(12) United States Patent
Kwon et al.

(10) Patent No.: US 11,965,038 B2
(45) Date of Patent: *Apr. 23, 2024

(54) PHARMACEUTICAL COMPOSITION COMPRISING ANTIBODY BINDING SPECIFICALLY TO LYSYL-TRNA SYNTHETASE N-TERMINUS AS EFFECTIVE INGREDIENT FOR PREVENTING OR TREATING IMMUNE CELL MIGRATION-RELATED DISEASE

(71) Applicant: Zymedi Co., Ltd., Incheon (KR)

(72) Inventors: Nam Hoon Kwon, Gyeonggi-do (KR); Jin Young Lee, Gyeonggi-do (KR); Sunghoon Kim, Gyeonggi-Do (KR)

(73) Assignee: Zymedi Co., Ltd., Incheon (KR)

( * ) Notice: Subject to any disclaimer, the term of this patent is extended or adjusted under 35 U.S.C. 154(b) by 291 days.

This patent is subject to a terminal disclaimer.

(21) Appl. No.: 16/646,240

(22) PCT Filed: Sep. 17, 2018

(86) PCT No.: PCT/KR2018/010903
§ 371 (c)(1),
(2) Date: May 15, 2020

(87) PCT Pub. No.: WO2019/054819
PCT Pub. Date: Mar. 21, 2019

(65) Prior Publication Data
US 2021/0070880 A1 Mar. 11, 2021

(30) Foreign Application Priority Data
Sep. 15, 2017 (KR) .................. 10-2017-0118917

(51) Int. Cl.
*C07K 16/40* (2006.01)
(52) U.S. Cl.
CPC ........ *C07K 16/40* (2013.01); *C07K 2317/565* (2013.01); *C07K 2317/622* (2013.01)
(58) Field of Classification Search
None
See application file for complete search history.

(56) References Cited

U.S. PATENT DOCUMENTS

| 9,511,085 | B2 | 12/2016 | Kim et al. |
| 9,945,859 | B2 | 4/2018 | Kim et al. |
| 2005/0277157 | A1 | 12/2005 | Rose et al. |
| 2016/0377619 | A1 | 12/2016 | Kim et al. |

FOREIGN PATENT DOCUMENTS

| JP | 2012-500256 A | 1/2012 |
| JP | 2017-502672 A | 1/2017 |
| KR | 10-2015-0079476 A | 7/2015 |
| WO | 2010021415 A1 | 2/2010 |
| WO | 2011/153277 A2 | 12/2011 |
| WO | 2019054819 A1 | 3/2019 |

OTHER PUBLICATIONS

Standen et al. (N Engl J Med 2000, 343:447-448.*
Kounis et al. OncoImmunology 3, e27987; 2014.*
Piche-Nicholas et al. MABS 2018, 10:81-94.*
Lamminmaki et al. (JBC 2001, 276:36687-36694).*
Padlan et al. (PNAS 1989, 86:5938-5942).*
Wu et al. (J. Mol. Biol. (1999) 294, 151-162).*
Chen et al. (J. Mol. Bio. (1999) 293, 865-881).*
Vajdos et al. (J. Mol. Biol. (2002) 320, 415-428).*
Casset et al. (BBRC 2003, 307:198-205).*
Pascalis et al. (The Journal of Immunology (2002) 169, 3076-3084).*
MacCallum et al. (J. Mol. Biol. 1996 262, 732-745).*
Rudikoff et al. (Proc Natl Acad Sci USA 1982 vol. 79 p. 1979).*
Lloyd et al. Protein Engineering, Design & Selection 2009, 22:159-168.*
Schroeder et al. J Allergy Clin Immunol 2010, 125:S41-S52.*
Kim et al. "Chemical inhibition of prometastatic lysyl-tRNA synthetase-laminin receptor interaction" Nature Chemical Biology, vol. 10, Jan. 2014.
Supplementary Information—Kim et al. "Chemical inhibition of prometastatic lysyl-tRNA synthetase-laminin receptor interaction". Nature Chemical Biology, vol. 10, Jan. 2014.
Jeon et al. "Function of membranous lysyl-tRNA synthetase and its implication for tumorigenesis" Biochimica et Biophysica Acta 1864 (2016) 1707-1713.
Choi et al. "A general strategy for generating intact, full-length IgG antibodies that penetrates into the cytosol of living cells" mAbs, 6:6, 1402-1414, DOI: 10.4161/mAbs.36389.
Tolkunova et al. "The Human Lysyl-tRNA Synthetase Gene Encodes Both the Cytoplasmic and Mitochondrial Enzymes by Means of an Unusual Alternative Splicing of the Primary Transcript". The Journal of Biological Chemistry, vol. 275, No. 45, Nov. 10, 2000, pp. 35063-35069.

(Continued)

*Primary Examiner* — Sharon X Wen
(74) *Attorney, Agent, or Firm* — Banner & Witcoff, Ltd.

(57) ABSTRACT

The present invention relates to a novel use of an antibody biding specifically to the N-terminus of lysyl-tRNA synthetase and, more particularly, to a pharmaceutical composition comprising an antibody biding specifically to an epitope including the sequence of SEQ ID NO: 117 in the N-terminal domain of lysyl-tRNA synthetase (KRS) or a functional fragment thereof as an effective ingredient for preventing and treating an immune cell migration-related disease. A KRS N-terminus-specific antibody provided by the present invention can regulate the migration of immune cells, thereby exhibiting very remarkable effects in the prevention, alleviation, and treatment of immune cell migration-related diseases.

12 Claims, 25 Drawing Sheets
(17 of 25 Drawing Sheet(s) Filed in Color)
Specification includes a Sequence Listing.

(56) References Cited

OTHER PUBLICATIONS

Kwon et al. "Aminoacyl-tRNA synthetases as therapeutic targets" Nature Reviews, Drug Discovery, vol. 18, Aug. 2019.
Park. S. G. el al., "Human Lysyl-tRNA Syn1hetase is Secreted to Trigger Proinfiammatory Response", Proceedings of the National Academy of Sciences of the United States of America, May 3, 2005, vol. 102, No. 18, pp. 63.56-636 See the entire document.
Yoshifuji, H. el al., "Anli-aminoacyl-tRNA Syn1hetase An1ibodies in Clinic31 Course Prediction of Interstitial Lung Disease Complicated with Idiopathic Inflamma1ory Myopathies", Autoimmunity, May 2006, vol. 39, No. 3, pp. 233-241 See the entire document.

\* cited by examiner

SF

LN111

LN211

LN221

LN411

LN421

LN511

LN521

SEQUENCE LISTING

```
<160> NUMBER OF SEQ ID NOS: 156

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 Ab CDR H1 amino acid

<400> SEQUENCE: 1

Ser Tyr Asp Met Ser
1               5
```

```
<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: N3 Ab CDR H1 DNA

<400> SEQUENCE: 2
agttatgata tgagc                                                            15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 Ab CDR H2 amino acid

<400> SEQUENCE: 3

Ala Ile Ser Tyr Asp Asn Gly Asn Thr Tyr Tyr Ala Asp Ser Val Lys
1               5                   10                  15

Gly

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: N3 Ab CDR H2 DNA

<400> SEQUENCE: 4
gcgatctctt atgataatgg taatacatat tacgctgatt ctgtaaaagg t                    51

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 Ab CDR H3 amino acid

<400> SEQUENCE: 5

Met Ala Leu Asp Phe Asp Tyr
1               5

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: N3 Ab CDR H3 DNA

<400> SEQUENCE: 6
atggcgcttg atttcgacta c                                                     21
```

```
<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 Ab CDR L1 amino acid

<400> SEQUENCE: 7

Thr Gly Ser Ser Ser Asn Ile Gly Ser Asn Tyr Val Thr
1               5                   10

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: N3 Ab CDR L1 DNA

<400> SEQUENCE: 8
actggctctt catctaatat tggcagtaat tatgtcacc                              39

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 Ab CDR L2 amino acid

<400> SEQUENCE: 9

Asp Asn Ser Asn Arg Pro Ser
1               5

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: N3 Ab CDR L2 DNA

<400> SEQUENCE: 10
gataatagta atcggccaag c                                                 21

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 Ab CDR L3 amino acid

<400> SEQUENCE: 11

Ala Ser Trp Asp Asp Ser Leu Ser Ala Tyr Val
1               5                   10

<210> SEQ ID NO 12
```

<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: N3 Ab CDR L3 DNA

<400> SEQUENCE: 12
gcttcttggg atgatagcct gagtgcttat gtc            33

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L3 mutant 1 amino acid

<400> SEQUENCE: 13

Ala Ser Phe Ser Asp Glu Leu Gly Ala Tyr Val
1               5                   10

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: CDR L3 mutant 1 DNA

<400> SEQUENCE: 14
gcttctttta gtgatgagtt ggggcttat gtc            33

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L3 mutant 2 amino acid

<400> SEQUENCE: 15

Ser Ser Phe Ser Asp Glu Leu Gly Ala Tyr Val
1               5                   10

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: CDR L3 mutant 2 DNA

<400> SEQUENCE: 16
tcttctttta gtgatgagtt gggggcttat gtc            33

<210> SEQ ID NO 17
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 1 amino acid

<400> SEQUENCE: 17

Ala Ile Ser Pro Gln Met Gly Arg Val Tyr Tyr Ala Asp Ser Val Lys
1               5                   10                  15
Gly

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 mutant 1 DNA

<400> SEQUENCE: 18
gcgatctcgc cgcagatggg tcgggtgtat tacgctgatt ctgtaaaagg t            51

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 2 amino acid

<400> SEQUENCE: 19

Ala Ile Asp Pro Leu Gly Gly Asn Ile Tyr Tyr Ala Asp Ser Val Lys
1               5                   10                  15
Gly

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 mutant 2 DNA

<400> SEQUENCE: 20
gcgatcgatc cgttgggggg taatatttat tacgctgatt ctgtaaaagg t            51

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 3 amino acid

<400> SEQUENCE: 21

Ala Ile Ser Pro Tyr Ser Gly Arg Ile Tyr Tyr Ala Asp Ser Val Lys
1               5                   10                  15
Gly
```

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: CDR H2 mutant 3 DNA

<400> SEQUENCE: 22
gcgatctctc cgtattcggg taggatttat tacgctgatt ctgtaaaagg t      51

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDR H2 mutant 4 amino acid

<400> SEQUENCE: 23

Ala Ile Gly Ala Asp Gly Gly Pro Ser Tyr Tyr Ala Asp Ser Val Lys
1               5                   10                  15

Gly

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: CDR H2 mutant 4 DNA

<400> SEQUENCE: 24
gcgatcgggg ctgatggggg tccgtcttat tacgctgatt ctgtaaaagg t      51

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDR H3 mutant 1 amino acid

<400> SEQUENCE: 25

Leu Ala Leu Asp Phe Asp Tyr
1               5

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: CDR H3 mutant 1 DNA

<400> SEQUENCE: 26
ctggcgcttg atttcgacta c                                       21

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L2 mutant 1 amino acid

<400> SEQUENCE: 27

Ser Asn Asn Gln Arg Pro Ser
1               5

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L2 mutant 1 DNA

<400> SEQUENCE: 28
agtaataatc agcggccaag c                                              21

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L2 mutant 2 amino acid

<400> SEQUENCE: 29

Arg Asn Asn Gln Arg Pro Ser
1               5

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L2 mutant 2 DNA

<400> SEQUENCE: 30
cggaataatc agcggccaag c                                              21

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH

<400> SEQUENCE: 31

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Tyr Asp Asn Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
        115

<210> SEQ ID NO 32
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH

<400> SEQUENCE: 32
gaggtgcagc tgttggagtc tgggggaggc ttggtacagc ctggggggtc cctgagactc     60
tcctgtgcag cctctggatt cacctttagc agttatgata tgagctgggt ccgccaggct    120
ccagggaagg ggctggagtg ggtctcagcg atctcttatg ataatggtaa tacatattac    180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctca                 348

<210> SEQ ID NO 33
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
            35                  40                  45

Ile Tyr Asp Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ala Tyr Val Phe Gly Gly Gly Thr Lys Leu Thr Val Leu
            100                 105                 110

<210> SEQ ID NO 34
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL

<400> SEQUENCE: 34

```
cagtctgtgc tgactcagcc accctcagcg tctgggaccc cggggcagag ggtcaccatc      60
tcttgtactg gctcttcatc taatattggc agtaattatg tcacctggta ccagcagctc     120
ccaggaacgg cccccaaact cctcatctat gataatagta atcggccaag cggggtccct     180
gaccgattct ctggctccaa gtctggcacc tcagcctccc tggccatcag tgggctccgg     240
tccgaggatg aggctgatta ttactgtgct tcttgggatg atagcctgag tgcttatgtc     300
ttcggcggag gcaccaagct gacggtccta                                      330
```

<210> SEQ ID NO 35
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 1

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
            85                  90                  95

Ala Arg Met Ala Leu Asp Phe Asp Tyr Trp Gly Gln Gly Thr Leu Val
        100                 105                 110

Thr Val Ser Ser
        115
```

<210> SEQ ID NO 36
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 1

<400> SEQUENCE: 36

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
```

```
ccagggaagg ggctggagtg ggtctcagtg atctcttctg atggtggtaa tacatattac    180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctca                 348
```

<210> SEQ ID NO 37
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 2

<400> SEQUENCE: 37

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
        115
```

<210> SEQ ID NO 38
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 2

<400> SEQUENCE: 38

```
gaggtgcagc tgttggagtc tgggggaggc ttggtacagc ctgggggtc cctgagactc     60 tcctgtgcag cctctggatt cacctttagc agttatgata tgagctgggt ccgccaggct   120
ccagggaagg ggctggagtg ggtctcagcg atctcgccgc agatgggtcg ggtgtattac   180
gctgattctg taaaaggtcg gttcaccatc tccagagaca attccaagaa cacgctgtat   240
ctgcaaatga acagcctgag agccgaggac acggccgtgt attactctgc gagaatggcg   300
cttgatttcg actactgggg ccagggtaca ctggtcaccg tgagctca                348
```

<210> SEQ ID NO 39
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: N3 VH mutant 3

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
            115

<210> SEQ ID NO 40
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 3

<400> SEQUENCE: 40
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg gtctcagcg atcgatccgt tgggggtaa tatttattac      180 gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctca                   348

<210> SEQ ID NO 41
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 4

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
        115

<210> SEQ ID NO 42
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 4

<400> SEQUENCE: 42
gaggtgcagc tgttggagtc tgggggaggc ttggtacagc ctgggggtc cctgagactc      60 tcctgtgcag cctctggatt cacctttagc agttatgata tgagctgggt ccgccaggct    120
ccagggaagg ggctggagtg ggtctcagcg atctctccgt attcgggtag gatttattac    180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctca                 348

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 5

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
        115

<210> SEQ ID NO 44
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 5

<400> SEQUENCE: 44

```
gaggtgcagc tgttggagtc tgggggaggc ttggtacagc ctggggggtc cctgagactc    60
tcctgtgcag cctctggatt cacctttagc agttatgata tgagctgggt ccgccaggct   120
ccagggaagg ggctggagtg ggtctcagcg atcggggctg atggggggtcc gtcttattac   180 gctgattctg taaaaggtcg gttcaccatc tccagagaca attccaagaa cacgctgtat   240
ctgcaaatga acagcctgag agccgaggac acggccgtgt attactctgc gagaatggcg   300
cttgatttcg actactgggg ccagggtaca ctggtcaccg tgagctca              348
```

<210> SEQ ID NO 45
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 6

<400> SEQUENCE: 45

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser
        115

<210> SEQ ID NO 46
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 6

<400> SEQUENCE: 46

```
gaggtgcagc tgttggagtc tgggggaggc ttggtacagc ctggggggtc cctgagactc    60
tcctgtgcag cctctggatt cacctttagc agttatgata tgagctgggt ccgccaggct   120
ccagggaagg ggctggagtg ggtctcagcg atctctccgt attcgggtag gatttattac   180
gctgattctg taaaaggtcg gttcaccatc tccagagaca attccaagaa cacgctgtat   240
ctgcaaatga acagcctgag agccgaggac acggccgtgt attactgtgc gagaatggcg   300
```

```
cttgatttcg actactgggg ccagggtaca ctggtcaccg tgagctca          348
```

<210> SEQ ID NO 47
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 7

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser
        115
```

<210> SEQ ID NO 48
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 7

<400> SEQUENCE: 48

```
gaggtgcagc tgttggagtc tgggggaggc ttggtacagc ctggggggtc cctgagactc     60
tcctgtgcag cctctggatt cacctttagc agttatgata tgagctgggt ccgccaggct    120
ccagggaagg gctggagtg gtctcagcg atctctccgt attcgggtag gatttattac     180
gctgattctg taaaaggtcg gttcaccatc tccagagaca attccaagaa cacgctgtat    240
ctgcaaatga acagcctgag agccgaggac acggccgtgt attactgtgc gagactggcg    300
cttgatttcg actactgggg ccagggtaca ctggtcaccg tgagctca               348
```

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL mutant 1

<400> SEQUENCE: 49

```
Gln Ser Val Leu Thr Gln Pro Pro Ser Ala Ser Gly Thr Pro Gly Gln
```

```
            1               5                   10                  15
Arg Val Thr Ile Ser Cys Thr Gly Ser Ser Ser Asn Ile Gly Ser Asn
                20                  25                  30

Tyr Val Thr Trp Tyr Gln Gln Leu Pro Gly Thr Ala Pro Lys Leu Leu
            35                  40                  45

Ile Tyr Asp Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Phe Ser Asp Glu Leu
                85                  90                  95

Gly Ala Tyr Val Phe Gly Gly Gly Thr Lys Leu Thr Val Leu
                100                 105                 110
```

<210> SEQ ID NO 50
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 1

<400> SEQUENCE: 50

```
cagtctgtgc tgactcagcc accctcagcg tctgggaccc ccgggcagag ggtcaccatc    60
tcttgtactg gctcttcatc taatattggc agtaattatg tcacctggta ccagcagctc   120
ccaggaacgg cccccaaact cctcatctat gataatagta atcggccaag cggggtccct   180
gaccgattct ctggctccaa gtctggcacc tcagcctccc tggccatcag tgggctccag   240
tccgaggatg aggctgatta ttactgtgct tcttttagtg atgagttggg ggcttatgtc   300
ttcggcggag gcaccaagct gacggtccta                                    330
```

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL mutant 2

<400> SEQUENCE: 51

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Tyr Val Thr Trp Tyr Gln Gln Leu Pro Gly Thr Ala Pro Lys Leu Leu
            35                  40                  45

Ile Tyr Asp Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu
                100                 105                 110
```

<210> SEQ ID NO 52
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 2

<400> SEQUENCE: 52

```
cagtctgtgc tgactcagcc accctcagcg tctgggaccc ccgggcagag ggtcaccatc    60
tcttgtactg gctcttcatc taatattggc agtaattatg tcacctggta ccagcagctc   120
ccaggaacgg cccccaaact cctcatctat gataatagta atcggccaag cggggtccct   180
gaccgattct ctggctccaa gtctggcacc tcagcctccc tggccatcag tgggctccag   240
tccgaggatg aggctgatta ttactgttct tcttttagtg atgagttggg ggcttatgtc   300
ttcggcggag gcaccaagct gacggtccta                                    330
```

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL mutant 3

<400> SEQUENCE: 53

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Tyr Val Thr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu
            100                 105                 110
```

<210> SEQ ID NO 54
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 3

<400> SEQUENCE: 54

```
cagtctgtgc tgactcagcc accctcagcg tctgggaccc ccgggcagag ggtcaccatc    60
tcttgtactg gctcttcatc taatattggc agtaattatg tcacctggta ccagcagctc   120
ccaggaacgg cccccaaact cctcatctat agtaataatc agcggccaag cggggtccct   180
gaccgattct ctggctccaa gtctggcacc tcagcctccc tggccatcag tgggctccag   240
```

```
tccgaggatg aggctgatta ttactgttct tcttttagtg atgagttggg ggcttatgtc    300
ttcggcggag gcaccaagct gacggtccta                                     330
```

<210> SEQ ID NO 55
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL mutant 4

<400> SEQUENCE: 55

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu
            100                 105                 110
```

<210> SEQ ID NO 56
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 4

<400> SEQUENCE: 56

```
cagtctgtgc tgactcagcc accctcagcg tctgggaccc ccgggcagag ggtcaccatc    60
tcttgtactg gctcttcatc taatattggc agtaattatg tcacctggta ccagcagctc   120
ccaggaacgg cccccaaact cctcatctat cggaataatc agcggccaag cggggtccct   180
gaccgattct ctggctccaa gtctggcacc tcagcctccc tggccatcag tgggctccag   240
tccgaggatg aggctgatta ttactgttct tcttttagtg atgagttggg ggcttatgtc   300
ttcggcggag gcaccaagct gacggtccta                                    330
```

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker for scFv

<400> SEQUENCE: 57

```
Gly Gly Gly Gly Ser Gly Gly Gly Gly Ser Gly Gly Gly Gly Ser
1               5                   10                  15
```

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Linker for scFv

<400> SEQUENCE: 58
ggtggaggcg gttcaggcgg aggtggatcc ggcggtggcg gatcg     45

<210> SEQ ID NO 59
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 scFv (VH+linker+VL)

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Ala Ser Trp Asp
    210                 215                 220

Asp Ser Leu Ser Ala Tyr Val Phe Gly Gly Gly Thr Lys Leu Thr Val
225                 230                 235                 240

Leu

<210> SEQ ID NO 60
<211> LENGTH: 723

<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N3 scFv (VH+linker+VL)

<400> SEQUENCE: 60

```
gaggtgcagc tgttggagtc tgggggaggc ttggtacagc ctgggggtc cctgagactc      60
tcctgtgcag cctctggatt cacctttagc agttatgata tgagctgggt ccgccaggct     120
ccagggaagg gctggagtg gtctcagcg atctcttatg ataatggtaa tacatattac      180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccacccctca    420
gcgtctggga cccccgggca gagggtcacc atctcttgta ctggctcttc atctaatatt     480
ggcagtaatt atgtcacctg gtaccagcag ctcccaggaa cggccccca actcctcatc     540
tatgataata gtaatcggcc aagcggggtc cctgaccgat tctctggctc caagtctggc     600
acctcagcct ccctggccat cagtgggctc cggtccgagg atgaggctga ttattactgt     660
gcttcttggg atgatagcct gagtgcttat gtcttcggcg aggcaccaa gctgacggtc     720
cta                                                                   723
```

<210> SEQ ID NO 61
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N3-1 scFv (VH+linker+VL)

<400> SEQUENCE: 61

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160
```

```
Gly Ser Asn Tyr Val Thr Trp Tyr Gln Gln Leu Pro Gly Thr Ala Pro
            165                 170                 175

Lys Leu Leu Ile Tyr Asp Asn Ser Asn Arg Pro Ser Gly Val Pro Asp
        180                 185                 190

Arg Phe Ser Gly Ser Lys Ser Gly Thr Ser Ala Ser Leu Ala Ile Ser
            195                 200                 205

Gly Leu Gln Ser Glu Asp Glu Ala Asp Tyr Tyr Cys Ala Ser Phe Ser
        210                 215                 220

Asp Glu Leu Gly Ala Tyr Val Phe Gly Gly Thr Lys Leu Thr Val
225                 230                 235                 240

Leu

<210> SEQ ID NO 62
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-1 scFv (VH+linker+VL)

<400> SEQUENCE: 62
gaggtgcagc tgttggagtc tgggggaggc ttggtacagc ctggggggtc cctgagactc      60
tcctgtgcag cctctggatt caccttagc agttatgata tgagctgggt ccgccaggct      120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccacccctca    420 gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatgataata gtaatcggcc aagcggggtc cctgaccgat tctctggctc caagtctggc    600
acctcagcct ccctggccat cagtgggctc cagtccgagg atgaggctga ttattactgt    660 gcttcttta gtgatgagtt gggggcttat gtcttcggcg aggcaccaa gctgacggtc     720 cta                                                                  723

<210> SEQ ID NO 63
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-3 scFv (VH+linker+VL)

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
```

```
                50              55               60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Ser
                 85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu
```

```
<210> SEQ ID NO 64
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-3 scFv (VH+linker+VL)

<400> SEQUENCE: 64
gaggtgcagc tgttggagtc tgggggaggc ttggtacagc ctggggggtc cctgagactc      60
tcctgtgcag cctctggatt caccttagc agttatgata tgagctgggt ccgccaggct      120
ccagggaagg ggctggagtg gtctcagcg atctcttatg ataatggtaa tacatattac      180
gctgattctg taaaaggtcg gttcaccatc tccagadaca attccaagaa cacgctgtat      240
ctgcaaatga acagcctgag agccgaggac acggccgtgt attactctgc gagaatggcg      300
cttgatttcg actactgggg ccagggtaca ctggtcaccg tgagctcagg tggaggcggt      360
tcaggcggag gtggatccgg cggtggcgga tcgcagtctg tgctgactca gccaccctca      420
gcgtctggga cccccgggca gagggtcacc atctcttgta ctggctcttc atctaatatt      480
ggcagtaatt atgtcacctg gtaccagcag ctcccaggaa cggcccccaa actcctcatc      540
tatgataata gtaatcggcc aagcgggtc cctgaccgat tctctggctc caagtctggc      600
acctcagcct ccctggccat cagtgggctc cagtccgagg atgaggctga ttattactgt      660
tcttctttta gtgatgagtt gggggcttat gtcttcggcg aggcaccaa gctgacggtc      720 cta                                                                   723
```

```
<210> SEQ ID NO 65
<211> LENGTH: 241
```

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-4 scFv (VH+linker+VL)

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ala Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 66
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-4 scFv (VH+linker+VL)

<400> SEQUENCE: 66
gaggtgcagc tgttggagtc tgggggaggc ttggtacagc ctgggggtc cctgagactc      60 tcctgtgcag cctctggatt cacctttagc agttatgata tgagctgggt ccgccaggct    120
ccagggaagg gctggagtg gtctcagtg atctcttctg atggtggtaa tacatattac      180
gctgattctg taaaaggtcg gttcaccatc tccagagaca attccaagaa cacgctgtat    240
ctgcaaatga acagcctgag agccgaggac acggccgtgt attactctgc gagaatggcg    300

```
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga ccccgggca gagggtcacc atctcttgta ctggctcttc atctaatatt    480
ggcagtaatt atgtcacctg gtaccagcag ctcccaggaa cggcccccaa actcctcatc    540
tatgataata gtaatcggcc aagcggggtc cctgaccgat tctctggctc caagtctggc    600
acctcagcct ccctggccat cagtgggctc cagtccgagg atgaggctga ttattactgt    660
gcttctttta gtgatgagtt gggggcttat gtcttcggcg aggcaccaa gctgacggtc    720 cta                                                                  723
```

<210> SEQ ID NO 67
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-5 scFv (VH+linker+VL)

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 68

```
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-5 scFv (VH+linker+VL)

<400> SEQUENCE: 68
gaggtgcagc tgttggagtc tgggggaggc ttggtacagc ctgggggtc cctgagactc      60 tcctgtgcag cctctggatt caccttagc agttatgata tgagctgggt ccgccaggct     120
ccagggaagg gctggagtg gtctcagtg atctcttctg atggtggtaa tacatattac     180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatgataata gtaatcggcc aagcggggtc cctgaccgat tctctggctc caagtctggc    600
acctcagcct ccctggccat cagtgggctc cagtccgagg atgaggctga ttattactgt    660 tcttcttttta gtgatgagtt gggggcttat gtcttcggcg gaggcaccaa gctgacggtc    720
cta                                                                  723

<210> SEQ ID NO 69
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-6 scFv (VH+linker+VL)

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160
```

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 70
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-6 scFv (VH+linker+VL)

<400> SEQUENCE: 70
gaggtgcagc tgttggagtc tgggggaggc ttggtacagc ctgggggtc cctgagactc        60 tcctgtgcag cctctggatt cacctttagc agttatgata tgagctgggt ccgccaggct      120
ccagggaagg gctggagtg gtctcagcg atctcgccgc agatgggtcg ggtgtattac       180
gctgattctg taaaaggtcg gttcaccatc tccagagaca attccaagaa cacgctgtat     240
ctgcaaatga acagcctgag agccgaggac acggccgtgt attactctgc gagaatggcg    300
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatgataata gtaatcggcc aagcggggtc cctgaccgat tctctggctc caagtctggc    600
acctcagcct ccctggccat cagtgggctc cagtccgagg atgaggctga ttattactgt    660 tcttcttta gtgatgagtt gggggcttat gtcttcggcg aggcaccaa gctgacggtc      720 cta                                                                  723

<210> SEQ ID NO 71
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-7 scFv (VH+linker+VL)

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

```
Ser Ala Ile Asp Pro Leu Gly Gly Asn Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Ser
                 85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
210                 215                 220

Asp Glu Leu Gly Ala Tyr Val Phe Gly Gly Gly Thr Lys Leu Thr Val
225                 230                 235                 240

Leu

<210> SEQ ID NO 72
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-7 scFv (VH+linker+VL)

<400> SEQUENCE: 72
gaggtgcagc tgttggagtc tgggggaggc ttggtacagc ctgggggtc cctgagactc        60 tcctgtgcag cctctggatt caccttagc agttatgata tgagctgggt ccgccaggct       120
ccagggaagg gctggagtg gtctcagcg atcgatccgt tgggggtaa tatttattac        180 gctgattctg taaaaggtcg gttcaccatc tccagagaca attccaagaa cacgctgtat      240
ctgcaaatga acagcctgag agccgaggac acggccgtgt attactctgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga ccccggca gagggtcacc atctcttgta ctggctcttc atctaatatt      480
ggcagtaatt atgtcacctg gtaccagcag ctcccaggaa cggcccccaa actcctcatc     540
tatgataata gtaatcggcc aagcggggtc cctgaccgat tctctggctc caagtctggc    600
acctcagcct ccctggccat cagtgggctc cagtccgagg atgaggctga ttattactgt    660 tcttcttta gtgatgagtt gggggcttat gtcttcggcg aggcaccaa gctgacggtc      720 cta                                                                    723

<210> SEQ ID NO 73
```

```
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8 scFv, N3-8-7 scFv (VH+linker+VL)

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 74
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8 scFv, N3-8-7 scFv (VH+linker+VL)

<400> SEQUENCE: 74
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg gctggagtg gtctcagcg atctctccgt attcgggtag gatttattac       180
gctgattctg taaaaggtcg gttcaccatc tccagagaca attccaagaa cacgctgtat     240
```

```
ctgcaaatga acagcctgag agccgaggac acggccgtgt attactctgc gagaatggcg    300
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatgataata gtaatcggcc aagcggggtc cctgaccgat tctctggctc caagtctggc    600
acctcagcct ccctggccat cagtgggctc cagtccgagg atgaggctga ttattactgt    660
tcttctttta gtgatgagtt gggggcttat gtcttcggcg aggcaccaa gctgacggtc    720 cta                                                                  723
```

<210> SEQ ID NO 75
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-9 scFv (VH+linker+VL)

<400> SEQUENCE: 75

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu
```

<210> SEQ ID NO 76
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N3-9 scFv (VH+linker+VL)

<400> SEQUENCE: 76

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atcggggctg atggggggtcc gtcttattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccacccctca    420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgataata gtaatcggcc aagcggggtc cctgaccgat tctctggctc caagtctggc     600
acctcagcct ccctggccat cagtgggctc cagtccgagg atgaggctga ttattactgt     660
tcttctttta gtgatgagtt gggggcttat gtcttcggcg aggcaccaa gctgacggtc      720
cta                                                                  723
```

<210> SEQ ID NO 77
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N3-8-1 scFv (VH+linker+VL)

<400> SEQUENCE: 77

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
```

```
                145                 150                 155                 160
Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
                180                 185                 190

Arg Phe Ser Gly Ser Lys Ser Gly Thr Ser Ala Ser Leu Ala Ile Ser
                195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 78
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-1 scFv (VH+linker+VL)

<400> SEQUENCE: 78
gaggtgcagc tgttggagtc tgggggaggc ttggtacagc ctgggggtc cctgagactc       60 tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgataata gtaatcggcc aagcggggtc cctgaccgat tctctggctc caagtctggc     600
acctcagcct ccctggccat cagtgggctc cagtccgagg atgaggctga ttattactgt     660
tcttctttta gtgatgagtt gggggcttat gtcttcggcg gaggcaccaa gctgacggtc     720
cta                                                                   723

<210> SEQ ID NO 79
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-2 scFv (VH+linker+VL)

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45
```

```
Ser Ala Ile Ser Pro Tyr Ser Gly Arg Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Ala Leu Asp Phe Asp Tyr Trp Gly Gln Gly Thr Leu Val
            100                 105                 110

Thr Val Ser Ser Gly Gly Gly Ser Gly Gly Gly Ser Gly Gly
            115                 120                 125

Gly Gly Ser Gln Ser Val Leu Thr Gln Pro Pro Ser Ala Ser Gly Thr
        130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Ser Asn Asn Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu
```

<210> SEQ ID NO 80
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-2 scFv (VH+linker+VL)

<400> SEQUENCE: 80

```
gaggtgcagc tgttggagtc tgggggaggc ttggtacagc ctgggggtc cctgagactc      60 tcctgtgcag cctctggatt caccttagc agttatgata tgagctgggt ccgccaggct     120
ccagggaagg gctggagtg gtctcagcg atctctccgt attcgggtag gatttattac     180
gctgattctg taaaaggtcg gttcaccatc tccagagaca attccaagaa cacgctgtat    240
ctgcaaatga acagcctgag agccgaggac acggccgtgt attactgtgc gagaatggcg    300
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatagtaata atcagcggcc aagcggggtc cctgaccgat tctctggctc caagtctggc    600
acctcagcct ccctggccat cagtgggctc cagtccgagg atgaggctga ttattactgt    660
tcttctttta gtgatgagtt gggggcttat gtcttcggcg gaggcaccaa gctgacggtc    720
cta                                                                  723
```

<210> SEQ ID NO 81
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N3-8-3 scFv (VH+linker+VL)

<400> SEQUENCE: 81

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Arg Asn Asn Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu
```

<210> SEQ ID NO 82
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N3-8-3 scFv (VH+linker+VL)

<400> SEQUENCE: 82

```
gaggtgcagc tgttggagtc tgggggaggc ttggtacagc ctggggggtc cctgagactc     60
tcctgtgcag cctctggatt cacctttagc agttatgata tgagctgggt ccgccaggct    120
ccagggaagg ggctggagtg ggtctcagcg atctctccgt attcgggtag gatttattac    180
gctgattctg taaaaggtcg gttcaccatc tccagagaca attccaagaa cacgctgtat    240
```

```
ctgcaaatga acagcctgag agccgaggac acggccgtgt attactgtgc gagaatggcg      300
cttgatttcg actactgggg ccagggtaca ctggtcaccg tgagctcagg tggaggcggt      360
tcaggcggag gtggatccgg cggtggcgga tcgcagtctg tgctgactca gccacccatca     420 gcgtctggga cccccgggca gagggtcacc atctcttgta ctggctcttc atctaatatt      480
ggcagtaatt atgtcacctg gtaccagcag ctcccaggaa cggcccccaa actcctcatc      540
tatcggaata atcagcggcc aagcggggtc cctgaccgat tctctggctc caagtctggc      600
acctcagcct ccctggccat cagtgggctc cagtccgagg atgaggctga ttattactgt      660
tcttctttta gtgatgagtt gggggcttat gtcttcggcg aggcaccaa  gctgacggtc      720 cta                                                                    723
```

```
<210> SEQ ID NO 83
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-4 scFv (VH+linker+VL)

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu
```

<210> SEQ ID NO 84
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N3-8-4 scFv (VH+linker+VL)

<400> SEQUENCE: 84

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgataata gtaatcggcc aagcggggtc cctgaccgat tctctggctc caagtctggc     600
acctcagcct ccctggccat cagtgggctc cagtccgagg atgaggctga ttattactgt     660
tcttctttta gtgatgagtt gggggcttat gtcttcggcg aggcaccaa gctgacggtc     720
cta                                                                  723
```

<210> SEQ ID NO 85
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N3-8-5 scFv (VH+linker+VL)

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140
```

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
            165                 170                 175

Lys Leu Leu Ile Tyr Ser Asn Asn Gln Arg Pro Ser Gly Val Pro Asp
        180                 185                 190

Arg Phe Ser Gly Ser Lys Ser Gly Thr Ser Ala Ser Leu Ala Ile Ser
    195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Thr Lys Leu Thr Val
225                 230                 235                 240

Leu

<210> SEQ ID NO 86
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-5 scFv (VH+linker+VL)

<400> SEQUENCE: 86
gaggtgcagc tgttggagtc tgggggaggc ttggtacagc ctgggggtc cctgagactc      60 tcctgtgcag cctctggatt cacctttagc agttatgata tgagctgggt ccgccaggct    120
ccagggaagg ggctggagtg ggtctcagcg atctctccgt attcgggtag gatttattac    180
gctgattctg taaaaggtcg gttcaccatc tccagagaca attccaagaa cacgctgtat    240
ctgcaaatga acagcctgag agccgaggac acggccgtgt attactgtgc gagactggcg    300
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatagtaata atcagcggcc aagcggggtc cctgaccgat tctctggctc caagtctggc    600
acctcagcct ccctggccat cagtgggctc cagtccgagg atgaggctga ttattactgt    660
tcttctttta gtgatgagtt gggggcttat gtcttcggcg aggcaccaa gctgacggtc      720 cta                                                                   723

<210> SEQ ID NO 87
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-6 scFv (VH+linker+VL)

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val

```
                    35                  40                  45
Ser Ala Ile Ser Pro Tyr Ser Gly Arg Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Ala Leu Asp Phe Asp Tyr Trp Gly Gln Gly Thr Leu Val
                100                 105                 110

Thr Val Ser Ser Gly Gly Gly Gly Ser Gly Gly Gly Gly Ser Gly Gly
                115                 120                 125

Gly Gly Ser Gln Ser Val Leu Thr Gln Pro Pro Ser Ala Ser Gly Thr
 130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Arg Asn Asn Gln Arg Pro Ser Gly Val Pro Asp
                180                 185                 190

Arg Phe Ser Gly Ser Lys Ser Gly Thr Ser Ala Ser Leu Ala Ile Ser
                195                 200                 205

Gly Leu Gln Ser Glu Asp Glu Ala Asp Tyr Tyr Cys Ser Ser Phe Ser
 210                 215                 220

Asp Glu Leu Gly Ala Tyr Val Phe Gly Gly Gly Thr Lys Leu Thr Val
225                 230                 235                 240

Leu
```

<210> SEQ ID NO 88
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N3-8-6 scFv (VH+linker+VL)

<400> SEQUENCE: 88

```
gaggtgcagc tgttggagtc tgggggaggc ttggtacagc ctgggggtc cctgagactc      60
tcctgtgcag cctctggatt cacctttagc agttatgata tgagctgggt ccgccaggct     120
ccagggaagg gctggagtg gtctcagcg atctctccgt attcgggtag gatttattac      180
gctgattctg taaaaggtcg gttcaccatc tccagagaca attccaagaa cacgctgtat    240
ctgcaaatga acagcctgag agccgaggac acggccgtgt attactgtgc gagactggcg    300
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatcggaata atcagcggcc aagcggggtc cctgaccgat tctctggctc caagtctggc    600
acctcagcct ccctggccat cagtgggctc cagtccgagg atgaggctga ttattactgt    660
tcttctttta gtgatgagtt gggggcttat gtcttcggcg gaggcaccaa gctgacggtc    720
cta                                                                  723
```

<210> SEQ ID NO 89
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N3 IgG heavy chain

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 90
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 IgG heavy chain

<400> SEQUENCE: 90
gaggtgcagc tgttggagtc tgggggaggc ttggtacagc ctgggggtc cctgagactc      60 tcctgtgcag cctctggatt cacctttagc agttatgata tgagctgggt ccgccaggct    120
ccagggaagg gctggagtg gtctcagcg atctcttatg ataatggtaa tacatattac      180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtataccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                 1338

<210> SEQ ID NO 91
```

<211> LENGTH: 217
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N3 IgG light chain

<400> SEQUENCE: 91

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 92
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N3 IgG light chain

<400> SEQUENCE: 92
cagtctgtgc tgactcagcc accctcagcg tctgggaccc ccgggcagag ggtcaccatc        60
tcttgtactg gctcttcatc taatattggc agtaattatg tcacctggta ccagcagctc       120
ccaggaacgg cccccaaact cctcatctat gataatagta tcggccaag cggggtccct        180 gaccgattct ctggctccaa gtctggcacc tcagcctccc tggccatcag tgggctccgg       240
tccgaggatg aggctgatta ttactgtgct tcttgggatg atagcctgag tgcttatgtc       300
ttcggcggag gcaccaagct gacggtccta cgtacggtgg ctgccaccatc tgtcttcatc      360 ttcccgccat ctgatgagca gttgaaatct ggaactgcct ctgttgtgtg cctgctgaat       420

```
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaag tctacgcctg cgaagtcacc      600
catcagggcc tgagctcgcc cgtcacaaag agcttcaaca ggggagagtg t               651
```

<210> SEQ ID NO 93
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1

<400> SEQUENCE: 93

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 94
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1

<400> SEQUENCE: 94
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg gctggagtg gtctcagtg atctcttctg atggtggtaa tacatattac      180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
```

-continued

```
ggctccttct tcctctacag caagctcacc gtggacaaga gcaggtggca gcagggggaac    1260 gtcttctcat gctccgtgat gcatgaggct ctgcacaacc actacacgca gaagagcctc    1320
tccctgtccc cgggtaaa                                                   1338
```

<210> SEQ ID NO 95
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 2

<400> SEQUENCE: 95

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 96
<211> LENGTH: 1338
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: IgG heavy chain 2

<400> SEQUENCE: 96
gaggtgcagc tgttggagtc tgggggaggc ttggtacagc ctgggggtc cctgagactc      60 tcctgtgcag cctctggatt cacctttagc agttatgata tgagctgggt ccgccaggct    120
ccagggaagg gctggagtg gtctcagcg atctcgccgc agatgggtcg gtgtattac       180 gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctcagc tccaccaag    360 ggcccatcgg tcttccccct ggcaccctcc tccaagagca cctctggggg cacagcggcc    420
ctgggctgcc tggtcaagga ctacttcccc gaaccggtga cggtgtcgtg aactcaggc    480 gccctgacca gcggcgtgca caccttcccg gctgtcctac agtcctcagg actctactcc    540
ctcagcagcg tggtgaccgt gcctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260

-continued

```
gtcttctcat gctccgtgat gcatgaggct ctgcacaacc actacacgca gaagagcctc   1320
tccctgtccc cgggtaaa                                                  1338
```

<210> SEQ ID NO 97
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 3

<400> SEQUENCE: 97

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
            325                 330                 335
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 98
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 3

<400> SEQUENCE: 98
gaggtgcagc tgttggagtc tgggggaggc ttggtacagc ctgggggtc cctgagactc       60 tcctgtgcag cctctggatt cacctttagc agttatgata tgagctgggt ccgccaggct     120
ccagggaagg gctggagtg gtctcagcg atcgatccgt tggggggtaa tatttattac       180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtataccctg cccccatccc gggatgagct gaccaagaac   1080
caggtcagcc tgacctgcct ggtcaaaggc ttctatccca gcgacatcgc cgtggagtgg   1140
gagagcaatg gcagccggga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
```
tccctgtccc cgggtaaa                                                  1338

<210> SEQ ID NO 99
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

```
Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 100
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4

<400> SEQUENCE: 100
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg gctggagtg gtctcagcg atctctccgt attcgggtag gatttattac       180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggaccctga ggtcacatgc       780 gtggtggtgg acgtgagcca cgaagaccct gaggtcaagt tcaactggta cgtgacggc       840 gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

<210> SEQ ID NO 101
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 102
<211> LENGTH: 1338
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: IgG heavy chain 5

<400> SEQUENCE: 102

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atcggggctg atggggggtcc gtcttattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtatccctg ccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc tcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

```
<210> SEQ ID NO 103
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
```

```
              355                 360                 365
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 104
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6

<400> SEQUENCE: 104
gaggtgcagc tgttggagtc tgggggaggc ttggtacagc ctggggggtc cctgagactc      60
tcctgtgcag cctctggatt caccttagc agttatgata tgagctgggt ccgccaggct     120
ccagggaagg gctggagtg gtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtatacctg ccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                 1338

<210> SEQ ID NO 105
<211> LENGTH: 446
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 106
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7

<400> SEQUENCE: 106
gaggtgcagc tgttggagtc tgggggaggc ttggtacagc ctggggggtc cctgagactc        60
tcctgtgcag cctctggatt cacctttagc agttatgata tgagctgggt ccgccaggct       120
ccagggaagg ggctggagtg ggtctcagcg atctctccgt attcgggtag gatttattac       180
gctgattctg taaaaggtcg gttcaccatc tccagagaca attccaagaa cacgctgtat       240
ctgcaaatga acagcctgag agccgaggac acggccgtgt attactgtgc gagactggcg       300
cttgatttcg actactgggg ccagggtaca ctggtcaccg tgagctcagc ctccaccaag       360
ggcccatcgg tcttccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaactcc tggggggacc gtcagtcttc       720
ctcttccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cacgtaccgt       900
gtggtcagcg tcctcaccgt cctgcaccag gactggctga atggcaagga gtacaagtgc       960
aaggtctcca acaaagccct cccagccccc atcgagaaaa ccatctccaa agccaaaggg      1020
cagccccgag aaccacaggt gtataccctg cccccatccc gggatgagct gaccaagaac      1080
caggtcagcc tgacctgcct ggtcaaaggc ttctatccca gcgacatcgc cgtggagtgg      1140
gagagcaatg ggcagccgga gaacaactac aagaccacgc tcccgtgct ggactccgac      1200 ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                    1338

<210> SEQ ID NO 107
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG light chain 1

<400> SEQUENCE: 107

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Phe Ser Asp Glu Leu
                85                  90                  95

Gly Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 108
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG light chain 1

<400> SEQUENCE: 108

```
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat gataatagta atcggccaag cggggtccct     180
gaccgattct ctggctccaa gtctggcacc tcagcctccc tggccatcag tgggctccag     240
tccgaggatg aggctgatta ttactgtgct tcttttagtg atgagttggg ggcttatgtc     300
ttcggcggag gcaccaagct gacggtccta cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
```

```
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 109
<211> LENGTH: 217
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: IgG light chain 2

<400> SEQUENCE: 109

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 110
<211> LENGTH: 651
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: IgG light chain 2

<400> SEQUENCE: 110

```
cagtctgtgc tgactcagcc acccctcagcg tctgggaccc ccgggcagag ggtcaccatc    60
tcttgtactg gctcttcatc taatattggc agtaattatg tcacctggta ccagcagctc    120
ccaggaacgg cccccaaact cctcatctat gataatagta atcggccaag cggggtccct    180
```

```
gaccgattct ctggctccaa gtctggcacc tcagcctccc tggccatcag tgggctccag    240
tccgaggatg aggctgatta ttactgttct tcttttagtg atgagttggg ggcttatgtc    300
ttcggcggag gcaccaagct gacggtccta cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 111
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG light chain 3

<400> SEQUENCE: 111

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
            35                  40                  45

Ile Tyr Asp Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215
```

<210> SEQ ID NO 112
<211> LENGTH: 648
<212> TYPE: DNA
<213> ORGANISM: Artificial Sequence
<220> FEATURE:
<223> OTHER INFORMATION: Description of Artificial Sequence: Synthetic

```
           polynucleotide
<220> FEATURE:
<223> OTHER INFORMATION: IgG light chain 3

<400> SEQUENCE: 112
cagtctgtgc tgactcagcc accctcagcg tctgggaccc ccggggcagag ggtcaccatc      60 tcttgtactg gctcttcatc taatattggc agtaattatg tcacctggta ccagcagctc     120
ccaggaacgg cccccaaact cctcatctat gataatagta atcggccaag cggggtccct     180
gaccgattct ctggctccaa gtctggcacc tcagcctccc tggccatcag tgggctccag     240
tccgaggatg aggctgatta ttactgttct tcttttagtg atgagttggg ggcttatgtc     300
ttcggcggag gcaccaagct gaccgtccta ggtcagccca aggctgcccc ctcggtcacg     360
ctcttcccac cctcctctga ggagcttcaa gccaacaagg ccacactggt gtgtctcata     420
agtgacttct acccgggagc cgtgacagtg gcctggaagg cagatagcag ccccgtcaag     480 gcggagtgg agaccaccac acccctccaaa caaagcaaca acaagtacgc ggccagcagc     540
tacctgagcc tgacgcctga gcagtggaag tcccacagaa gctacagctg ccaggtcacg     600
catgaaggga gcaccgtgga agacagtg gcccctacag aatgctct                   648

<210> SEQ ID NO 113
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG light chain 4

<400> SEQUENCE: 113

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Tyr Val Thr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205
```

Thr Val Ala Pro Thr Glu Cys Ser
    210                 215

<210> SEQ ID NO 114
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG light chain 4

<400> SEQUENCE: 114
cagtctgtgc tgactcagcc accctcagcg tctgggaccc ccgggcagag ggtcaccatc       60
tcttgtactg ctcttcatc taatattggc agtaattatg tcacctggta ccagcagctc      120
ccaggaacgg ccccccaaact cctcatctat agtaataatc agcggccaag cggggtccct    180
gaccgattct ctggctccaa gtctggcacc tcagcctccc tggccatcag tgggctccag    240
tccgaggatg aggctgatta ttactgttct tcttttagtg atgagttggg ggcttatgtc    300
ttcggcggag gcaccaagct gacggtccta agtcagccca aggctgcccc ctcggtcacg    360
ctcttcccac cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tacctgagcc tgacgcctga gcagtggaag tcccacagaa gctacagctg ccaggtcacg    600
catgaaggga gcaccgtgga gaagacagtg gcccctacag aatgctct                 648

<210> SEQ ID NO 115
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG light chain 5

<400> SEQUENCE: 115

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 116
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG light chain 5

<400> SEQUENCE: 116
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat cggaataatc agcggccaag cggggtccct     180
gaccgattct ctggctccaa gtctggcacc tcagcctccc tggccatcag tgggctccag     240
tccgaggatg aggctgatta ttactgttct tcttttagtg atgagttggg ggcttatgtc     300
ttcggcggag gcaccaagct gacggtccta ggtcagccca aggctgcccc ctcggtcacg     360
ctcttcccac cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc      540 tacctgagcc tgacgcctga cagtggaag tcccacagaa gctacagctg ccaggtcacg      600
catgaaggga gcaccgtgga agacagtg gcccctacag aatgctct                    648

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: main binding site of N3 Ab series

<400> SEQUENCE: 117

Lys Leu Ser Lys Asn Glu Leu Lys Arg Arg Leu Lys Ala
1               5                   10

<210> SEQ ID NO 118
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of Lysyl-tRNA synthetase
      (KRS, Homo sapiens)

<400> SEQUENCE: 118

```
Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Thr Asn His Thr Thr Asp Asn Gly Val
    50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
                100                 105                 110

Ser His Leu Gln Pro Gly Asp His Leu Thr Asp Ile Thr Leu Lys Val
            115                 120                 125

Ala Gly Arg Ile His Ala Lys Arg Ala Ser Gly Gly Lys Leu Ile Phe
        130                 135                 140

Tyr Asp Leu Arg Gly Glu Gly Val Lys Leu Gln Val Met Ala Asn Ser
145                 150                 155                 160

Arg Asn Tyr Lys Ser Glu Glu Phe Ile His Ile Asn Asn Lys Leu
                165                 170                 175

Arg Arg Gly Asp Ile Ile Gly Val Gln Gly Asn Pro Gly Lys Thr Lys
            180                 185                 190

Lys Gly Glu Leu Ser Ile Ile Pro Tyr Glu Ile Thr Leu Leu Ser Pro
        195                 200                 205

Cys Leu His Met Leu Pro His Leu His Phe Gly Leu Lys Asp Lys Glu
    210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255

Phe Leu Asp Glu Leu Gly Phe Leu Glu Ile Glu Thr Pro Met Met Asn
            260                 265                 270

Ile Ile Pro Gly Gly Ala Val Ala Lys Pro Phe Ile Thr Tyr His Asn
        275                 280                 285

Glu Leu Asp Met Asn Leu Tyr Met Arg Ile Ala Pro Glu Leu Tyr His
    290                 295                 300

Lys Met Leu Val Val Gly Gly Ile Asp Arg Val Tyr Glu Ile Gly Arg
305                 310                 315                 320

Gln Phe Arg Asn Glu Gly Ile Asp Leu Thr His Asn Pro Glu Phe Thr
                325                 330                 335

Thr Cys Glu Phe Tyr Met Ala Tyr Ala Asp Tyr His Asp Leu Met Glu
            340                 345                 350

Ile Thr Glu Lys Met Val Ser Gly Met Val Lys His Ile Thr Gly Ser
        355                 360                 365

Tyr Lys Val Thr Tyr His Pro Asp Gly Pro Glu Gly Gln Ala Tyr Asp
370                 375                 380

Val Asp Phe Thr Pro Pro Phe Arg Arg Ile Asn Met Val Glu Glu Leu
385                 390                 395                 400

Glu Lys Ala Leu Gly Met Lys Leu Pro Glu Thr Asn Leu Phe Glu Thr
            405                 410                 415
```

```
Glu Glu Thr Arg Lys Ile Leu Asp Asp Ile Cys Val Ala Lys Ala Val
            420                 425                 430
Glu Cys Pro Pro Pro Arg Thr Thr Ala Arg Leu Leu Asp Lys Leu Val
        435                 440                 445
Gly Glu Phe Leu Glu Val Thr Cys Ile Asn Pro Thr Phe Ile Cys Asp
    450                 455                 460
His Pro Gln Ile Met Ser Pro Leu Ala Lys Trp His Arg Ser Lys Glu
465                 470                 475                 480
Gly Leu Thr Glu Arg Phe Glu Leu Phe Val Met Lys Lys Glu Ile Cys
                485                 490                 495
Asn Ala Tyr Thr Glu Leu Asn Asp Pro Met Arg Gln Arg Gln Leu Phe
            500                 505                 510
Glu Glu Gln Ala Lys Ala Lys Ala Ala Gly Asp Asp Glu Ala Met Phe
        515                 520                 525
Ile Asp Glu Asn Phe Cys Thr Ala Leu Glu Tyr Gly Leu Pro Pro Thr
    530                 535                 540
Ala Gly Trp Gly Met Gly Ile Asp Arg Val Ala Met Phe Leu Thr Asp
545                 550                 555                 560
Ser Asn Asn Ile Lys Glu Val Leu Leu Phe Pro Ala Met Lys Pro Glu
                565                 570                 575
Asp Lys Lys Glu Asn Val Ala Thr Thr Asp Thr Leu Glu Ser Thr Thr
            580                 585                 590
Val Gly Thr Ser Val
        595
```

<210> SEQ ID NO 119
<211> LENGTH: 1794
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of KRS

<400> SEQUENCE: 119

| | | |
|---|---|---|
| atggcggccg tgcaggcggc cgaggtgaaa gtggatggca gcgagccgaa actgagcaag | 60 |
| aatgagctga agagacgcct gaaagctgag aagaaagtag cagagaagga ggccaaacag | 120 |
| aaagagctca gtgagaaaca gctaagccaa gccactgctg ctgccaccaa ccacaccact | 180 |
| gataatggtg tgggtcctga ggaagagagc gtggacccaa tcaatacta caaaatccgc | 240 |
| agtcaagcaa ttcatcagct gaaggtcaat ggggaagacc catcccaca caagttccat | 300 |
| gtagacatct cactcactga cttcatccaa aaatatagtc acctgcagcc tgggatcac | 360 |
| ctgactgaca tcaccttaaa ggtggcaggt aggatccatg ccaaaagagc ttctggggga | 420 |
| aagctcatct tctatgatct tcgaggagag ggggtgaagt tgcaagtcat ggccaattcc | 480 |
| agaaattata atcagaaga agaatttatt catattaata caaactgcg tcggggagac | 540 |
| ataattggag ttcagggaa tcctggtaaa accaagaagg gtgagctgag catcattccg | 600 |
| tatgagatca cactgctgtc tccctgtttg catatgttac ctcatcttca ctttgggctc | 660 |
| aaagacaagg aaacaaggta tcgccagaga tacttggact tgatcctgaa tgactttgtg | 720 |
| aggcagaaat ttatcatccg ctctaagatc atcacatata taagaagttt cttagatgag | 780 |
| ctgggattcc tagagattga aactcccatg atgaacatca tcccagggg agccgtggcc | 840 |
| aagccttca tcacttatca caacgagctg gacatgaact tatatatgag aattgctcca | 900 |

```
gaactctatc ataagatgct tgtggttggt ggcatcgacc gggtttatga aattggacgc    960
cagttccgga atgagtggat tgatttgacg cacaatcctg agttcaccac ctgtgagttc   1020
tacatggcct atgcagacta tcacgatctc atggaaatca cggagaagat ggtttcaggg   1080
atggtgaagc atattacagg cagttacaag gtcacctacc acccagatgg cccagagggc   1140
caagcctacg atgttgactt caccccaccc ttccggcgaa tcaacatggt agaagagctt   1200
gagaaagccc tggggatgaa gctgccagaa acgaacctct ttgaaactga gaaaactcgc   1260
aaaattcttg atgatatctg tgtggcaaaa gctgttgaat gccctccacc tcggaccaca   1320
gccaggctcc ttgacaagct tgttggggag ttcctggaag tgacttgcat caatcctaca   1380
ttcatctgtg atcacccaca gataatgagc cctttggcta atggcaccg ctctaaagag    1440
ggtctgactg agcgctttga gctgtttgtc atgaagaaag agatatgcaa tgcgtatact   1500
gagctgaatg atcccatgcg gcagcggcag cttttgaag aacaggccaa ggccaaggct    1560
gcaggtgatg atgaggccat gttcatagat gaaaacttct gtactgccct ggaatatggg   1620
ctgccccca cagctggctg gggcatgggc attgatcgag tcgccatgtt ctctcacggac   1680
tccaacaaca tcaaggaagt acttctgttt cctgccatga aacccgaaga caagaaggag   1740
aatgtagcaa ccactgatac actggaaagc acaacagttg gcacttctgt ctag          1794
```

<210> SEQ ID NO 120
<211> LENGTH: 1823
<212> TYPE: PRT
<213> ORGANISM: Artificial Sequence
<220> FEATURE:
<223> OTHER INFORMATION: Description of Artificial Sequence: Synthetic
   polypeptide
<220> FEATURE:
<223> OTHER INFORMATION: Amino acid sequence of Laminin subunit alpha-4
   (Homo sapiens)

<400> SEQUENCE: 120

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
                20                  25                  30

Pro Phe Asp Ile Glu Gly Ser Ser Ala Val Gly Arg Gln Asp Pro Pro
            35                  40                  45

Glu Thr Ser Glu Pro Arg Val Ala Leu Gly Arg Leu Pro Pro Ala Ala
        50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

-continued

```
Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
                260                 265                 270

Cys Asp Lys Cys Val Trp Asp Leu Thr Asp Ala Leu Arg Leu Ala Ala
            275                 280                 285

Leu Ser Ile Glu Glu Gly Lys Ser Gly Val Leu Ser Val Ser Ser Gly
        290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
                340                 345                 350

Val Glu Leu Val Glu Lys Glu Asn Gln Ala Ser Arg Lys Gly Gln
            355                 360                 365

Leu Val Gln Lys Glu Ser Met Asp Thr Ile Asn His Ala Ser Gln Leu
    370                 375                 380

Val Glu Gln Ala His Asp Met Arg Asp Lys Ile Gln Glu Ile Asn Asn
385                 390                 395                 400

Lys Met Leu Tyr Tyr Gly Glu Glu His Glu Leu Ser Pro Lys Glu Ile
                405                 410                 415

Ser Glu Lys Leu Val Leu Ala Gln Lys Met Leu Glu Glu Ile Arg Ser
            420                 425                 430

Arg Gln Pro Phe Phe Thr Gln Arg Glu Leu Val Asp Glu Glu Ala Asp
        435                 440                 445

Glu Ala Tyr Glu Leu Leu Ser Gln Ala Glu Ser Trp Gln Arg Leu His
    450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
                485                 490                 495

Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
        515                 520                 525

Val Val Asn Met Ser Leu Ser Thr Ser Ala Asp Ser Leu Thr Thr Pro
    530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575

Ser Asn Leu Ser Asn Leu Ser His Asp Leu Val Gln Glu Ala Ile Asp
            580                 585                 590

His Ala Gln Asp Leu Gln Gln Glu Ala Asn Glu Leu Ser Arg Lys Leu
        595                 600                 605
```

-continued

His Ser Ser Asp Met Asn Gly Leu Val Gln Lys Ala Leu Asp Ala Ser
610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
            645                 650                 655

Gly Ile Asp Thr Gln Ile Ile Tyr His Lys Asp Glu Ser Glu Asn Leu
            660                 665                 670

Leu Asn Gln Ala Arg Glu Leu Gln Ala Lys Ala Glu Ser Ser Ser Asp
            675                 680                 685

Glu Ala Val Ala Asp Thr Ser Arg Arg Val Gly Gly Ala Leu Ala Arg
690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
            725                 730                 735

Ile Thr Glu Glu Ala Asn Arg Thr Thr Met Glu Val Gln Ala Thr
            740                 745                 750

Ala Pro Met Ala Asn Asn Leu Thr Asn Trp Ser Gln Asn Leu Gln His
            755                 760                 765

Phe Asp Ser Ser Ala Tyr Asn Thr Ala Val Asn Ser Ala Arg Asp Ala
770                 775                 780

Val Arg Asn Leu Thr Glu Val Val Pro Gln Leu Asp Gln Leu Arg
785                 790                 795                 800

Thr Val Glu Gln Lys Arg Pro Ala Ser Asn Val Ser Ala Ser Ile Gln
            805                 810                 815

Arg Ile Arg Glu Leu Ile Ala Gln Thr Arg Ser Val Ala Ser Lys Ile
            820                 825                 830

Gln Val Ser Met Met Phe Asp Gly Gln Ser Ala Val Glu Val His Ser
            835                 840                 845

Arg Thr Ser Met Asp Asp Leu Lys Ala Phe Thr Ser Leu Ser Leu Tyr
850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
            885                 890                 895

Leu Ala Ile Lys Asn Asp Asn Leu Val Tyr Val Tyr Asn Leu Gly Thr
            900                 905                 910

Lys Asp Val Glu Ile Pro Leu Asp Ser Lys Pro Val Ser Ser Trp Pro
            915                 920                 925

Ala Tyr Phe Ser Ile Val Lys Ile Glu Arg Val Gly Lys His Gly Lys
930                 935                 940

Val Phe Leu Thr Val Pro Ser Leu Ser Ser Thr Ala Glu Glu Lys Phe
945                 950                 955                 960

Ile Lys Lys Gly Glu Phe Ser Gly Asp Asp Ser Leu Leu Asp Leu Asp
            965                 970                 975

Pro Glu Asp Thr Val Phe Tyr Val Gly Gly Val Pro Ser Asn Phe Lys
            980                 985                 990

Leu Pro Thr Ser Leu Asn Leu Pro Gly Phe Val Gly Cys Leu Glu Leu
            995                 1000                1005

Ala Thr Leu Asn Asn Asp Val Ile Ser Leu Tyr Asn Phe Lys His
            1010                1015                1020

Ile Tyr Asn Met Asp Pro Ser Thr Ser Val Pro Cys Ala Arg Asp

```
         1025                1030                1035
Lys Leu Ala Phe Thr Gln Ser Arg Ala Ala Ser Tyr Phe Phe Asp
    1040                1045                1050
Gly Ser Gly Tyr Ala Val Val Arg Asp Ile Thr Arg Arg Gly Lys
    1055                1060                1065
Phe Gly Gln Val Thr Arg Phe Asp Ile Glu Val Arg Thr Pro Ala
    1070                1075                1080
Asp Asn Gly Leu Ile Leu Leu Met Val Asn Gly Ser Met Phe Phe
    1085                1090                1095
Arg Leu Glu Met Arg Asn Gly Tyr Leu His Val Phe Tyr Asp Phe
    1100                1105                1110
Gly Phe Ser Gly Gly Pro Val His Leu Glu Asp Thr Leu Lys Lys
    1115                1120                1125
Ala Gln Ile Asn Asp Ala Lys Tyr His Glu Ile Ser Ile Ile Tyr
    1130                1135                1140
His Asn Asp Lys Lys Met Ile Leu Val Val Asp Arg Arg His Val
    1145                1150                1155
Lys Ser Met Asp Asn Glu Lys Met Lys Ile Pro Phe Thr Asp Ile
    1160                1165                1170
Tyr Ile Gly Gly Ala Pro Pro Glu Ile Leu Gln Ser Arg Ala Leu
    1175                1180                1185
Arg Ala His Leu Pro Leu Asp Ile Asn Phe Arg Gly Cys Met Lys
    1190                1195                1200
Gly Phe Gln Phe Gln Lys Lys Asp Phe Asn Leu Leu Glu Gln Thr
    1205                1210                1215
Glu Thr Leu Gly Val Gly Tyr Gly Cys Pro Glu Asp Ser Leu Ile
    1220                1225                1230
Ser Arg Arg Ala Tyr Phe Asn Gly Gln Ser Phe Ile Ala Ser Ile
    1235                1240                1245
Gln Lys Ile Ser Phe Phe Asp Gly Phe Glu Gly Gly Phe Asn Phe
    1250                1255                1260
Arg Thr Leu Gln Pro Asn Gly Leu Leu Phe Tyr Tyr Ala Ser Gly
    1265                1270                1275
Ser Asp Val Phe Ser Ile Ser Leu Asp Asn Gly Thr Val Ile Met
    1280                1285                1290
Asp Val Lys Gly Ile Lys Val Gln Ser Val Asp Lys Gln Tyr Asn
    1295                1300                1305
Asp Gly Leu Ser His Phe Val Ile Ser Ser Val Ser Pro Thr Arg
    1310                1315                1320
Tyr Glu Leu Ile Val Asp Lys Ser Arg Val Gly Ser Lys Asn Pro
    1325                1330                1335
Thr Lys Gly Lys Ile Glu Gln Thr Gln Ala Ser Glu Lys Lys Phe
    1340                1345                1350
Tyr Phe Gly Gly Ser Pro Ile Ser Ala Gln Tyr Ala Asn Phe Thr
    1355                1360                1365
Gly Cys Ile Ser Asn Ala Tyr Phe Thr Arg Val Asp Arg Asp Val
    1370                1375                1380
Glu Val Glu Asp Phe Gln Arg Tyr Thr Glu Lys Val His Thr Ser
    1385                1390                1395
Leu Tyr Glu Cys Pro Ile Glu Ser Ser Pro Leu Phe Leu Leu His
    1400                1405                1410
Lys Lys Gly Lys Asn Leu Ser Lys Pro Lys Ala Ser Gln Asn Lys
    1415                1420                1425
```

```
Lys Gly Gly Lys Ser Lys Asp Ala Pro Ser Trp Asp Pro Val Ala
    1430            1435                1440

Leu Lys Leu Pro Glu Arg Asn Thr Pro Arg Asn Ser His Cys His
    1445            1450                1455

Leu Ser Asn Ser Pro Arg Ala Ile Glu His Ala Tyr Gln Tyr Gly
    1460            1465                1470

Gly Thr Ala Asn Ser Arg Gln Glu Phe Glu His Leu Lys Gly Asp
    1475            1480                1485

Phe Gly Ala Lys Ser Gln Phe Ser Ile Arg Leu Arg Thr Arg Ser
    1490            1495                1500

Ser His Gly Met Ile Phe Tyr Val Ser Asp Gln Glu Glu Asn Asp
    1505            1510                1515

Phe Met Thr Leu Phe Leu Ala His Gly Arg Leu Val Tyr Met Phe
    1520            1525                1530

Asn Val Gly His Lys Lys Leu Lys Ile Arg Ser Gln Glu Lys Tyr
    1535            1540                1545

Asn Asp Gly Leu Trp His Asp Val Ile Phe Ile Arg Glu Arg Ser
    1550            1555                1560

Ser Gly Arg Leu Val Ile Asp Gly Leu Arg Val Leu Glu Glu Ser
    1565            1570                1575

Leu Pro Pro Thr Glu Ala Thr Trp Lys Ile Lys Gly Pro Ile Tyr
    1580            1585                1590

Leu Gly Gly Val Ala Pro Gly Lys Ala Val Lys Asn Val Gln Ile
    1595            1600                1605

Asn Ser Ile Tyr Ser Phe Ser Gly Cys Leu Ser Asn Leu Gln Leu
    1610            1615                1620

Asn Gly Ala Ser Ile Thr Ser Ala Ser Gln Thr Phe Ser Val Thr
    1625            1630                1635

Pro Cys Phe Glu Gly Pro Met Glu Thr Gly Thr Tyr Phe Ser Thr
    1640            1645                1650

Glu Gly Gly Tyr Val Val Leu Asp Glu Ser Phe Asn Ile Gly Leu
    1655            1660                1665

Lys Phe Glu Ile Ala Phe Glu Val Arg Pro Arg Ser Ser Ser Gly
    1670            1675                1680

Thr Leu Val His Gly His Ser Val Asn Gly Glu Tyr Leu Asn Val
    1685            1690                1695

His Met Lys Asn Gly Gln Val Ile Val Lys Val Asn Asn Gly Ile
    1700            1705                1710

Arg Asp Phe Ser Thr Ser Val Thr Pro Lys Gln Ser Leu Cys Asp
    1715            1720                1725

Gly Arg Trp His Arg Ile Thr Val Ile Arg Asp Ser Asn Val Val
    1730            1735                1740

Gln Leu Asp Val Asp Ser Glu Val Asn His Val Val Gly Pro Leu
    1745            1750                1755

Asn Pro Lys Pro Ile Asp His Arg Glu Pro Val Phe Val Gly Gly
    1760            1765                1770

Val Pro Glu Ser Leu Leu Thr Pro Arg Leu Ala Pro Ser Lys Pro
    1775            1780                1785

Phe Thr Gly Cys Ile Arg His Phe Val Ile Asp Gly His Pro Val
    1790            1795                1800

Ser Phe Ser Lys Ala Ala Leu Val Ser Gly Ala Val Ser Ile Asn
    1805            1810                1815
```

Ser Cys Pro Ala Ala
    1820

<210> SEQ ID NO 121
<211> LENGTH: 5472
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of Laminin subunit alpha-4 (Homo
      sapiens)

<400> SEQUENCE: 121

```
atggctttga gctcagcctg gcgctcggtt ctgcctctgt ggctcctctg gagcgctgcc      60
tgctcccgcg ccgcgtccgg ggacgacaac gcttttcctt ttgacattga agggagctca     120
gcggttggca ggcaagaccc gcctgagacg agcgaacccc gcgtggctct gggacgcctg     180
ccgcctgcgg ccgagaaatg caatgctgga ttctttcaca ccctgtcggg agaatgtgtg     240
ccctgcgact gtaatggcaa ttccaacgag tgtttggacg gctcaggata ctgtgtgcac     300
tgccagcgga acacaacagg agagcactgt gaaaagtgtc tggatggtta tatcggagat     360
tccatcaggg gagcacccca attctgccag ccgtgcccct gtccctgcc  ccacttggcc     420 aattttgcag aatcctgcta taggaaaaat ggagctgttc ggtgcatttg taacgaaaat     480
tatgctggac taactgtga  agatgtgct  cccggttact atggaaaccc cttactcatt     540
ggaagcacct gtaagaaatg tgactgcagt ggaaattcag atcccaacct gatctttgaa     600
gattgtgatg aagtcactgg ccagtgtagg aattgcttac aacaccac  cggattcaag     660 tgtgaacgtt gcgctcctgg ctactatggg acgccagga  tagccaagaa ctgtgcagtg     720
tgcaactgcg ggggaggccc atgtgacagt gtaaccggag aatgcttgga agaaggtttt     780
gaacccccta caggcatgga ctgcccaacc ataagctgtg ataagtgcgt ctgggacctg     840
actgatgacc tgcggttagc agcgctctcc atcgaggaag gcaaatccgg ggtgctgagc     900
gtatcctctg ggccgccgc  tcataggcac gtgaatgaaa tcaacgccac catctacctc     960
ctcaaaacaa aattgtcaga aagagaaaac caatacgccc taagaaagat acaaatcaac    1020
aatgctgaga cacgatgaa  aagccttctg tctgacgtag aggaattagt tgaaaaggaa    1080
aatcaagcct ccagaaaagg acaacttgtt cagaaggaaa gcatggacac cattaaccac    1140
gcaagtcagc tggtagagca agcccatgat atgagggata aaatccaaga gatcaacaac    1200
aagatgctct attatgggga gagcatgaa  cttagcccca ggaaatctc  tgagaagctg    1260 gtgttggccc agaagatgct tgaagagatt agaagccgtc aaccattttt cacccaacgg    1320
gagctcgtgg atgaggaggc agatgaggct tacgaactac tgagccaggc tgagagctgg    1380
cagcggctgc acaatgagac ccgcactctg tttcctgtcg tcctggagca gctggatgac    1440
tacaatgcta agttgtcaga tctccaggaa gcacttgacc aggcccttaa ctatgtcagg    1500
gatgccgaag acatgaacag ggccacagca gccaggcagc gggaccatga aaacaacag     1560 gaaagagtga gggaacaaat ggaagtggtg aacatgtctc tgagcacatc tgcggactct    1620
ctgacaacac ctcgtctaac tctttcagaa cttgatgata taataagaa  tgcgtcaggg    1680 atttatgcag aaatagatgg agccaaaagt gaactacaag taaaactatc taacctaagt    1740
aacctcagcc atgatttagt ccaagaagct attgaccatg cacaggacct tcaacaagaa    1800
gctaatgaat tgagcaggaa gttgcacagt tcagatatga acgggctggt acagaaggct    1860
```

```
ttggatgcat caaatgtcta tgaaaatatt gttaattatg ttagtgaagc caatgaaaca    1920
gcagaatttg ctttgaacac cactgaccga atttatgatg cggtgagtgg gattgatact    1980
caaatcattt accataaaga tgaaagtgag aacctcctca atcaagccag agaactgcaa    2040
gcaaaggcag agtctagcag tgatgaagca gtggctgaca ctagcaggcg tgtgggtgga    2100
gccctagcaa ggaaaagtgc ccttaaaacc agactcagtg atgccgttaa gcaactacaa    2160
gcagcagaga gaggggatgc ccagcagcgc ctggggcagt ctagactgat caccgaggaa    2220
gccaacagga cgacgatgga ggtgcagcag gccactgccc ccatggccaa caatctaacc    2280
aactggtcac agaatcttca acattttgac tcttctgctt acaacactgc agtgaactct    2340
gctagggatg cagtaagaaa tctgaccgag gttgtccctc agctcctgga tcagcttcgt    2400
acggttgagc agaagcgacc tgcaagcaac gtttctgcca gcatccagag gatccgagag    2460
ctcattgctc agaccagaag tgttgccagc aagatccaag tctccatgat gtttgatggc    2520
cagtcagctg tggaagtgca ctcgagaacc agtatggatg acttaaaggc cttcacgtct    2580
ctgagcctgt acatgaaacc ccctgtgaag cggccgaaac tgaccgagac tgcagatcag    2640
tttatcctgt acctcggaag caaaaacgcc aaaaaagagt atatgggtct tgcaatcaaa    2700
aatgataatc tggtatacgt ctataatttg ggaactaaag atgtggagat tccccctggac   2760 tccaagcccg tcagttcctg gcctgcttac ttcagcattg tcaagattga aggggtggga    2820
aaacatggaa aggtgttttt aacagtcccg agtctaagta gcacagcaga ggaaaagttc    2880
attaaaaagg gggaatttc gggagatgac tctctgctgg acctggaccc tgaggacaca    2940
gtgttttatg ttggtggagt gccttccaac ttcaagctcc ctaccagctt aaacctgcct    3000
ggctttgttg gctgcctgga actggccact ttgaataatg atgtgatcag cttgtacaac    3060
tttaagcaca tctataatat ggaccctcc acatcagtgc catgtgcccg agataagctg    3120
gccttcactc agagtcgggc tgccagttac ttcttcgatg gctccggtta gccgtggtg    3180 agagacatca aaggagagg gaaatttggt caggtgactc gctttgacat agaagttcga    3240
acaccagctg acaacggcct tattctcctg atggtcaatg gaagtatgtt tttcagactg    3300
gaaatgcgca atggttacct acatgtgttc tatgattttg gattcagcgg tggccctgtg    3360
catcttgaag atacgttaaa gaaagctcaa attaatgatg caaaatacca tgagatctca    3420
atcatttacc acaatgataa gaaaatgatc ttggtagttg acagaaggca tgtcaagagc    3480
atggataatg aaaagatgaa aatacctttt acagatatat acattggagg agctcctcca    3540
gaaatcttac aatccaggc cctcagagca caccttcccc tagatatcaa cttcagagga    3600
tgcatgaagg gcttccagtt ccaaaagaag gacttcaatt tactggagca gacagaaacc    3660
ctgggagttg gttatggatg cccagaagac tcacttatat ctcgcagagc atatttcaat    3720
ggacagagct tcattgcttc aattcagaaa atatctttct ttgatggctt tgaaggaggt    3780
tttaatttcc gaacattaca accaaatggg ttactattct attatgcttc agggtcagac    3840
gtgttctcca tctcactgga taatggtact gtcatcatga tgtaaaggg aatcaaagtt    3900 cagtcagtag ataagcagta caatgatggg ctgtcccact tcgtcattag ctctgtctca    3960
cccacaagat atgaactgat agtagataaa agcagagttg ggagtaagaa tcctaccaaa    4020
gggaaaatag aacagacaca agcaagtgaa aagaagtttt acttcggtgg ctcaccaatc    4080
agtgctcagt atgctaattt cactggctgc ataagtaatg cctactttac cagggtggat    4140
agagatgtgg aggttgaaga tttccaacgg tatactgaaa aggtccacac ttctctttat    4200
gagtgtccca ttgagtcttc accattgttt ctcctccata aaaaaggaaa aaatttatcc    4260
```

```
aagcctaaag caagtcagaa taaaaaggga gggaaaagta aagatgcacc ttcatgggat    4320
cctgttgctc tgaaactccc agagcggaat actccaagaa actctcattg ccacctttcc    4380
aacagcccta gagcaataga gcacgcctat caatatggag gaacagccaa cagccgccaa    4440
gagtttgaac acttaaaagg agattttggt gccaaatctc agttttccat tcgtctgaga    4500
actcgttcct cccatggcat gatcttctat gtctcagatc aagaagagaa tgacttcatg    4560
actctatttt tggcccatgg ccgcttggtt tacatgttta atgttggtca caaaaaactg    4620
aagattagaa gccaggagaa atacaatgat ggcctgtggc atgatgtgat atttattcga    4680
gaaaggagca gtggccgact ggtaattgat ggtctccgag tcctagaaga aagtcttcct    4740
cctactgaag ctacctggaa atcaagggt cccatttatt tgggaggtgt ggctcctgga    4800
aaggctgtga aaatgttca gattaactcc atctacagtt ttagtggctg tctcagcaat    4860
ctccagctca atggggcctc catcaccttct gcttctcaga cattcagtgt gacccccttgc    4920 tttgaaggcc ccatggaaac aggaacttac ttttcaacag aaggaggata cgtggttcta    4980
gatgaatctt tcaatattgg attgaagttt gaaattgcat ttgaagtccg tcccagaagc    5040
agttccggaa ccctggtcca cggccacagt gtcaatgggg agtacctaaa tgttcacatg    5100
aaaaatggac aggtcatagt gaaagtcaat aatggcatca gagattttc cacctcagtt    5160 acacccaagc agagtctctg tgatggcaga tggcacagaa ttacagttat tagagattct    5220
aatgtggttc agttggatgt ggactctgaa gtgaaccatg tggttggacc cctgaatcca    5280
aaaccaattg atcacaggga gcctgtgttt gttggaggtg ttccagaatc tctactgaca    5340
ccacgcttgg cccccagcaa acccttcaca ggctgcatac gccactttgt gattgatgga    5400
cacccagtga gcttcagtaa agcagccctg gtcagcggcg ccgtaagcat caactcctgt    5460
ccagcagcct ga                                                       5472
```

<210> SEQ ID NO 122
<211> LENGTH: 1798
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence of Laminin subunit beta-2 (Homo sapiens)

<400> SEQUENCE: 122

```
Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Gly Asp Leu Leu Val Gly Arg Ala Asp Arg Leu Thr Ala
    50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
```

```
            115                 120                 125
Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
        195                 200                 205

Ile Glu Pro Ser Thr Glu Gly Glu Val Ile Tyr Arg Val Leu Asp Pro
    210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
    290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

Thr His Ser Cys His Phe Asp Met Ala Val Tyr Leu Ala Ser Gly Asn
        355                 360                 365

Val Ser Gly Gly Val Cys Asp Gly Cys Gln His Asn Thr Ala Gly Arg
    370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Asp Pro Ala Leu Gly
            420                 425                 430

Leu Val Ser Gly Gln Cys Arg Cys Lys Glu His Val Val Gly Thr Arg
        435                 440                 445

Cys Gln Gln Cys Arg Asp Gly Phe Phe Gly Leu Ser Ile Ser Asp Arg
    450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
    530                 535                 540
```

-continued

```
Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
                580                 585                 590

Ser Trp Thr Gly Ser Gly Phe Val Arg Leu Gln Glu Gly Gln Thr Leu
                595                 600                 605

Glu Phe Leu Val Ala Ser Val Pro Lys Ala Met Asp Tyr Asp Leu Leu
610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
                675                 680                 685

Tyr Lys Leu His Leu Lys Leu Val Arg Thr Gly Gly Ser Ala Gln Pro
690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
                755                 760                 765

Leu Ile Ser Leu Ser Thr Leu Ile Tyr Asn Gly Ala Leu Pro Cys Gln
770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
                805                 810                 815

Ala Pro Gly Tyr Tyr Gly Phe Gly Pro Thr Gly Cys Gln Ala Cys Gln
                820                 825                 830

Cys Ser His Glu Gly Ala Leu Ser Ser Leu Cys Glu Lys Thr Ser Gly
                835                 840                 845

Gln Cys Leu Cys Arg Thr Gly Ala Phe Gly Leu Arg Cys Asp Arg Cys
                850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
                900                 905                 910

His Gly Asp Pro Arg Leu Pro Tyr Gly Gly Gln Cys Arg Pro Cys Pro
                915                 920                 925

Cys Pro Glu Gly Pro Gly Ser Gln Arg His Phe Ala Thr Ser Cys His
930                 935                 940

Gln Asp Glu Tyr Ser Gln Gln Ile Val Cys His Cys Arg Ala Gly Tyr
945                 950                 955                 960
```

```
Thr Gly Leu Arg Cys Glu Ala Cys Ala Pro Gly His Phe Gly Asp Pro
                965                 970                 975

Ser Arg Pro Gly Gly Arg Cys Gln Leu Cys Glu Cys Ser Gly Asn Ile
            980                 985                 990

Asp Pro Met Asp Pro Asp Ala Cys Asp Pro His Thr Gly Gln Cys Leu
        995                 1000                1005

Arg Cys Leu His His Thr Glu Gly Pro His Cys Ala His Cys Lys
    1010                1015                1020

Pro Gly Phe His Gly Gln Ala Ala Arg Gln Ser Cys His Arg Cys
    1025                1030                1035

Thr Cys Asn Leu Leu Gly Thr Asn Pro Gln Gln Cys Pro Ser Pro
    1040                1045                1050

Asp Gln Cys His Cys Asp Pro Ser Ser Gly Gln Cys Pro Cys Leu
    1055                1060                1065

Pro Asn Val Gln Gly Pro Ser Cys Asp Arg Cys Ala Pro Asn Phe
    1070                1075                1080

Trp Asn Leu Thr Ser Gly His Gly Cys Gln Pro Cys Ala Cys His
    1085                1090                1095

Pro Ser Arg Ala Arg Gly Pro Thr Cys Asn Glu Phe Thr Gly Gln
    1100                1105                1110

Cys His Cys Arg Ala Gly Phe Gly Gly Arg Thr Cys Ser Glu Cys
    1115                1120                1125

Gln Glu Leu His Trp Gly Asp Pro Gly Leu Gln Cys His Ala Cys
    1130                1135                1140

Asp Cys Asp Ser Arg Gly Ile Asp Thr Pro Gln Cys His Arg Phe
    1145                1150                1155

Thr Gly His Cys Ser Cys Arg Pro Gly Val Ser Gly Val Arg Cys
    1160                1165                1170

Asp Gln Cys Ala Arg Gly Phe Ser Gly Ile Phe Pro Ala Cys His
    1175                1180                1185

Pro Cys His Ala Cys Phe Gly Asp Trp Asp Arg Val Val Gln Asp
    1190                1195                1200

Leu Ala Ala Arg Thr Gln Arg Leu Glu Gln Arg Ala Gln Glu Leu
    1205                1210                1215

Gln Gln Thr Gly Val Leu Gly Ala Phe Glu Ser Ser Phe Trp His
    1220                1225                1230

Met Gln Glu Lys Leu Gly Ile Val Gln Gly Ile Val Gly Ala Arg
    1235                1240                1245

Asn Thr Ser Ala Ala Ser Thr Ala Gln Leu Val Glu Ala Thr Glu
    1250                1255                1260

Glu Leu Arg Arg Glu Ile Gly Glu Ala Thr Glu His Leu Thr Gln
    1265                1270                1275

Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Asp Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
```

```
            1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470

Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530

Glu Met Val Ala Thr Arg Val Leu Glu Leu Ser Ile Pro Ala Ser
    1535                1540                1545

Ala Glu Gln Ile Gln His Leu Ala Gly Ala Ile Ala Glu Arg Val
    1550                1555                1560

Arg Ser Leu Ala Asp Val Asp Ala Ile Leu Ala Arg Thr Val Gly
    1565                1570                1575

Asp Val Arg Arg Ala Glu Gln Leu Leu Gln Asp Ala Arg Arg Ala
    1580                1585                1590

Arg Ser Trp Ala Glu Asp Glu Lys Gln Lys Ala Glu Thr Val Gln
    1595                1600                1605

Ala Ala Leu Glu Glu Ala Gln Arg Ala Gln Gly Ile Ala Gln Gly
    1610                1615                1620

Ala Ile Arg Gly Ala Val Ala Asp Thr Arg Asp Thr Glu Gln Thr
    1625                1630                1635

Leu Tyr Gln Val Gln Glu Arg Met Ala Gly Ala Glu Arg Ala Leu
    1640                1645                1650

Ser Ser Ala Gly Glu Arg Ala Arg Gln Leu Asp Ala Leu Leu Glu
    1655                1660                1665

Ala Leu Lys Leu Lys Arg Ala Gly Asn Ser Leu Ala Ala Ser Thr
    1670                1675                1680

Ala Glu Glu Thr Ala Gly Ser Ala Gln Gly Arg Ala Gln Glu Ala
    1685                1690                1695

Glu Gln Leu Leu Arg Gly Pro Leu Gly Asp Gln Tyr Gln Thr Val
    1700                1705                1710

Lys Ala Leu Ala Glu Arg Lys Ala Gln Gly Val Leu Ala Ala Gln
    1715                1720                1725

Ala Arg Ala Glu Gln Leu Arg Asp Glu Ala Arg Asp Leu Leu Gln
    1730                1735                1740

Ala Ala Gln Asp Lys Leu Gln Arg Leu Gln Glu Leu Glu Gly Thr
    1745                1750                1755
```

```
Tyr Glu  Glu Asn Glu Arg Ala  Leu Glu Ser Lys Ala  Ala Gln Leu
    1760             1765                 1770

Asp Gly  Leu Glu Ala Arg Met  Arg Ser Val Leu Gln  Ala Ile Asn
    1775             1780                 1785

Leu Gln  Val Gln Ile Tyr Asn  Thr Cys Gln
    1790             1795

<210> SEQ ID NO 123
<211> LENGTH: 5397
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of Laminin subunit beta-2 (Homo
      sapiens)

<400> SEQUENCE: 123
```

| | | | | | |
|---|---|---|---|---|---|
| atggagctga | cctcaaggga | agagggagg | ggacagcctc | tgccctggga | acttcgactg | 60 |
| ggcctactgc | taagcgtgct | ggctgccaca | ctggcacagg | cccctgcccc | ggatgtgcct | 120 |
| ggctgttcca | ggggaagctg | ctaccccgcc | acgggcgacc | tgctggtggg | ccgagctgac | 180 |
| agactgactg | cctcatccac | ttgtggcctg | aatggccccc | agccctactg | catcgtcagt | 240 |
| cacctgcagg | acgaaaagaa | gtgcttcctt | tgtgactccc | ggcgcccctt | ctctgctaga | 300 |
| gacaacccac | acagccatcg | catccagaat | gtagtcacca | gctttgcacc | acagcggcgg | 360 |
| gcagcctggt | ggcagtcaga | gaatggtatc | cctgcggtca | ccatccagct | ggacctggag | 420 |
| gctgagtttc | atttcacaca | cctcattatg | accttcaaga | catttcgccc | tgctgccatg | 480 |
| ctggtggaac | gctcagcaga | ctttggccgc | acctggcatg | tgtaccgata | tttctcctat | 540 |
| gactgtgggg | ctgacttccc | aggagtccca | ctagcacccc | cacggcactg | ggatgatgta | 600 |
| gtctgtgagt | cccgctactc | agagattgag | ccatccactg | aaggcgaggt | catctatcgt | 660 |
| gtgctggacc | ctgccatccc | tatcccagac | ccctacagct | cacggattca | gaacctgttg | 720 |
| aagatcacca | acctacgggt | gaacctgact | cgtctacaca | cgttgggaga | caacctactc | 780 |
| gacccacgga | gggagatccg | agagaagtac | tactatgccc | tctatgagct | ggttgtacgt | 840 |
| ggcaactgct | tctgctacgg | acacgcctca | gagtgtgcac | cgcccccagg | ggcaccagcc | 900 |
| catgctgagg | gcatggtgca | cggagcttgc | atctgcaaac | acaacacacg | tggcctcaac | 960 |
| tgcgagcagt | gtcaggattt | ctatcgtgac | ctgccctggc | gtccggctga | ggacggccat | 1020 |
| agtcatgcct | gtaggaagtg | tgagtgccat | gggcacaccc | acagctgcca | cttcgacatg | 1080 |
| gccgtatacc | tggcatctgg | caatgtgagt | ggaggtgtgt | gtgatggatg | tcagcataac | 1140 |
| acagctgggc | gccactgtga | gctctgtcgg | cccttcttct | accgtgaccc | aaccaaggac | 1200 |
| ctgcgggatc | cggctgtgtg | ccgctcctgt | gattgtgacc | ccatgggttc | tcaagacggt | 1260 |
| ggtcgctgtg | attccatga | tgaccctgca | ctgggactgg | tctccggcca | gtgtcgctgc | 1320 |
| aaagaacatg | tggtgggcac | tcgctgccag | caatgccgtg | atggcttctt | tgggctcagc | 1380 |
| atcagtgacc | gtctgggctg | ccggcgatgt | caatgtaatg | cacggggcac | agtgcctggg | 1440 |
| agcactcctt | gtgaccccaa | cagtggatcc | tgttactgca | aacgtctagt | gactggacgt | 1500 |
| ggatgtgacc | gctgcctgcc | tggccactgg | ggcctgagcc | acgacctgct | cggctgccgc | 1560 |
| ccctgtgact | cgcacgtggg | tggtgctttg | gatcccagt | gtgatgaggg | cacaggtcaa | 1620 |
| tgccactgcc | gccagcacat | ggttgggcga | cgctgtgagc | aggtgcaacc | tggctacttc | 1680 |

```
cggcccttcc tggaccacct aatttgggag gctgaggaca cccgagggca ggtgctcgat    1740
gtggtggagc gcctggtgac ccccggggaa actccatcct ggactggctc aggcttcgtg    1800
cggctacagg aaggtcagac cctggagttc ctggtggcct ctgtgccgaa ggctatggac    1860
tatgacctgc tgctgcgctt agagcccag gtccctgagc aatgggcaga gttggaactg     1920
attgtgcagc gtccagggcc tgtgcctgcc cacagcctgt gtgggcattt ggtgcccaag    1980
gatgatcgca tccaagggac tctgcaacca catgccaggt acttgatatt tcctaatcct    2040
gtctgccttg agcctggtat ctcctacaag ctgcatctga agctggtacg dacaggggga    2100
agtgcccagc ctgagactcc ctactctgga cctggcctgc tcattgactc gctggtgctg    2160
ctgccccgtg tcctggtgct agagatgttt agtgggggtg atgctgctgc cctggagcgc    2220
caggccacct ttgaacgcta ccaatgccat gaggagggtc tggtgcccag caagacttct    2280
ccctctgagg cctgcgcacc cctcctcatc agcctgtcca ccctcatcta caatggtgcc    2340
ctgccatgtc agtgcaaccc tcaaggttca ctgagttctg agtgcaaccc tcatggtggt    2400
cagtgcctgt gcaagcctgg agtggttggg cgccgctgtg acctctgtgc ccctggctac    2460
tatggctttg gccccacagg ctgtcaagcc tgccagtgca ccacgagggg ggcactcagc    2520
agtctctgtg aaaagaccag tgggcaatgt ctctgtcgaa ctggtgcctt tgggcttcgc    2580
tgtgaccgct gccagcgtgg ccagtgggga ttccctagct gccggccatg tgtctgcaat    2640
gggcatgcag atgagtgcaa cacccacaca ggcgcttgcc tgggctgccg tgatcacaca    2700
gggggtgagc actgtgaaag gtgcattgct ggtttccacg gggacccacg gctgccatat    2760
gggggccagt gccggccctg tccctgtcct gaaggccctg ggagccaacg gcactttgct    2820
acttcttgcc accaggatga atattcccag cagattgtgt gccactgccg ggcaggctat    2880
acggggctgc gatgtgaagc ttgtgcccct gggcactttg ggacccatc aaggccaggt    2940 ggccggtgcc aactgtgtga gtgcagtggg aacattgacc caatggatcc tgatgcctgt    3000
gacccccaca cggggcaatg cctgcgctgt ttacaccaca cagagggtcc acactgtgcc    3060
cactgcaagc ctggcttcca tgggcaggct gcccgacaga gctgtcaccg ctgcacatgc    3120
aacctgctgg gcacaaatcc gcagcagtgc ccatctcctg accagtgcca ctgtgatcca    3180
agcagtgggc agtgcccatg cctccccaat gtccagggcc ctagctgtga ccgctgtgcc    3240
cccaacttct ggaacctcac cagtggccat ggttgccagc cttgtgcctg ccacccaagc    3300
cgggccagag gccccacctg caacgagttc acagggcagt gccactgccg tgccggcttt    3360
ggagggcgga cttgttctga gtgccaagag ctccactggg gagaccctgg gttgcagtgc    3420
catgcctgtg attgtgactc tcgtggaata gatacacctc agtgtcaccg cttcacaggt    3480
cactgcagct gccgccagg ggtgtctggt gtgcgctgtg accagtgtgc ccgtggcttc    3540
tcaggaatct ttcctgcctg ccatcccctgc catgcatgct cggggattg ggaccgagtg    3600 gtgcaggact tggcagcccg tacacagcgc ctagagcagc gggcgcagga gttgcaacag    3660
acgggtgtgc tgggtgcctt tgagagcagc ttctggcaca tgcaggagaa gctgggcatt    3720
gtgcagggca tcgtaggtgc ccgcaacacc tcagccgcct ccactgcaca gcttgtggag    3780
gccacagagg agctgcggcg tgaaattggg gaggccactg agcacctgac tcagctcgag    3840
gcagacctga cagatgtgca agatgagaac ttcaatgcca accatgcact aagtggtctg    3900
gagcgagata ggcttgcact taatctcaca ctgcggcagc tcgaccagca tcttgacttg    3960
ctcaaacatt caaacttcct gggtgccat gacagcatcc ggcatgccca tagccagtct    4020
```

```
gcagaggcag aacgtcgtgc caatacctca gccctggcag tacctagccc tgtgagcaac    4080
tcggcaagtg ctcggcatcg acagaggca ctgatggatg ctcagaagga ggacttcaac     4140
agcaaacaca tggccaacca gcgggcactt ggcaagctct ctgcccatac ccacaccctg    4200
agcctgacag acataaatga gctggtgtgt ggggcaccag gggatgcacc ctgtgctaca    4260
agcccttgtg ggggtgccgg ctgtcgagat gaggatgggc agccgcgctg tggggcctc     4320 agctgcaatg gggcagcggc tacagcagac ctagcactgg gccgggcccg gcacacacag    4380
gcagagctgc agcgggcact ggcagaaggt ggtagcatcc tcagcagagt ggctgagact    4440
cgtcggcagg caagcgaggc acagcagcgg gcccaggcag ccctggacaa ggctaatgct    4500
tccaggggac aggtggaaca ggccaaccag gaacttcaag aacttatcca gagtgtgaag    4560
gacttcctca accaggaggg ggctgatcct gatagcattg aaatggtggc cacacgggtg    4620
ctagagctct ccatcccagc ttcagctgag cagatccagc acctggcggg tgcgattgca    4680
gagcgagtcc ggagcctggc agatgtggat gcgatcctgg cacgtactgt aggagatgtg    4740
cgtcgtgccg agcagctact gcaggatgca cggcgggcaa ggagctgggc tgaggatgag    4800
aaacagaagg cagagacagt acaggcagca ctggaggagg cccagcgggc acagggtatt    4860
gcccagggtg ccatccgggg ggcagtggct gacacacggg acacagagca gaccctgtac    4920
caggtacagg agaggatggc aggtgcagag cgggcactga gctctgcagg tgaaagggct    4980
cggcagttgg atgctctcct ggaggctctg aaattgaaac gggcaggaaa tagtctggca    5040
gcctctacag cagaagaaac ggcaggcagt gcccagggtc gtgcccagga ggctgagcag    5100
ctgctacgcg gtcctctggg tgatcagtac cagacggtga aggccctagc tgagcgcaag    5160
gcccaaggtg tgctggctgc acaggcaagg gcagaacaac tgcgggatga ggctcgggac    5220
ctgttgcaag ccgctcagga caagctgcag cggctacagg aattggaagg cacctatgag    5280
gaaaatgagc gggcactgga gagtaaggca gcccagttgg acgggttgga ggccaggatg    5340
cgcagcgtgc ttcaagccat caacttgcag gtgcagatct acaacacctg ccagtga      5397
```

<210> SEQ ID NO 124
<211> LENGTH: 1609
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of Laminin subunit gamma-1
      (Homo sapiens)

<400> SEQUENCE: 124

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
            20                  25                  30

Ala Gln Ala Ala Met Asp Glu Cys Thr Asp Glu Gly Gly Arg Pro Gln
        35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln

```
               100                 105                 110
Ala Asp Thr Thr Trp Trp Gln Ser Gln Thr Met Leu Ala Gly Val Gln
            115                 120                 125

Tyr Pro Ser Ser Ile Asn Leu Thr Leu His Leu Gly Lys Ala Phe Asp
            130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
            195                 200                 205

Phe Ser Asp Ile Ser Pro Leu Thr Gly Gly Asn Val Ala Phe Ser Thr
            210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
            275                 280                 285

Asn Gly His Ala Ser Glu Cys Met Lys Asn Glu Phe Asp Lys Leu Val
290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
            355                 360                 365

Asn Cys Gln Asp Asn Thr Asp Gly Ala His Cys Glu Arg Cys Arg Glu
            370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
            405                 410                 415

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
            435                 440                 445

Pro Ser Gly Ser Ile Asp Glu Cys Asn Ile Glu Thr Gly Arg Cys Val
            450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
            485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
            515                 520                 525
```

```
Glu Gln Arg Asp Gly Ser Glu Ala Ser Leu Glu Trp Ser Ser Glu Arg
    530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                565                 570                 575

Leu Ser Phe Ser Phe Arg Val Asp Arg Arg Asp Thr Arg Leu Ser Ala
            580                 585                 590

Glu Asp Leu Val Leu Glu Gly Ala Gly Leu Arg Val Ser Val Pro Leu
        595                 600                 605

Ile Ala Gln Gly Asn Ser Tyr Pro Ser Glu Thr Thr Val Lys Tyr Val
    610                 615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
                645                 650                 655

Arg Gly Thr Tyr Ser Glu Arg Ser Ala Gly Tyr Leu Asp Asp Val Thr
            660                 665                 670

Leu Ala Ser Ala Arg Pro Gly Pro Gly Val Pro Ala Thr Trp Val Glu
        675                 680                 685

Ser Cys Thr Cys Pro Val Gly Tyr Gly Gln Phe Cys Glu Met Cys
    690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
                725                 730                 735

Thr Gly Val Cys Asn Cys Arg Asp Asn Thr Ala Gly Pro His Cys Glu
            740                 745                 750

Lys Cys Ser Asp Gly Tyr Tyr Gly Asp Ser Thr Ala Gly Thr Ser Ser
        755                 760                 765

Asp Cys Gln Pro Cys Pro Cys Pro Gly Gly Ser Ser Cys Ala Val Val
    770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
                805                 810                 815

Gly Arg Asn Gly Pro Val Arg Leu Cys Arg Leu Cys Gln Cys Ser Asp
            820                 825                 830

Asn Ile Asp Pro Asn Ala Val Gly Asn Cys Asn Arg Leu Thr Gly Glu
        835                 840                 845

Cys Leu Lys Cys Ile Tyr Asn Thr Ala Gly Phe Tyr Cys Asp Arg Cys
    850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
                885                 890                 895

Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
    930                 935                 940
```

```
Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
            965                 970                 975

Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
        995                 1000                1005

Gly Asn Arg Cys Asp Gln Cys Glu Glu Asn Tyr Phe Tyr Asn Arg
    1010                1015                1020

Ser Trp Pro Gly Cys Gln Glu Cys Pro Ala Cys Tyr Arg Leu Val
    1025                1030                1035

Lys Asp Lys Val Ala Asp His Arg Val Lys Leu Gln Glu Leu Glu
    1040                1045                1050

Ser Leu Ile Ala Asn Leu Gly Thr Gly Asp Glu Met Val Thr Asp
    1055                1060                1065

Gln Ala Phe Glu Asp Arg Leu Lys Glu Ala Glu Arg Glu Val Met
    1070                1075                1080

Asp Leu Leu Arg Glu Ala Gln Asp Val Lys Asp Val Asp Gln Asn
    1085                1090                1095

Leu Met Asp Arg Leu Gln Arg Val Asn Asn Thr Leu Ser Ser Gln
    1100                1105                1110

Ile Ser Arg Leu Gln Asn Ile Arg Asn Thr Ile Glu Glu Thr Gly
    1115                1120                1125

Asn Leu Ala Glu Gln Ala Arg Ala His Val Glu Asn Thr Glu Arg
    1130                1135                1140

Leu Ile Glu Ile Ala Ser Arg Glu Leu Glu Lys Ala Lys Val Ala
    1145                1150                1155

Ala Ala Asn Val Ser Val Thr Gln Pro Glu Ser Thr Gly Asp Pro
    1160                1165                1170

Asn Asn Met Thr Leu Leu Ala Glu Glu Ala Arg Lys Leu Ala Glu
    1175                1180                1185

Arg His Lys Gln Glu Ala Asp Asp Ile Val Arg Val Ala Lys Thr
    1190                1195                1200

Ala Asn Asp Thr Ser Thr Glu Ala Tyr Asn Leu Leu Leu Arg Thr
    1205                1210                1215

Leu Ala Gly Glu Asn Gln Thr Ala Phe Glu Ile Glu Glu Leu Asn
    1220                1225                1230

Arg Lys Tyr Glu Gln Ala Lys Asn Ile Ser Gln Asp Leu Glu Lys
    1235                1240                1245

Gln Ala Ala Arg Val His Glu Glu Ala Lys Arg Ala Gly Asp Lys
    1250                1255                1260

Ala Val Glu Ile Tyr Ala Ser Val Ala Gln Leu Ser Pro Leu Asp
    1265                1270                1275

Ser Glu Thr Leu Glu Asn Glu Ala Asn Asn Ile Lys Met Glu Ala
    1280                1285                1290

Glu Asn Leu Glu Gln Leu Ile Asp Gln Lys Leu Lys Asp Tyr Glu
    1295                1300                1305

Asp Leu Arg Glu Asp Met Arg Gly Lys Glu Leu Glu Val Lys Asn
    1310                1315                1320

Leu Leu Glu Lys Gly Lys Thr Glu Gln Gln Thr Ala Asp Gln Leu
    1325                1330                1335

Leu Ala Arg Ala Asp Ala Ala Lys Ala Leu Ala Glu Glu Ala Ala
```

Lys Lys Gly Arg Asp Thr Leu Gln Glu Ala Asn Asp Ile Leu Asn
1355                1360                1365

Asn Leu Lys Asp Phe Asp Arg Arg Val Asn Asp Asn Lys Thr Ala
1370                1375                1380

Ala Glu Ala Leu Arg Lys Ile Pro Ala Ile Asn Gln Thr Ile
1385                1390                1395

Thr Glu Ala Asn Glu Lys Thr Arg Glu Ala Gln Gln Ala Leu Gly
1400                1405                1410

Ser Ala Ala Asp Ala Thr Glu Ala Lys Asn Lys Ala His Glu
1415                1420                1425

Ala Glu Arg Ile Ala Ser Ala Val Gln Lys Asn Ala Thr Ser Thr
1430                1435                1440

Lys Ala Glu Ala Glu Arg Thr Phe Ala Glu Val Thr Asp Leu Asp
1445                1450                1455

Asn Glu Val Asn Asn Met Leu Lys Gln Leu Gln Glu Ala Glu Lys
1460                1465                1470

Glu Leu Lys Arg Lys Gln Asp Asp Ala Asp Gln Asp Met Met Met
1475                1480                1485

Ala Gly Met Ala Ser Gln Ala Ala Gln Glu Ala Glu Ile Asn Ala
1490                1495                1500

Arg Lys Ala Lys Asn Ser Val Thr Ser Leu Leu Ser Ile Ile Asn
1505                1510                1515

Asp Leu Leu Glu Gln Leu Gly Gln Leu Asp Thr Val Asp Leu Asn
1520                1525                1530

Lys Leu Asn Glu Ile Glu Gly Thr Leu Asn Lys Ala Lys Asp Glu
1535                1540                1545

Met Lys Val Ser Asp Leu Asp Arg Lys Val Ser Asp Leu Glu Asn
1550                1555                1560

Glu Ala Lys Lys Gln Glu Ala Ala Ile Met Asp Tyr Asn Arg Asp
1565                1570                1575

Ile Glu Glu Ile Met Lys Asp Ile Arg Asn Leu Glu Asp Ile Arg
1580                1585                1590

Lys Thr Leu Pro Ser Gly Cys Phe Asn Thr Pro Ser Ile Glu Lys
1595                1600                1605

Pro

<210> SEQ ID NO 125
<211> LENGTH: 4830
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of Laminin subunit gamma-1 (Homo
      sapiens)

<400> SEQUENCE: 125
atgagaggga gccatcgggc cgcgccggcc ctgcggcccc gggggcgggct ctggcccgtg      60 ctggccgtgc tggcggcggc cgccgcgcg ggctgtgccc aggcagccat ggacgagtgc     120
acggacgagg gcgggcggcc gcagcgctgc atgcccgagt cgtcaacgc cgccttcaac     180 gtgactgtgg tggccaccaa cacgtgtggg actccgccg aggaatactg tgtgcagacc     240
ggggtgaccg gggtcaccaa gtcctgtcac ctgtgcgacg ccgggcagcc ccacctgcag     300

```
cacggggcag ccttcctgac cgactacaac aaccaggccg acaccacctg gtggcaaagc    360
cagaccatgc tggccggggt gcagtacccc agctccatca acctcacgct gcacctggga    420
aaagcttttg acatcaccta tgtgcgtctc aagttccaca ccagccgccc ggagagcttt    480
gccatttaca agcgcacacg ggaagacggg ccctggattc cttaccagta ctacagtggt    540
tcctgtgaga cacctactc caaggcaaac cgcggcttca tcaggacagg aggggacgag    600
cagcaggcct tgtgtactga tgaattcagt gacatttctc ccctcactgg gggcaacgtg    660
gccttttcta ccctggaagg aaggcccagc gcctataact ttgacaatag ccctgtgctg    720
caggaatggg taactgccac tgacatcaga gtaactctta atcgcctgaa cacttttgga    780
gatgaagtgt ttaacgatcc caaagttctc aagtcctatt attatgccat ctctgatttt    840
gctgtaggtg gcagatgtaa atgtaatgga cacgcaagcg agtgtatgaa gaacgaattt    900
gataagctgg tgtgtaattg caaacataac acatatggag tagactgtga aaagtgtctt    960
cctttcttca atgaccggcc gtggaggagg gcaactgcgg aaagtgccag tgaatgcctg   1020
ccctgtgatt gcaatggtcg atcccaggaa tgctacttcg accctgaact ctatcgttcc   1080
actggccatg ggggccactg taccaactgc caggataaca cagatggcgc ccactgtgag   1140
aggtgccgag agaacttctt ccgccttggc aacaatgaag cctgctcttc atgccactgt   1200
agtcctgtgg gctctctaag cacacagtgt gatagttacg gcagatgcag ctgtaagcca   1260
ggagtgatgg gggacaaatg tgaccgttgc cagcctggat ccattctct cactgaagca   1320
ggatgcaggc catgctcttg tgatccctct ggcagcatag atgaatgtaa tattgaaaca   1380
ggaagatgtg tttgcaaaga caatgtcgaa ggcttcaatt gtgaaagatg caaacctgga   1440
tttttttaatc tggaatcatc taatcctcgg ggttgcacac cctgcttctg ctttgggcat   1500
tcttctgtct gtacaaacgc tgttggctac agtgtttatt ctatctcctc tacctttcag   1560
attgatgagg atgggtggcg tgcggaacag agagatggct ctgaagcatc tctcgagtgg   1620
tcctctgaga ggcaagatat cgccgtgatc tcagacagct actttcctcg gtacttcatt   1680
gctcctgcaa agttcttggg caagcaggtg ttgagttatg gtcagaacct ctccttctcc   1740
tttcgagtgg acaggcgaga tactcgcctc tctgcagaag accttgtgct tgagggagct   1800
ggcttaagag tatctgtacc cttgatcgct cagggcaatt cctatccaag tgagaccact   1860
gtgaagtatg tcttcaggct ccatgaagca acagattacc cttggaggcc tgctcttacc   1920
ccttttgaat ttcagaagct cctaaacaac ttgacctcta tcaagatacg tgggacatac   1980
agtgagagaa gtgctggata tttgatgat gtcaccctgg caagtgctcg tcctgggcct   2040
ggagtccctg caacttgggt ggagtcctgc acctgtcctg tgggatatgg agggcagttt   2100
tgtgagatgt gcctctcagg ttacagaaga gaaactccta atcttggacc atacagtcca   2160
tgtgtgcttt gcgcctgcaa tggacacagc gagacctgtg atcctgagac aggtgtttgt   2220
aactgcagag acaatacggc tggcccgcac tgtgagaagt gcagtgatgg gtactatgga   2280
gattcaactg caggcaccct ctccgattgc aaccctgtc cgtgtcctgg aggttcaagt   2340
tgtgctgttg ttcccaagac aaaggaggtg gtgtgcacca actgtcctac tggcaccact   2400
ggtaagagat gtgagctctg tgatgatggc tactttggag accccctggg tagaaacggc   2460
cctgtgagac tttgccgcct gtgccagtgc agtgacaaca tcgatcccaa tgcagttgga   2520
aattgcaatc gcttgacggg agaatgcctg aagtgcatct ataacactgc tggcttctat   2580
tgtgaccggt gcaaagacgg atttttttgga aatcccctgg ctcccaatcc agcagacaaa   2640
tgcaaagcct gcaattgcaa tctgtatggg accatgaagc agcagagcag ctgtaacccc   2700
```

```
gtgacggggc agtgtgaatg tttgcctcac gtgactggcc aggactgtgg tgcttgtgac    2760
cctggattct acaatctgca gagtgggcaa ggctgtgaga ggtgtgactg ccatgccttg    2820
ggctccacca atgggcagtg tgacatccgc accggccagt gtgagtgcca gcccggcatc    2880
actggtcagc actgtgagcg ctgtgaggtc aaccactttg ggtttggacc tgaaggctgc    2940
aaaccctgtg actgtcatcc tgagggatct ctttcacttc agtgcaaaga tgatggtcgc    3000
tgtgaatgca gagaaggctt tgtgggaaat cgctgtgacc agtgtgaaga aaactatttc    3060
tacaatcggt cttggcctgg ctgccaggaa tgtccagctt gttaccggct ggtaaaggat    3120
aaggttgctg atcatagagt gaagctccag gaattagaga gtctcatagc aaaccttgga    3180
actggggatg agatggtgac agatcaagcc ttcgaggata gactaaagga agcagagagg    3240
gaagttatgg acctccttcg tgaggcccag gatgtcaaag atgttgacca gaatttgatg    3300
gatcgcctac agagagtgaa taacactctg tccagccaaa ttagccgttt acagaatatc    3360
cggaatacca ttgaagagac tggaaaacttg gctgaacaag cgcgtgccca tgtagagaac    3420
acagagcggt tgattgaaat cgcatccaga gaacttgaga aagcaaaagt cgctgctgcc    3480
aatgtgtcag tcactcagcc agaatctaca ggggacccaa acaacatgac tcttttggca    3540
gaagaggctc gaaagcttgc tgaacgtcat aaacaggaag ctgatgacat tgttcgagtg    3600
gcaaagacag ccaatgatac gtcaactgag gcatacaacc tgcttctgag gacactggca    3660
ggagaaaatc aaacagcatt tgagattgaa gagcttaata ggaagtatga acaagcgaag    3720
aacatctcac aggatctgga aaaacaagct gcccgagtac atgaggaggc aaaagggcc     3780 ggtgacaaag ctgtggagat ctatgccagc gtggctcagc tgagccctttt ggactctgag    3840 acactggaga atgaagcaaa taacataaag atggaagctg agaatctgga acaactgatt    3900
gaccagaaat taaagatta tgaggacctc agagaagata tgagagggaa ggaacttgaa    3960
gtcaagaacc ttctggagaa aggcaagact gaacagcaga ccgcagacca actcctagcc    4020
cgagctgatg ctgccaaggc cctcgctgaa gaagctgcaa agaagggacg ggatacctta    4080
caagaagcta atgacattct caacaacctg aaagattttg ataggcgtgt gaacgataac    4140
aagacggccg cagaggaggc actaaggaag attcctgcca tcaaccagac catcactgaa    4200
gccaatgaaa agaccagaga agcccagcag gccctgggca gtgctgcggc ggatgccaca    4260
gaggccaaga caaggcccta tgaggcgag aggatcgcga gcgctgtcca aaagaatgcc    4320
accagcacca aggcagaagc tgaaagaact tttgcagaag ttacagatct ggataatgag    4380
gtgaacaata tgttgaagca actgcaggaa gcagaaaaag agctaaagag aaaacaagat    4440
gacgctgacc aggacatgat gatggcaggg atggcttcac aggctgctca agaagccgag    4500
atcaatgcca gaaaagccaa aaactctgtt actagcctcc tcagcattat taatgacctc    4560
ttggagcagc tggggcagct ggatacagtg gacctgaata agctaaacga gattgaaggc    4620
accctaaaca agccaaaga tgaaatgaag gtcagcgatc ttgataggaa agtgtctgac    4680
ctggagaatg aagccaagaa gcaggaggct gccatcatgg actataaccg agatatcgag    4740
gagatcatga aggacattcg caatctggag gacatcagga agaccttacc atctggctgc    4800
ttcaacaccc cgtccattga aaagccctag                                    4830
```

<210> SEQ ID NO 126  
<211> LENGTH: 3122  
<212> TYPE: PRT  
<213> ORGANISM: Artificial Sequence  
<220> FEATURE:

<223> OTHER INFORMATION: Description of Artificial Sequence: Synthetic
polypeptide
<220> FEATURE:
<223> OTHER INFORMATION: Amino acid sequence of Laminin subunit alpha-2
(Homo sapiens)

<400> SEQUENCE: 126

```
Met Pro Gly Ala Ala Gly Val Leu Leu Leu Leu Leu Ser Gly Gly
1               5                   10                  15

Leu Gly Gly Val Gln Ala Gln Arg Pro Gln Gln Gln Arg Gln Ser Gln
            20                  25                  30

Ala His Gln Gln Arg Gly Leu Phe Pro Ala Val Leu Asn Leu Ala Ser
        35                  40                  45

Asn Ala Leu Ile Thr Thr Asn Ala Thr Cys Gly Glu Lys Gly Pro Glu
    50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Ser Asn Pro Asn Gln Arg
                85                  90                  95

His Pro Ile Thr Asn Ala Ile Asp Gly Lys Asn Thr Trp Trp Gln Ser
            100                 105                 110

Pro Ser Ile Lys Asn Gly Ile Glu Tyr His Tyr Val Thr Ile Thr Leu
        115                 120                 125

Asp Leu Gln Gln Val Phe Gln Ile Ala Tyr Val Ile Val Lys Ala Ala
    130                 135                 140

Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
            180                 185                 190

Lys Asp Asp Glu Val Ile Cys Thr Ser Phe Tyr Ser Lys Ile His Pro
        195                 200                 205

Leu Glu Asn Gly Glu Ile His Ile Ser Leu Ile Asn Gly Arg Pro Ser
    210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Tyr Ser Val Lys Asp Ile Ser Val Gly Gly Met Cys Ile
        275                 280                 285

Cys Tyr Gly His Ala Arg Ala Cys Pro Leu Asp Pro Ala Thr Asn Lys
    290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile
        355                 360                 365

Arg Gly Lys Tyr Ile Gly Gly Val Cys Ile Asn Cys Thr Gln Asn
    370                 375                 380
```

```
Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
        435                 440                 445

Gly Gly Val Ser Cys Asp Arg Cys Ala Arg Gly Tyr Thr Gly Tyr Pro
    450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
        515                 520                 525

Ser Ser Tyr Trp Thr Tyr Gly Lys Ile Gln Asp Met Ser Gly Trp Tyr
    530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
        595                 600                 605

Asp Leu Glu Glu Glu Glu Glu Asp Thr Glu Arg Val Leu Gln Leu Met
    610                 615                 620

Ile Ile Leu Glu Gly Asn Asp Leu Ser Ile Ser Thr Ala Gln Asp Glu
625                 630                 635                 640

Val Tyr Leu His Pro Ser Glu Glu His Thr Asn Val Leu Leu Leu Lys
                645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
        675                 680                 685

Thr Tyr Ser Phe Gly Met Asp Ala Ile Phe Arg Leu Ser Ser Val Asn
    690                 695                 700

Leu Glu Ser Ala Val Ser Tyr Pro Thr Asp Gly Ser Ile Ala Ala Ala
705                 710                 715                 720

Val Glu Val Cys Gln Cys Pro Pro Gly Tyr Thr Gly Ser Ser Cys Glu
                725                 730                 735

Ser Cys Trp Pro Arg His Arg Arg Val Asn Gly Thr Ile Phe Gly Gly
            740                 745                 750

Ile Cys Glu Pro Cys Gln Cys Phe Gly His Ala Glu Ser Cys Asp Asp
        755                 760                 765

Val Thr Gly Glu Cys Leu Asn Cys Lys Asp His Thr Gly Gly Pro Tyr
    770                 775                 780

Cys Asp Lys Cys Leu Pro Gly Phe Tyr Gly Glu Pro Thr Lys Gly Thr
785                 790                 795                 800
```

Ser Glu Asp Cys Gln Pro Cys Ala Cys Pro Leu Asn Ile Pro Ser Asn
                805                 810                 815

Asn Phe Ser Pro Thr Cys His Leu Asp Arg Ser Leu Gly Leu Ile Cys
        820                 825                 830

Asp Gly Cys Pro Val Gly Tyr Thr Gly Pro Arg Cys Glu Arg Cys Ala
            835                 840                 845

Glu Gly Tyr Phe Gly Gln Pro Ser Val Pro Gly Ser Cys Gln Pro
850                 855                 860

Cys Gln Cys Asn Asp Asn Leu Asp Phe Ser Ile Pro Gly Ser Cys Asp
865                 870                 875                 880

Ser Leu Ser Gly Ser Cys Leu Ile Cys Lys Pro Gly Thr Thr Gly Arg
            885                 890                 895

Tyr Cys Glu Leu Cys Ala Asp Gly Tyr Phe Gly Asp Ala Val Asp Ala
                900                 905                 910

Lys Asn Cys Gln Pro Cys Arg Cys Asn Ala Gly Gly Ser Phe Ser Glu
            915                 920                 925

Val Cys His Ser Gln Thr Gly Gln Cys Glu Cys Arg Ala Asn Val Gln
    930                 935                 940

Gly Gln Arg Cys Asp Lys Cys Lys Ala Gly Thr Phe Gly Leu Gln Ser
945                 950                 955                 960

Ala Arg Gly Cys Val Pro Cys Asn Cys Asn Ser Phe Gly Ser Lys Ser
            965                 970                 975

Phe Asp Cys Glu Glu Ser Gly Gln Cys Trp Cys Gln Pro Gly Val Thr
        980                 985                 990

Gly Lys Lys Cys Asp Arg Cys Ala His Gly Tyr Phe Asn Phe Gln Glu
            995                 1000                1005

Gly Gly Cys Thr Ala Cys Glu Cys Ser His Leu Gly Asn Asn Cys
    1010                1015                1020

Asp Pro Lys Thr Gly Arg Cys Ile Cys Pro Pro Asn Thr Ile Gly
    1025                1030                1035

Glu Lys Cys Ser Lys Cys Ala Pro Asn Thr Trp Gly His Ser Ile
    1040                1045                1050

Thr Thr Gly Cys Lys Ala Cys Asn Cys Ser Thr Val Gly Ser Leu
    1055                1060                1065

Asp Phe Gln Cys Asn Val Asn Thr Gly Gln Cys Asn Cys His Pro
    1070                1075                1080

Lys Phe Ser Gly Ala Lys Cys Thr Glu Cys Ser Arg Gly His Trp
    1085                1090                1095

Asn Tyr Pro Arg Cys Asn Leu Cys Asp Cys Phe Leu Pro Gly Thr
    1100                1105                1110

Asp Ala Thr Thr Cys Asp Ser Glu Thr Lys Lys Cys Ser Cys Ser
    1115                1120                1125

Asp Gln Thr Gly Gln Cys Thr Cys Lys Val Asn Val Glu Gly Ile
    1130                1135                1140

His Cys Asp Arg Cys Arg Pro Gly Lys Phe Gly Leu Asp Ala Lys
    1145                1150                1155

Asn Pro Leu Gly Cys Ser Ser Cys Tyr Cys Phe Gly Thr Thr Thr
    1160                1165                1170

Gln Cys Ser Glu Ala Lys Gly Leu Ile Arg Thr Trp Val Thr Leu
    1175                1180                1185

Lys Ala Glu Gln Thr Ile Leu Pro Leu Val Asp Glu Ala Leu Gln
    1190                1195                1200

His Thr Thr Thr Lys Gly Ile Val Phe Gln His Pro Glu Ile Val

```
                    1205                    1210                    1215

Ala His Met Asp Leu Met Arg Glu Asp Leu His Leu Glu Pro Phe
                    1220                    1225                    1230

Tyr Trp Lys Leu Pro Glu Gln Phe Glu Gly Lys Lys Leu Met Ala
                    1235                    1240                    1245

Tyr Gly Gly Lys Leu Lys Tyr Ala Ile Tyr Phe Glu Ala Arg Glu
                    1250                    1255                    1260

Glu Thr Gly Phe Ser Thr Tyr Asn Pro Gln Val Ile Ile Arg Gly
                    1265                    1270                    1275

Gly Thr Pro Thr His Ala Arg Ile Ile Val Arg His Met Ala Ala
                    1280                    1285                    1290

Pro Leu Ile Gly Gln Leu Thr Arg His Glu Ile Glu Met Thr Glu
                    1295                    1300                    1305

Lys Glu Trp Lys Tyr Tyr Gly Asp Asp Pro Arg Val His Arg Thr
                    1310                    1315                    1320

Val Thr Arg Glu Asp Phe Leu Asp Ile Leu Tyr Asp Ile His Tyr
                    1325                    1330                    1335

Ile Leu Ile Lys Ala Thr Tyr Gly Asn Phe Met Arg Gln Ser Arg
                    1340                    1345                    1350

Ile Ser Glu Ile Ser Met Glu Val Ala Glu Gln Gly Arg Gly Thr
                    1355                    1360                    1365

Thr Met Thr Pro Pro Ala Asp Leu Ile Glu Lys Cys Asp Cys Pro
                    1370                    1375                    1380

Leu Gly Tyr Ser Gly Leu Ser Cys Glu Ala Cys Leu Pro Gly Phe
                    1385                    1390                    1395

Tyr Arg Leu Arg Ser Gln Pro Gly Gly Arg Thr Pro Gly Pro Thr
                    1400                    1405                    1410

Leu Gly Thr Cys Val Pro Cys Gln Cys Asn Gly His Ser Ser Leu
                    1415                    1420                    1425

Cys Asp Pro Glu Thr Ser Ile Cys Gln Asn Cys Gln His His Thr
                    1430                    1435                    1440

Ala Gly Asp Phe Cys Glu Arg Cys Ala Leu Gly Tyr Tyr Gly Ile
                    1445                    1450                    1455

Val Lys Gly Leu Pro Asn Asp Cys Gln Gln Cys Ala Cys Pro Leu
                    1460                    1465                    1470

Ile Ser Ser Ser Asn Asn Phe Ser Pro Ser Cys Val Ala Glu Gly
                    1475                    1480                    1485

Leu Asp Asp Tyr Arg Cys Thr Ala Cys Pro Arg Gly Tyr Glu Gly
                    1490                    1495                    1500

Gln Tyr Cys Glu Arg Cys Ala Pro Gly Tyr Thr Gly Ser Pro Gly
                    1505                    1510                    1515

Asn Pro Gly Gly Ser Cys Gln Glu Cys Glu Cys Asp Pro Tyr Gly
                    1520                    1525                    1530

Ser Leu Pro Val Pro Cys Asp Pro Val Thr Gly Phe Cys Thr Cys
                    1535                    1540                    1545

Arg Pro Gly Ala Thr Gly Arg Lys Cys Asp Gly Cys Lys His Trp
                    1550                    1555                    1560

His Ala Arg Glu Gly Trp Glu Cys Val Phe Cys Gly Asp Glu Cys
                    1565                    1570                    1575

Thr Gly Leu Leu Leu Gly Asp Leu Ala Arg Leu Glu Gln Met Val
                    1580                    1585                    1590

Met Ser Ile Asn Leu Thr Gly Pro Leu Pro Ala Pro Tyr Lys Met
                    1595                    1600                    1605
```

```
Leu Tyr Gly Leu Glu Asn Met Thr Gln Glu Leu Lys His Leu Leu
    1610            1615            1620

Ser Pro Gln Arg Ala Pro Glu Arg Leu Ile Gln Leu Ala Glu Gly
    1625            1630            1635

Asn Leu Asn Thr Leu Val Thr Glu Met Asn Glu Leu Leu Thr Arg
    1640            1645            1650

Ala Thr Lys Val Thr Ala Asp Gly Glu Gln Thr Gly Gln Asp Ala
    1655            1660            1665

Glu Arg Thr Asn Thr Arg Ala Lys Ser Leu Gly Glu Phe Ile Lys
    1670            1675            1680

Glu Leu Ala Arg Asp Ala Glu Ala Val Asn Glu Lys Ala Ile Lys
    1685            1690            1695

Leu Asn Glu Thr Leu Gly Thr Arg Asp Glu Ala Phe Glu Arg Asn
    1700            1705            1710

Leu Glu Gly Leu Gln Lys Glu Ile Asp Gln Met Ile Lys Glu Leu
    1715            1720            1725

Arg Arg Lys Asn Leu Glu Thr Gln Lys Glu Ile Ala Glu Asp Glu
    1730            1735            1740

Leu Val Ala Ala Glu Ala Leu Leu Lys Lys Val Lys Lys Leu Phe
    1745            1750            1755

Gly Glu Ser Arg Gly Glu Asn Glu Glu Met Glu Lys Asp Leu Arg
    1760            1765            1770

Glu Lys Leu Ala Asp Tyr Lys Asn Lys Val Asp Asp Ala Trp Asp
    1775            1780            1785

Leu Leu Arg Glu Ala Thr Asp Lys Ile Arg Glu Ala Asn Arg Leu
    1790            1795            1800

Phe Ala Val Asn Gln Lys Asn Met Thr Ala Leu Glu Lys Lys Lys
    1805            1810            1815

Glu Ala Val Glu Ser Gly Lys Arg Gln Ile Glu Asn Thr Leu Lys
    1820            1825            1830

Glu Gly Asn Asp Ile Leu Asp Glu Ala Asn Arg Leu Ala Asp Glu
    1835            1840            1845

Ile Asn Ser Ile Ile Asp Tyr Val Glu Asp Ile Gln Thr Lys Leu
    1850            1855            1860

Pro Pro Met Ser Glu Glu Leu Asn Asp Lys Ile Asp Asp Leu Ser
    1865            1870            1875

Gln Glu Ile Lys Asp Arg Lys Leu Ala Glu Lys Val Ser Gln Ala
    1880            1885            1890

Glu Ser His Ala Ala Gln Leu Asn Asp Ser Ser Ala Val Leu Asp
    1895            1900            1905

Gly Ile Leu Asp Glu Ala Lys Asn Ile Ser Phe Asn Ala Thr Ala
    1910            1915            1920

Ala Phe Lys Ala Tyr Ser Asn Ile Lys Asp Tyr Ile Asp Glu Ala
    1925            1930            1935

Glu Lys Val Ala Lys Glu Ala Lys Asp Leu Ala His Glu Ala Thr
    1940            1945            1950

Lys Leu Ala Thr Gly Pro Arg Gly Leu Leu Lys Glu Asp Ala Lys
    1955            1960            1965

Gly Cys Leu Gln Lys Ser Phe Arg Ile Leu Asn Glu Ala Lys Lys
    1970            1975            1980

Leu Ala Asn Asp Val Lys Glu Asn Glu Asp His Leu Asn Gly Leu
    1985            1990            1995
```

-continued

Lys Thr Arg Ile Glu Asn Ala Asp Ala Arg Asn Gly Asp Leu Leu
2000                2005                2010

Arg Thr Leu Asn Asp Thr Leu Gly Lys Leu Ser Ala Ile Pro Asn
2015                2020                2025

Asp Thr Ala Ala Lys Leu Gln Ala Val Lys Asp Lys Ala Arg Gln
2030                2035                2040

Ala Asn Asp Thr Ala Lys Asp Val Leu Ala Gln Ile Thr Glu Leu
2045                2050                2055

His Gln Asn Leu Asp Gly Leu Lys Lys Asn Tyr Asn Lys Leu Ala
2060                2065                2070

Asp Ser Val Ala Lys Thr Asn Ala Val Val Lys Asp Pro Ser Lys
2075                2080                2085

Asn Lys Ile Ile Ala Asp Ala Asp Ala Thr Val Lys Asn Leu Glu
2090                2095                2100

Gln Glu Ala Asp Arg Leu Ile Asp Lys Leu Lys Pro Ile Lys Glu
2105                2110                2115

Leu Glu Asp Asn Leu Lys Lys Asn Ile Ser Glu Ile Lys Glu Leu
2120                2125                2130

Ile Asn Gln Ala Arg Lys Gln Ala Asn Ser Ile Lys Val Ser Val
2135                2140                2145

Ser Ser Gly Gly Asp Cys Ile Arg Thr Tyr Lys Pro Glu Ile Lys
2150                2155                2160

Lys Gly Ser Tyr Asn Asn Ile Val Val Asn Val Lys Thr Ala Val
2165                2170                2175

Ala Asp Asn Leu Leu Phe Tyr Leu Gly Ser Ala Lys Phe Ile Asp
2180                2185                2190

Phe Leu Ala Ile Glu Met Arg Lys Gly Lys Val Ser Phe Leu Trp
2195                2200                2205

Asp Val Gly Ser Gly Val Gly Arg Val Glu Tyr Pro Asp Leu Thr
2210                2215                2220

Ile Asp Asp Ser Tyr Trp Tyr Arg Ile Val Ala Ser Arg Thr Gly
2225                2230                2235

Arg Asn Gly Thr Ile Ser Val Arg Ala Leu Asp Gly Pro Lys Ala
2240                2245                2250

Ser Ile Val Pro Ser Thr His His Ser Thr Ser Pro Pro Gly Tyr
2255                2260                2265

Thr Ile Leu Asp Val Asp Ala Asn Ala Met Leu Phe Val Gly Gly
2270                2275                2280

Leu Thr Gly Lys Leu Lys Lys Ala Asp Ala Val Arg Val Ile Thr
2285                2290                2295

Phe Thr Gly Cys Met Gly Glu Thr Tyr Phe Asp Asn Lys Pro Ile
2300                2305                2310

Gly Leu Trp Asn Phe Arg Glu Lys Glu Gly Asp Cys Lys Gly Cys
2315                2320                2325

Thr Val Ser Pro Gln Val Glu Asp Ser Glu Gly Thr Ile Gln Phe
2330                2335                2340

Asp Gly Glu Gly Tyr Ala Leu Val Ser Arg Pro Ile Arg Trp Tyr
2345                2350                2355

Pro Asn Ile Ser Thr Val Met Phe Lys Phe Arg Thr Phe Ser Ser
2360                2365                2370

Ser Ala Leu Leu Met Tyr Leu Ala Thr Arg Asp Leu Arg Asp Phe
2375                2380                2385

Met Ser Val Glu Leu Thr Asp Gly His Ile Lys Val Ser Tyr Asp

-continued

```
                2390                2395                2400
Leu Gly Ser Gly Met Ala Ser Val Val Ser Asn Gln Asn His Asn
    2405                2410                2415
Asp Gly Lys Trp Lys Ser Phe Thr Leu Ser Arg Ile Gln Lys Gln
    2420                2425                2430
Ala Asn Ile Ser Ile Val Asp Ile Asp Thr Asn Gln Glu Glu Asn
    2435                2440                2445
Ile Ala Thr Ser Ser Ser Gly Asn Asn Phe Gly Leu Asp Leu Lys
    2450                2455                2460
Ala Asp Asp Lys Ile Tyr Phe Gly Gly Leu Pro Thr Leu Arg Asn
    2465                2470                2475
Leu Ser Met Lys Ala Arg Pro Glu Val Asn Leu Lys Lys Tyr Ser
    2480                2485                2490
Gly Cys Leu Lys Asp Ile Glu Ile Ser Arg Thr Pro Tyr Asn Ile
    2495                2500                2505
Leu Ser Ser Pro Asp Tyr Val Gly Val Thr Lys Gly Cys Ser Leu
    2510                2515                2520
Glu Asn Val Tyr Thr Val Ser Phe Pro Lys Pro Gly Phe Val Glu
    2525                2530                2535
Leu Ser Pro Val Pro Ile Asp Val Gly Thr Glu Ile Asn Leu Ser
    2540                2545                2550
Phe Ser Thr Lys Asn Glu Ser Gly Ile Ile Leu Leu Gly Ser Gly
    2555                2560                2565
Gly Thr Pro Ala Pro Pro Arg Arg Lys Arg Arg Gln Thr Gly Gln
    2570                2575                2580
Ala Tyr Tyr Ala Ile Leu Leu Asn Arg Gly Arg Leu Glu Val His
    2585                2590                2595
Leu Ser Thr Gly Ala Arg Thr Met Arg Lys Ile Val Ile Arg Pro
    2600                2605                2610
Glu Pro Asn Leu Phe His Asp Gly Arg Glu His Ser Val His Val
    2615                2620                2625
Glu Arg Thr Arg Gly Ile Phe Thr Val Gln Val Asp Glu Asn Arg
    2630                2635                2640
Arg Tyr Met Gln Asn Leu Thr Val Glu Gln Pro Ile Glu Val Lys
    2645                2650                2655
Lys Leu Phe Val Gly Gly Ala Pro Pro Glu Phe Gln Pro Ser Pro
    2660                2665                2670
Leu Arg Asn Ile Pro Pro Phe Glu Gly Cys Ile Trp Asn Leu Val
    2675                2680                2685
Ile Asn Ser Val Pro Met Asp Phe Ala Arg Pro Val Ser Phe Lys
    2690                2695                2700
Asn Ala Asp Ile Gly Arg Cys Ala His Gln Lys Leu Arg Glu Asp
    2705                2710                2715
Glu Asp Gly Ala Ala Pro Ala Glu Ile Val Ile Gln Pro Glu Pro
    2720                2725                2730
Val Pro Thr Pro Ala Phe Pro Thr Pro Thr Pro Val Leu Thr His
    2735                2740                2745
Gly Pro Cys Ala Ala Glu Ser Glu Pro Ala Leu Leu Ile Gly Ser
    2750                2755                2760
Lys Gln Phe Gly Leu Ser Arg Asn Ser His Ile Ala Ile Ala Phe
    2765                2770                2775
Asp Asp Thr Lys Val Lys Asn Arg Leu Thr Ile Glu Leu Glu Val
    2780                2785                2790
```

```
Arg Thr Glu Ala Glu Ser Gly Leu Leu Phe Tyr Met Ala Arg Ile
2795                2800                2805

Asn His Ala Asp Phe Ala Thr Val Gln Leu Arg Asn Gly Leu Pro
2810                2815                2820

Tyr Phe Ser Tyr Asp Leu Gly Ser Gly Asp Thr His Thr Met Ile
2825                2830                2835

Pro Thr Lys Ile Asn Asp Gly Gln Trp His Lys Ile Lys Ile Met
2840                2845                2850

Arg Ser Lys Gln Glu Gly Ile Leu Tyr Val Asp Gly Ala Ser Asn
2855                2860                2865

Arg Thr Ile Ser Pro Lys Lys Ala Asp Ile Leu Asp Val Val Gly
2870                2875                2880

Met Leu Tyr Val Gly Gly Leu Pro Ile Asn Tyr Thr Thr Arg Arg
2885                2890                2895

Ile Gly Pro Val Thr Tyr Ser Ile Asp Gly Cys Val Arg Asn Leu
2900                2905                2910

His Met Ala Glu Ala Pro Ala Asp Leu Glu Gln Pro Thr Ser Ser
2915                2920                2925

Phe His Val Gly Thr Cys Phe Ala Asn Ala Gln Arg Gly Thr Tyr
2930                2935                2940

Phe Asp Gly Thr Gly Phe Ala Lys Ala Val Gly Gly Phe Lys Val
2945                2950                2955

Gly Leu Asp Leu Leu Val Glu Phe Glu Phe Arg Thr Thr Thr Thr
2960                2965                2970

Thr Gly Val Leu Leu Gly Ile Ser Ser Gln Lys Met Asp Gly Met
2975                2980                2985

Gly Ile Glu Met Ile Asp Glu Lys Leu Met Phe His Val Asp Asn
2990                2995                3000

Gly Ala Gly Arg Phe Thr Ala Val Tyr Asp Ala Gly Val Pro Gly
3005                3010                3015

His Leu Cys Asp Gly Gln Trp His Lys Val Thr Ala Asn Lys Ile
3020                3025                3030

Lys His Arg Ile Glu Leu Thr Val Asp Gly Asn Gln Val Glu Ala
3035                3040                3045

Gln Ser Pro Asn Pro Ala Ser Thr Ser Ala Asp Thr Asn Asp Pro
3050                3055                3060

Val Phe Val Gly Gly Phe Pro Asp Asp Leu Lys Gln Phe Gly Leu
3065                3070                3075

Thr Thr Ser Ile Pro Phe Arg Gly Cys Ile Arg Ser Leu Lys Leu
3080                3085                3090

Thr Lys Gly Thr Gly Lys Pro Leu Glu Val Asn Phe Ala Lys Ala
3095                3100                3105

Leu Glu Leu Arg Gly Val Gln Pro Val Ser Cys Pro Ala Asn
3110                3115                3120

<210> SEQ ID NO 127
<211> LENGTH: 3695
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of Laminin subunit alpha-5
      (Homo sapiens)
```

<400> SEQUENCE: 127

```
Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
            20                  25                  30

Ala Arg Ala Arg Glu Glu Ala Gly Gly Phe Ser Leu His Pro Pro
        35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Asp Pro Asn Gln
                85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
        115                 120                 125

Gln Ser Pro Pro Leu Ser Arg Gly Leu Glu Tyr Asn Glu Val Asn Val
    130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
            180                 185                 190

Arg Asp Cys Leu Glu Arg Phe Gly Pro Gln Thr Leu Glu Arg Ile Thr
        195                 200                 205

Arg Asp Asp Ala Ala Ile Cys Thr Thr Glu Tyr Ser Arg Ile Val Pro
    210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
    290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
        355                 360                 365

Tyr Tyr Asp Pro Glu Val Asp Arg Arg Ala Ser Gln Ser Leu Asp
    370                 375                 380

Gly Thr Tyr Gln Gly Gly Val Cys Ile Asp Cys Gln His Thr
385                 390                 395                 400

Thr Gly Val Asn Cys Glu Arg Cys Leu Pro Gly Phe Tyr Arg Ser Pro
                405                 410                 415
```

```
Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
        435                 440                 445

Cys Arg Pro Asn Phe Ser Gly Glu Arg Cys Asp Val Cys Ala Glu Gly
    450                 455                 460

Phe Thr Gly Phe Pro Ser Cys Tyr Pro Thr Pro Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
                500                 505                 510

Gly Arg Cys Leu Cys Lys Pro Asn Phe Gln Gly Thr His Cys Glu Leu
            515                 520                 525

Cys Ala Pro Gly Phe Tyr Gly Pro Gly Cys Gln Pro Cys Gln Cys Ser
        530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575

Gly Tyr Phe His Phe Pro Leu Cys Gln Leu Cys Gly Cys Ser Pro Ala
                580                 585                 590

Gly Thr Leu Pro Glu Gly Cys Asp Glu Ala Gly Arg Cys Leu Cys Gln
            595                 600                 605

Pro Glu Phe Ala Gly Pro His Cys Asp Arg Cys Arg Pro Gly Tyr His
    610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
        675                 680                 685

Cys Asp Pro Arg Ser Gly Gln Cys Ser Cys Arg Pro Arg Val Thr Gly
    690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
        755                 760                 765

Asn Pro Glu Gly Cys Thr Arg Cys Ser Cys Asp Leu Arg Gly Thr Leu
    770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
            820                 825                 830
```

```
Ile Gly Gly Ala Leu Gly Gln Ser Cys Glu Pro Arg Thr Gly Val Cys
            835                 840                 845

Arg Cys Arg Pro Asn Thr Gln Gly Pro Thr Cys Ser Glu Pro Ala Arg
850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe
        915                 920                 925

Trp Leu Val Phe Arg Tyr Val Asn Arg Gly Ala Met Ser Val Ser Gly
    930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Ser Thr Glu Pro Ala
                965                 970                 975

Phe Ile Thr Val Pro Gln Arg Gly Phe Gly Glu Pro Phe Val Leu Asn
            980                 985                 990

Pro Gly Thr Trp Ala Leu Arg Val Glu Ala Glu Gly Val Leu Leu Asp
        995                 1000                1005

Tyr Val Val Leu Leu Pro Ser Ala Tyr Glu Ala Ala Leu Leu
    1010                1015                1020

Gln Leu Arg Val Thr Glu Ala Cys Thr Tyr Arg Pro Ser Ala Gln
    1025                1030                1035

Gln Ser Gly Asp Asn Cys Leu Leu Tyr Thr His Leu Pro Leu Asp
    1040                1045                1050

Gly Phe Pro Ser Ala Ala Gly Leu Glu Ala Leu Cys Arg Gln Asp
    1055                1060                1065

Asn Ser Leu Pro Arg Pro Cys Pro Thr Glu Gln Leu Ser Pro Ser
    1070                1075                1080

His Pro Pro Leu Ile Thr Cys Thr Gly Ser Asp Val Asp Val Gln
    1085                1090                1095

Leu Gln Val Ala Val Pro Gln Pro Gly Arg Tyr Ala Leu Val Val
    1100                1105                1110

Glu Tyr Ala Asn Glu Asp Ala Arg Gln Glu Val Gly Val Ala Val
    1115                1120                1125

His Thr Pro Gln Arg Ala Pro Gln Gln Gly Leu Leu Ser Leu His
    1130                1135                1140

Pro Cys Leu Tyr Ser Thr Leu Cys Arg Gly Thr Ala Arg Asp Thr
    1145                1150                1155

Gln Asp His Leu Ala Val Phe His Leu Asp Ser Glu Ala Ser Val
    1160                1165                1170

Arg Leu Thr Ala Glu Gln Ala Arg Phe Phe Leu His Gly Val Thr
    1175                1180                1185

Leu Val Pro Ile Glu Glu Phe Ser Pro Glu Phe Val Glu Pro Arg
    1190                1195                1200

Val Ser Cys Ile Ser Ser His Gly Ala Phe Gly Pro Asn Ser Ala
    1205                1210                1215

Ala Cys Leu Pro Ser Arg Phe Pro Lys Pro Pro Gln Pro Ile Ile
    1220                1225                1230

Leu Arg Asp Cys Gln Val Ile Pro Leu Pro Pro Gly Leu Pro Leu
```

```
                1235                1240                1245

Thr His Ala Gln Asp Leu Thr Pro Ala Met Ser Pro Ala Gly Pro
    1250                1255                1260

Arg Pro Arg Pro Pro Thr Ala Val Asp Pro Asp Ala Glu Pro Thr
    1265                1270                1275

Leu Leu Arg Glu Pro Gln Ala Thr Val Val Phe Thr Thr His Val
    1280                1285                1290

Pro Thr Leu Gly Arg Tyr Ala Phe Leu Leu His Gly Tyr Gln Pro
    1295                1300                1305

Ala His Pro Thr Phe Pro Val Glu Val Leu Ile Asn Ala Gly Arg
    1310                1315                1320

Val Trp Gln Gly His Ala Asn Ala Ser Phe Cys Pro His Gly Tyr
    1325                1330                1335

Gly Cys Arg Thr Leu Val Val Cys Glu Gly Gln Ala Leu Leu Asp
    1340                1345                1350

Val Thr His Ser Glu Leu Thr Val Thr Val Arg Val Pro Lys Gly
    1355                1360                1365

Arg Trp Leu Trp Leu Asp Tyr Val Leu Val Val Pro Glu Asn Val
    1370                1375                1380

Tyr Ser Phe Gly Tyr Leu Arg Glu Glu Pro Leu Asp Lys Ser Tyr
    1385                1390                1395

Asp Phe Ile Ser His Cys Ala Ala Gln Gly Tyr His Ile Ser Pro
    1400                1405                1410

Ser Ser Ser Ser Leu Phe Cys Arg Asn Ala Ala Ala Ser Leu Ser
    1415                1420                1425

Leu Phe Tyr Asn Asn Gly Ala Arg Pro Cys Gly Cys His Glu Val
    1430                1435                1440

Gly Ala Thr Gly Pro Thr Cys Glu Pro Phe Gly Gly Gln Cys Pro
    1445                1450                1455

Cys His Ala His Val Ile Gly Arg Asp Cys Ser Arg Cys Ala Thr
    1460                1465                1470

Gly Tyr Trp Gly Phe Pro Asn Cys Arg Pro Cys Asp Cys Gly Ala
    1475                1480                1485

Arg Leu Cys Asp Glu Leu Thr Gly Gln Cys Ile Cys Pro Pro Arg
    1490                1495                1500

Thr Ile Pro Pro Asp Cys Leu Leu Cys Gln Pro Gln Thr Phe Gly
    1505                1510                1515

Cys His Pro Leu Val Gly Cys Glu Glu Cys Asn Cys Ser Gly Pro
    1520                1525                1530

Gly Ile Gln Glu Leu Thr Asp Pro Thr Cys Asp Thr Asp Ser Gly
    1535                1540                1545

Gln Cys Lys Cys Arg Pro Asn Val Thr Gly Arg Arg Cys Asp Thr
    1550                1555                1560

Cys Ser Pro Gly Phe His Gly Tyr Pro Arg Cys Arg Pro Cys Asp
    1565                1570                1575

Cys His Glu Ala Gly Thr Ala Pro Gly Val Cys Asp Pro Leu Thr
    1580                1585                1590

Gly Gln Cys Tyr Cys Lys Glu Asn Val Gln Gly Pro Lys Cys Asp
    1595                1600                1605

Gln Cys Ser Leu Gly Thr Phe Ser Leu Asp Ala Ala Asn Pro Lys
    1610                1615                1620

Gly Cys Thr Arg Cys Phe Cys Phe Gly Ala Thr Glu Arg Cys Arg
    1625                1630                1635
```

```
Ser Ser Ser Tyr Thr Arg Gln Glu Phe Val Asp Met Glu Gly Trp
    1640                1645                1650

Val Leu Leu Ser Thr Asp Arg Gln Val Pro His Glu Arg Gln
    1655                1660                1665

Pro Gly Thr Glu Met Leu Arg Ala Asp Leu Arg His Val Pro Glu
    1670                1675                1680

Ala Val Pro Glu Ala Phe Pro Glu Leu Tyr Trp Gln Ala Pro Pro
    1685                1690                1695

Ser Tyr Leu Gly Asp Arg Val Ser Ser Tyr Gly Gly Thr Leu Arg
    1700                1705                1710

Tyr Glu Leu His Ser Glu Thr Gln Arg Gly Asp Val Phe Val Pro
    1715                1720                1725

Met Glu Ser Arg Pro Asp Val Val Leu Gln Gly Asn Gln Met Ser
    1730                1735                1740

Ile Thr Phe Leu Glu Pro Ala Tyr Pro Thr Pro Gly His Val His
    1745                1750                1755

Arg Gly Gln Leu Gln Leu Val Glu Gly Asn Phe Arg His Thr Glu
    1760                1765                1770

Thr Arg Asn Thr Val Ser Arg Glu Glu Leu Met Met Val Leu Ala
    1775                1780                1785

Ser Leu Glu Gln Leu Gln Ile Arg Ala Leu Phe Ser Gln Ile Ser
    1790                1795                1800

Ser Ala Val Phe Leu Arg Arg Val Ala Leu Glu Val Ala Ser Pro
    1805                1810                1815

Ala Gly Gln Gly Ala Leu Ala Ser Asn Val Glu Leu Cys Leu Cys
    1820                1825                1830

Pro Ala Ser Tyr Arg Gly Asp Ser Cys Gln Glu Cys Ala Pro Gly
    1835                1840                1845

Phe Tyr Arg Asp Val Lys Gly Leu Phe Leu Gly Arg Cys Val Pro
    1850                1855                1860

Cys Gln Cys His Gly His Ser Asp Arg Cys Leu Pro Gly Ser Gly
    1865                1870                1875

Val Cys Val Asp Cys Gln His Asn Thr Glu Gly Ala His Cys Glu
    1880                1885                1890

Arg Cys Gln Ala Gly Phe Val Ser Ser Arg Asp Asp Pro Ser Ala
    1895                1900                1905

Pro Cys Val Ser Cys Pro Cys Pro Leu Ser Val Pro Ser Asn Asn
    1910                1915                1920

Phe Ala Glu Gly Cys Val Leu Arg Gly Gly Arg Thr Gln Cys Leu
    1925                1930                1935

Cys Lys Pro Gly Tyr Ala Gly Ala Ser Cys Glu Arg Cys Ala Pro
    1940                1945                1950

Gly Phe Phe Gly Asn Pro Leu Val Leu Gly Ser Ser Cys Gln Pro
    1955                1960                1965

Cys Asp Cys Ser Gly Asn Gly Asp Pro Asn Leu Leu Phe Ser Asp
    1970                1975                1980

Cys Asp Pro Leu Thr Gly Ala Cys Arg Gly Cys Leu Arg His Thr
    1985                1990                1995

Thr Gly Pro Arg Cys Glu Ile Cys Ala Pro Gly Phe Tyr Gly Asn
    2000                2005                2010

Ala Leu Leu Pro Gly Asn Cys Thr Arg Cys Asp Cys Thr Pro Cys
    2015                2020                2025
```

```
Gly Thr Glu Ala Cys Asp Pro His Ser Gly His Cys Leu Cys Lys
    2030                2035            2040

Ala Gly Val Thr Gly Arg Arg Cys Asp Arg Cys Gln Glu Gly His
    2045                2050            2055

Phe Gly Phe Asp Gly Cys Gly Gly Cys Arg Pro Cys Ala Cys Gly
    2060                2065            2070

Pro Ala Ala Glu Gly Ser Glu Cys His Pro Gln Ser Gly Gln Cys
    2075                2080            2085

His Cys Arg Pro Gly Thr Met Gly Pro Gln Cys Arg Glu Cys Ala
    2090                2095            2100

Pro Gly Tyr Trp Gly Leu Pro Glu Gln Gly Cys Arg Arg Cys Gln
    2105                2110            2115

Cys Pro Gly Gly Arg Cys Asp Pro His Thr Gly Arg Cys Asn Cys
    2120                2125            2130

Pro Pro Gly Leu Ser Gly Glu Arg Cys Asp Thr Cys Ser Gln Gln
    2135                2140            2145

His Gln Val Pro Val Pro Gly Gly Pro Val Gly His Ser Ile His
    2150                2155            2160

Cys Glu Val Cys Asp His Cys Val Val Leu Leu Leu Asp Asp Leu
    2165                2170            2175

Glu Arg Ala Gly Ala Leu Leu Pro Ala Ile His Glu Gln Leu Arg
    2180                2185            2190

Gly Ile Asn Ala Ser Ser Met Ala Trp Ala Arg Leu His Arg Leu
    2195                2200            2205

Asn Ala Ser Ile Ala Asp Leu Gln Ser Gln Leu Arg Ser Pro Leu
    2210                2215            2220

Gly Pro Arg His Glu Thr Ala Gln Gln Leu Glu Val Leu Glu Gln
    2225                2230            2235

Gln Ser Thr Ser Leu Gly Gln Asp Ala Arg Arg Leu Gly Gly Gln
    2240                2245            2250

Ala Val Gly Thr Arg Asp Gln Ala Ser Gln Leu Leu Ala Gly Thr
    2255                2260            2265

Glu Ala Thr Leu Gly His Ala Lys Thr Leu Leu Ala Ala Ile Arg
    2270                2275            2280

Ala Val Asp Arg Thr Leu Ser Glu Leu Met Ser Gln Thr Gly His
    2285                2290            2295

Leu Gly Leu Ala Asn Ala Ser Ala Pro Ser Gly Glu Gln Leu Leu
    2300                2305            2310

Arg Thr Leu Ala Glu Val Glu Arg Leu Leu Trp Glu Met Arg Ala
    2315                2320            2325

Arg Asp Leu Gly Ala Pro Gln Ala Ala Ala Glu Ala Glu Leu Ala
    2330                2335            2340

Ala Ala Gln Arg Leu Leu Ala Arg Val Gln Glu Gln Leu Ser Ser
    2345                2350            2355

Leu Trp Glu Glu Asn Gln Ala Leu Ala Thr Gln Thr Arg Asp Arg
    2360                2365            2370

Leu Ala Gln His Glu Ala Gly Leu Met Asp Leu Arg Glu Ala Leu
    2375                2380            2385

Asn Arg Ala Val Asp Ala Thr Arg Glu Ala Gln Glu Leu Asn Ser
    2390                2395            2400

Arg Asn Gln Glu Arg Leu Glu Glu Ala Leu Gln Arg Lys Gln Glu
    2405                2410            2415

Leu Ser Arg Asp Asn Ala Thr Leu Gln Ala Thr Leu His Ala Ala
```

```
                2420                2425                2430

Arg Asp Thr Leu Ala Ser Val Phe Arg Leu Leu His Ser Leu Asp
    2435                2440                2445

Gln Ala Lys Glu Glu Leu Glu Arg Leu Ala Ala Ser Leu Asp Gly
    2450                2455                2460

Ala Arg Thr Pro Leu Leu Gln Arg Met Gln Thr Phe Ser Pro Ala
    2465                2470                2475

Gly Ser Lys Leu Arg Leu Val Glu Ala Ala Glu Ala His Ala Gln
    2480                2485                2490

Gln Leu Gly Gln Leu Ala Leu Asn Leu Ser Ser Ile Ile Leu Asp
    2495                2500                2505

Val Asn Gln Asp Arg Leu Thr Gln Arg Ala Ile Glu Ala Ser Asn
    2510                2515                2520

Ala Tyr Ser Arg Ile Leu Gln Ala Val Gln Ala Ala Glu Asp Ala
    2525                2530                2535

Ala Gly Gln Ala Leu Gln Gln Ala Asp His Thr Trp Ala Thr Val
    2540                2545                2550

Val Arg Gln Gly Leu Val Asp Arg Ala Gln Gln Leu Leu Ala Asn
    2555                2560                2565

Ser Thr Ala Leu Glu Glu Ala Met Leu Gln Glu Gln Gln Arg Leu
    2570                2575                2580

Gly Leu Val Trp Ala Ala Leu Gln Gly Ala Arg Thr Gln Leu Arg
    2585                2590                2595

Asp Val Arg Ala Lys Lys Asp Gln Leu Glu Ala His Ile Gln Ala
    2600                2605                2610

Ala Gln Ala Met Leu Ala Met Asp Thr Asp Glu Thr Ser Lys Lys
    2615                2620                2625

Ile Ala His Ala Lys Ala Val Ala Ala Glu Ala Gln Asp Thr Ala
    2630                2635                2640

Thr Arg Val Gln Ser Gln Leu Gln Ala Met Gln Glu Asn Val Glu
    2645                2650                2655

Arg Trp Gln Gly Gln Tyr Glu Gly Leu Arg Gly Gln Asp Leu Gly
    2660                2665                2670

Gln Ala Val Leu Asp Ala Gly His Ser Val Ser Thr Leu Glu Lys
    2675                2680                2685

Thr Leu Pro Gln Leu Leu Ala Lys Leu Ser Ile Leu Glu Asn Arg
    2690                2695                2700

Gly Val His Asn Ala Ser Leu Ala Leu Ser Ala Ser Ile Gly Arg
    2705                2710                2715

Val Arg Glu Leu Ile Ala Gln Ala Arg Gly Ala Ala Ser Lys Val
    2720                2725                2730

Lys Val Pro Met Lys Phe Asn Gly Arg Ser Gly Val Gln Leu Arg
    2735                2740                2745

Thr Pro Arg Asp Leu Ala Asp Leu Ala Ala Tyr Thr Ala Leu Lys
    2750                2755                2760

Phe Tyr Leu Gln Gly Pro Glu Pro Glu Pro Gln Gly Thr Glu
    2765                2770                2775

Asp Arg Phe Val Met Tyr Met Gly Ser Arg Gln Ala Thr Gly Asp
    2780                2785                2790

Tyr Met Gly Val Ser Leu Arg Asp Lys Lys Val His Trp Val Tyr
    2795                2800                2805

Gln Leu Gly Glu Ala Gly Pro Ala Val Leu Ser Ile Asp Glu Asp
    2810                2815                2820
```

-continued

Ile Gly Glu Gln Phe Ala Ala Val Ser Leu Asp Arg Thr Leu Gln
2825                2830                2835

Phe Gly His Met Ser Val Thr Val Glu Arg Gln Met Ile Gln Glu
2840                2845                2850

Thr Lys Gly Asp Thr Val Ala Pro Gly Ala Glu Gly Leu Leu Asn
2855                2860                2865

Leu Arg Pro Asp Asp Phe Val Phe Tyr Val Gly Gly Tyr Pro Ser
2870                2875                2880

Thr Phe Thr Pro Pro Pro Leu Leu Arg Phe Pro Gly Tyr Arg Gly
2885                2890                2895

Cys Ile Glu Met Asp Thr Leu Asn Glu Glu Val Val Ser Leu Tyr
2900                2905                2910

Asn Phe Glu Arg Thr Phe Gln Leu Asp Thr Ala Val Asp Arg Pro
2915                2920                2925

Cys Ala Arg Ser Lys Ser Thr Gly Asp Pro Trp Leu Thr Asp Gly
2930                2935                2940

Ser Tyr Leu Asp Gly Thr Gly Phe Ala Arg Ile Ser Phe Asp Ser
2945                2950                2955

Gln Ile Ser Thr Thr Lys Arg Phe Glu Gln Glu Leu Arg Leu Val
2960                2965                2970

Ser Tyr Ser Gly Val Leu Phe Phe Leu Lys Gln Gln Ser Gln Phe
2975                2980                2985

Leu Cys Leu Ala Val Gln Glu Gly Ser Leu Val Leu Leu Tyr Asp
2990                2995                3000

Phe Gly Ala Gly Leu Lys Lys Ala Val Pro Leu Gln Pro Pro Pro
3005                3010                3015

Pro Leu Thr Ser Ala Ser Lys Ala Ile Gln Val Phe Leu Leu Gly
3020                3025                3030

Gly Ser Arg Lys Arg Val Leu Val Arg Val Glu Arg Ala Thr Val
3035                3040                3045

Tyr Ser Val Glu Gln Asp Asn Asp Leu Glu Leu Ala Asp Ala Tyr
3050                3055                3060

Tyr Leu Gly Gly Val Pro Pro Asp Gln Leu Pro Pro Ser Leu Arg
3065                3070                3075

Arg Leu Phe Pro Thr Gly Gly Ser Val Arg Gly Cys Val Lys Gly
3080                3085                3090

Ile Lys Ala Leu Gly Lys Tyr Val Asp Leu Lys Arg Leu Asn Thr
3095                3100                3105

Thr Gly Val Ser Ala Gly Cys Thr Ala Asp Leu Leu Val Gly Arg
3110                3115                3120

Ala Met Thr Phe His Gly His Gly Phe Leu Arg Leu Ala Leu Ser
3125                3130                3135

Asn Val Ala Pro Leu Thr Gly Asn Val Tyr Ser Gly Phe Gly Phe
3140                3145                3150

His Ser Ala Gln Asp Ser Ala Leu Leu Tyr Tyr Arg Ala Ser Pro
3155                3160                3165

Asp Gly Leu Cys Gln Val Ser Leu Gln Gln Gly Arg Val Ser Leu
3170                3175                3180

Gln Leu Leu Arg Thr Glu Val Lys Thr Gln Ala Gly Phe Ala Asp
3185                3190                3195

Gly Ala Pro His Tyr Val Ala Phe Tyr Ser Asn Ala Thr Gly Val
3200                3205                3210

```
Trp Leu Tyr Val Asp Asp Gln Leu Gln Gln Met Lys Pro His Arg
3215                3220                3225

Gly Pro Pro Pro Glu Leu Gln Pro Gln Pro Glu Gly Pro Pro Arg
3230                3235                3240

Leu Leu Leu Gly Gly Leu Pro Glu Ser Gly Thr Ile Tyr Asn Phe
3245                3250                3255

Ser Gly Cys Ile Ser Asn Val Phe Val Gln Arg Leu Leu Gly Pro
3260                3265                3270

Gln Arg Val Phe Asp Leu Gln Gln Asn Leu Gly Ser Val Asn Val
3275                3280                3285

Ser Thr Gly Cys Ala Pro Ala Leu Gln Ala Gln Thr Pro Gly Leu
3290                3295                3300

Gly Pro Arg Gly Leu Gln Ala Thr Ala Arg Lys Ala Ser Arg Arg
3305                3310                3315

Ser Arg Gln Pro Ala Arg His Pro Ala Cys Met Leu Pro Pro His
3320                3325                3330

Leu Arg Thr Thr Arg Asp Ser Tyr Gln Phe Gly Gly Ser Leu Ser
3335                3340                3345

Ser His Leu Glu Phe Val Gly Ile Leu Ala Arg His Arg Asn Trp
3350                3355                3360

Pro Ser Leu Ser Met His Val Leu Pro Arg Ser Ser Arg Gly Leu
3365                3370                3375

Leu Leu Phe Thr Ala Arg Leu Arg Pro Gly Ser Pro Ser Leu Ala
3380                3385                3390

Leu Phe Leu Ser Asn Gly His Phe Val Ala Gln Met Glu Gly Leu
3395                3400                3405

Gly Thr Arg Leu Arg Ala Gln Ser Arg Gln Arg Ser Arg Pro Gly
3410                3415                3420

Arg Trp His Lys Val Ser Val Arg Trp Glu Lys Asn Arg Ile Leu
3425                3430                3435

Leu Val Thr Asp Gly Ala Arg Ala Trp Ser Gln Glu Gly Pro His
3440                3445                3450

Arg Gln His Gln Gly Ala Glu His Pro Gln Pro His Thr Leu Phe
3455                3460                3465

Val Gly Gly Leu Pro Ala Ser Ser His Ser Ser Lys Leu Pro Val
3470                3475                3480

Thr Val Gly Phe Ser Gly Cys Val Lys Arg Leu Arg Leu His Gly
3485                3490                3495

Arg Pro Leu Gly Ala Pro Thr Arg Met Ala Gly Val Thr Pro Cys
3500                3505                3510

Ile Leu Gly Pro Leu Glu Ala Gly Leu Phe Phe Pro Gly Ser Gly
3515                3520                3525

Gly Val Ile Thr Leu Asp Leu Pro Gly Ala Thr Leu Pro Asp Val
3530                3535                3540

Gly Leu Glu Leu Glu Val Arg Pro Leu Ala Val Thr Gly Leu Ile
3545                3550                3555

Phe His Leu Gly Gln Ala Arg Thr Pro Pro Tyr Leu Gln Leu Gln
3560                3565                3570

Val Thr Glu Lys Gln Val Leu Leu Arg Ala Asp Asp Gly Ala Gly
3575                3580                3585

Glu Phe Ser Thr Ser Val Thr Arg Pro Ser Val Leu Cys Asp Gly
3590                3595                3600

Gln Trp His Arg Leu Ala Val Met Lys Ser Gly Asn Val Leu Arg
```

```
                3605                3610                3615

Leu Glu  Val Asp Ala Gln Ser  Asn His Thr Val Gly  Pro Leu Leu
    3620             3625              3630

Ala Ala  Ala Ala Gly Ala Pro  Ala Pro Leu Tyr Leu  Gly Gly Leu
    3635             3640              3645

Pro Glu  Pro Met Ala Val Gln  Pro Trp Pro Pro Ala  Tyr Cys Gly
    3650             3655              3660

Cys Met  Arg Arg Leu Ala Val  Asn Arg Ser Pro Val  Ala Met Thr
    3665             3670              3675

Arg Ser  Val Glu Val His Gly  Ala Val Gly Ala Ser  Gly Cys Pro
    3680             3685              3690

Ala Ala
    3695

<210> SEQ ID NO 128
<211> LENGTH: 1786
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of Laminin subunit beta-1
      (Homo sapiens)

<400> SEQUENCE: 128

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240
```

-continued

```
His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
    290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
            340                 345                 350

Ala Thr Gly Asn Val Ser Gly Val Cys Asp Asp Cys Gln His Asn
        355                 360                 365

Thr Met Gly Arg Asn Cys Glu Gln Cys Lys Pro Phe Tyr Tyr Gln His
    370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

Glu Gly Glu His Cys Asp Val Cys Lys Glu Gly Phe Tyr Asp Leu Ser
        435                 440                 445

Ser Glu Asp Pro Phe Gly Cys Lys Ser Cys Ala Cys Asn Pro Leu Gly
    450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
            500                 505                 510

Asp Leu Gly Gly Ala Leu Asn Asn Ser Cys Phe Ala Glu Ser Gly Gln
        515                 520                 525

Cys Ser Cys Arg Pro His Met Ile Gly Arg Gln Cys Asn Glu Val Glu
    530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
        595                 600                 605

Glu Tyr Asp Ile Leu Ile Arg Tyr Glu Pro Gln Leu Pro Asp His Trp
    610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
```

-continued

```
              660                 665                 670
Glu Lys Gly Thr Asn Tyr Thr Val Arg Leu Glu Leu Pro Gln Tyr Thr
                675                 680                 685

Ser Ser Asp Ser Asp Val Glu Ser Pro Tyr Thr Leu Ile Asp Ser Leu
    690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
                740                 745                 750

Asp Val Cys Arg Asn Ile Ile Phe Ser Ile Ser Ala Leu Leu His Gln
            755                 760                 765

Thr Gly Leu Ala Cys Glu Cys Asp Pro Gln Gly Ser Leu Ser Ser Val
            770                 775                 780

Cys Asp Pro Asn Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
                820                 825                 830

Cys Asn Pro Val Thr Gly Gln Cys His Cys Phe Gln Gly Val Tyr Ala
            835                 840                 845

Arg Gln Cys Asp Arg Cys Leu Pro Gly His Trp Gly Phe Pro Ser Cys
        850                 855                 860

Gln Pro Cys Gln Cys Asn Gly His Ala Asp Asp Cys Asp Pro Val Thr
865                 870                 875                 880

Gly Glu Cys Leu Asn Cys Gln Asp Tyr Thr Met Gly His Asn Cys Glu
                885                 890                 895

Arg Cys Leu Ala Gly Tyr Tyr Gly Asp Pro Ile Ile Gly Ser Gly Asp
                900                 905                 910

His Cys Arg Pro Cys Pro Cys Pro Asp Gly Pro Asp Ser Gly Arg Gln
            915                 920                 925

Phe Ala Arg Ser Cys Tyr Gln Asp Pro Val Thr Leu Gln Leu Ala Cys
930                 935                 940

Val Cys Asp Pro Gly Tyr Ile Gly Ser Arg Cys Asp Asp Cys Ala Ser
945                 950                 955                 960

Gly Tyr Phe Gly Asn Pro Ser Glu Val Gly Gly Ser Cys Gln Pro Cys
                965                 970                 975

Gln Cys His Asn Asn Ile Asp Thr Thr Asp Pro Glu Ala Cys Asp Lys
            980                 985                 990

Glu Thr Gly Arg Cys Leu Lys Cys Leu Tyr His Thr Glu Gly Glu His
                995                1000                1005

Cys Gln Phe Cys Arg Phe Gly Tyr Tyr Gly Asp Ala Leu Gln Gln
            1010                1015                1020

Asp Cys Arg Lys Cys Val Cys Asn Tyr Leu Gly Thr Val Gln Glu
            1025                1030                1035

His Cys Asn Gly Ser Asp Cys Gln Cys Asp Lys Ala Thr Gly Gln
            1040                1045                1050

Cys Leu Cys Leu Pro Asn Val Ile Gly Gln Asn Cys Asp Arg Cys
            1055                1060                1065

Ala Pro Asn Thr Trp Gln Leu Ala Ser Gly Thr Gly Cys Asp Pro
            1070                1075                1080
```

```
Cys Asn Cys Asn Ala Ala His Ser Phe Gly Pro Ser Cys Asn Glu
    1085                1090                1095

Phe Thr Gly Gln Cys Gln Cys Met Pro Gly Phe Gly Gly Arg Thr
    1100                1105                1110

Cys Ser Glu Cys Gln Glu Leu Phe Trp Gly Asp Pro Asp Val Glu
    1115                1120                1125

Cys Arg Ala Cys Asp Cys Asp Pro Arg Gly Ile Glu Thr Pro Gln
    1130                1135                1140

Cys Asp Gln Ser Thr Gly Gln Cys Val Cys Val Glu Gly Val Glu
    1145                1150                1155

Gly Pro Arg Cys Asp Lys Cys Thr Arg Gly Tyr Ser Gly Val Phe
    1160                1165                1170

Pro Asp Cys Thr Pro Cys His Gln Cys Phe Ala Leu Trp Asp Val
    1175                1180                1185

Ile Ile Ala Glu Leu Thr Asn Arg Thr His Arg Phe Leu Glu Lys
    1190                1195                1200

Ala Lys Ala Leu Lys Ile Ser Gly Val Ile Gly Pro Tyr Arg Glu
    1205                1210                1215

Thr Val Asp Ser Val Glu Arg Lys Val Ser Glu Ile Lys Asp Ile
    1220                1225                1230

Leu Ala Gln Ser Pro Ala Ala Glu Pro Leu Lys Asn Ile Gly Asn
    1235                1240                1245

Leu Phe Glu Glu Ala Glu Lys Leu Ile Lys Asp Val Thr Glu Met
    1250                1255                1260

Met Ala Gln Val Glu Val Lys Leu Ser Asp Thr Thr Ser Gln Ser
    1265                1270                1275

Asn Ser Thr Ala Lys Glu Leu Asp Ser Leu Gln Thr Glu Ala Glu
    1280                1285                1290

Ser Leu Asp Asn Thr Val Lys Glu Leu Ala Glu Gln Leu Glu Phe
    1295                1300                1305

Ile Lys Asn Ser Asp Ile Arg Gly Ala Leu Asp Ser Ile Thr Lys
    1310                1315                1320

Tyr Phe Gln Met Ser Leu Glu Ala Glu Glu Arg Val Asn Ala Ser
    1325                1330                1335

Thr Thr Glu Pro Asn Ser Thr Val Glu Gln Ser Ala Leu Met Arg
    1340                1345                1350

Asp Arg Val Glu Asp Val Met Met Glu Arg Glu Ser Gln Phe Lys
    1355                1360                1365

Glu Lys Gln Glu Glu Gln Ala Arg Leu Leu Asp Glu Leu Ala Gly
    1370                1375                1380

Lys Leu Gln Ser Leu Asp Leu Ser Ala Ala Ala Glu Met Thr Cys
    1385                1390                1395

Gly Thr Pro Pro Gly Ala Ser Cys Ser Glu Thr Glu Cys Gly Gly
    1400                1405                1410

Pro Asn Cys Arg Thr Asp Glu Gly Glu Arg Lys Cys Gly Gly Pro
    1415                1420                1425

Gly Cys Gly Gly Leu Val Thr Val Ala His Asn Ala Trp Gln Lys
    1430                1435                1440

Ala Met Asp Leu Asp Gln Asp Val Leu Ser Ala Leu Ala Glu Val
    1445                1450                1455

Glu Gln Leu Ser Lys Met Val Ser Glu Ala Lys Leu Arg Ala Asp
    1460                1465                1470
```

```
Glu Ala Lys Gln Ser Ala Glu Asp Ile Leu Leu Lys Thr Asn Ala
1475                1480                1485

Thr Lys Glu Lys Met Asp Lys Ser Asn Glu Glu Leu Arg Asn Leu
1490                1495                1500

Ile Lys Gln Ile Arg Asn Phe Leu Thr Gln Asp Ser Ala Asp Leu
1505                1510                1515

Asp Ser Ile Glu Ala Val Ala Asn Glu Val Leu Lys Met Glu Met
1520                1525                1530

Pro Ser Thr Pro Gln Gln Leu Gln Asn Leu Thr Glu Asp Ile Arg
1535                1540                1545

Glu Arg Val Glu Ser Leu Ser Gln Val Glu Val Ile Leu Gln His
1550                1555                1560

Ser Ala Ala Asp Ile Ala Arg Ala Glu Met Leu Leu Glu Glu Ala
1565                1570                1575

Lys Arg Ala Ser Lys Ser Ala Thr Asp Val Lys Val Thr Ala Asp
1580                1585                1590

Met Val Lys Glu Ala Leu Glu Glu Ala Glu Lys Ala Gln Val Ala
1595                1600                1605

Ala Glu Lys Ala Ile Lys Gln Ala Asp Glu Asp Ile Gln Gly Thr
1610                1615                1620

Gln Asn Leu Leu Thr Ser Ile Glu Ser Glu Thr Ala Ala Ser Glu
1625                1630                1635

Glu Thr Leu Phe Asn Ala Ser Gln Arg Ile Ser Glu Leu Glu Arg
1640                1645                1650

Asn Val Glu Glu Leu Lys Arg Lys Ala Ala Gln Asn Ser Gly Glu
1655                1660                1665

Ala Glu Tyr Ile Glu Lys Val Val Tyr Thr Val Lys Gln Ser Ala
1670                1675                1680

Glu Asp Val Lys Lys Thr Leu Asp Gly Glu Leu Asp Glu Lys Tyr
1685                1690                1695

Lys Lys Val Glu Asn Leu Ile Ala Lys Lys Thr Glu Glu Ser Ala
1700                1705                1710

Asp Ala Arg Arg Lys Ala Glu Met Leu Gln Asn Glu Ala Lys Thr
1715                1720                1725

Leu Leu Ala Gln Ala Asn Ser Lys Leu Gln Leu Leu Lys Asp Leu
1730                1735                1740

Glu Arg Lys Tyr Glu Asp Asn Gln Arg Tyr Leu Glu Asp Lys Ala
1745                1750                1755

Gln Glu Leu Ala Arg Leu Gly Glu Val Arg Ser Leu Leu Lys
1760                1765                1770

Asp Ile Ser Gln Lys Val Ala Val Tyr Ser Thr Cys Leu
1775                1780                1785

<210> SEQ ID NO 129
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer for scFv VH

<400> SEQUENCE: 129
agagagtgta cactcccagg cggccgaggt gcag                            34
```

<210> SEQ ID NO 130
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer for scFv VH

<400> SEQUENCE: 130
cgccgctggg cccttggtgg aggctgagct cacggtgacc ag           42

<210> SEQ ID NO 131
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer for scFv VL

<400> SEQUENCE: 131
aagcggccgc caccatggga tggagctgta tcatcctctt cttggtagca acagctacag     60
gtgtacactc ccagtctgtg ctgactcag                                       89

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer for scFv VL

<400> SEQUENCE: 132
cgccgccgta cgtaggaccg tcagcttggt                         30

<210> SEQ ID NO 133
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 epitope F1

<400> SEQUENCE: 133

Met Ala Ala Val Gln Ala Ala Glu Val Lys Val Asp Gly Ser Glu Pro
1               5                   10                  15
Lys Leu Ser Lys Asn Glu Leu Lys Arg Arg Leu Lys Ala
            20                  25

<210> SEQ ID NO 134
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 epitope F2

<400> SEQUENCE: 134

Gln Ala Ala Glu Val Lys Val Asp Gly Ser Glu Pro Lys Leu Ser Lys

```
1               5                   10                  15

Asn Glu Leu Lys Arg Arg Leu Lys Ala Glu Lys Lys Val Ala
            20                  25                  30

<210> SEQ ID NO 135
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 epitope F3

<400> SEQUENCE: 135

Lys Val Asp Gly Ser Glu Pro Lys Leu Ser Lys Asn Glu Leu Lys Arg
1               5                   10                  15

Arg Leu Lys Ala Glu Lys Lys Val Ala Glu Lys Glu Ala
            20                  25

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 epitope F4

<400> SEQUENCE: 136

Glu Pro Lys Leu Ser Lys Asn Glu Leu Lys Arg Arg Leu Lys Ala Glu
1               5                   10                  15

Lys Lys Val Ala Glu Lys Glu Ala Lys Gln Lys Glu
            20                  25

<210> SEQ ID NO 137
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N3 epitope F5

<400> SEQUENCE: 137

Lys Arg Arg Leu Lys Ala Glu Lys Lys Val Ala Glu Lys Glu Ala Lys
1               5                   10                  15

Gln Lys Glu Leu Ser Glu Lys Gln Leu Ser
            20                  25

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mouse N3 epitope F1(mF1)

<400> SEQUENCE: 138

Met Ala Thr Leu Gln Glu Ser Glu Val Lys Val Asp Gly Glu Gln Lys
1               5                   10                  15

Leu Ser Lys Asn Glu Leu Lys Arg Arg Leu Lys Ala
```

```
            20                  25

<210> SEQ ID NO 139
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mouse N3 epitope F2(mF2)

<400> SEQUENCE: 139

Gln Glu Ser Glu Val Lys Val Asp Gly Glu Gln Lys Leu Ser Lys Asn
1               5                   10                  15

Glu Leu Lys Arg Arg Leu Lys Ala Glu Lys Lys Leu Ala
            20                  25

<210> SEQ ID NO 140
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mouse N3 epitope F3(mF3)

<400> SEQUENCE: 140

Lys Val Asp Gly Glu Gln Lys Leu Ser Lys Asn Glu Leu Lys Arg Arg
1               5                   10                  15

Leu Lys Ala Glu Lys Lys Leu Ala Glu Lys Glu Ala
            20                  25

<210> SEQ ID NO 141
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mouse N3 epitope F4(mF4)

<400> SEQUENCE: 141

Gln Lys Leu Ser Lys Asn Glu Leu Lys Arg Arg Leu Lys Ala Glu Lys
1               5                   10                  15

Lys Leu Ala Glu Lys Glu Ala Lys Gln Lys Glu
            20                  25

<210> SEQ ID NO 142
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mouse N3 epitope F5(mF5)

<400> SEQUENCE: 142

Arg Arg Leu Lys Ala Glu Lys Lys Leu Ala Glu Lys Glu Ala Lys Gln
1               5                   10                  15

Lys Glu Leu Ser Glu Lys Gln Leu Asn
            20                  25
```

```
<210> SEQ ID NO 143
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rat N3 epitope F1(rF1)

<400> SEQUENCE: 143

Met Ala Thr Leu Arg Glu Gly Glu Val Lys Leu Asp Gly Glu Pro Lys
1               5                   10                  15

Leu Ser Lys Asn Glu Leu Lys Arg Arg Leu Lys Ala
            20                  25

<210> SEQ ID NO 144
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rat N3 epitope F2(rF2)

<400> SEQUENCE: 144

Arg Glu Gly Glu Val Lys Leu Asp Gly Glu Pro Lys Leu Ser Lys Asn
1               5                   10                  15

Glu Leu Lys Arg Arg Leu Lys Ala Glu Lys Lys Leu Ala
            20                  25

<210> SEQ ID NO 145
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rat N3 epitope F3(rF3)

<400> SEQUENCE: 145

Lys Leu Asp Gly Glu Pro Lys Leu Ser Lys Asn Glu Leu Lys Arg Arg
1               5                   10                  15

Leu Lys Ala Glu Lys Lys Leu Ala Glu Lys Glu Ala
            20                  25

<210> SEQ ID NO 146
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rat N3 epitope F4(rF4)

<400> SEQUENCE: 146

Pro Lys Leu Ser Lys Asn Glu Leu Lys Arg Arg Leu Lys Ala Glu Lys
1               5                   10                  15

Lys Leu Ala Glu Lys Glu Ala Lys Gln Lys Glu
            20                  25

<210> SEQ ID NO 147
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: rat N3 epitope F5(rF5)

<400> SEQUENCE: 147

Arg Arg Leu Lys Ala Glu Lys Lys Leu Ala Glu Lys Glu Ala Lys Gln
1               5                   10                  15

Lys Glu Leu Ser Glu Lys Gln Leu Asn
            20                  25

<210> SEQ ID NO 148
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: membrane exposed Lysyl-tRNA synthetase
      N-term(Homo sapiens)

<400> SEQUENCE: 148

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr
    50

<210> SEQ ID NO 149
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Lysyl-tRNA synthetase N-term(mouse)

<400> SEQUENCE: 149

Met Ala Thr Leu Gln Glu Ser Glu Val Lys Val Asp Gly Glu Gln Lys
1               5                   10                  15

Leu Ser Lys Asn Glu Leu Lys Arg Arg Leu Lys Ala Glu Lys Lys Leu
            20                  25                  30

Ala Glu Lys Glu Ala Lys Gln Lys Glu Leu Ser Glu Lys Gln Leu Asn
        35                  40                  45

<210> SEQ ID NO 150
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Lysyl-tRNA synthetase N-term(rat)

<400> SEQUENCE: 150

Met Ala Thr Leu Arg Glu Gly Glu Val Lys Leu Asp Gly Glu Pro Lys
1               5                   10                  15
```

Leu Ser Lys Asn Glu Leu Lys Arg Arg Leu Lys Ala Glu Lys Lys Leu
            20                  25                  30

Ala Glu Lys Glu Ala Lys Gln Lys Glu Leu Ser Glu Lys Gln Leu Asn
        35                  40                  45

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 5 amino acid

<400> SEQUENCE: 151

Val Ile Ser Ser Asp Gly Gly Asn Thr Tyr Tyr Ala Asp Ser Val Lys
1               5                   10                  15

Gly

<210> SEQ ID NO 152
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 mutant 5 DNA

<400> SEQUENCE: 152
gtgatctctt ctgatggtgg taatacatat tacgctgatt ctgtaaaagg t         51

<210> SEQ ID NO 153
<211> LENGTH: 16
<212> TYPE: PRT
<213> ORGANISM: Artificial
<220> FEATURE:
<223> OTHER INFORMATION: claim 13 heavy chain complementarity
      determining region 2 wherein X1 is A or V, X2 is S, D or G, X3 is
      Y, P, S or A and X4 is D, Q, L or Y, X5 is N, M, S, or G, X6 is N,
      R
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 153

Xaa Xaa Xaa Xaa Xaa Gly Xaa Xaa Tyr Tyr Ala Asp Ser Val Lys Gly
1               5                   10                  15

<210> SEQ ID NO 154
<211> LENGTH: 14
<212> TYPE: PRT
<213> ORGANISM: Artificial
<220> FEATURE:
<223> OTHER INFORMATION: claim 13 heavy chain complementarity
      determining region 3 wherein X8 is M or L
<220> FEATURE:
<221> NAME/KEY: misc_feature
<222> LOCATION: (1)..(8)
<223> OTHER INFORMATION: Xaa can be any naturally occurring amino acid

<400> SEQUENCE: 154

Xaa Xaa Xaa Xaa Xaa Xaa Xaa Xaa Ala Leu Asp Phe Asp Tyr

```
<210> SEQ ID NO 155
<211> LENGTH: 34
<212> TYPE: PRT
<213> ORGANISM: Artificial
<220> FEATURE:
<223> OTHER INFORMATION: claim 13 light chain complementarity
      determining region 2 wherein X9 is D, S or R, X10 is S or N, and
      X11 is N or Q
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (11)..(31)
<223> OTHER INFORMATION: Xaa can be any naturally occurring amino acid

<400> SEQUENCE: 155

Xaa Xaa Xaa Xaa Xaa Xaa Xaa Xaa Xaa Asn Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Arg
            20                  25                  30

Pro Ser

<210> SEQ ID NO 156
<211> LENGTH: 22
<212> TYPE: PRT
<213> ORGANISM: Artificial
<220> FEATURE:
<223> OTHER INFORMATION: claim 13 light chain complementarity
      determining region 3 wherein X12 is A or S
<220> FEATURE:
<221> NAME/KEY: misc_feature
<222> LOCATION: (1)..(12)
<223> OTHER INFORMATION: Xaa can be any naturally occurring amino acid

<400> SEQUENCE: 156

Xaa Xaa Xaa Xaa Xaa Xaa Xaa Xaa Xaa Xaa Xaa Xaa Ser Phe Ser Asp
1               5                   10                  15

Glu Leu Gly Ala Tyr Val
            20
```

PHARMACEUTICAL COMPOSITION COMPRISING ANTIBODY BINDING SPECIFICALLY TO LYSYL-TRNA SYNTHETASE N-TERMINUS AS EFFECTIVE INGREDIENT FOR PREVENTING OR TREATING IMMUNE CELL MIGRATION-RELATED DISEASE

RELATED APPLICATION DATA

This application is a National Stage Application under 35 U.S.C. 371 of co-pending PCT application number PCT/KR2018/010903 designating the United States and filed Sep. 17, 2018; which claims the benefit of KR application number 10-2017-0118917 and filed Sep. 15, 2017 each of which are hereby incorporated by reference in their entireties.

SEQUENCE LISTING

The instant application contains a Sequence Listing which has been filed electronically in ASCII format and is hereby incorporated by reference in its entirety. Said ASCII copy, created on Jan. 31 2022, is named Corrected Sequence Listing 009041.00005 and is 315,201 bytes in size.

TECHNICAL FIELD

The present invention relates to a novel use of an antibody biding specifically to the N-terminus of lysyl-tRNA synthetase and, more particularly, to a pharmaceutical composition comprising an antibody biding specifically to an epitope containing the sequence of SEQ ID NO: 117 in the N-terminus of lysyl-tRNA synthetase (KRS) or a functional fragment thereof as an effective ingredient for preventing or treating an immune cell migration-related disease.

BACKGROUND OF THE INVENTION

This application claims priority from Korean Patent Application No. 10-2017-0118917, filed on Sep. 15, 2017, the entire contents of which are incorporated herein by reference.

In many tissues of the body, each cell migrates in different ways depending on their genetic characteristics and environment. Uncontrolled cell migration involves various disease states such as inflammatory disease, and cancer metastasis, but the migration signaling and mechanism characteristics of each cell are not fully characterized. In particular, each cell is reported to have a different way of relating to the same factors, which further increases the difficulty in identifying signaling processes and mechanisms. For example, water channel aquaporin-1 (AQP1) is known to promote cell migration in epithelial cells and the like, and in particular to promote cancer metastasis (Hara-Chikuma M et al., Aquaporin-1 facilitates epithelial cell migration in kidney proximal tubule, J Am Soc Nephrol. 2006 January; 17(1):39-45; Jiang Y, Aquaporin-1 activity of plasma membrane affects HT20 colon cancer cell migration, IUBMB Life. 2009 October; 61(10):1001-9), but aquaporin-1 have been reported to inhibit the migration of macrophages despite macrophages express AQP1 (Tyteca D et al., Regulation of Macrophage Motility by the Water Channel Aquaporin-1: Crucial Role of MO/M2 Phenotype Switch, PLoS One. 2015 Feb. 26; 10(2):e0117398). As these different types of cells have various ways and characteristics in their migration, drugs designed to prevent the migration of specific cells have been shown to be quite limited and insufficient in efficacy. Therefore, there is a demand for a new strategy for controlling migratory switches of cells and treating migration-related diseases.

On the other hand, although immune cells are also the first defense system in the body, excessive activation of immune cells has recently been reported to be one of the major pathogenesis. In general, an increase in the mobility of immune cells is observed upon activation of inflammatory immune cells. Specifically, it has been reported that such immune cell migration and invasion are closely related to the pathology of the disease in the following diseases.

Cardiovascular diseases, for example, are diseases of the heart and major arteries, including atherosclerosis and coronary artery disease (Ross R et al., New Engl J Med, 1999: 340 (2): 115-26, Poli G et al., Redox Biol 2013; 1 (1): 125-30, Libby P et al., Circulation 2002; 5; 105 (9): 1135-43). Atherosclerosis is an inflammatory disease related with cholesterol and is caused by atheromas consisting of cholesterol deposited on the inner artery membrane and immune cells that migrated from the blood into the arteries. In other words, atheromas are formed by the migration of immune cells, such as monocytes, to the site of cholesterol oxide inflammation. When atheromas are formed, the inner surface of the blood vessel becomes stiff and the wall becomes thick, and the diameter of the inside of the blood flowing narrows, which causes a problem in blood circulation. When the fibrous cap around the atheromas bursts, blood clots develop in the blood vessels, and bleeding into the atheromas causes the vessel's internal diameter to narrow sharply or become blocked. It mainly occurs in blood vessels that supply blood to the heart, blood vessels that supply blood to the brain, blood vessels and peripheral blood vessels that supply blood to the kidneys, causing ischemic heart disease, ischemic cerebrovascular disease (stroke), kidney failure, and limb ischemic artery disease. Conventionally, CCL2 (CC-Chemokine ligand 2, MCP-1), which causes inflammatory reactions by inducing the migration of monocytes, is known to play an important role in the occurance and development of such cardiovascular diseases. A new method for treating such cardiovascular diseases by inhibiting the action of CCL2 and thus monocyte migration has been proposed (Gu L et al., Mol Cell, 1998; 2(2):275-81, Aiello R J et al., Arterioscler Thromb Vasc Biol 1999; 19(6):1518-25, Gosling J1 et al., Clin Invest 1999; 103(6):773-8, Harrington J R et al., Stem Cells 2000; 18(1):65-6, Ikeda U et al., Clin Cardiol 2002; 25(4):143-7).

In addition, even in high blood pressure, various immune cells that secrete inflammatory cytokines are excessively moved into blood vessels, resulting in pathologies in which the walls of blood vessels become thick and which lose the elasticity of blood vessels.

Pulmonary arterial hypertension (PAH) is classified as Group 1 in the clinical classification system (ESC Guidelines, European Heart Journal 2015) of the World Health Organization (WHO), and is a rare disease clinically characterized by difficulty in breathing, an increase in mean pulmonary artery pressure (mPAP, mPAP>25 mm Hg), and right ventricular dysfunction. Although pulmonary hypertension is involved in many preexisting factors such as heredity, infection, and related diseases, the immune response due to endothelial cell injury is known to be a key pathological factor (Huertas et al., Circulation, 129:1332-1340, 2014). In this phenomenon, a series of processes due to invasion and dysfunction of immune cells are known to be deeply associated with pathology. In particular, the interactions of immune and vascular endothelial cells are known to be important in PAH. In addition, in Alport syndrome, invasion of monocytes and macrophages has recently been reported to promote the progression of the disease.

On the other hand, in fibrosis-related diseases, a persistent (chronic) inflammatory response activates a wound-healing program, which leads to fibrosis. After tissue damage, inflammatory immune cells, such as monocytes, macrophages, neutrophils, eosinophils, and mast cells, rapidly penetrate into the site of injury and activate several cytokines, which reactivate surrounding fibroblasts, epithelial cells, and smooth muscle to activate them into myoblast type cells. These myoblast type cells produce and secrete a large amount of extracellular matrix protein, ultimately causing a large amount of extracellular matrix protein to accumulate in the tissue, leaving a wound and inducing tissue fibrosis or enlargement (Gurtner G C et al., Trends Cell Biol. 15: 599-607, 2005). This pathological mechanism is one of the fundamental causes of scar formation in the skin tissue caused by wounds, burns and bedsores or sclerogenic fibrosis of tissues such as liver, kidney, blood vessels and lungs. Fibrosis is also a major pathological feature in chronic autoimmune diseases such as scleroderma, rheumatoid arthritis, Crohn's disease, ulcerative colitis, myelofibrosis, and systemic lupus erythematosus. In addition, the activation of inflammatory immune cells is known to contribute to the pathology in atopic diseases, asthma, COPD, psoriasis, keloids, and proliferative retinopathy.

In particular, the fibroblasts activated by myoblast type cells in the wound-healing program are called myofibroblasts. Since the myofibroblast is at the center of all fibrosis-related disease pathologies, eliminating the molecular biological or immunological mechanisms that induce myofibroblast activity is a key component of disease treatment. It is well known that many innate or adaptive immune responses are important for the activity and differentiation of fibroblasts. Therefore, eliminating the inflammatory response in the wound is a key factor in stopping tissue remodeling with fibrosis and in maintaining normal tissue morphology. In practice, however, it is not easy to eliminate the inflammatory response, so understanding the mechanisms of innate or adaptive immunity to find key mediators is important to slow down fibrosis.

Monocytes, macrophages, and the like contribute to wound healing, but they release reactive oxygen and nitrogen, which can have harmful effects on surrounding cells. Therefore, the lack of rapid removal of monocytes and macrophages will cause more tissue damage and result in fibrosis. Therefore, limiting monocytes and macrophages which respond first in the early stages of the disease, is considered a therapeutic strategy for various chronic inflammatory and fibrotic related diseases.

When the wound-healing mechanism triggers a fibrosis reaction, platelet-derived growth factor (PDGF) involved in hemagglutination recruits other inflammatory immune cells into the wound and TGF-β1 is known to promote extracellular matrix synthesis from topical fibroblasts. However, it has been reported that the factors related to the hemagglutination response induce fibrosis even when they are deficient.

As mentioned above, target factors have been suggested to prevent the migration (and invasion) of previous immune cells in diseases in which excessive immune cell activation is a problem. Attempts have been made to devise therapeutic methods for the disease, but the limitations are reported. Accordingly, it is still required to find out what are the key mediators and strategies for controlling the immune cell migration for effective disease treatment.

DETAILED DESCRIPTION OF THE INVENTION

Technical Problem

Therefore, while the present inventors have been searching for a new therapeutic strategy for immune cell migration (invasion)—related diseases, increasing KRS levels in the cell membrane region of immune cells (monocytes/macrophages) was confirmed to be an important pathological phenomenon for immune cell migration and invasion-related diseases. They have completed the present invention after they have confirmed that the KRS N-terminal binding antibody provided in the present invention reduces the increased KRS level in the cell membrane region of immune cells and has an effect of treating related diseases by actually inhibiting the migration and invasion of immune cells.

Accordingly, an aspect of the present invention is to provide a use of an antibody or functional fragments thereof that specifically bind to an epitope containing the sequence of SEQ ID NO: 117 in the N-terminus of lysyltRNA synthetase (KRS) for preventing or treating immune cell migration-related diseases.

Technical Solution

Accordingly, an aspect of the present invention is to provide to a pharmaceutical composition comprising an antibody biding specifically to an epitope containing the sequence of SEQ ID NO: 117 in the N-terminus of lysyl-tRNA synthetase (KRS) or a functional fragment thereof as an effective ingredient for preventing or treating an immune cell migration-related disease.

Another aspect of the present invention is to provide use of an antibody or functional fragments thereof that specifically bind to an epitope containing the sequence of SEQ ID NO: 117 in the N-terminus of lysyl tRNA synthetase (KRS) for preparing an agent for preventing or treating immune cell migration-related diseases.

Still another aspect of the present invention is to provide a method for treating immune cell migration-related diseases in a subject, the method comprising administering to the subject in need thereof an effective amount of a composition comprising an antibody biding specifically to an epitope containing the sequence of SEQ ID NO: 117 in the N-terminus of lysyl-tRNA synthetase (KRS) or a functional fragment thereof as an effective ingredient.

Definition

Unless defined otherwise, all technical and scientific terms used herein have the same meaning as commonly understood by one of ordinary skill in the art. The following references provide one of the skills having a general definition of several terms used in the present invention: Singleton et al., DICTIONARY OF MICROBIOLOGY AND MOLECULAR BIOLOTY (2d ed. 1994); THE CAMBRIDGE DICTIONARY OF SCIENCE AND TECHNOLOGY (Walker ed., 1988); And Hale & Marham, THE HARPER COLLINS DICTIONARY OF BIOLOGY. In addition, the following definitions are provided to assist readers in carrying out the present invention.

As used herein, the one letter (three letters) amino acid means the following amino acids in accordance with standard abbreviation provisions in the field of biochemistry: A(Ala); C(Cys); D(Asp); E(Glu); F(Phe); G(Gly); H(His); I(Ile); K(Lys); L(Leu); M(Met); N(Asn); O(Ply); P(Pro); Q(Gln); R(Arg); S(Ser); T(Thr); U(Sec); V(Val); W(Trp); Y(Tyr).

As used herein, "expression" refers to the production of proteins or nucleic acids in cells.

In the present invention, the term "host cell" refers to a prokaryotic or eukaryotic cell containing heterologous DNA introduced into the cell by any means (e.g., electroshock, calcium phosphatase precipitation, microinjection, transformation, viral infection, etc.).

As used herein, the term "polypeptide" is used interchangeably with "protein" or "peptide" and for example, refers to a polymer of amino acid residues as commonly found in proteins of nature.

As used herein, "nucleic acid", "DNA sequence" or "polynucleotide" refers to deoxyribonucleotides or ribonucleotides in the form of single- or double-strands. The term "polynucleotide" or "nucleic acid" in the present invention refers to deoxyribonucleotides or ribonucleotides in single- or double-stranded form. Unless otherwise constrained, it also includes known analogs of natural nucleotides that hybridize to nucleic acids in a manner similar to naturally occurring nucleotides.

In the present invention, the term "laminin" is a heterotrimeric molecule consisting of α, β, and γ chains, and is an extracellular matrix protein in which isoforms (subforms) having different subunit chain compositions exist. Specifically, laminin has about 15 types of isoforms in combination of heterotrimers of five kinds of α chains, four kinds of β chains, and three kinds of γ chains. The names of laminin are determined by combining the respective numbers of α chains (α1 to α5), β chains (β1 to β4) and γ chains (γ1 to γ3). For example, laminin by a combination of α1 chain, β1 chain, and γ1 chain is called LN111, laminin by a combination of α5 chain, β1 chain, and γ1 chain is called LN511, and laminin by a combination of α5 chain, β2 chain, and γ1 chain is called LN521. In the present invention, the term laminin may refer to a single component of one laminin subtype, or may mean a laminin mixture in which two or more laminin subtypes are mixed.

In one embodiment said "LN421 protein" refers to a polypeptide known as laminin subtype, α4β2γ1. If it is known in the art as the LN421, the specific origin and sequence (configuration of amino acid sequence) is not particularly limited, but preferably the α4 chain in the LN421 may include an amino acid sequence defined by SEQ ID NO: 120, β2 chain may include an amino acid sequence defined by number 122, and γ1 chain may include an amino acid sequence defined by SEQ ID NO: 124. More preferably in the LN421 α4 chain may be composed of an amino acid sequence defined by SEQ ID NO: 120, β2 chain may be composed of an amino acid sequence defined by SEQ ID NO: 122, and γ1 chain may be composed of an amino acid defined by SEQ ID NO: 124, but are not limited thereto.

In addition, the LN421 as used herein includes functional equivalents thereof. The functional equivalents thereof are described below for the functional equivalents of KRS, in which "substantially homogeneous physiological activity" refers to regulating the specific (selective) migration of immune cells such as monocytes, macrophages and neutrophils In the present invention, the "N-terminus or N-terminal region of lysyl-tRNA synthetase (KRS)" refers to a specific sequence that is exposed to the extracellular region or to the cell membrane surface when KRS produced in the cell moves and is located on the cell membrane (or plasma membrane). As a specific sequence, it may mean a part or full length sequence of 1 to 72 amino acid region of the N-terminus of KRS. In a more preferred example, humans include the sequence defined by SEQ ID NO: 148, mouse includes the sequence defined by SEQ ID NO: 149 and rats include the sequence defined by SEQ ID NO: 150. The N-terminal region of KRS has sequence similarity between species, in particular comprising the amino acid sequence defined by SEQ ID NO: 117.

"KRS protein" in the present invention refers to polypeptides known as lysyl-tRNA synthetases. KRS is an enzyme that mediates the aminoacylation reaction of lysine, an amino acid, and tRNA. In the present invention, the KRS is not particularly limited when the specific sequence is known in the art as a lysyl-tRNA synthetase, and may preferably include the amino acid sequence defined by SEQ ID NO: 117 (especially at the N-terminus). For instance, KRS of the present invention includes: a sequence derived from a human (*Homo sapiens*) and known as NCBI (Genbank) Accession No. NP_005539.1 or the like; a sequence derived from a mouse (*Mus musculus*) and known as NCBI (Genbank) Accession No. NP_444322.1 or the like; and a sequence derived from a rat (*Rattus norvegicus*) and known as NCBI (Genbank) Accession No. XP_006255692.1 or the like, and besides, reference may be made to the following sequence information, but is not limited thereto: XP_005004655.1 (guinea-pig: *Cavia porcellus*), XP_021503253.1 (gerbil, *Meriones unguiculatus*), XP_002711778.1 (rabbit, *Oryctolagus cuniculus*), XP_536777.2 (dog, *Canis lupus familiaris*), XP_003126904.2 (swine, *Sus scrofa*), XP_011755768.1 (monkey, *Macaca nemestrina*), XP_008984479.1 (marmoset, *Callithrix jacchus*), XP_019834275.1 (cow, *Bos indicus*), XP_511115.2 (chimpanzee, Pan troglodytes).

In the present invention, the entire KRS protein may comprise an amino acid sequence defined by SEQ ID NO: 118, and more preferably, may be a polypeptide consisting of the amino acid sequence defined by SEQ ID NO: 118 (Genbank Accession No. NP_005539.1). Also in the present invention, the KRS includes functional equivalents thereof.

The KRS protein in the present invention preferably means intracellular KRS or KRS inherent in the cell membrane, which is different from KRS secreted completely extracellularly.

The intracellular KRS has two subtypes (isoforms): cytoplasmic form (lysyl-tRNA synthetase, cytoplasmic) and mitochondrial form (lysyl-tRNA synthetase, mitochondrial). The KRS in the present invention is preferably a cytoplasmic form.

The functional equivalent refers to a polypeptide having at least 70% or more, preferably 80% or more, more preferably 90% or more sequence homology (or identity) with amino acid sequences consisting of a known KRS protein (as a preferred example, the amino acid sequence defined by SEQ ID NO: 118).

For example, it includes polypeptides having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence homology, and refers to a polypeptide that exhibits substantially the same physiological activity as the known KRS protein as the mother (as a preferred example, the amino acid sequence defined by SEQ ID NO: 118).

Here, the term "substantially homogeneous physiological activity" means regulating immune cell migration. Preferably, the functional equivalent of KRS in the present invention may be a result of the addition, substitution or deletion of a part of the amino acid sequence of SEQ ID NO: 118. Substitution of amino acids in the above is preferably a conservative substitution. Examples of conservative substitutions of amino acids present in nature are as follows; Aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gin, Asn) and sulfur-containing amino acids (Cys, Met). Functional equivalent of the KRS also includes variants in which some of the amino acids are deleted on the amino acid sequence of the KRS protein. Deletion or substitution of the amino acid is preferably located in a region that is not directly related to the physiological activity of KRS.

In addition, the deletion of the amino acid is preferably located at a region not directly involved in the physiological activity of KRS. Also, variants in which some amino acids are added at both ends of the amino acid sequence or in the sequence of the KRS are included. Also, the scope of functional equivalents of the present invention also includes polypeptide derivatives in which some chemical structures of the polypeptide are modified while maintaining the basic skeleton of KRS and its physiological activity. For example, this includes structural modifications to alter the stability, storability, volatility or solubility of the protein.

The homology and identity of sequences herein are defined as the percentage of identical matching residues (amino acid residues or bases) in the candidate sequence to the original sequence after aligning the original (as examples, SEQ ID NO: 118 for preferred amino acid sequences or SEQ ID NO: 119 for preferred nucleic acid sequences) sequences and candidate sequences and introducing gaps. If necessary, conservative substitutions as part of sequence homogeneity are not considered in order to obtain the maximum percentage of sequence homogeneity. Also, in the case of determining homogeneity or homology of protein sequence, the N-terminus, C-terminus or internal extension, deletion or insertion of the KRS amino acid sequence is not to be interpreted as a sequence affecting homogeneity or homology of sequence. In addition, the homogeneity of sequence can be determined by common standard methods used to compare similar portions of the amino acid sequences of two proteins or polypeptides. Computer programs such as BLAST or FASTA align the two polypeptides so that their respective amino acids are optimally matched (along the full length of one or two sequences or along the predicted portion of one or two sequences). The program provides a default opening penalty and a default gap penalty and provides a scoring matrix such as PAM250 (Standard scoring matrix; Dayhoff et al., in Atlas of Protein Sequence and Structure, vol 5, supp 3, 1978) that can be used in conjunction with a computer program. For example, percentage homogeneity can be calculated as follows. The total number of identical matches is multiplied by 100 and then divided by the sum of the length of the longer sequence in the matched span and the number of gaps introduced into the longer sequence to align the two sequences.

As used herein, the term 'transfer of KRS proteins to the cell membrane' refers to that the endogenous protein (proteins made inside cells, such as those present in the cytoplasm) of a cell moves to the cell membrane in the intracellular direction of the same cell, unless otherwise indicated. In this case, KRS may be completely present only in the intracellular direction, or may be partially exposed (preferably, N-terminal part of KRS) to the extracellular cell because it is interposed between cell membranes. However, in either case, it may be desirable to exclude the resulting protein from completely separating out of the cells. That is, in the present invention, the movement to the cell membrane is distinguished from the extracellular interaction of proteins completely separated and secreted in one cell with other cells or tissues, unless otherwise indicated.

The term "cell membrane site" in the present invention is meant to include both the cell membrane itself and the neighborhood (near) that is very close to the cell membrane and is substantially interacting with the cell membrane.

In the present invention, 'antibody' is also called immunoglobulin (Ig), and is a generic term for proteins that selectively bind to antigens and are involved in biological immunity. All antibodies found in nature generally consist of two pairs of light chains (LCs) and heavy chains (HCs), which are polypeptides of several domains, or are based on two pairs of HC/LC. There are five types of heavy chains constituting the antibodies of mammals defined by the Greek letters a, δ, ε, γ, and α, and different types of antibodies, such as IgA, IgD, IgE, IgG and IgM, respectively, will be constructed depending on the type of heavy chain. There are two kinds of light chains constituting the antibody of mammals defined by λ and κ.

The heavy and light chains of an antibody are structurally divided into variable and constant regions according to amino acid sequence variability. The constant region of the heavy chain is composed of three or four heavy chain constant regions, such as CH1, CH2 and CH3 (IgA, IgD and IgG antibodies) and CH4 (IgE and IgM antibodies), depending on the type of antibody. The light chain is composed of CL, one constant region. The heavy chain variable region and light chain variable region consist of one domain of the heavy chain variable region (VH) or light chain variable region (VL), respectively. The light and heavy chains are arranged side by side with each variable and constant region connected by one covalent disulfide bond, and the heavy chains of the two molecules linked with the light chain are connected via two covalent disulfide bonds to form the whole antibody to form the whole antibody. The whole antibody specifically binds to the antigen through the variable regions of the heavy and light chains, and since the whole antibody consists of two heavy and light chain pairs (HC/LC), the whole antibody of one molecule has bivalent monospecificity that binds to the same two antigens through two variable regions.

The variable region including the site where an antibody binds to an antigen is subdivided into a framework region (FR) having low sequence variability and a complementarity determining region (CDR) which is a hypervariable region with high sequence variability. VH and VL each have three CDRs and four FRs arranged in the order of FR1-CDR1-FR2-CDR2-FR3-CDR3-FR4 in the direction from N-terminus to C-terminus. The CDRs with the highest sequence variability within the variable region of the antibody directly bind to the antigen, which is most important for the antigen specificity of the antibody.

As used herein, 'treatment' refers to inhibiting the occurrence or recurrence of a disease, alleviating symptoms, reducing the direct or indirect pathological consequences of the disease, decreasing the rate of disease progression, improving the disease state, improving, alleviating or improving the prognosis. As used herein, the term "prevention" refers to any action that inhibits the onset of a disease or delays its progression.

Hereinafter, the present invention will be described in detail.

The inventors have identified for the first time that it is important pathological phenomenon that KRS raises its specific level in the cell membrane relative to the cytoplasm of immune cells in relation to immune cell migration and invasive state, and particularly, have identified the specific regulatory function of KRS in immune cell migration with a special association with LN421 (laminin subtype α4β2γ1). Therefore, the specific antibody binding to a specific epitope (SEQ ID NO: 117 region) of the KRS N-terminus provided by the present invention significantly reduces the KRS level of the cell membrane, and indeed, it has been shown to have significant therapeutic effects in diseases such as pulmonary hypertension, which are deeply related to the pathology of migration and invasion of immune cells.

Accordingly, the present invention thus provides the use of an antibody or functional fragment thereof that specifically binds to an epitope containing the sequence of SEQ ID NO: 117 in the N-terminus of lysyl tRNA synthetase (KRS) for manufacturing an agent for preventing or treating immune cell migration-related diseases.

The present invention is to provide to a pharmaceutical composition comprising an antibody biding specifically to an epitope containing the sequence of SEQ ID NO: 117 at the N-terminus of lysyl-tRNA synthetase (KRS) or a functional fragment thereof as an effective ingredient for preventing or treating an immune cell migration-related disease.

The present invention is also to provide to a pharmaceutical composition consisting of an antibody biding specifically to an epitope containing the sequence of SEQ ID NO: 117 at the N-terminus of lysyl-tRNA synthetase (KRS) or a functional fragment thereof for preventing or treating an immune cell migration-related disease.

The present invention is to provide to a pharmaceutical composition consisting essentially of an antibody biding specifically to an epitope containing the sequence of SEQ ID NO: 117 at the N-terminal domain of lysyl-tRNA synthetase (KRS) or a functional fragment thereof for preventing or treating an immune cell migration-related disease.

In the present invention, the term 'comprising' is used in the same way as 'containing' or 'characteristic', and does not exclude additional component elements or method steps not mentioned in the composition or method. The term 'consisting of' is used in the same manner as 'composed of' and means to exclude additional elements, steps, or components, which are not separately described. The term "consisting essentially of" means in the scope of the composition or method, including the component elements or steps described, as well as the component elements or steps that do not substantially affect their basic properties.

In the present invention, the term 'epitope' refers to a specific portion of an antibody that specifically determines the specificity of an antigen-antibody reaction in any object to which an antibody specifically binds. In the present invention, the epitope is derived from the KRS N-terminal sequence (regardless of species), and the specific sequence thereof is not particularly limited as long as it is a contiguous region including (essentially) the amino acid sequence of SEQ ID NO. 117. In general, the amino acid sequence of SEQ ID NO: 117 may consist of 13, to 52, more preferably 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid sequences.

As a preferred example, in the present invention, the epitope derived from human KRS N-terminus and may consist of SEQ ID NO: 133, SEQ ID NO: 134, SEQ ID NO: 135, SEQ ID NO: 136 or SEQ ID NO: 148. The epitope derived from mouse KRS N-terminus may consist of SEQ ID NO: 138, SEQ ID NO: 139, SEQ ID NO: 140, SEQ ID NO: 141 or SEQ ID NO: 149. The epitope derived from rat KRS N-terminus may consist of SEQ ID NO: 143, SEQ ID NO: 144, SEQ ID NO: 145, SEQ ID NO: 146 or SEQ ID NO: 150.

Antibodies or functional fragments thereof of the present invention are characterized by reducing KRS levels of cell membranes through specific binding in the epitope. It was first identified by the present inventors that immune cell migration and invasion can be inhibited when the level of KRS is specifically reduced in the cell membrane, and thus a therapeutic effect of related diseases is possible. The present inventors have confirmed that the antibody specifically binding to the epitope (N3 antibody and improved antibodies therefrom) effectively inhibits and decreases (through endocytosis) KRS levels increased in the immune cell membrane accompanied by immune cell migration and invasion, and inhibits immune cell migration. Indeed, they have confirmed that this antibody has a significant therapeutic effect when applied in animal models with the pathological diseases (e.g., pulmonary hypertension, etc.) of excessive immune cell migration and invasion.

The specific sequence is not particularly limited as long as the antibody or functional fragment thereof specifically binding to the epitope comprising the sequence of SEQ ID NO: 117 in the N-terminus of the lysyl-tRNA synthetase (KRS) exhibits substantially homogeneous physiological activity.

However, for example, it may be characterized by comprising a heavy chain variable region comprising a heavy chain complementarity determining region 1 (CDR1) containing an amino acid sequence defined by SEQ ID NO: 1, a heavy chain complementarity determining region 2 (CDR2) containing an amino acid sequence defined by SEQ ID NO: 3, and a heavy chain complementarity determining region 3 (CDR3) containing an amino acid sequence defined by SEQ ID NO: 5; and a light chain variable region comprising a light chain complementarity determining region 1 (CDR1) containing an amino acid sequence defined by SEQ ID NO: 7, a light chain complementarity determining region 2 (CDR2) containing an amino acid sequence defined by SEQ ID NO: 9, and a light chain complementarity determining region 3 (CDR3) containing an amino acid sequence defined by SEQ ID NO: 11. Antibodies having these sequences are designated as N3 antibodies in the present invention.

More preferably, the antibody or functional fragment thereof according to the present invention may comprise a heavy chain variable region (VH) containing an amino acid sequence defined by SEQ ID NO: 31; and a light chain variable region (VL) containing an amino acid sequence defined by SEQ ID NO: 33. Antibodies having these sequences are designated as N3 antibodies in the present invention.

The antibody according to the present invention is not limited thereto, but may be one selected from the group consisting of IgG, IgA, IgM, IgE, and IgD, and may be preferably an IgG antibody. Most preferably, the antibody of the present invention may consist of a heavy chain comprising an amino acid sequence defined by SEQ ID NO: 89 and a light chain comprising an amino acid sequence defined by SEQ ID NO: 91 (named N3 antibody as used herein).

In addition, the present inventors have prepared improved antibodies (N3-1, N3-3, N3-4, N3-5, N3-6, N3-7, N3-8, N3-9, N3-8-1, N3-8-2, N3-8-3, N3-8-4, N3-8-5, N3-8-6, N3-8-7) having high usefulness as therapeutic antibodies based on the variable region sequence of the N3 antibody (heavy chain variable region (VH) comprising an amino acid sequence defined by SEQ ID NO: 31; and light chain variable region (VL) sequence comprising an amino acid sequence defined by SEQ ID NO: 33). N3 antibodies and these improved antibodies have commonalities and features on the CDR sequences of (a) and (b) below.

Therefore, the present invention provides, as an improved antibody, an antibody or a functional fragment thereof comprising
(a) a heavy chain variable region (VH) comprising
(a-1) heavy chain complementarity determining region 1 (CDR1) containing the amino acid sequence SYDMS (SEQ ID NO: 1);
(a-2) heavy chain complementarity determining region 2 (CDR2) containing the amino acid sequence $X_1X_2X_3X_4X_5GX_6X_7YYADSVKG$ (SEQ ID NO: 153), and wherein $X_1$ is A or V, $X_2$ is S, D or G, $X_3$ is Y, P, S or A and $X_4$ is D, Q, L or Y, $X_5$ is N, M, S, or G, $X_6$ is N, R or P, $X_7$ is T, V, I or S; and
(a-3) heavy chain complementarity determining region 3 (CDR3) containing an amino acid sequence $X_8$ALDFDY (SEQ ID NO: 154), and wherein $X_8$ is M or L, and
(b) a light chain variable region (VL) comprising
(b-1) light chain complementarity determining region 1 (CDR1) containing the amino acid sequence TGSSSNIGSNYVT (SEQ ID NO: 7);
(b-2) light chain complementarity determining region 2 (CDR2) containing amino acid sequence $X_9NX_{10}X_{11}RPS$ (SEQ ID NO: 155), wherein $X_9$ is D, S or R, $X_{10}$ is S or N, and $X_{11}$ is N or Q; and
(b-3) a light chain complementarity determining region 3 (CDR3) containing an amino acid sequence $X_{12}$SFSDELGAYV (SEQ ID NO: 156), and wherein $X_{12}$ is A or S.

Specifically, the antibody and functional fragment thereof provided in the present invention comprises (a) the heavy chain variable region (VH), wherein VH comprises a heavy chain complementarity determining region 1 (CDR1) containing the amino acid sequence defined by SEQ ID NO: 1; and heavy chain complementarity determining region 2 (CDR2) containing at least one amino acid sequence selected from the group consisting of SEQ ID NO: 3, SEQ ID NO: 17, SEQ ID NO: 19, SEQ ID NO: 21, SEQ ID NO: 23, and SEQ ID NO: 151, and heavy chain complementarity determining region 3 (CDR3) containing at least one amino acid sequence selected from the group consisting of SEQ ID NO: 5 and SEQ ID NO: 25.

(b) the light chain variable region (VL), wherein VL comprises a light chain complementarity determining region 1 (CDR1) containing the amino acid sequence defined by SEQ ID NO: 7; a light chain complementarity determining regions 2 (CDR2) containing at least one amino acid sequence selected from the group consisting of SEQ ID NO: 9, SEQ ID NO: 27 and SEQ ID NO: 29; a light chain complementarity determining region 3 (CDR3) containing at least one amino acid sequence selected from the group consisting of SEQ ID NO: 13 and SEQ ID NO: 15.

Antibodies consisted of the CDR sequences (N3 antibody and N3 derivatives) have an excellent ability to specifically bind to the N-terminal region of KRS exposed to the outer membrane, and significantly inhibit and reduce immune cell migration/invasion, showing an excellent therapeutic effect on an immune cell migration-related disease. It is demonstrated well in the examples of the specification in the present invention.

The antibody or fragment thereof (functional fragment) that specifically binds to the N-terminal region of KRS exposed to the extracellular membrane according to the present invention, but is not limited thereto, preferably is an antibody comprising the CDRs of the heavy chain variable region and the light chain variable region as follows, and the following i, ii, iii, iv, v, vi, vii, viii, ix, x, xi, xii and xiii represent CDR combinations of N3-1, N3-3, N3-4, N3-5, N3-6, N3-7, N3-8, N3-9, N3-8-1, N3-8-2, N3-8-3, N3-8-4, N3-8-5 and N3-8-6, and N3-8-7 antibody of the example, respectively:

The antibodies or fragment thereof comprises
i) a heavy chain variable region (VH) comprising a heavy chain complementarity determining region 1 (CDR1) comprising an amino acid sequence defined by SEQ ID NO: 1, a heavy chain complementarity determining region 2 (CDR2) comprising an amino acid sequence defined by SEQ ID NO: 3, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 13;

ii) a heavy chain variable region (VH) comprising a heavy chain complementarity determining region 1 (CDR1) comprising an amino acid sequence defined by SEQ ID NO: 1, a heavy chain complementarity determining region 2 (CDR2) comprising an amino acid sequence defined by SEQ ID NO: 3, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 15;

iii) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 151, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 13;

iv) a heavy chain variable region (VH) of an antibody comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 151, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 15;

v) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 17, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 15;

vi) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 19, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 15;

vii) a heavy chain variable region (VH) of comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 21, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 15;

viii) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 23, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 15;

ix) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 21, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 27, and a light chain complementarity determining region 3 (CDR3) comprising an amino acid sequence defined by SEQ ID NO: 15;

x) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 21, and a heavy chain complementarity determining region 3 (CDR3) comprising an amino acid sequence defined by SEQ ID NO: 5; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 29, and a light chain complementarity determining region 3 (CDR3) comprising an amino acid sequence defined by SEQ ID NO: 15;

xi) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 21, and a heavy chain complementarity determining region 3 (CDR3) comprising the amino acid sequence defined by SEQ ID NO: 25; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 9, and a light chain complementarity determining region 3 (CDR3) comprising an amino acid sequence defined by SEQ ID NO: 15;

xii) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 21, and a heavy chain complementarity determining region 3 (CDR3) comprising the amino acid sequence defined by SEQ ID NO: 25; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 27, and a light chain complementarity determining region 3 (CDR3) comprising an amino acid sequence defined by SEQ ID NO: 15; And xiii) a heavy chain variable region (VH) comprising a heavy chain complementarity determining region 1 (CDR1) comprising the amino acid sequence defined by SEQ ID NO: 1, a heavy chain complementarity determining region 2 (CDR2) comprising the amino acid sequence defined by SEQ ID NO: 21, and a heavy chain complementarity determining region 3 (CDR3) comprising the amino acid sequence defined by SEQ ID NO: 25; and a light chain variable region (VL) comprising a light chain complementarity determining region 1 (CDR1) comprising the amino acid sequence defined by SEQ ID NO: 7, a light chain complementarity determining region 2 (CDR2) comprising the amino acid sequence defined by SEQ ID NO: 29, and a light chain complementarity determining region 3 (CDR3) comprising an amino acid sequence defined by SEQ ID NO: 15.

Most preferably, the antibody or fragment thereof according to the present invention comprises a heavy chain variable region (VH) and a light chain variable region (VL) as follows: In the antibody or fragment thereof, the heavy chain variable region includes at least one amino acid sequence selected from the group consisting of SEQ ID NO: 31, SEQ ID NO: 35, SEQ ID NO: 37, SEQ ID NO: 39, SEQ ID NO: 41, SEQ ID NO: 43, SEQ ID NO: 45, and SEQ ID NO: 47, and the light chain variable region includes at least one amino acid sequence selected from the group consisting of SEQ ID NO: 49, SEQ ID NO: 51, SEQ ID NO: 53, and SEQ ID NO: 55.

Preferably, it is an antibody comprising a heavy chain variable region comprising an amino acid sequence defined by SEQ ID NO: 31 and the light chain variable region comprising an amino acid sequence defined by SEQ ID NO: 49; a heavy chain variable region comprising an amino acid sequence defined by SEQ ID NO: 31 and a light chain variable region comprising an amino acid sequence defined by SEQ ID NO: 51; a heavy chain variable region comprising an amino acid sequence defined by SEQ ID NO: 35 and a light chain variable region comprising an amino acid sequence defined by SEQ ID NO: 49; a heavy chain variable region comprising an amino acid sequence defined by SEQ ID NO: 35 and a light chain variable region comprising an amino acid sequence defined by SEQ ID NO: 51; a heavy chain variable region comprising an amino acid sequence defined by SEQ ID NO: 37 and a light chain variable region comprising an amino acid sequence defined by SEQ ID NO: 51; a heavy chain variable region comprising an amino acid sequence defined by SEQ ID NO: 39 and a light chain variable region comprising an amino acid sequence defined by SEQ ID NO: 51; a heavy chain variable region comprising an amino acid sequence defined by SEQ ID NO: 41 and a light chain variable region comprising an amino acid sequence defined by SEQ ID NO: 51; a heavy chain variable region comprising an amino acid sequence defined by SEQ ID NO: 43 and a light chain variable region comprising an amino acid sequence defined by SEQ ID NO: 51; a heavy chain variable region comprising an amino acid sequence defined by SEQ ID NO: 45 and a light chain variable region comprising an amino acid sequence defined by SEQ ID NO: 51; a heavy chain variable region comprising an amino acid sequence defined by SEQ ID NO: 45 and a light chain variable region comprising an amino acid sequence defined by SEQ ID NO: 53; a heavy chain variable region comprising an amino acid sequence defined by SEQ ID NO: 45 and a light chain variable region comprising an amino acid sequence defined by SEQ ID NO: 55; a heavy chain variable region comprising an amino acid sequence defined by SEQ ID NO: 47 and a light chain variable region comprising an amino acid sequence defined by SEQ ID NO: 51; a heavy chain variable region comprising an amino acid sequence defined by SEQ ID NO: 47 and a light chain variable region comprising an amino acid sequence defined by SEQ ID NO: 53; a heavy chain variable region comprising an amino acid sequence defined by SEQ ID NO: 47 and a light chain variable region comprising an amino acid sequence defined by SEQ ID NO: 55.

The IgG type antibody including the heavy chain variable region (VH) and light chain variable region (VL) may specifically be an antibody characterized in that consisting of a heavy chain (HC) comprising at least one amino acid sequence selected from the group consisting of SEQ ID NO: 89, SEQ ID NO: 93, SEQ ID NO: 95, SEQ ID NO: 97, SEQ ID NO: 99, SEQ ID NO: 101, SEQ ID NO: 103, and SEQ ID NO: 105, and a light chain (LC) comprising at least one amino acid sequence selected from the group consisting of SEQ ID NO: 107, SEQ ID NO: 109, SEQ ID NO: 111, SEQ ID NO: 113 and SEQ ID NO: 115. It is an antibody including, most preferably, a heavy chain comprising an amino acid sequence defined by SEQ ID NO: 89 and a light chain comprising an amino acid sequence defined by SEQ ID NO: 107; a heavy chain comprising an amino acid sequence defined by SEQ ID NO: 89 and a light chain comprising an amino acid sequence defined by SEQ ID NO: 109; a heavy chain comprising an amino acid sequence defined by SEQ ID NO: 93 and a light chain comprising an amino acid sequence defined by SEQ ID NO: 107; a heavy chain comprising an amino acid sequence defined by SEQ ID NO: 93 and a light chain comprising an amino acid sequence defined by SEQ ID NO: 109; a heavy chain comprising an amino acid sequence defined by SEQ ID NO: 95 and a light chain comprising an amino acid sequence defined by SEQ ID NO: 109; a heavy chain comprising an amino acid sequence defined by SEQ ID NO: 97 and a light chain comprising an amino acid sequence defined by SEQ ID NO: 109; a heavy chain comprising an amino acid sequence defined by SEQ ID NO: 99 and a light chain comprising an amino acid sequence defined by SEQ ID NO: 109; a heavy chain comprising an amino acid sequence defined by SEQ ID NO: 101 and a light chain comprising an amino acid sequence defined by SEQ ID NO: 109; a heavy chain comprising an amino acid sequence defined by SEQ ID NO: 103 and a light chain comprising an amino acid sequence defined by SEQ ID NO: 111; a heavy chain comprising an amino acid sequence defined by SEQ ID NO: 103 and a light chain comprising an amino acid sequence defined by SEQ ID NO: 113; a heavy chain comprising an amino acid sequence defined by SEQ ID NO: 103 and a light chain comprising an amino acid sequence defined by SEQ ID NO: 115; a heavy chain comprising an amino acid sequence defined by SEQ ID NO: 105 and a light chain comprising an amino acid sequence defined by SEQ ID NO: 111; a heavy chain comprising an amino acid sequence defined by SEQ ID NO: 105 and a light chain comprising an amino acid sequence defined by SEQ ID NO: 113; A heavy chain comprising an amino acid sequence defined by SEQ ID NO: 105 and a light chain comprising an amino acid sequence defined by SEQ ID NO: 115; a heavy chain comprising the amino acid sequence defined by SEQ ID NO: 99 and a light chain comprising the amino acid sequence defined by SEQ ID NO: 111.

The antibody of the present invention refers to include a monoclonal (monoclonal) antibody, a polyclonal antibody and a recombinant antibody. For the purposes of the present invention, it may be desirable for the monoclonal antibody to be a population of antibodies in which the amino acid sequences of the heavy and light chains of the antibody are substantially identical. Monoclonal antibodies can be prepared using hybridoma methods (hybridoma method) (Kohler and Milstein (1976) European Journal of Immunology 6:511-519) or phage antibody library techniques (Clackson et al, Nature, 352:624-628, 1991; Marks et al, J. Mol. Biol., 222:58, 1-597, 1991) that are well known in the art.

Antibodies of the invention may be derived from mammals, including humans, or any animal, and including birds, and preferably may be a chimeric antibody including a portion of an antibody derived from a human, or a portion of an antibody derived from an animal of a different species from a human. That is, the present invention includes all chimeric antibodies, humanized antibodies, and human antibodies, and preferably may be human antibodies.

The antibodies of the invention also include functional fragments of antibody molecules, as well as complete forms having, for example, two full length light chains and two full length heavy chains as IgGs. The functional fragment refers to a fragment of an antibody that retains the antigen-specific binding ability of the whole antibody, and preferably has a binding affinity with the KRS N-terminus of the parent antibody at least 50%, 60%. 70%, 80%, 90%, 95% or 90%, 95%, 100%, or more. Specifically, it may be in the form of Fab, F(ab)2, Fab', F(ab')2, Fv, diabody, and scFv. Fab (fragment antigen-binding) is an antigen-binding fragment of the antibody, and is composed of one variable domain and a constant domain of each of the heavy and light chains. F(ab')2 is a fragment produced by hydrolyzing an antibody with pepsin, and two Fabs are connected by disulfide bonds at the heavy chain hinges. F(ab') is a monomer antibody fragment in which a heavy chain hinge is added to a Fab separated by reducing the disulfide bond of the F(ab')2 fragment. A variable fragment (Fv) is an antibody fragment composed only of the variable regions of each of the heavy and light chains. A single chain variable fragment (scFv) is a recombinant antibody fragment in which a heavy chain variable region (VH) and a light chain variable region (VL) are linked by a flexible peptide linker. Diabody that VH and VL of scFv are linked by a very short linker and cannot bind to each other refers to the form of a fragment that binds to VL and VH of the other scFv of the same form, respectively, to form a dimer.

The functional fragment of the antibody for the purposes of the present invention is not limited in structure or form when it retains binding specificity for the N-terminal region of human KRS exposed to the outside of the cell and exhibit the same physiological activity, but may preferably be scFv. The scFv according to the present invention is not particularly limited when it has substantially the same physiological activity as the above-described antibody, but preferably has a specific CDR configuration to the N-terminal region of KRS or a VH and VL configuration. VH and VL may be connected via a linker. The linker is not particularly limited when it is known in the art as a linker applied to scFv. Preferably, the peptide may include an amino acid sequence defined by SEQ ID NO: 57. Accordingly, N3 scFv in the present invention may specifically include an amino acid sequence defined by SEQ ID NO: 59, and more preferably, may be composed of an amino acid sequence defined by SEQ ID NO: 59. In addition, according to the VH and VL sequence configuration of the N3 improved antibody, the present invention can provide the following scFVs: ScFV comprising an amino acid sequence selected from the group consisting of SEQ ID NO: 61, SEQ ID NO: 63, SEQ ID NO: 65, SEQ ID NO: 67, SEQ ID NO: 69, SEQ ID NO: 71, SEQ ID 73, SEQ ID 75, SEQ ID 77, SEQ ID 79, SEQ ID 81, SEQ ID 83, SEQ ID 85 and SEQ ID 87.

The antibody or fragment thereof of the invention may comprise conservative amino acid substitutions (called conservative variants of the antibody), deletions or additions that do not substantially alter their biological activity. In the present invention, "substantially homogeneous physiological activity" means binding to the N-terminal region of KRS and inhibiting immune cell migration and invasion.

In the present invention, the polynucleotide sequence for providing the antibody or fragment thereof is not particularly limited in its specific nucleotide sequence configuration as long as the above-described sequence configuration is satisfied. The polynucleotide provided in the present invention is not particularly limited in sequence, as long as it encodes the antibody or fragment thereof of the present invention. The polynucleotide encoding the above-described CDR sequences in the antibody according to the present invention is not particularly limited in sequence, but may preferably include a base sequence defined by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, or SEQ ID NO: 152. The proteins encoded by each sequence are listed in the Sequence Listing.

In addition, the polynucleotide encoding the above-mentioned VH and VL in the antibody according to the present invention, but is not particularly limited in sequence, may preferably include a nucleotide sequence defined by SEQ ID NO: 32 (VH), SEQ ID NO: 36 (VH), SEQ ID NO: 38 (VH), sequence SEQ ID NO: 40 (VH), SEQ ID NO: 42 (VH), SEQ ID NO: 44 (VH), SEQ ID NO: 46 (VH), SEQ ID NO: 48 (VH), SEQ ID NO: 34 (VL), SEQ ID NO: 50 (VL), SEQ ID NO: 52 (VL), SEQ ID NO: 54 (VL) or SEQ ID NO: 56 (VL).

In one embodiment, the polynucleotide encoding the antibody of the IgG form comprising the heavy chain variable region (VH) and light chain variable region (VL) preferably may include the following base sequence: The polynucleotide encoding the heavy chain (HC) may be to include at least one nucleotide sequence selected from the group consisting of SEQ ID NO: 90, SEQ ID NO: 94, SEQ ID NO: 96, SEQ ID NO: 98, SEQ ID NO: 100, SEQ ID NO: 102, SEQ ID NO: 104, and SEQ ID NO: 106. The polynucleotide encoding the light chain (LC) may include one or more nucleotide sequences selected from the group consisting of SEQ ID NO: 92, SEQ ID NO: 108, SEQ ID NO: 110, SEQ ID NO: 112, SEQ ID NO: 114, and SEQ ID NO: 116.

In addition, the polynucleotide encoding the fragment of the antibody may preferably include any one base sequence selected from the group consisting of SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86 and SEQ ID NO: 88 encoding the scFv according to the present invention.

Polynucleotides encoding the antibodies or fragments thereof in the present invention can be obtained by methods well known in the art. For example, based on DNA sequences or corresponding amino acid sequences encoding part or all of the heavy and light chains of the antibody, the oligonucleotides well known in the art can be synthesized using a synthetic technique such as polymerase chain reaction (PCR).

The polynucleotide is introduced into a suitable host cell through a vector, and then expresses the antibody protein of the present invention. The host cell is transformed into a recombinant expression vector operably linked to the polynucleotide encoding the antibody or fragment thereof. After culturing the transformed host cell to produce a polypeptide of the heavy chain, light chain or antibody fragment of the antibody from the recombinant expression vector introduced into the host cell, specific methods for isolating and obtaining antibodies therefrom are well known in the art.

First, a nucleic acid encoding the antibody is constructed according to a conventional method. The nucleic acid can be generated by PCR amplification using appropriate primers. Alternatively, DNA sequences may be synthesized by standard methods known in the art, such as using automated DNA synthesizers (such as those sold by Biosearch or Applied Biosystems). The constructed nucleic acid is inserted into a vector comprising one or more expression control sequences (e.g., promoters, enhancers, etc.) operably linked to regulate expression of the nucleic acid and the host cell is transformed with the recombinant expression vector formed therefrom.

The term 'transformation' refers to the modification of the genotype of a host cell by the introduction of an exogenous polynucleotide and refers to the introduction of the exogenous polynucleotide into the host cell, regardless of the method used for the transformation. Exogenous polynucleotides introduced into a host cell may remain integrated or unintegrated into the genome of the host cell, and the invention includes both cases.

Recombinant expression vectors expressing antibodies or fragments thereof that specifically bind to the N-terminal region of KRS according to the present invention may be introduced and transformed into cells to produce antibodies or fragments thereof by methods known in the art, for example, transient transfection, microinjection, transduction, cell fusion, calcium phosphate precipitation, liposome-mediated transfection, DEAE dextran-mediated transfection, Polybrene-mediated transfection, electroporation, gene guns and known methods for introducing nucleic acids into cells, but the methods are not limited to. A person skilled in the art can select and perform an appropriate transformation method according to the selected host cell and the recombinant expression vector.

Recombinant expression vectors comprising the heavy and light chain sequences may be co-transformed into the same host cell so that the heavy and light chains are expressed in a single cell, and recombinant expression vectors comprising the nucleotide sequences of the heavy and light chains may be transformed into separate host cells, respectively, so that the heavy and light chains are expressed separately. The medium composition, culture conditions and culture time for culturing the host cell can be appropriately selected according to methods commonly used in the art. The antibody molecule produced in the host cell may be accumulated in the cytoplasm of the cell, secreted outside the cell or into culture medium by an appropriate signal sequence, or targeted to periplasm. It is also preferred that the antibodies according to the invention have protein refolding and functional conformation using methods known in the art to maintain binding specificity for the KRS N-terminus. In addition, when producing an IgG form of the antibody, the heavy and light chains may be expressed in separate cells, and the heavy and light chains may be contacted to form a complete antibody in a separate step. The heavy and light chains may be expressed in the same cells, and may also be made to form a complete antibody inside the cell.

Those skilled in the art can appropriately select and control the obtaining method, considering the characteristics of the antibody or fragment polypeptide produced in the host cell, the characteristics of the host cell, the expression method or whether the polypeptide is targeted. For example, the antibody secreted in the culture medium or fragments thereof can recover the antibody by obtaining a medium in which the host cells are cultured, and centrifuged to remove impurities. If necessary, the cells may be lysed in a range that does not affect the functional structure of the antibody or fragment thereof in order to release and recover the antibody present in a specific organelle or cytoplasm in the cell. In addition, the obtained antibody may further include a process of further removing impurities and concentrating through filtration and dialysis by chromatography and filters.

The polypeptide of the manufacturing (production) method of the present invention may be the antibody or a fragment thereof of the present invention, and a polypeptide to which another amino acid sequence other than the antibody or fragment thereof of the present invention is further bound. In this case, the amino acid sequence may be removed from the antibody or fragment thereof of the present invention using methods well known to those skilled in the art.

For genetic engineering methods for polypeptide synthesis of the present invention, references may be made to the following documents: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998) and Third (2000) Editions; Gene Expression Technology, Method in Enzymology, Genetics and Molecular Biology, Method in Enzymology, Guthrie & Fink (eds.), Academic Press, San Diego, Calif, 1991; —Hitzeman et al., J. Biol. Chem., 255:12073-12080, 1990.

In the present invention, the term "immune cells" refers to cells involved in the immune response in the body. If it is known in the art as an immune cell, and especially if it is known as an immune cell present in the human body, the type is not particularly limited, but monocytes, macrophages, neutrophils, eosinophils, basophils, dendritic cells, natural killer cells, megakaryocytes, T cells and B cells are included. It may preferably mean monocytes, macrophages or neutrophils. Immune cells express KRS.

In the present invention, the term immune cell migration-related disease, for example, may be selected from the group consisting of cardiovascular disease, fibrotic disease, inflammatory disease and Alport syndrome, but if excessive immune cell migration (and/or invasion) is known in the art as the major pathogenesis, then the specific type of disease is not particularly limited.

The cardiovascular disease may be, for example, selected from the group consisting of hypertension (including inflammatory complications caused by hypertension), pulmonary arterial hypertension, atherosclerosis, angina pectoris, myocardial infarction, ischemic cerebrovascular disease, arteriosclerosis, and mesenteric sclerosis, but the kind of the specific disease is not particularly limited.

The fibrotic disease may be selected from the group consisting of, for example, scleroderma, rheumatoid arthritis, Crohn's disease, ulcerative colitis, myelofibrosis, pulmonary fibrosis, hepathic fibrosis, liver cirrhosis, kidney fibrosis, glomerulosclerosis, myofibrosis, myofibrosis cordis, interstitial fibrosis, pancreatic fibrosis, splenic fibrosis, mediastinal fibrosis, vascular fibrosis, skin fibrosis, eye fibrosis, macular degeneration, joint fibrosis, thyroid fibrosis, endomyocardial fibrosis, peritoneal fibrosis, retroperitoneal fibrosis, progressive mass fibrosis, nephrogenic systemic fibrosis, systemic lupus erythematosus, hereditary fibrosis, infectious fibrosis, irritant fibrosis, fibrosis due to chronic autoimmunity, fibrosis due to antigen incompatibility during organ transplantation, fibrotic complications during surgery, fibrosis due to hyperlipidemia, fibrosis due to obesity, diabetic fibrosis, fibrosis due to hypertension, and occlusion due to fibrosis at the time of stent insertion, but the specific disease type is not particularly limited.

In the present invention, the inflammatory disease may preferably be selected from the group consisting of an autoimmune disease, inflammatory bowel disease, dermatitis (for example, atopic dermatitis, eczema, psoriasis, etc.), diabetic eye disease (diabetic retinopathy, etc.), peritonitis, osteomyelitis, cellulites, meningitis, encephalitis, pancreatitis, trauma-induced shock, bronchial asthma, rhinitis, sinusitis, tympanitis, pneumonia, gastritis, enteritis, cystic fibrosis, apoplexy (apoplexy, stroke, etc.), bronchitis, bronchiolitis, hepatitis (cirrhosis, steatohepatitis, non-alcoholic steatohepatitis, etc.), nephritis (diabetic renal failure, etc.), proteinuria, arthritis (such as psoriatic arthritis, osteoarthritis), neuritis (diabetic neuropathy, multiple sclerosis, etc.), gout, spondylitis, Reiter's syndrome, polyarteritis nodosa, vasculitis, amyotrophic lateral sclerosis, Wegener's granulomatosis, hypercytokinemia, Polymyalgia rheumatica, articular cell arteritis, calcium crystalline arthritis, pseudogout, non-articular rheumatoid, bursitis, tendosynovitis, epicondylitis (tennis elbow), Charcot's joint, hemarthrosis, Henoch-Schonlein purpura, hypertrophic osteoarthritis, multicentric reticulocytoma, sarcoidosis, hemochromatosis, drepanocytosis, hyperlipoproteinemia, hypogammaglobulinemia, hyperparathyroidism, acromegaly, familial Mediterranean fever, systemic lupus erythematosus, recurrent fever, psoriasis, multiple sclerosis, sepsis, septic shock, acute respiratory distress syndrome, multiple organs dysfunction, chronic obstructive pulmonary disease, acute lung injury, and broncho-pulmonary dysplasia, and also includes chronic inflammatory diseases, but the disease type is not particularly limited.

In the present invention, autoimmune diseases may be selected from the group consisting of rheumatoid arthritis, systemic scleroderma, systemic lupus erythematosus, psoriasis, asthma, ulcerative colitis, Behcet's disease, Crohn's disease, multiple sclerosis, dermatitis, collagen disease, vasculitis, arthritis, granulomatosis, organ specificity autoimmune diseases and GvHD (graft-versus-host disease).

The chronic inflammatory disease refers to a condition in which they are chronicized with reference to the types of inflammatory diseases described above, and preferred examples thereof include asthma, atopic dermatitis, eczema, psoriasis, osteoarthritis, gout, psoriatic arthritis, cirrhosis, steatohepatitis, nonalcoholic steatohepatitis, chronic obstructive pulmonary disease, rhinitis, diabetic retinopathy, diabetic renal failure, diabetic neuropathy and multiple sclerosis, but are not limited thereto.

The pharmaceutical compositions according to the invention may only comprise the antibodies or functional fragments thereof in the invention or may be formulated in a suitable form with one or more pharmaceutically acceptable carriers and may further contain excipients or diluents. As used herein, 'pharmaceutically acceptable' refers to a non-toxic composition that is physiologically acceptable and does not cause allergic reactions or similar reactions, such as gastrointestinal disorders, and dizziness when administered to humans.

Pharmaceutically acceptable carriers may further include, for example, carriers for oral administration or carriers for parenteral administration. The carriers for oral administration may include lactose, starch, cellulose derivatives, magnesium stearate and stearic acid. In addition, it may include various drug delivery materials used for oral administration to a peptide agent. In addition, the carriers for parenteral administration may include water, suitable oils, saline, aqueous glucose and glycols, and further include stabilizers and preservatives. Suitable stabilizers include antioxidants such as sodium hydrogen sulfite, sodium sulfite or ascorbic acid. Suitable preservatives include benzalkonium chloride, methyl- or propyl-parabens and chlorobutanol.

The pharmaceutical composition of the present invention may further include a lubricant, a humectant, a sweetener, a flavoring agent, an emulsifier and a suspension agent in addition to the above components. Other pharmaceutically acceptable carriers and formulations may be referred to as described in the following documents.

The composition of the present invention can be administered to any mammal, including humans. For example, it can be administered orally or parenterally.

Specifically, the route of administration of the composition of the present invention may be a known antibody administration method, for example, the injection or infusion by an intravenous, intraperitoneal, intracranial, subcutaneous, intramuscular, intraocular, intraarterial, cerebrospinal, or intralesional route, or the injection or infusion by the sustained release system described below. For example, the antibody of the present invention may be administered systemically or locally.

The pharmaceutical composition of the present invention may be formulated into an agent for oral or parenteral administration according to the route of administration as described above.

In the pharmaceutical composition according to the present invention, the antibody or fragment thereof may be administered in several oral and parental dosage forms during clinical administration. The antibody or fragment thereof, when formulated, may be prepared using a diluent or an excipient, such as a filler, an extender, a binder, a wetting agent, a disintegrant, or a surfactant, which is normally used. Solid formulations for oral administration include a tablet, a pill, a powder, granules, a capsule, a troche, and the like. These solid formulations may be prepared by mixing an aryl derivative of chemical formula 1 of the present invention or a pharmaceutically acceptable salt thereof with at least one excipient, for example, starch, calcium carbonate, sucrose or lactose, or gelatin. In addition, lubricants, such as magnesium stearate and talc, may be used besides to the simple excipients. Liquid formulations for oral administration include a suspension, a solution for internal use, an emulsion, a syrup, and the like. Besides simple diluents that are frequently used, such as water and liquid paraffin, several excipients, for example, a wetting agent, a sweetener, an aroma, a preservative, and the like may be contained in the liquid formulations.

Agents for parenteral administration include sterile aqueous solutions, non-aqueous solvents, suspensions, emulsions, lyophilized agents and suppositories. The therapeutic compositions of the invention may be prepared in the form of a lyophilized cake or aqueous solution for storage after mixing any physiologically acceptable carrier, excipient or stabilizer (Remington: The Science and Practice of Pharmacy, 19th Edition, Alfonso, R., ed, Mack Publishing Co. (Easton, PA: 1995)) with the antibody having the desired purity. Acceptable carriers, excipients or stabilizers are nontoxic to recipients at the dosages and concentrations employed, and include complete solutions such as phosphoric acid, citric acid and other organic acids; Antioxidants including ascorbic acid; Low molecular weight (less than about 10 residues) polypeptides; Proteins such as serum albumin, gelatin or immunoglobulins; Hydrophilic polymers such as polyvinylpyridone; Amino acids such as glycine, glutamine, asparagine, arginine or lysine; Monosaccharides, disaccharides, and other carbohydrates including glucose, mannose, or dextrins; Chelating agents such as EDTA; Sugar alcohols such as manny or sorbitan; Salt-forming counterions such as sodium; And (or) nonionic surfactants, such as tween, pluronics or polyethylene glycol (PEG).

Agents for parenteral administration may be formulated by methods known in the art in the form of injections, creams, lotions, external preprations, oils, moisturizers, gels, aerosols and nasal inhalants. These formulations are described in the literature, which is a prescription generally known in all pharmaceutical chemistry (Remington's Pharmaceutical Science, 19th ed., Mack Publishing Company, Easton, PA, 1995).

The total effective amount of an antibody or functional fragment thereof of the present invention may be administered in a single dose, or may be administered by a fractionated treatment protocol in which multiple doses are administered for a long time.

The pharmaceutical composition of the present invention may vary the content of the active ingredient (an antibody or a functional fragment thereof of the present invention) according to the extent and/or purpose of the disease, but may be repeatedly administered several times a day at an effective dose of usually 0.01 µg to 10000 mg, or preferably 0.1 µg to 1000 mg, in a single dose. However, the dosage of the pharmaceutical composition is determined in consideration of various factors such as the formulation method, route of administration and frequency of treatment, as well as various factors such as the patient's age, weight, health status, sex, severity of the disease, diet and excretion rate. In view of this, those of ordinary skill in the art will be able to determine the appropriate effective dosage of the compositions of the present invention. The pharmaceutical composition according to the present invention is not particularly limited to its formulation, route of administration and method of administration as long as the effect of the present invention is shown.

Also, the present invention is to provide a method for treating immune cell migration-related diseases, the method comprising administering to a subject in need thereof an effective amount of a composition comprising an antibody biding specifically to an epitope including the sequence of SEQ ID NO: 117 at the N-terminus of lysyl-tRNA synthetase (KRS) or a functional fragment thereof as an effective ingredient.

An embodiment according to an aspect of the present invention provides a method for treating immune cell migration-related diseases, the method comprising administering to a subject in need thereof an effective amount of a composition consisting of an antibody biding specifically to an epitope including the sequence of SEQ ID NO: 117 at the N-terminal domain of lysyl-tRNA synthetase (KRS) or a functional fragment thereof.

An embodiment according to another aspect of the present invention provides a method for treating immune cell migration-related diseases, the method comprising administering to a subject in need thereof an effective amount of a composition consisting essentially of an antibody biding specifically to an epitope including the sequence of SEQ ID NO: 117 at the N-terminal domain of lysyl-tRNA synthetase (KRS) or a functional fragment thereof.

As used herein, 'treatment' refers to a concept that includes inhibiting the occurrence or recurrence of a disease, alleviating symptoms, reducing direct or indirect pathological consequences of the disease, decreasing the rate of disease progression, improving the disease state, improving, alleviating, improved prognosis and/or prevention. As used herein, the term "prevention" refers to any action that inhibits the onset of a disease or delays its progression.

The 'effective amount' of the present invention, when administered to a subject, refers to an amount that exhibits a change in immune cell migration or immune cell invasion, or an improvement, treatment, and preventive effect of a disease caused by the same, and is understood with reference to the foregoing with respect to the dosage.

The 'subject' may be an animal, preferably a mammal, particularly an animal including a human, or may be a cell, tissue, organ, or the like derived from the animal.

The subject may be a patient in need of treatment.

The 'agent or composition' may be in the form of a food composition, cosmetic composition, pharmaceutical composition, etc., and preferably may be a pharmaceutical composition. A detailed description of the pharmaceutical composition is as described above.

Advantageous Effect

The KRS N-terminal specific antibodies provided by the present invention can regulate the migration of immune cells, thereby showing a very significant effect in the prevention, improvement and treatment of diseases related to immune cell migration.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODE FOR CARRYING OUT INVENTION

Hereinafter, the present invention will be described in detail.

However, the following examples are illustrative of the present invention, and the present invention is not limited to the following examples.

Example 1: Verification of Laminin Signal Role in Immune Cell Migration and Invasion In the extracellular matrix (ECM) that make up the blood vessels, it was identified which promotes the migration and invasion of monocytes/macrophages. Transwell migration assay was performed using collagen (collagen, Col), fibronectin (FN) and laminin (LN) as extracellular matrix. The specific experimental method is as follows. After transwells (Corning, #3421-5 mm) were coated with gelatin (0.5 mg/ml), RAW 264.7 cells (1×10$^5$ cells/well) were seeded into the top chamber. Fibronectin or Collagen was placed in the bottom chamber. Serum Free DMEM (500 μl) containing 10 μg/ml of Laminin (laminin mixture, Biolamina), Fibronectin or Collagen, respectively, was placed in the bottom chamber. After 24 hours, the cells were treated with 70% methanol for 30 minutes and fixed, and then stained with 50% Hematoxylin for 30 minutes. After removing non-migrating cells from the top of the membrane with a cotton swab, the membrane was taken and mounted on the slide. The migrating cells on the underside of the membrane were observed and quantified under a high magnification microscope.

Figure 1:
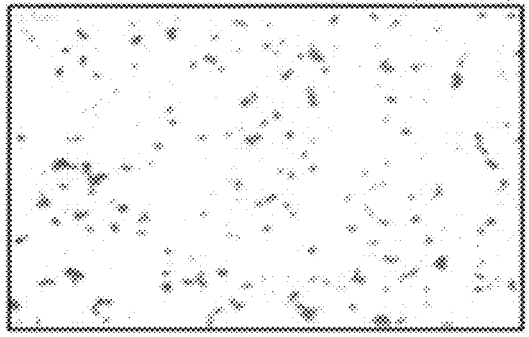
FIG. 1 is a result of comparing the effects of collagen, fibronectin, and laminin on immune cell (monocyte/macrophage) migration by a transwell migration assay, showing microscopic images of the migrating cells.
Figure 1:
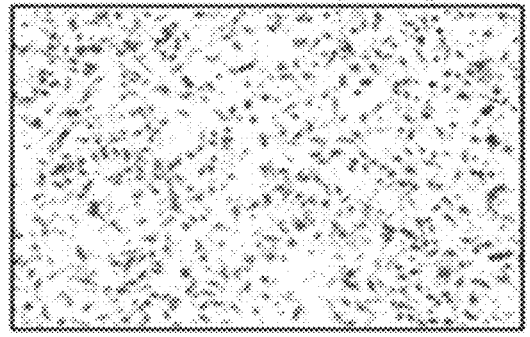
Figure 1:
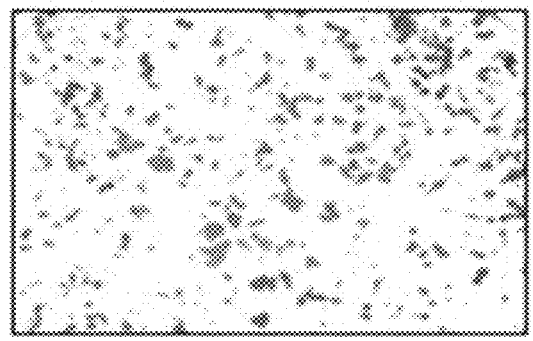
Figure 1:
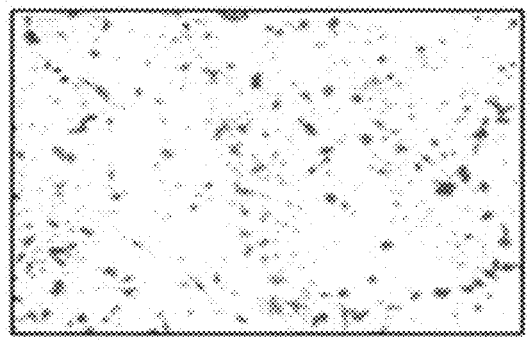
Figure 2:
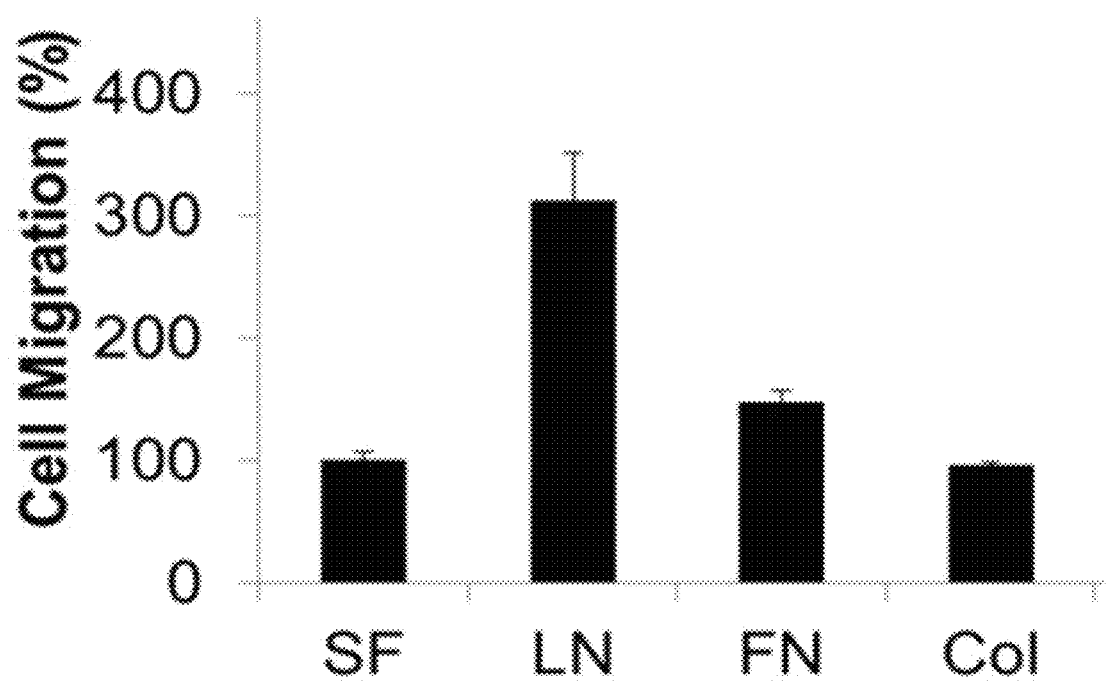
FIG. 2 is a graph showing the number of cells measured (quantified) in the microscope image of FIG. 1.

As shown in FIGS. 1 and 2, it was confirmed that laminin in the various extracellular matrix most strongly promotes the migration of monocytes/macrophages. Therefore, it was confirmed that the migration of monocytes/macrophages responded most strongly to laminin (LN) signals in the extracellular matrix (ECM).

Example 2: Immune Cell Migration and Invasion Effects by Laminin Subtypes

The effects of laminin subtypes on immune cell migration and invasion were evaluated. A transwell cell migration assay was performed in the same manner as in the Example 1 using LN111, LN211, LN221, LN411, LN421, LN511, and LN521 at 1 μg/ml as various laminin subtype proteins (purchased from Biolamina). The specific sequence of the laminin subtypes can be referenced according to the chains consisting of each laminin subtype, α4 chain of SEQ ID NO: 120, α2 chain of SEQ ID NO: 126, α5 chain of SEQ ID NO: 127, β2 chain of SEQ ID NO: 122, β1 chain of SEQ ID NO: 128, γ1 chain of SEQ ID NO: 124

Figure 3:
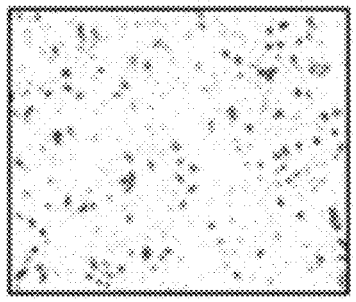
FIG. 3 is the result of comparing the effects of various laminin subtypes (LN111, LN211, LN221, LN411, LN421, LN511, LN521) on immune cell (monocyte/macrophage) migration by a transwell migration assay, showing microscopic images of the migrating cells.
Figure 3:
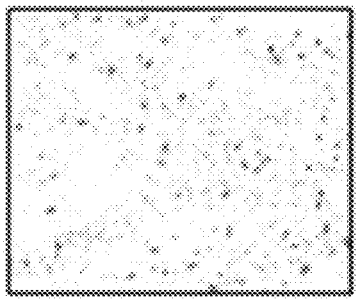
Figure 3:
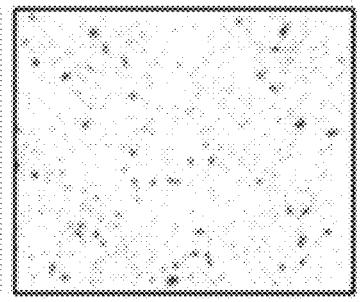
Figure 3:
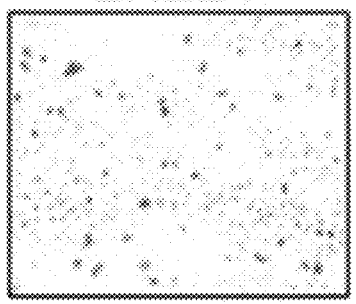
Figure 3:
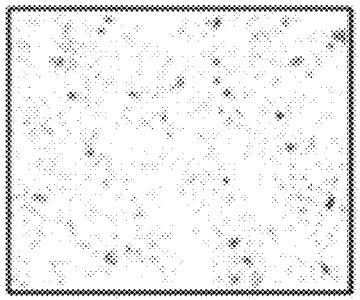
Figure 3:
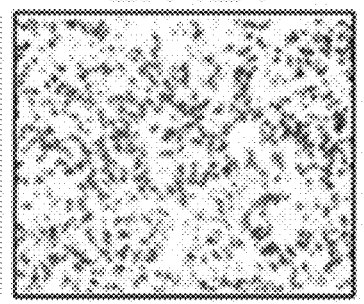
Figure 3:
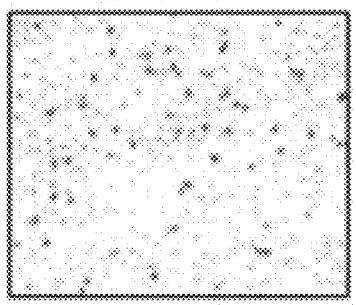
Figure 3:
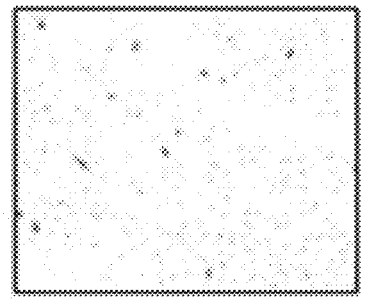
Figure 4:
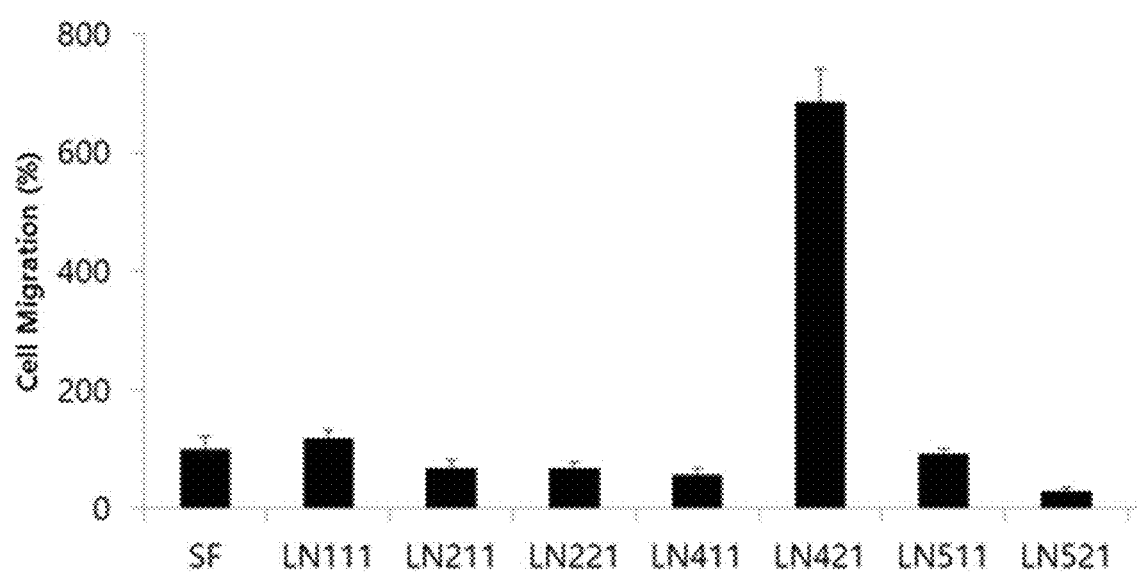
FIG. 4 is a graph showing the number of cells measured (quantified) in the microscope image of FIG. 3.

As shown in FIG. 3 and FIG. 4, it was confirmed that monocytes/macrophages specifically move in response to a α4β2γ1 subtype (LN421) among laminin subtypes. Therefore, it was confirmed that the migration of monocytes/macrophages is specific for LN421 among laminin subtypes.

Example 3: Movement of Cytoplasmic KRS to Cell Membrane Following Laminin Treatment of Immune Cells Identification of Novel Pathology of Immune Cell Migration-Related Diseases After seeding RAW 264.7 cells (2×10$^6$ cells) in 100 pie plate and incubating for 18 hr, the serum free-DMEM media was treated with 1 μg/ml LN421 and the cells were harvested at 0 h, 12 h, and 24 h. RAW 264.7 cell proteins were separated into cytosol and membrane fractions using the ProteoExtract® Subcellular Proteome Extraction Kit (Calbiotech, cat #539790). The obtained protein was subjected to electrophoresis, transferred to PVDF membrane (Millipore) and blocked with 3% skim milk. KRS was then detected by the western blotting. Specifically, KRS polyclonal antibody (rabbit, Neomics, Co. Ltd. #NMS-01-0005) was added to bind for 1 hour. Unbound antibody was removed and then anti-rabbit secondary antibody (Thermo Fisher Scientific, #31460) was added. After reacting with the secondary antibody, the film was developed in the dark room using ECL reagent as a substrate. The detected bands were compared to standard molecular markers to identify the bands corresponding to the size of the KRS. Antibodies against Na+/K+ATPase (Abcam, ab76020) and tubulin (Santa cruz SC-5286) were used to identify plasma membrane and cytosol markers, respectively.

Figure 5:
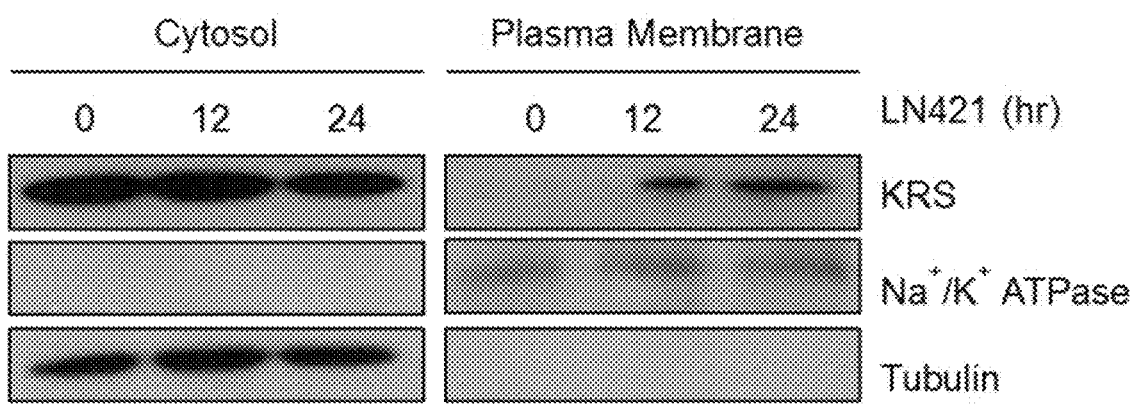
FIG. 5 shows the western blotting results of confirming that KRS increased in the monocyte/macrophage membrane by LN421 treatment.

As shown in FIG. 5, it was confirmed that the amount of KRS detected in the cell membrane region was increased compared to a partial decrease in the amount of KRS detected in the cytosol region when the LN421 was treated to monocytes/macrophages. These results suggest that KRS which is expressed in the cells of monocytes/macrophages and is generally present in the cytoplasmic region migrates to the cell membrane region by LN421 treatment. It is thought that KRS specifically increases in the immune cell membrane region is an important pathological phenomenon in the diseases associated with immune cell migration and invasion.

Example 4: Control of Immune Cell Migration/Invasion Through Reduction of KRS Levels in Cell Membrane Location and Confirmation of Therapeutic Effects of Immune Cell Migration-Related Diseases Use of Compounds that Inhibit KRS Migration to Cell Membrane The present inventors confirmed that the intracellular behavior of KRS significantly influences the migration of monocytes/macrophages from the results of the above-described examples. In particular, the phenomenon that KRS specifically increases in the area of the immune cell membrane as the KRS moves toward the cell membrane is considered to be an important pathology for diseases related to immune cell migration and invasion. Therefore, the present inventors have verified that suppressing this pathological phenomenon of KRS can be applied as one of the therapeutic strategies of diseases related to immune cell migration and invasion, which this has been disclosed in Korean applications 10-2017-0076718 and 10-2018-0069146.

In the above document, the present inventors have discovered compounds that inhibit the movement of KRS to the cell membrane in order to inhibit the KRS increase in the immune cell membrane in immune cell migration-related diseases, and their therapeutic effect on immune cell migration-related diseases was confirmed and examined.

Briefly, in order to suppress the KRS increase in immune cell membranes, compounds such as BC-KI-00053 (4-({(7-fluorobenzo [d] thiazol-2-yl) [2-(4-methoxyphenyl) ethyl] amino} methyl) benzoic acid) were found as a representative example of the inhibitor of migration of KRS to cell membranes. In inflammatory conditions such as acute inflammatory reactions (e.g., ear skin wound models) and ischemic immune responses (e.g., liver ischemia-reperfusion injury models), it was also confirmed that the migration and invasion of immune cells was inhibited by the administration of inhibitors of migration of KRS to the cell membrane (especially, BC-KI-00053) and the effect of alleviating disease appeared. In addition, in in vivo models of immune cell migration-related diseases such as hepatic fibrosis, pulmonary arterial hypertension (PAH), hypertension, proteinuria, glomerulosclerosis, kidney fibrosis and myofibrosis cordis, and Alport syndrome, the disease state caused by immune cell migration and invasion was confirmed, and here, the effect of treating the disease of the inhibitory compound of KRS migration to the cell membrane was confirmed.

Example 5: Construction of Antibody for Reducing Cellular Membrane KRS Level and Verification of Immune Cell Migration/Invasion Control Effect 5-1. Construction of KRS-N Term Specific Binding Antibody_N3 Antibody As the compound of Example 4 exhibited an effect of treating and improving immune cell migration/invasion-related diseases by inhibiting an increase in KRS level at the site of a cell membrane, the present inventors attempted to generate an antibody showing excellent therapeutic efficacy on a similar principle. On the other hand, the present inventors have identified that when KRS moves from the cytoplasm and is located in the cell membrane, some N-terminal regions are also exposed to the extracellular membranes (usually amino acid regions 1 to 72 of the KRS N-terminus). Therefore, among the anti-KRS antibodies, the antibody capable of binding to the KRS-N terminus was thought to have a more remarkable advantage in in vivo in the immune cell migration/invasion inhibition, and as a representative example, the present inventors confirmed these therapeutic advantages through the construction of N3 antibody as described below. N3 antibody was obtained by the following method.

Specifically, to select scFv that specifically binds only to the human KRS N-terminal (SEQ ID NO: 148) region exposed to the outer membrane when moved to the cell membrane by laminin signal from the human KRS full length sequence (SEQ ID NO: 118), a phage display panning experiment was performed using scFv phage library derived from human B cells labeled with HA tag. The scFv display phage library (Library size: app.7.6×109, Library produced by prof. Hyunbo Shim) used in this experiment is described in Korean Patent No. 10-0961392. Human KRS full-length sequences and KRS fragments of different specific regions of the N-terminal site were used as antigenic proteins for a phage display panning experiment.

The phage display panning experiment was specifically performed as follows. 1-10 µg of the antigenic protein was added to an Immuno-tube containing 1 ml of 1×PBS solution, and the antigen was coated on the inner surface of the tube by reacting at 37° C. and 200 rpm for 1 hour. The antigen solution was drained, and uncoated antigens were removed by washing once with tap water. In order to prevent nonspecific binding between antigen protein and phage, immuno-tube and scFv library were reacted with 1×PBST (PBS containing 0.05% tween20) containing 3% skim milk at room temperature for 1 hour. After removing the skim milk from the immuno-tube, the scFv library was added and reacted at 37° C. and 150 rpm for 1 hour to bind the scFv phage to the antigen. The scFv phage specifically bound to each antigen was separated within 10 minutes by adding 1 ml of triethylamine (100 mM) at room temperature and neutralized with Tris (1 M, pH 7.4). The filtered phage scFv was added to ER2537 $E. coli$ incubated with OD<1 and then infected it during incubating at 37° C. and 120 rpm for 1 hour and 30 minutes. $E. coli$ infected with phage were centrifuged to remove some of the culture supernatant, and redispersed to spread to agarose plates with a diameter of 15 cm containing ampicillin and glucose (2%). The next day 5 ml SB medium was spread to obtain all the cells grown on the plate, and glycerol (50%) was added to 0.5 times the total volume, mixed and aliquoted with 1 ml each to storage them at −80° C. (scFv panning stock). Twenty µl of the prepared stock was inoculated in a 20 ml SB solution and cultured, and a helper phage was used to prepare a scFv phage library (1 ml) for phage panning in the next step. The above procedure was repeated 2-3 times to isolate phage expressing an antigen specific scFv.

After the biopanning, the western blotting, and the immunoprecipitation were further performed to select scFv clones having high binding ability to the target protein.

The selected scFvs were converted to IgG (total antibody), and specific methods are as follows. First, polynucleotides encoding scFv in the genome of the scFv clone were amplified by PCR. The base sequences of the primers used to amplify the genes of the VH region of scFv are as follows: Forward (AGA GAG TGT ACA CTC C CA GGC GGC CGA GGT GCA G, SEQ ID NO: 129), and Reverse (CGC CGC TGG GCC CTT GGT GGA GGC) TGA GCT CAC GGT GAC CAG, SEQ ID NO: 130). The nucleotide sequence of the primers used to amplify the gene of the VL region of scFv is as follows: Forward (AAG CGG CCG CCA CCA TGG GAT GGA GCT GTA TCA TCC TCT TCT TGG TAG CAA CAG CTA CAG GTG TAC ACT CCC AGT CTG TGC TGA CTC AG, SEQ ID NO: 131), and Reverse (CGC CGC CGT ACG TAG GAC CGT CAG CTT GGT, SEQ ID NO: 132). PCR was performed with each phage DNA (50 ng) as a template by using the primers (10 pmol each) in conditions of: 95° C./3 min; 95° C./30 sec, 60° C./30 sec, 72° C./30 sec, 30 cycles; 72° C./5 min, thereby amplifying the VH or VL gene of scFv. The PCR product was inserted into the pcDNA3.4 vector (Thermo Fisher Scientific), a vector used for IgG production using restriction enzymes. The heavy and light chain proteins of IgG were individually expressed in plasmids respectively.

The vector containing the DNA encoding the light and heavy chains of the IgG including the variable region of scFv prepared in this way was cotransformed into freestyle 293F cells (ATCC) to allow the light and heavy chains to be expressed together in the cells. Transformed 293F cells were incubated at 37° C. and 8% $CO_2$ conditions for 7 days to obtain supernatants. The supernatants were filtered using a cellulose acetate membrane filter (0.22 µm pore size, Corning) and purified using CaptivA™ PriMAB protein A column (Repligen, USA). The obtained antibody concentration was measured using a BCA kit (Pierce, 23225), and the IgG antibody protein produced under reduced and non-reduced conditions was analyzed using a Bioanalyzer (Agilent 2100 Bioanalyzer).

5-2. Identification of the Inhibitory Efficacy on Immune Cell Migration and Invasion The effects on immune cell migration and invasion of the various candidate antibody generated in 5-1 were confirmed. The specific experimental method is as follows. Transwell (Corning #3421-5 mm) was coated with gelatin (0.5 mg/ml), and then RAW 264.7 cells (1×105 cells/well) were seeded into the top chamber. Serum Free DMEM (500 µl) containing Laminin 421 (1 µg/ml) was placed in the bottom chamber. Each antibody was treated at 100 nM concentration in the top chamber. After 24 hours, the cells were fixed with 70% methanol for 30 min and then stained with 50% Hematoxylin for 30 min. After removing the non-migrating cells in the upper part of the membrane with a cotton swab, the membrane was taken and mounted on the slide. The migrating cells on the underside of the membrane were observed under a high magnification microscope (FIG. 6), and the number of cells in the obtained image was measured and displayed graphically (FIG. 7).

In addition, the cells were incubated and harvested for 24 hours by treating Laminin 421 (1 µg/ml) and antibody (100 nM) in RAW 264.7 cells. Subsequently, using the Proteo-Extracttesubcellular proteom extraction kit (Calbiochem), the samples were divided into membrane and cytosol fractions, and then the western blotting was performed on KRS. The specific method is as described in the Example 2.

Figure 6:
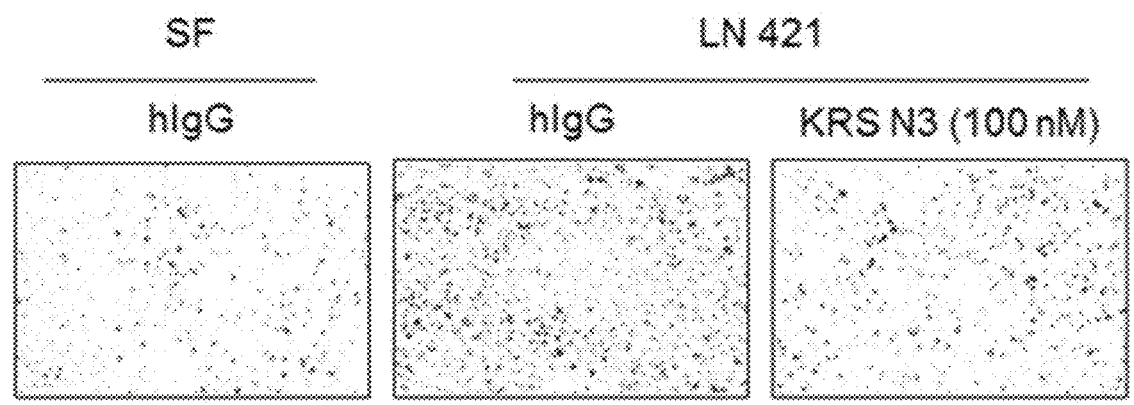
FIG. 6 is a result of comparing the migration inhibitory effect of the N3 antibody (antibody binding to the N-terminus of KRS) of the present invention on monocyte/macrophage migration specific to LN421 by a transwell migration assay, showing microscopic images of the migrating cells.
Figure 7:
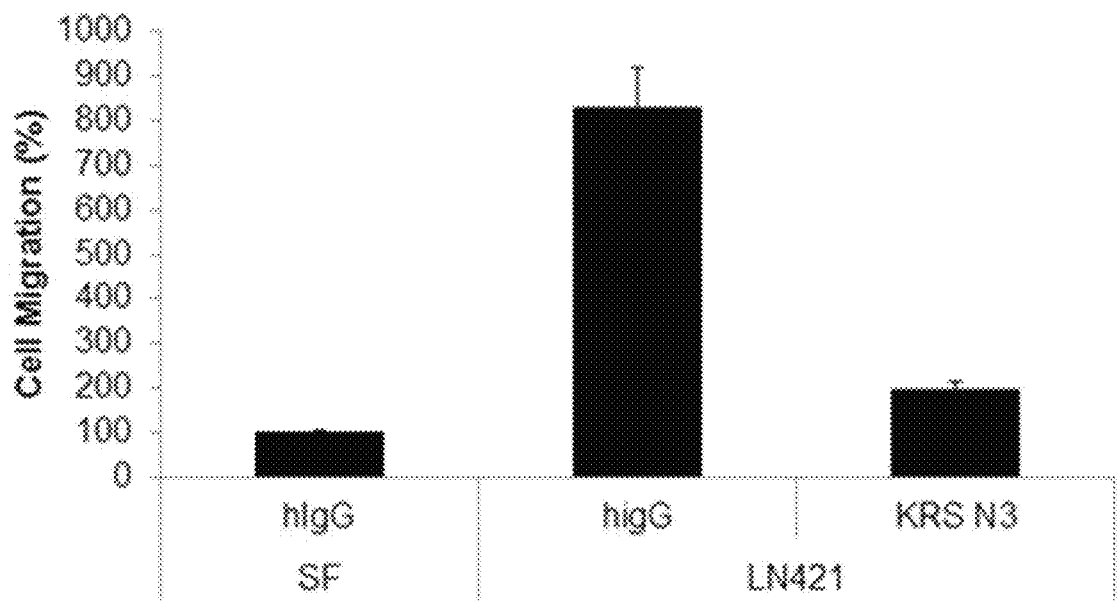
FIG. 7 is a graph showing the number of cells measured (quantified) in the microscope image of FIG. 6.
Figure 8:
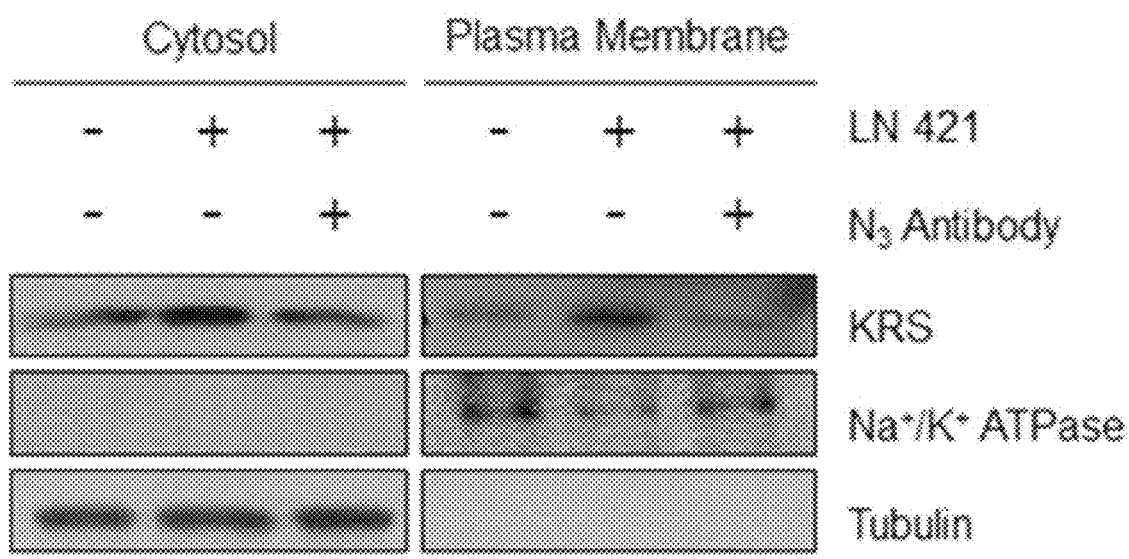
FIG. 8 shows the western blotting results of confirming that increased KRS levels in monocyte/macrophage membranes by LN421 treatment were reduced by treatment with the inventive N3 antibody (antibody binding to the N-terminus of KRS).
Figure 9:
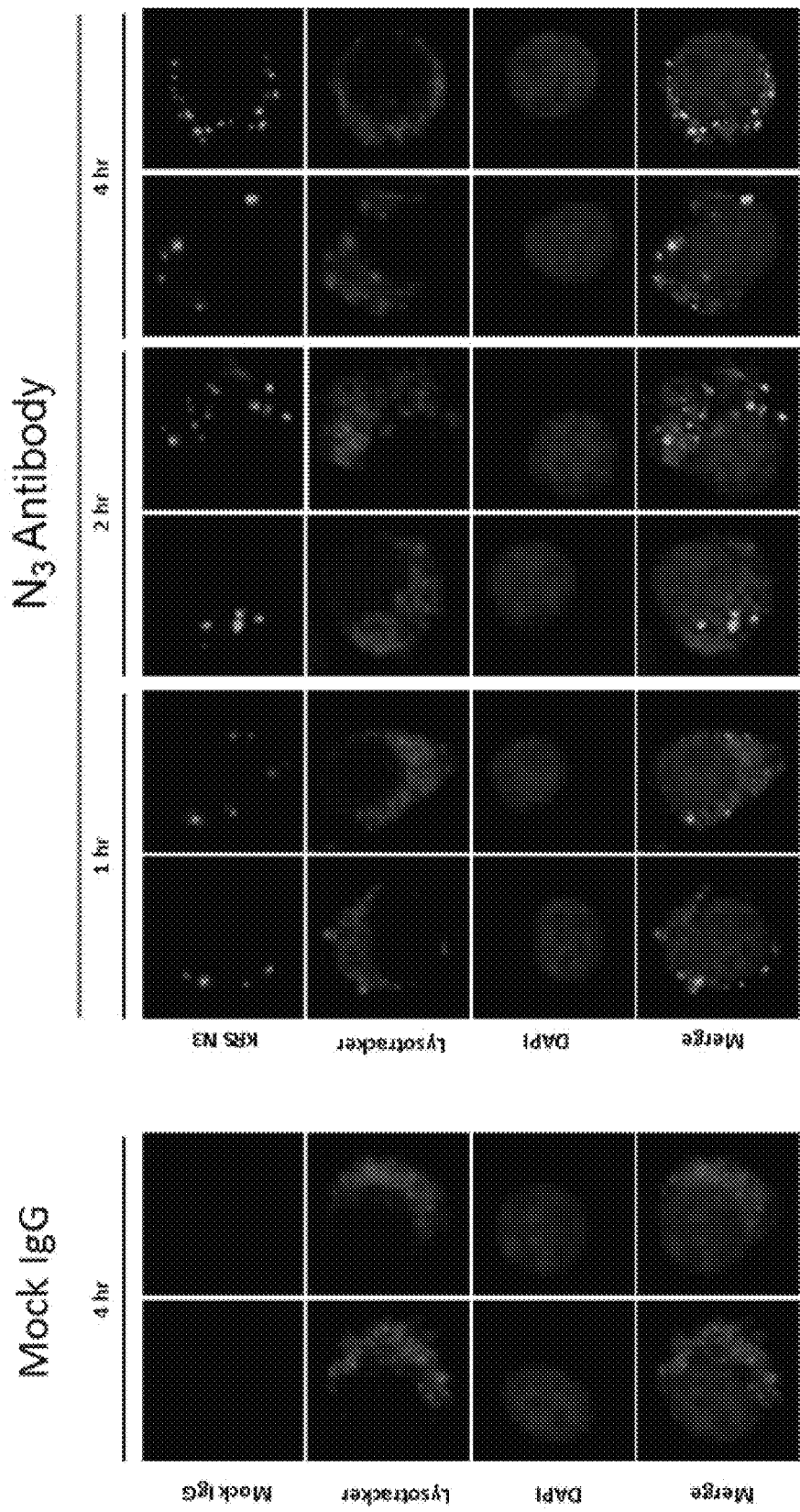
FIG. 9 shows the results of confirming that KRS in the cell membrane region is endocytosed by treatment with N3 antibody (antibody binding to the N-terminus of KRS). Anti-KRS antibody (N3) labeled with Alexa fluor 488 (Thermofisher) fluorescence probe and Mock IgG (Thermofisher), a control group, were treated and the antibody movement was monitored according to time. At this time, Lysotracker (Thermofisher) was used as a lysosome marker to confirm endocytosis.

As a result, it was confirmed that the N3 monoclonal antibody (an antibody specifically binding to KRS N-term) of the present invention effectively inhibits LN421-dependent monocyte/macrophage migration, which is shown in FIGS. 6 and 7. In addition, as shown in FIG. 8, LN421 treatment increased the KRS level at the cell membrane location of monocytes/macrophages, and it was confirmed that the KRS level was specifically decreased at the cell membrane location by N3 monoclonal antibody treatment. In addition, as shown in FIG. 9, it was confirmed that the endocytosis occurs when the N3 antibody binds to the KRS region (especially the N-terminal region) exposed to the extracellular. This not only inhibits the migration of KRS from the cytoplasm to the cell membrane, but it also suggests that it is possible to inhibit immune cell migration and treat diseases related to immune cell migration by actively removing KRS that has already migrated to the cell membrane using a substance (in particular, an agent specifically binding to the N-terminus exposed outside the cell) that specifically binds to KRS. These results confirmed that the antibody binding to the N-terminus of KRS has possibility as a novel therapeutic agent for immune cell migration/invasion-related diseases.

5-3. N3 Antibody Sequencing

The sequences of N3 scFv (SEQ ID NO: 59) and N3 IgG antibodies (SEQ ID NO: 89 and SEQ ID NO: 91) was confirmed using Omp primer according to the method described in Hye young Yang, et. al., 2009, Mol. Cells 27, 225-235. The sequence thus obtained was confirmed the sequence of the CDR region using the Bioedit program. The results of sequencing of the antigen binding site were shown in Table 1, and the scFv further included a linker of SEQ ID NO: 57.

TABLE 1

|   |   | Amino acid sequence | DNA sequence |
|---|---|---|---|
| VH | CDR-H1 | SYDMS (SEQ ID NO: 1) | agttatgatatgagc (SEQ ID NO: 2) |
|   | CDR-H2 | AISYDNGNTYYADSVKG (SEQ ID NO: 3) | gcgatctcttatgataatggtaatacatattacgctgattctgtaaaaggt (SEQ ID NO: 4) |
|   | CDR-H3 | MALDFDY (SEQ ID NO: 5) | atggcgcttgatttcgactac (SEQ ID NO: 6) |
|   | Full | (FR1-CDR1-FR2-CDR2-FR3-CDR3-FR4) EVQLLESGGGLVQPGGSLRLSCAASGFTFSSYDMSWVRQAPGKGLEWVSAISYDNGNTYYADSVKGRFTISRDNSKNTLYLQMNSLRAEDTAVYYSARMALDFDYWGQGTLVTVSS (SEQ ID NO: 31) | gaggtgcagctgttggagtctgggggaggcttggtacagcctggggggtccctgagactctcctgtgcagcctctggattcacctttagcagttatgatatgagctgggtccgccaggctccagggaaggggctggagtgggtctcagcgatctcttatgataatggtaatacatattacgctgattctgtaaaaggtcggttcaccatctccagagacaattccaagaacacgctgtatctgcaaatgaacagcctgagagccgaggacacggccgtgtattactctgcgagaatggcgcttgatttcgactactggggccagggtacactggtcaccgtgagctca (SEQ ID NO: 32) |
| VL | CDR-L1 | TGSSSNICSNYVT (SEQ ID NO: 7) | actggctcttcatctaatattggcagtaattatgtcacc (SEQ ID NO: 8) |
|   | CDR-L2 | DNSNRPS (SEQ ID NO: 9) | gataatagtaatcggccaagc (SEQ ID NO: 10) |
|   | CDR-L3 | ASWDDSLSAYV (SEQ ID NO: 11) | gcttcttgggatgatagcctgagtgcttatgtc (SEQ ID NO: 12) |
|   | Full | (FR1-CDR1-FR2-CDR2-FR3-CDR3-FR4) QSVLTQPPSASGTPGQRVTISCTGSSSNIGSNYVTWYQQLPGTAPKLLIYDNSNRPSGVPDRFSGSKSGTSASLAISGLRSEDEADYYCASWDDSLSAYVFGGGTKLTVL (SEQ ID NO: 33) | cagtctgtgctgactcagccaccctcagcgtctgggaccccgggcagagggtcaccatctcttgtactggctcttcatctaatattggcagtaattatgtcacctggtaccagcagctcccaggaacggccccaaaactoctcatctatgataatagtaatcggccaagcggggtccctgaccgattctctggctccaagtctggcacctcagcctccctggccatcagtgggctccggtccgaggatgaggctgattattactgtgcttcttgggatgatagcctgagtgcttatgtcttcggcggaggcaccaagctgacggtccta (SEQ ID NO: 34) |

5-4. Verification of Human KRS Binding Site of N3 Monoclonal Antibody

Figure 10:
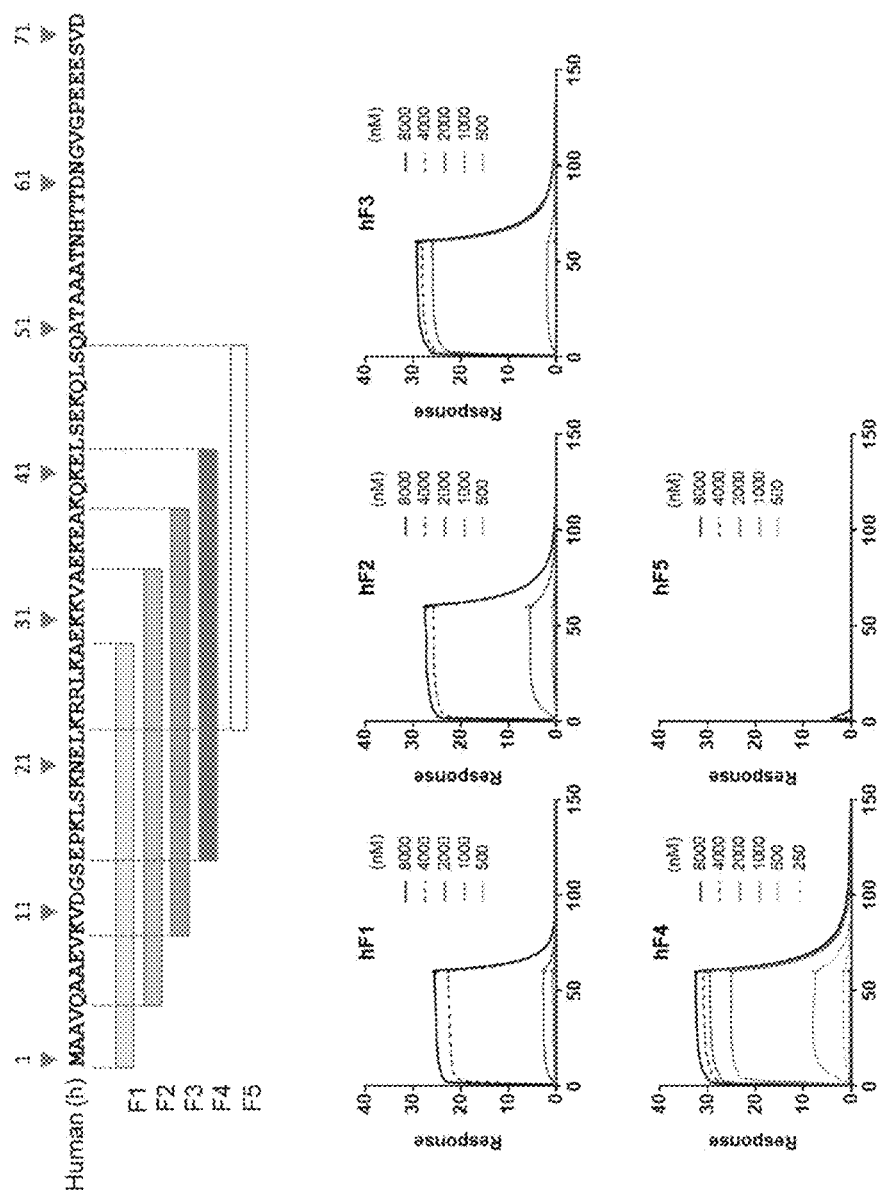
FIG. 10 shows the results of the binding site and the relative binding strength to the corresponding region of the N3 antibody of the present invention in the N-terminal region of human KRS by SPR (surface plasmon resonance) experiment (The gray bar at the bottom of the sequence indicates the binding ability of the N3 antibody to the corresponding region (F1 to F5), indicating the darker the bar, the higher the binding strength). The gray bar at the bottom of the sequence indicates the binding ability of the N3 antibody to the corresponding region (F1 to F5), and the darker the bar indicates the higher binding strength.

In the N-terminal region of human KRS, the following experiment was performed to confirm the N3 monoclonal antibody binding site. First, as shown in FIG. 10 and Table 2, the binding ability of N3 antibody was analyzed through Surface Plasmon Resonance (SPR) using the KRS fragment peptides F1 to F5 for slightly different sites in the KRS N-terminal region of SEQ ID NO: 148 as an antigen (epitope). The SPR experiment was performed using a Biacore T200 (GE Healthcare) equipped with Series S sensor chip CM5 (GE Healthcare) at 2500. After fixing the antibody to the chip with an amine coupling kit (GE Healthcare), each antigen peptide was dissolved in PBS solution, and then diluted twice in the range of 156 nM-1 5000 nM and flowed for 60 seconds. PBS was then flowed for 300 seconds. The data obtained were analyzed with Biacore 1200 Evaluation software v2.0 (GE Healthcare).

TABLE 2

|   |   | Species | MW |
|---|---|---|---|
| F1 (1-29) | MAAVQAAEVKVDGSEPKLSKNELKRRLKA (SEQ ID NO: 133) | Human | 3168 |

TABLE 2-continued

| | | Species | MW |
|---|---|---|---|
| F2 (5-34) | QAAEVKVDGSEPKLSKNELKRRLKAEKKVA (SEQ ID NO: 134) | Human | 3351 |
| F3 (10-38) | KVDGSEPKLSKNELKRRLKAEKKVAEKEA (SEQ ID NO: 135) | Human | 3310 |
| F4 (15-42) | EPKLSKNELKRRLKAEKKVAEKEAKQKE (SEQ ID NO: 136) | Human | 3337 |
| F5 (24-49) | KRRLKAEKKVAEKEAKQKELSEKQLS (SEQ ID NO: 137) | Human | 3084 |
| mF1 (1-28) | MATLQESEVKVDGEQKLSKNELKRRLKA (SEQ ID NO: 138) | Mouse | 3230 |
| mF2 (3-34) | QESEVKVDGEQKLSKNELKRRLKAEKKLA (SEQ ID NO: 139) | Mouse | 3383 |
| mF3 (10-37) | KVDGEQKLSKNELKRRLKAEKKLAEKEA (SEQ ID NO: 140) | Mouse | 3268 |
| mF4 (15-41) | QKLSKNELKRRLKAEKKLAEKEAKQKE (SEQ ID NO: 141) | Mouse | 3253 |
| mF5 (24-48) | RRLKAEKKLAEKEAKQKELSEKQLN (SEQ ID NO: 142) | Mouse | 2997 |
| rF1 (1-28) | MATLREGEVKLDGEPKLSKNELKRRLKA (SEQ ID NO: 143) | Rat | 3211 |
| rF2 (3-34) | REGEVKLDGEPKLSKNELKRRLKAEKKLA (SEQ ID NO: 144) | Rat | 3364 |
| rF3 (10-37) | KLDGEPKLSKNELKRRLKAEKKLAEKEA (SEQ ID NO: 145) | Rat | 3251 |
| rF4 (15-41) | PKLSKNELKRRLKAEKKLAEKEAKQKE (SEQ ID NO: 146) | Rat | 3222 |
| rF5 (24-48) | RRLKAEKKLAEKEAKQKELSEKQLN (SEQ ID NO: 147) | Rat | 2997 |

As shown in FIG. 10, the N3 IgG antibody did not bind to the F5 peptide at all, and showed binding ability in the order of F4>F3>F2>F1. The F4, F3, F2 and F1 share 15 to 29 amino acids in the N-terminus of human KRS defined by SEQ ID NO: 148. From this, it was confirmed that a 15-29 aa region (15-29 amino acid residue region) plays an important role in the binding of the N3 antibody to human KRS, and amino acids at position 15-42 in the human KRS which is corresponding to the F4 polypeptide within the amino acids at position 15-29 in the human KRS is considered to be the major binding site of the N3 antibody.

Figure 11:
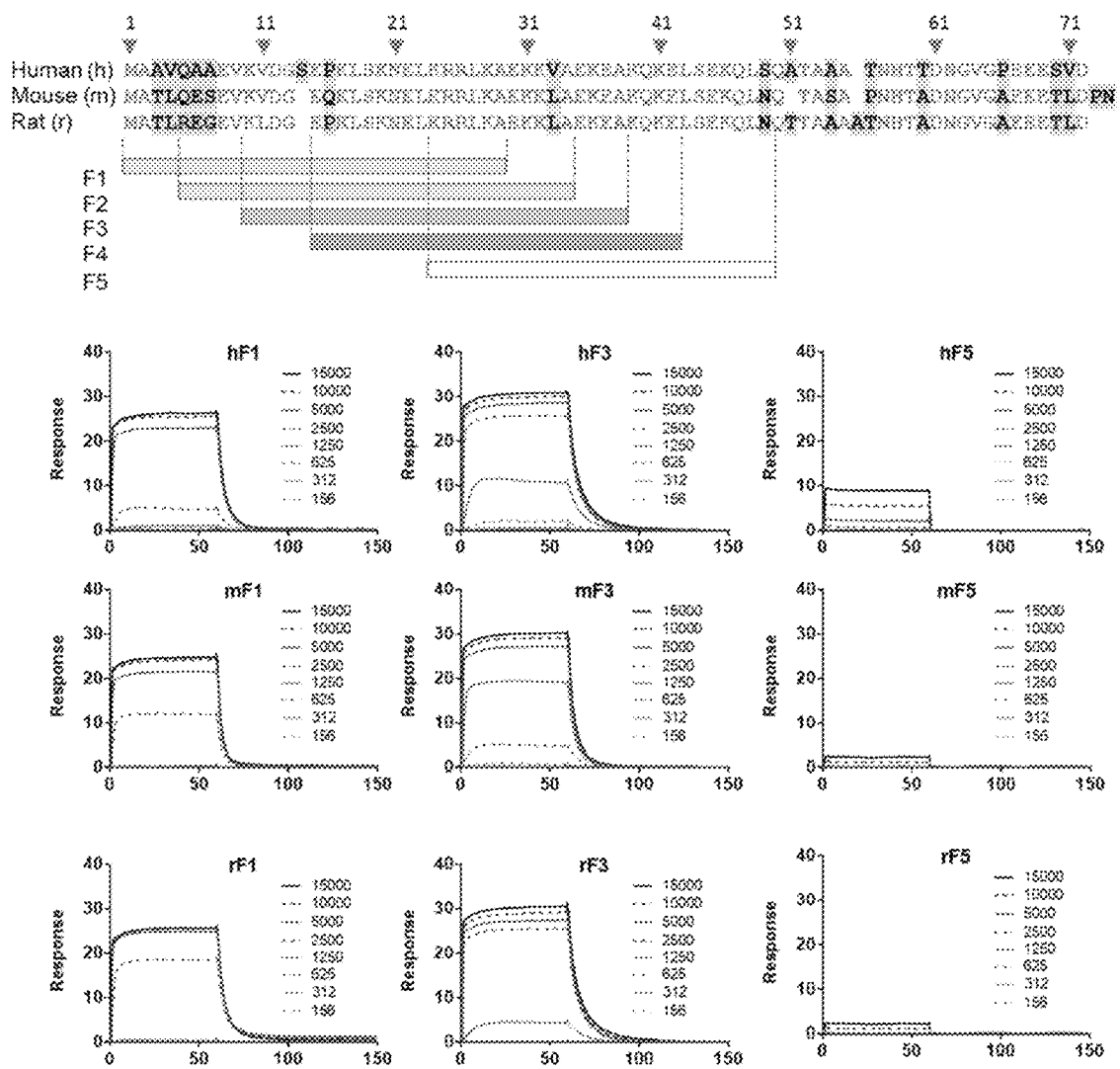
FIG. 11 shows the binding site and relative binding ability of the N3 antibody to the corresponding region of the present invention to the N-terminal region of human (h), mouse (m), or rat (r) KRS by SPR. The epitope sequence is shown (The gray bar at the bottom of the sequence indicates the binding strength of the N3 antibody to the corresponding region (F1 to F5), and the darker the bar indicates the higher binding strength).

5-5. Verification of Efficacy Evaluation of N3 Monoclonal Antibody in Other Animal Models In order to confirm whether the efficacy of the N3 antibody of the present invention can be evaluated by constructing disease animal models in mice and rats, sequence similarity across species in the KRS N-terminal sequences was analyzed. As shown in FIG. 11 and Table 2, KRS fragment peptides F1 to F5 for slightly different sites in KRS N-terminal regions of human (h), mouse (m), and let (r) were used as antigens (epitopes). The binding ability of N3 antibody was analyzed by Surface Plasmon Resonance (SPR). The specific method is as described in the Example <5-4>.

As shown in FIG. 11, since the N3 antibody showed the same binding pattern in human (h), mouse (m), and let (r), it did not bind to F5 peptide at all. It showed binding ability in the order of F4>F3>F2>F1. When comparing the F1 to F4 sequences of each species, they commonly included the KLSKNELKRRLKA sequence. It is thought that 17-29-amino acid region (SEQ ID NO: 117) plays an important role in antibody binding within the amino acids at position 15-29 in KRS identified in the Example 5-4. It is thought that cross-reactivity between species of N3 antibody is possible through this experiment, and this fact shows that mouse and rat models can be used for toxicity test and in vivo efficacy test of N3 antibody.

Example 6 Efficacy Verification of KRS-N Term Specific Binding Antibodies in Immune Cell Migration-Related Diseases in In Vivo Models_In Vivo Pulmonary Hypertension Models Treatment of an antibody that specifically binds to the KRS N-terminus inhibits immune cell migration/invasion through a decrease in KRS levels (through endocytosis, etc.) at the site of a cell membrane, resulting in the same effect as the compound of Example 4 (decrease of KRS level in a cell membrane). Therefore, it is apparent that the KRS N-term specific antibody of the present invention (typically N3 antibody) will show a therapeutic effect against the same indication (diseases related to immune cell migration) of the compound of Example 4, which is further demonstrated through the following examples.

Experiment Methods

1) Construction of Pulmonary Arterial Hypertension (PAH) Models and Administration of a Test Substance To induce PAH in 7-week-old SD rats (Oriental Bio), 60 mpk of MCT (monocrotaline) were subcutaneously injected. Thereafter, the rats were divided into four groups (tested with five animals in each group), and were administrated with 1 mpk of Mock human IgG (Thermo Fisher Scientific, negative control), 1mpk of N3 IgG antibody, 10mpk of N3 IgG antibody, and 25 mpk of sildenafil (positive control) for 3 weeks. All antibodies were i.v. injected twice a week and sildenafil was orally administered every day.

2) Blood Flow and Blood Pressure Measurement

After three weeks, the rats were anesthetized with isoflurane, and blood flow and pressure were measured using an MPVS Cardiovascular Pressure and Volume system (model name: MPVS Ultra, manufacturer: Millar Instruments). The right ventricular end-systolic pressure (RVESP), right ventricular end-diastolic pressure, left ventricular end-systolic pressure, left ventricular end-diastolic pressure were measured using an exclusive catheter (Mikro-Tip rat pressure catheter, manufacturer: Millar Instruments). The cardiac output was measured using a perivascular blood flow probe (Transonic Flow probes, manufacturer: Millar Instruments), and experimental method thereof was performed by the same method as disclosed in the following literature: Pacher P, Nagayama T, Mukhopadhyay P, Batkai S, Kass D A. Measurement of cardiac function using pressure-volume conductance catheter technique in mice and rats. Nat Protoc 2008; 3(9):1422-34.

3) Immunohistochemistry (IHC)

The collected lungs were fixed in PFA (paraformaldehyde) according to a conventional procedure, and then embedded in paraffin through washing, dehydration, and clearing. The paraffin blocks of Rat lung tissue were cut into 3 μm thickness and a slide were manufactured. The sample was first treated with xylene for 5 min three times, treated with 100% ethanol, 95% ethanol, 90% ethanol, and 70% ethanol, and DW in that order for 2 min, and washed with PBS for 5 min. After 0.3% $H_2O_2$ treatment, the sample was washed with PBS for 5 min twice. After soaking in 0.01 M citrate buffer and heated, the sample washed with PBS-T (0.03% tween 20), and then blocking was performed at room temperature for 30 minutes (2% BSA & 2% goat serum in PBS). It was stained overnight at 4° C. with anti-CD68 antibody (1:200, ED1 clone, Abcam). After washing three times with PBS-T for 5 minutes, the sample was treated with a polymer-HRP anti-mouse envision kit (DAKO) for 1 hour at 4° C. After washing three times with PBS-T, the sample was developed by treatment with DAB substrate buffer and DAB chromogen 20. The stained tissue was treated with Mayer's hematoxylin (Sigma) for 1 minute, and then treated twice for 2 minutes in order of 70% ethanol, 90% ethanol, 95% ethanol, and 100% ethanol. Finally, the tissue was treated with xylene three times for 5 min, and then observed under an optical microscope.

Results 6-1. Verification of Blood Pressure and Cardiac Output Changes.

The models of PAH, which is a disease having a close relation between immune cell invasion and pathological phenomena, were treated with N3 IgG antibody (1 mpk or 10 mpk) for 3 weeks (i.v., twice a week), and then measured for right ventricular end-systolic pressure (RVESP), right ventricular end-diastolic pressure (RVEDP), left ventricular end-systolic pressure (LVESP), left ventricular end-diastolic pressure (LVEDP), and cardiac output (CO). The results thereof are shown in Table 3.

to the movement of the interventricular septum and a decrease in the left ventricular end diastolic volume and cardiac output (Lee Woo-seok et al., 2007; 37: 265-270). As a result, pulmonary hypertension is primarily associated with the right ventricle, but also with the function of the left ventricle.

Figure 12:
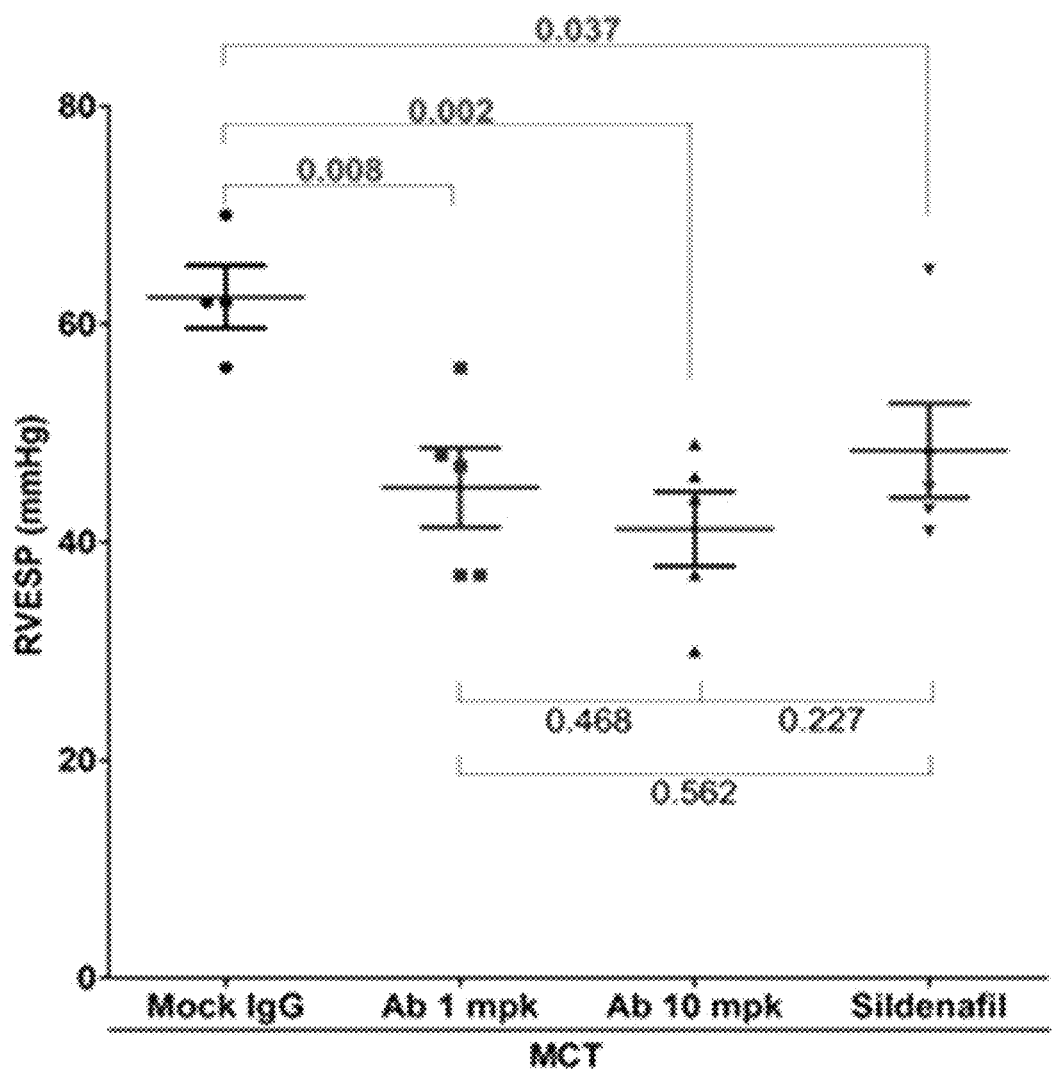
FIG. 12 shows the change of right ventricular end-systolic pressure (RVESP) in the pulmonary arterial hypertension (PAH) models by administration of the N3 antibody of the present invention (Mock IgG: negative control, Ab 1mpk: N3 antibody 1 mpk, Ab 10 mpk: N3 antibody 10 mpk, sildenafil: positive control).

PAH patients showed a RVESP increase, which has also been confirmed in the PAH animal models of this experiment. In contrast, as shown in FIG. 12, N3 antibody (an antibody specifically binding to KRS N-term) significantly reduced RVESP at both concentrations, and especially decreased RVESP better than Sildenafil, a positive control drug.

Figure 13:
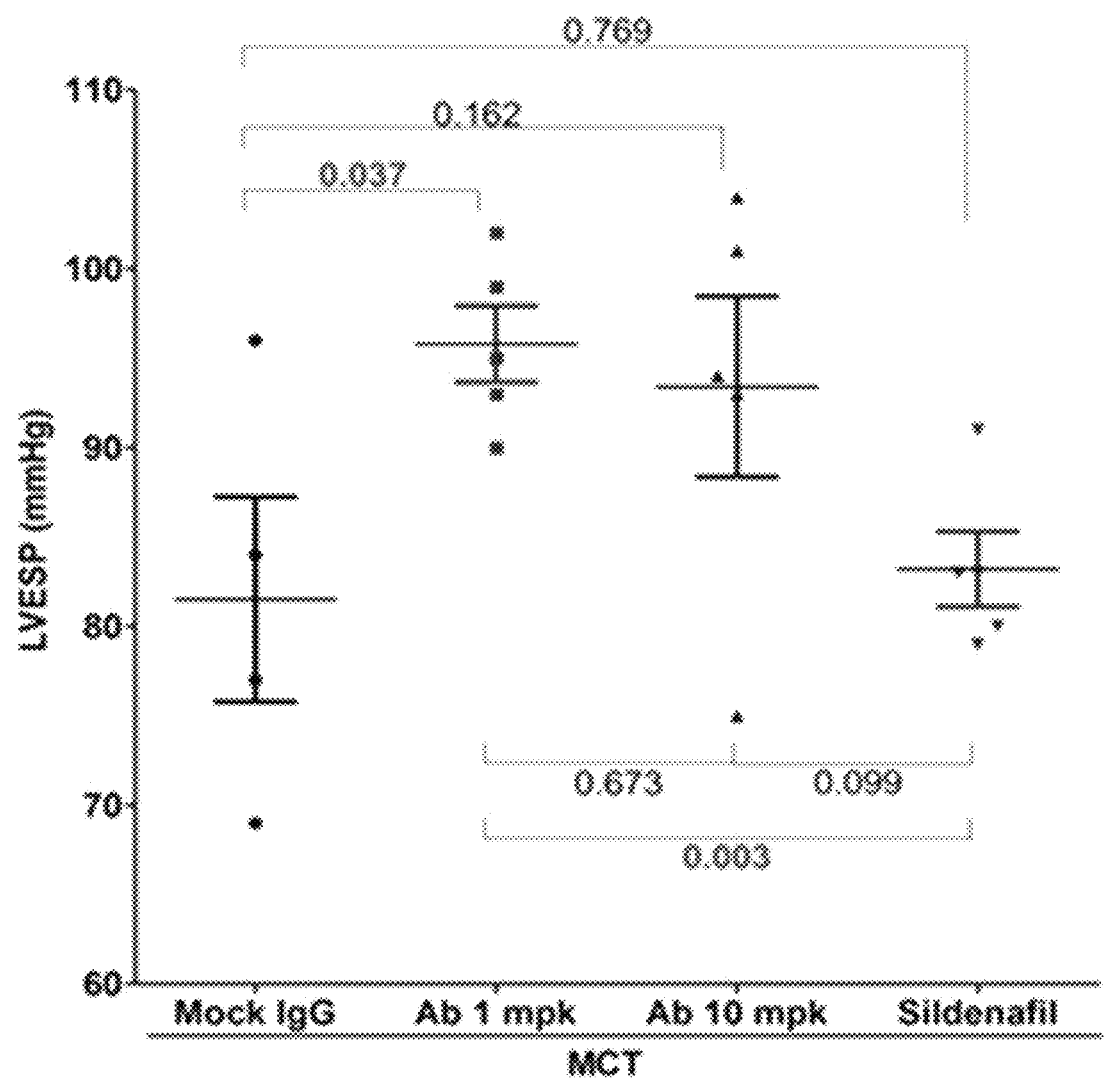
FIG. 13 shows the change of left ventricular end-systolic pressure (LVESP) in pulmonary hypertension (PAH) models by administration of N3 antibody of the present invention (Mock IgG: negative control, Ab 1mpk: N3 antibody 1mpk, Ab 10 mpk: N3 antibody 10 mpk, sildenafil: positive control).

In addition, there was no decrease in the left ventricular end systolic pressure (LVESP) following administration of the N3 antibody (an antibody specifically binding to KRS N-term). Instead, LVESP was significantly increased in the group administered with the antibody of the present invention as shown in FIG. 13. This is in contrast to the risk of lowering the systemic blood pressure by causing the expansion of the pulmonary artery, as well as the expansion of the systemic artery in the case of Sildenafil, which is used as a conventional treatment for pulmonary hypertension. That is, it was confirmed that the antibody of the present invention showed a tendency of having a low effect on systemic artery pressure compared with sildenafil, and this effect is thought to be a favorable characteristic of a therapeutic agent considering that sildenafil administration may be a risk of developing hypotension in clinical sites. Moreover, severe pulmonary arterial hypertension causes systolic RV failure, which may be accompanied by low cardiac output and systemic hypotension. Whereas, a treatment to alleviate pulmonary arterial hypertension by the N3 antibody of the present invention is expected to increase the cardiac output and systemic blood pressure, thereby normalizing the blood pressure.

In summary, it was confirmed that administration of the KRS N-term binding antibody (particularly, N3 antibody) of

TABLE 3

|  | MCT + Mock IgG (n = 4) | MCT + N3 Ab 1 mpk (n = 5) | MCT + N3 Ab 10 mpk (n = 5) | MCT + Sildenafil (n = 5) |
| --- | --- | --- | --- | --- |
| RVESP (mmHg) | 62.5 ± 5.7 | 45.0 ± 8.1 | 41.2 ± 7.7 | 48.4 ± 9.6 |
| RVEDP (mmHg) | 2.8 ± 1.5 | 1.4 ± 2.2 | 3.8 ± 1.3 | 2.6 ± 1.3 |
| LVESP (mmHg) | 81.5 ± 11.4 | 95.8 + 4.8 | 93.4 ± 11.3 | 83.2 ± 4.7 |
| LVEDP (mmHg) | 1.0 ± 0.8 | 2.6 ± 1.9 | 4.6 + 3.9 | 3.6 ± 2.3 |
| CO (ml/min) | 58 ± 4.7 (n = 4) | 74.0 ± 10.9 (n = 5) | 59.8 ± 12.9 (n = 5) | 49.6 ± 17.7 (n = 4) |

(CO was not measured in one animal of MCT+mock IgG group and one animal of sildenafil treatment group, since they died from anesthesia, and during surgery, respectively)

Pulmonary hypertension causes the right ventricular pressure to rise due to narrowing of the pulmonary artery, resulting in right ventricular failure. In addition, if the reward mechanism is destroyed by persistent hypertension, right ventricular enlargement is followed by right ventricular enlargement. This causes the left ventricle compression due the present invention reduced the risk of side effects of existing therapeutic drugs and showed PAH symptom alleviation and treatment effects.

6-2. Echocardiography

The D-shaped left ventricle finding indicating pressure overload in the right ventricle was observed in three animals in the MCT alone administration group (i.e., test substance non-administration PAH models) and three animals in the MCT+sildenafil administration group, but was not observed in the therapeutic antibody administration groups.

In addition, as shown in Table 4 below, the weight of each group was increased to a similar degree, with no significant difference. That is, the findings were not observed to indicate abnormal signs, including abnormal weight reduction, caused by the administration of the therapeutic antibody.

TABLE 4

|  | MCT + Mock IgG (n = 4) | MCT + Ab 1 mpk (n = 5) | MCT + Ab 10 mpk (n = 5) | MCT + Sildenafil (n = 5) |
|---|---|---|---|---|
| Absolute change (g) | 101.4 ± 14.2 | 113.5 ± 14.6 | 104.1 ± 12.3 | 104.1 ± 26.4 |
| Relative change (%) | 48.8 ± 7.8 | 43.6 ± 5.2 | 40.7 ± 5.0 | 49.8 ± 10.5 |

6-3. Verification of Monocyte/Macrophage Migration and Infiltration Degrees

Figure 14:
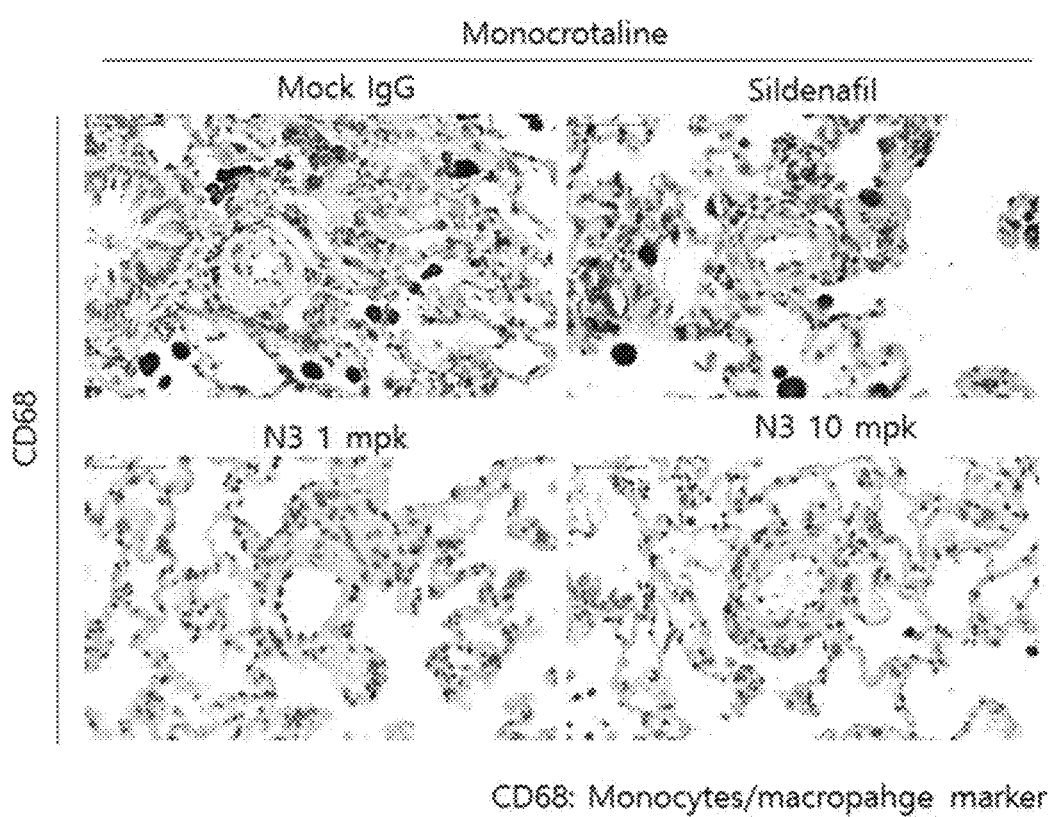
FIG. 14 is a result of confirming by IHC staining that immune cell migration and invasion are reduced by administration of the N3 antibody of the present invention in the pulmonary arterial hypertension (PAH) models.

IHC staining was performed with respect to CD68, which is a monocyte/macrophage marker, by using the lung tissues of each experimental group. As shown in FIG. 14, it was confirmed that the N3 antibody (KRS N-term binding antibody) treatment group of the present invention explicitly reduced the monocyte/macrophage infiltration into lung tissues, and such an effect was significantly excellent than that of sildenafil.

Example 7: Verification of KRS-N Term Specific Binding Antibody Effect on Immune Cell Migration-Related Diseases In Vivo Models Acute Lung Injury Models Methods
1) Construction of LPS-Induced Acute Lung Injury Models and Administration of Test Substance Mouse models of acute lung injury were constructed by intratracheal injection of 2.5 mg/kg LPS (Sigma) into 7-week-old male C57BL/6 mice (duothermal bio). To investigate the effects of KRS inhibitors on acute lung injury, first, the intravenous injection of N3 IgG antibody to C57BL/6 mice was performed at 1 mg/kg or 10 mg/kg, respectively, followed by endotracheal injection of 2.5 mg/kg of LPS after 24 hours. Twenty-four hours after the LPS injection, each mouse was sacrificed to collect and analyze lung tissue and BALF (Bronchoalveolar lavage fluid).
2) Immune Cell Count in Bronchoalveolar Lavage Fluid (BALF)

BALF obtained by washing the lungs with PBS was collected and pellets were collected by centrifugation at 800×g for 10 minutes at 4° C. After the cells were suspended, red blood cells were removed using RBC lysis buffer (eBioscience cat. no. 00-4333-57). After stopping the reaction with PBS, washed twice, and suspended in 400 µl PBS to measure the number of cells by hemocytometer and neutrophil number through Hema3 staining.
3) FACS on Immune Cells in Lung Tissue Lung tissues were collected and rotated for 45 min at 37° C. using gentleMACS Octo Dissociator (MACS Miltenyi Biotec, Order no. 130-095-937) to crush tissue. After filtering using a cell strainer (40 µm) was centrifuged at room temperature for 5 minutes at 1500 rpm. The pellet was collected and red blood cells were removed using RBC lysis buffer (eBioscience cat. no. 00-4333-57). The cells were collected and suspended in FACS buffer (PBS containing 1% NaN3 and 3% FBS), 50 µl were placed in a tube, mixed well with the same amount of antibody mxiture, and stained by blocking light at 4° C. for 1 hour. FITC Rat Anti-CD11 b (BD Pharmingen) and PE Rat Anti-Mouse F4/80 (BD Pharmingen) antibodies were used for analysis of interstitial macrophage (IM) moving to the lungs. After washing twice at 400×g for 5 minutes using FACS buffer, it was analyzed by Navios Flow Cytometer (Beckman).
4) Masson's Trichrome Staining for Lung Tissue Lung tissue was embedded in paraffin in the original manner and then cut out. Thereafter, the tissue slide from which paraffin was removed using xylene was washed with DW, and then treated with Bouin Fluid at 56-60° C. for 1 hour. After stained with Weigert's iron hematoxylin solution for 10 minutes, the tissue slide was washed. After stained again with Biebrich scarlet-acid fuchsin solution for 10-15 minutes, the silde was washed. Phosphomolybdic-phosphotungstic acid solution was treated to the slide for 10-15 minutes, and then the slide was transferred to aniline blue solution and stained for 5-10 minutes. After washing, the slide was treated with 1% acetic acid solution for 2-5 minutes. After washing and dehydration, the slide was treated with xylene and mounted.
Results
7-1. Verification of the Inhibitory Effect on Immune Cell Migration in Bronchoalveolar Lavage Fluid (BALF)

Figure 15:
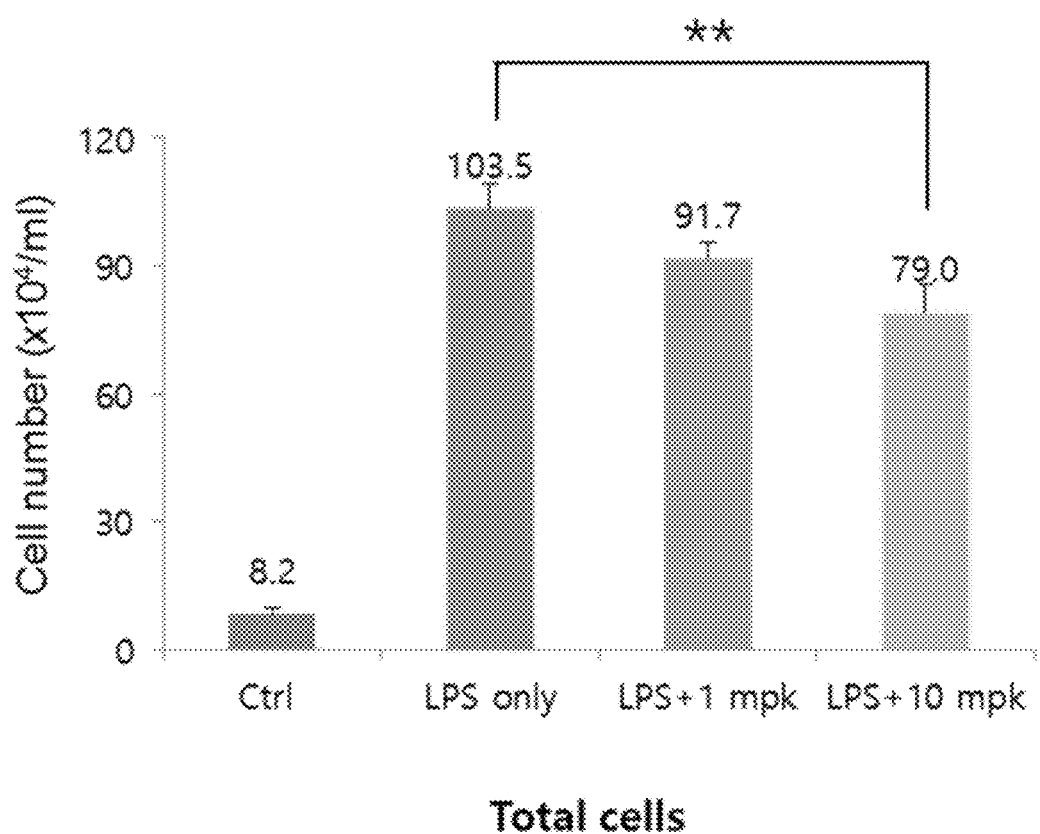
FIG. 15 shows the result of confirming that the total number of immune cells increased in the BALF (Bronchoalveolar lavage fluid) in the mouse models of acute lung injury were reduced depending on the treatment concentration of N3 antibody (antibody binding to the N-terminus of KRS).
Figure 16:
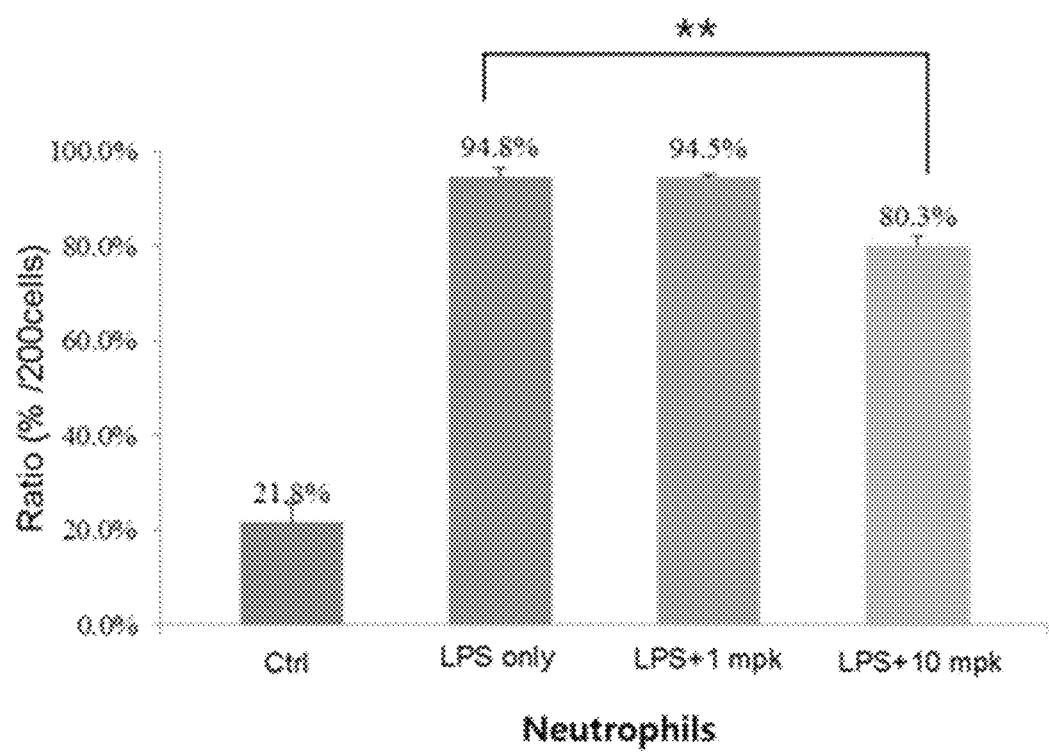
FIG. 16 shows the result of confirming that neutrophils which are particularly increased in bronchoalveolar lavage fluid (BALF) of the mouse models of acute lung injury were reduced depending on the treatment concentration of N3 antibody (antibody binding to the N-terminus of KRS).
Figure 17:
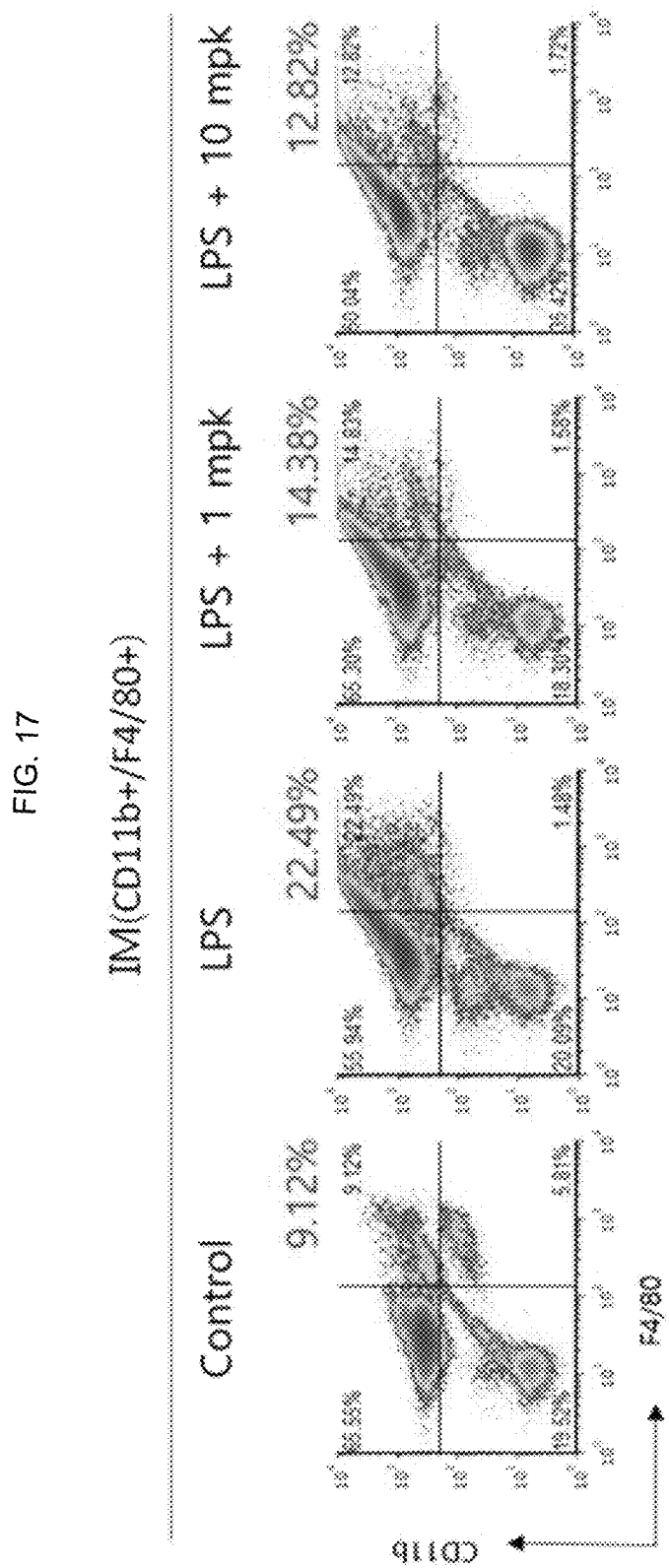
FIG. 17 shows the results of confirming by FACS that increased macrophage (IM, CD11b+/F4/80+) migration and invasion in the lung tissue of the mouse models of acute lung injury was reduced depending on the treatment concentration of N3 antibody (antibody binding to the N-terminus of KRS).
Figure 18:
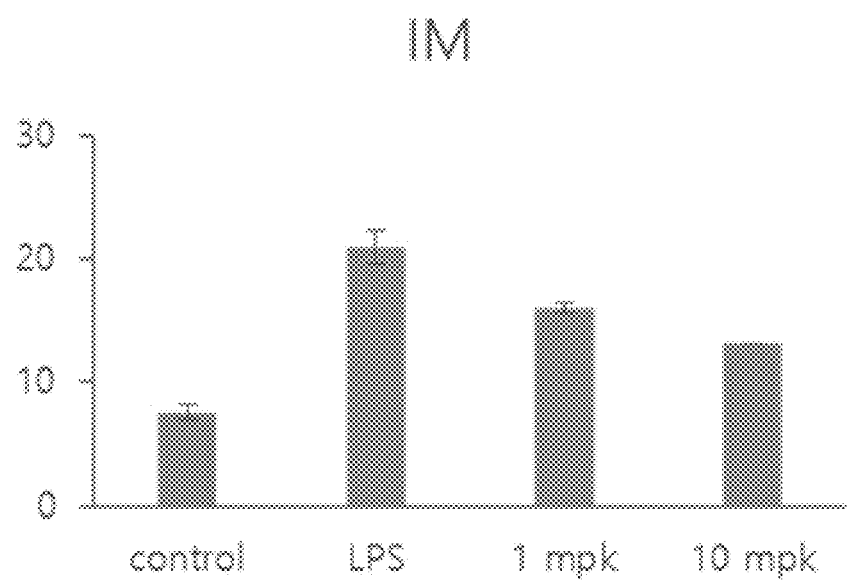
FIG. 18 is a graph quantifying the results of FIG. 17.
Figure 19:
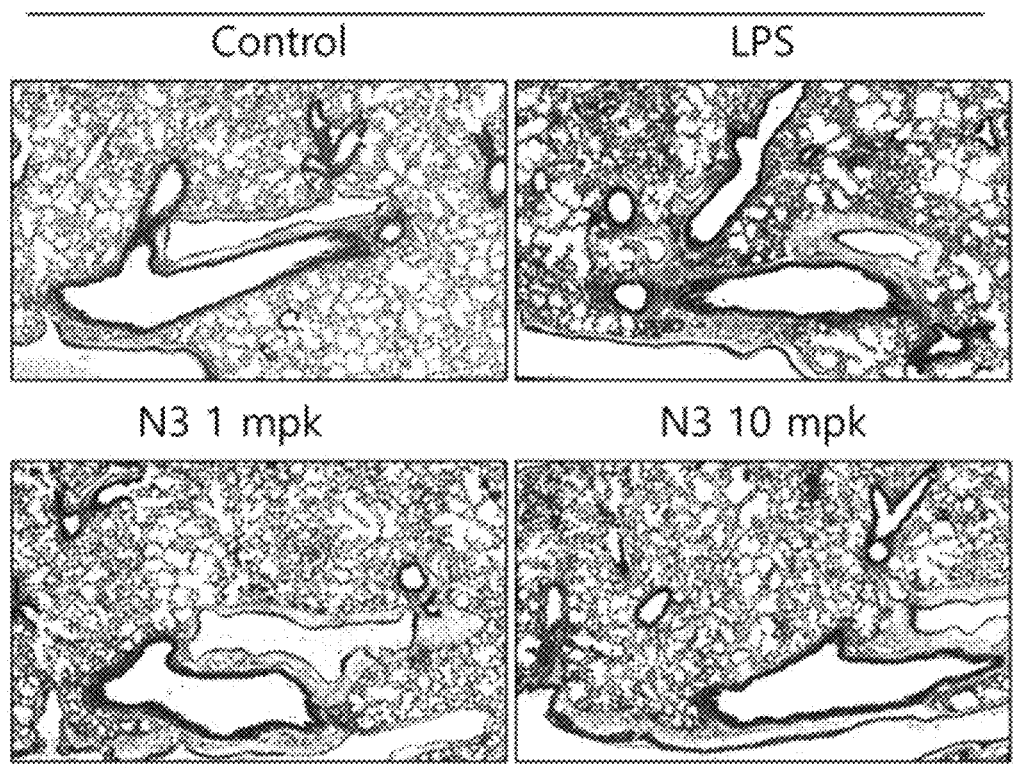
FIG. 19 is a tissue image showing that the tissue fibrosis advanced in lung tissue of the mouse models of acute lung injury mouse models is inhibited by treatment with an N3 antibody (KRS N-terminal binding antibody). Tissues of each experimental group and control group were observed under a microscope after Masson's trichrome staining.

As shown in FIG. 15, it was confirmed that the total number of immune cells in BALF was increased in mice induced by acute lung injury by LPS treatment, which was concentration-dependently reduced by N3 antibody (KRS N-term binding antibody) treatment. In particular, as shown in FIG. 16, it was confirmed that neutrophils were increased in mice with acute lung injury by LPS treatment, and N3 antibody (KRS N-term binding antibody) treatment reduced these neutrophil levels. As a result, it was confirmed that infiltratration of immune cells, particularly neutrophils, into lungs of BALF was significantly inhibited by treating the antibody specifically binding to KRS N-term.
7-2. Verification of the Antibody Inhibitory Effect on Immune Cell Migration in Lung Tissue FIGS. 17 and 18 showed the results of FACS analysis of macrophages migrated to lung tissue due to acute lung injury. Interstitial macrophage (IM) is CD11 b+/F4/80+ cells, which are migrating macrophages that do not reside in the lung but migrate to the lung in certain situations. LPS treatment increased the infiltration of IM into the lung, but N3 antibody treatment reduced the migration of IM to the lung in a concentration dependent manner. Through this, it was confirmed that the migration and invasion of immune cells such as macrophages/monocytes into lung tissues was inhibited by the treatment of antibodies (typically, N3 antibody) that specifically bind to KRS N-term. The excessive migration and invasion of immune cells, such as macrophages/monocytes, is an important pathological phenomenon in tissue fibrotic disease. As a result of observation of Masson's trichrome staining of lung tissue with respect to the acute lung injury model (FIG. 19), it was confirmed that fibrosis in the lung tissue proceeded considerably. In contrast, it was confirmed that the treatment of the N3 antibody (an antibody that specifically binds to KRS N-term) inhibited such fibrosis.

Example 8: Construction of N3 Modified Antibody with Increased Affinity for the N-Terminus of KRS The present inventors attempted to obtain an antibody having better affinity for the N-terminal region of KRS by modifying the N3 antibody in order to produce an antibody that shows better performance as a therapeutic antibody. Therefore, the light chain variable region and heavy chain variable region of the N3 antibody were improved by the following series of processes.

8-1. Construction of the scFab Library in N3 Antibody-Based Sequence Variants (Yeast Cell Surface Expression Library)_Primary Library Using the Homology modeling method, the rough structure of the N3 antibody was predicted, and through this, a random mutation was introduced into a CDR region predicted to play an important role in antigen binding to construct a library. Specifically, in the library based on the heavy chain variable region, NNK, which is a degenerated codon that can include all 20 amino acid sequences for residues in the heavy chain CDR2 or CDR3, was used. In the light chain variable region library, NNK, a degenerated codon that can contain all 20 amino acid sequences for residues in the light chain CDR2 or CDR3 of the N3 antibody, was used. The DNA encoding the designed library was amplified using a PCR technique, and then concentrated using an ethanol precipitation method.

Thereafter, a scFab library expressed on surface of yeast containing various variations of the light chain variable region was constructed with reference to the method described in the following literature: Baek D S and Kim Y S, Construction of a large synthetic human Fab antibody library on yeast cell surface by optimized yeast mating, J Microbiol Biotechnol. 2014 Mar. 28; 24(3):408-20.

Briefly, yeast surface expression vectors (C-aga2: pYDS) expressing aga2 protein at the C-terminus for homologous recombination were treated with NheI and MluI restriction enzymes, purified using agarose gel extraction, and concentrated using ethanol precipitation method.

A 4 μg of vector treated with the restriction enzyme in 12 μg of each library-coding DNA was transformed by electroporation into yeast EBY100 (yeast for surface expression), and the library size was confirmed by measuring the number of colonies grown in the selection medium, SD-CAA (20 g/L Glucose, 6.7 g/L Yeast nitrogen base without amino acids, 5.4 g/L $Na_2HPO_4$, 8.6 g/L $NaH_2PO_4$, 5 g/L casamino acids) through serial dilution.

8-2. Screening scFab with Improved Affinity for KRS (Residues 1-72 Aa) Peptide First Library Selection Fabs with increased affinity were selected for the library constructed in the Example 8-1 using GST-conjugated KRS (residues 1-72 aa, N-term) peptide as an antigen.

Specifically, 10 nM of GST-conjugated KRS peptide (residues 1-72 aa, purified state) using SG-CAA medium (20 g/L Galactose, 6.7 g/L Yeast nitrogen base without amino acids, 5.4 g/L $Na_2HPO_4$, 8.6 g/L $NaH_2PO_4$, 5 g/L casamino acids) for primary FACS screening was reacted with yeast inducing scFab library expression on the cell surface in Example 8-1 for 1 hour at room temperature. Thereafter, GST-conjugated KRS (residues 1-72) peptide and yeast expressing the library were reacted with PE-conjugated Streptavidin-R-phycoerythrin conjugate (SA-PE) at 4° C. for 20 minutes and were suspended by FACS (Fluorescence activated cell sorting, FACS Caliber; BD biosciences). Subsequently, a second FACS screening was performed with KRS (residues 1-72) peptide conjugated with 1 nM GST, and a third FACS screening was performed with KRS (residues 1-72) peptide conjugated with 0.5 nM GST.

Through the selection process using the FACS, clones with high affinity for the KRS (residues 1-72) peptide were selected compared to the N3 antibody. In this way, three excellent clones (N3-1, N3-3, N3-4) having high affinity and specificity for KRS (residues 1-72) peptide were selected through analysis of binding ability for individual clones, and another light chain variable region and heavy chain variable region were combined with each other to construct another unique clone N3-5. The N3-5 clone was also confirmed to have excellent affinity and specificity for the KRS (residues 1-72) peptide, and finally a total of four unique (magnetic activated cell sorting) clones, N3-1, N3-3, N3-4, and N3-5, was selected.

The CDR sequences of the light chain variable region and the heavy chain variable region of four individual clones, N3-1, N3-3, N3-4, and N3-5, showing high binding ability to the KRS (residues 1-72) peptide were shown in Table 5, and Table 6 showed the full sequences of heavy chain variable region and light chain variable region.

TABLE 5

| | Heavy | | | Light | | |
|---|---|---|---|---|---|---|
| | CDR H1 | CDR H2 | CDR H3 | CDR L1 | CDR L2 | CDR L3 |
| N3 | SYDMS (SEQ ID NO: 1) | AISYDNGNTYYADSV KG (SEQ ID NO: 3) | MALDFDY (SEQ ID NO: 5) | TGSSSNIGSNYVT (SEQ ID NO: 7) | DNSNRPS (SEQ ID NO: 9) | ASWDDSLSAYV (SEQ ID NO: 11) |
| N3-1 | SYDMS (SEQ ID NO: 1) | AISYDNGNTYYADSV KG (SEQ ID NO: 3) | MALDFDY (SEQ ID NO: 5) | TGSSSNIGSNYVT (SEQ ID NO: 7 | DNSNRPS (SEQ ID NO: 9) | ASFSDELGAYV (SEQ ID NO: 13) |
| N-3 | SYDMS (SEQ ID NO: 1) | AISYDNGNTYYADSV KG (SEQ ID NO: 3) | MALDFDY (SEQ ID NO: 5) | TGSSSNIGSNYVT (SEQ ID NO: 7) | DNSNRPS (SEQ ID NO: 9) | SSFSDELGAYV (SEQ ID NO: 15) |
| N3-4 | SYDMS (SEQ ID NO: 1) | VISSDGGNTYYADSV KG (SEQ ID NO: 151) | MALDFDY (SEQ ID NO: 5) | TGSSSNIGSNYVT (SEQ ID NO: 7) | DNSNRPS (SEQ ID NO: 9) | ASFSDELGAYV (SEQ ID NO: 13) |
| N3-5 | SYDMS (SEQ ID NO: 1) | VISSDGGNTYYADSV KG (SEQ ID NO: 151) | MALDFDY (SEQ ID NO: 5) | TGSSSNIGSNYVT (SEQ ID NO: 7) | DNSNRPS (SEQ ID NO: 9) | SSFSDELGAYV (SEQ ID NO: 15) |

TABLE 6

| | | Sequence | SEQ ID NO: (Sequence name) |
|---|---|---|---|
| N3 | VH | EVQLLESGGGLVQPGGSLRLSCAASGFTFSSYDMSWVRQA PGKGIEWVSAISYDNGNTYYADSVKGRFTISRDNSKNTLY LQMNSLRAEDTAVYYSARMALDFDYWGQGTLVTVSS | SEQ ID NO: 31 (N3 VH) |
| | VL | QSVLTQPPSASGTPGQRVTISCTGSSSNIGSNYVTWYQQL PGTAPKLLIYDNSNRPSGVPDRFSGSKSGTSASLAISGLR SEDEADYYCASWDDSLSAYVFGGGTKLTVL | SEQ ID NO: 33 (N3 VL) |
| N3-1 | VH | EVQLLESGGGLVQPGGSLRLSCAASGFTFSSYDMSWVRQA PGKGLEWVSAISYDNGNTYYADSVKGRFTISRDNSKNTLY LQMNSLRAEDTAVYYSARMALDFDYWGQGTLVTVSS | SEQ ID NO: 31 (N3 VH) |
| | VL | QSVLTQPPSASGTPGQRVTISCTGSSSNIGSNYVTWYQQL PGTAPKLLIYDNSNRPSGVPDRFSGSKSGTSASLAISGLQ SEDEADYYCASFSDELGAYVFGGGTKLTVL | SEQ ID NO: 49 (N3 VL mutant 1) |
| N3-3 | VH | EVQLLESGGGLVQPGGSLRLSCAASGFTFSSYDMSWVRQA PGKGLEWVSAISYDNGNTYYADSVKGRFTISRDNSKNILY LQMNSLRAEDTAVYYSARMALDFDYWGQGTLVTVSS | SEQ ID NO: 31 (N3 VH) |
| | VL | QSVLTQPPSASGTPGQRVTISCTGSSSNIGSNYVTWYQQL PGTAPKLLIYDNSNRPSGVPDRFSGSKEGTSASLAISGLQ SEDEADYYCSSFSDELGAYVFGGGTKLTVL | SEQ ID NO: 51 (N3 VL mutant 2) |
| N3-4 | VH | EVQLLESGGGLVQPGGSLRLSCAASGFTFSSYDMSWVRQA PGKGLEWVSVISSDGGNTYYADSVKGRFTISRDNSKNTLY LQMNSLRAEDTAVYYSARMALDFDYWGQGTLVTVSS | SEQ ID NO: 35 (N3 VH mutant 1) |
| | VL | QSVITQPPSASGTPGQRVTISCTGSSSNIGSNYVTWYQQL PGTAPKLLIYDNSNRPSGVPDRFSGSKSGTSASLAISGLQ SEDEADYYCASFSDELGAYVFGGGTKLTVL | SEQ ID NO: 49 (N3 VL mutant 1) |
| N3-5 | VH | EVQLLESGGGLVQPGGSLRLSCAASGFTFSSYDMSWVRQA PGKGLEWVSVISSDGGNTYYADSVKGRFTISRDNSKNTLY LQMNSLRAEDTAVYYSARMALDFDYWGQGTIVTVSS | SEQ ID NO: 35 (N3 VH mutant 1) |
| | VL | QSVLTQPPSASGTPGQRVTISCTGSSSNIGSNYVTWYQQL PGTAPKLLIYDNSNRPSGVPDRFSGSKSGTSASLAISGLQ SEDEADYYCSSFSDELGAYVFGGGTKLTVL | SEQ ID NO: 51 (N3 VL mutant 2) |

In addition, the affinity of the selected individual clones, N3-1, N3-3, N3-4, and N3-5, for the KRS N-terminus was reconfirmed using the ELISA method. In this experiment, the clones converted to IgG antibody were tested. The conversion to an IgG antibody refers to the method of Example 5-1 above.

Specifically, the N-terminal region (residues 1-72) peptide of KRS was treated in a 96-well EIA/RIA plate (COSTAR Corning) and bound at 25° C. for 1 hour, followed by washing 3 times with PBS (pH 7.4, 137 mM NaCl, 12 mM phosphate, 2.7 mM KCl) (SIGMA) for 10 minutes. Thereafter, 4% BSA PBS (4% Bovine Serum Albumin, pH7.4, 137 mM NaCl, 12 mM phosphate, 2.7 mM KCl) (SIGMA) was treated for 1 hour, and then washed 3 times with PBS for 10 minutes. Then, the N3 antibody, N3-1 antibody, N3-3 antibody, N3-4 antibody, and N3-5 antibody of IgG-type were treated and bound, respectively, and then washed three times with 0.1% PBST for 10 minutes. As a labeled antibody, Horseradish peroxidase-conjugated anti-human mAb (SIGMA) was used. Then, it was reacted with TMB (3,3′,5,5′-Tetramethylbenzidine) (Sigma) and measured at 450 nm absorbance to quantify.

Figure 20:
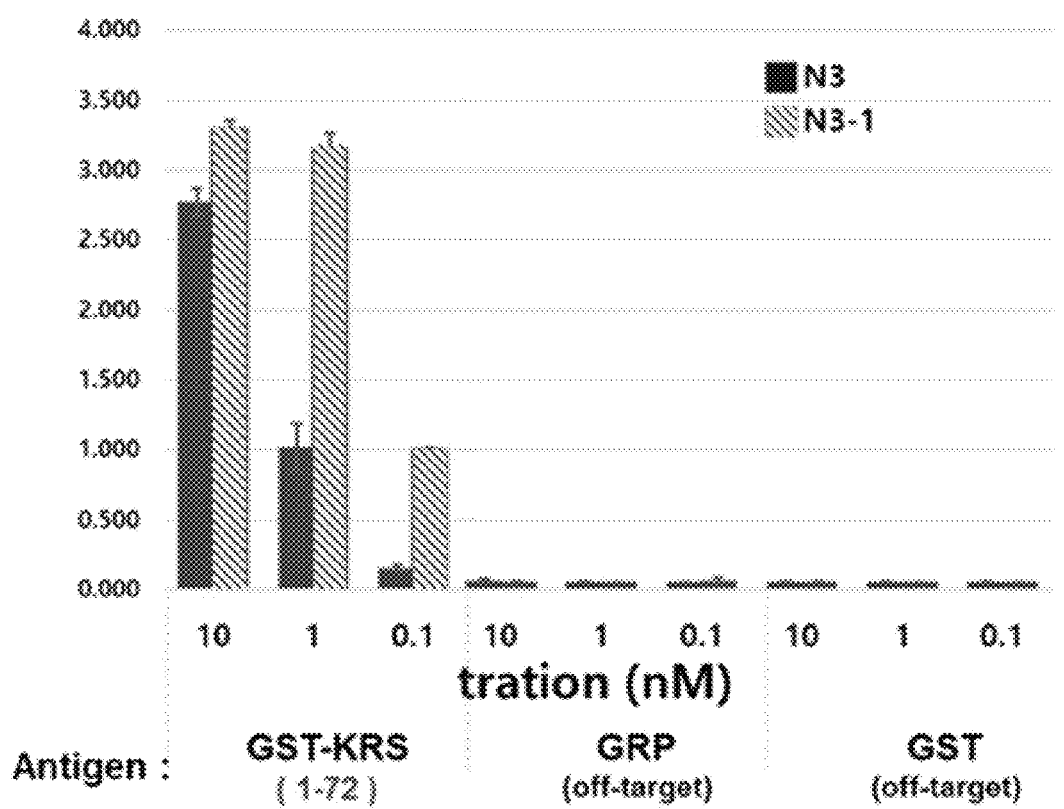
FIG. 20 shows ELISA results for measuring affinity for the N-terminus of KRS of the N3-1 antibody which is an improved antibody selected as having high affinity and specificity for the peptide of KRS N-term (residues 1-72) and N3 antibody as a control.
Figure 21:
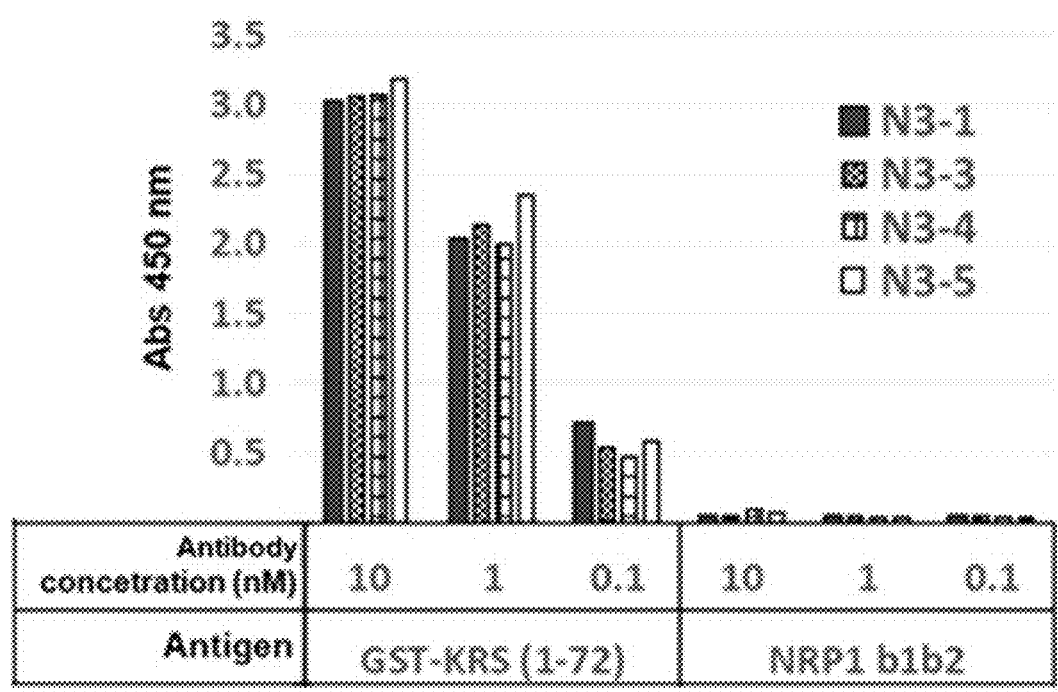
FIG. 21 shows ELISA results for measuring affinity for the N-terminus of KRS of the N3-1 antibody, N3-3 antibody, N3-4 antibody and N3-5 antibody selected as having high affinity and specificity for the peptide of KRS N-term (residues 1-72).

As a result, as shown in FIGS. 20 and 21, it was confirmed that the affinity of the N3-1, N3-3, N3-4, and N3-5 antibodies as improved antibodies was significantly increased compared to the N3 antibody. It was found that all clones did not bind to GST or NRP1-b1 b2 used as a negative control. There was no significant difference in the KRS binding ability within the mutant antibodies N3-1, N3-3, N3-4, and N3-5 (see FIG. 21).

8-3. Comparison of Affinity Between N3 Antibody and Primary Improved Antibody and Verification of their Inhibitory Effect on Cell Migration There was no significant difference in binding ability between KRS and the improved antibodies, N3-1, N3-3, N3-4, and N3-5. Thus, using the representative N3-1 IgG antibody among the improved antibodies selected in the Example 8-2, the affinity of the parent antibody, N3 antibody and KRS N-terminus was more specifically compared. Using KRS fragment (1-207 aa) purified protein as an antigen, the binding ability between N3 antibody and N3-1 antibody (IgG) was analyzed through Surface Plasmon Resonance (SPR). The SPR experiment was performed using a Biacore T200 (GE Healthcare) equipped with a Series S sensor chip CM5 (GE Healthcare) at 25° C. After the antibody was immobilized on the chip using an amine coupling kit (GE Healthcare), the antigen was diluted 4 times in PBS solution in the range of 4.8 nM-1250 nM and flowed for 60 seconds. Thereafter, PBS was flowed for 300 seconds. The obtained data was analyzed with Biacore T200 Evaluation software v2.0 (GE Healthcare).

Figure 22:
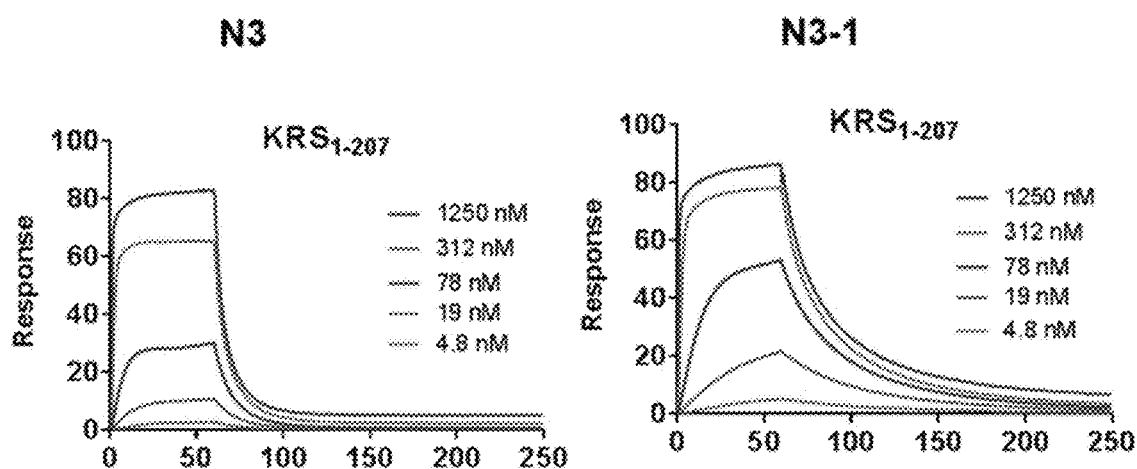
FIG. 22 shows the result of comparing the affinity for KRS of N3 antibody and N3-1 antibody by SPR (surface plasmon resonance) method.

As a result, as shown in FIG. 22, the KD value of the N3-1 antibody was measured to be 31 nM, indicating that the binding ability to the KRS protein was increased compared to the N3 antibody. In addition, the result of the inhibitory effect on cell migration by treating the antibody (refer to the above-described Examples) was confirmed that the N3-1 antibody significantly inhibited cell migration compared to the N3 antibody. 8-4. Construction of the scFab Library in N3 antibody-based sequence variants (Yeast cell surface expression library)_Secondary library The N3-1, N3-3, N3-4, and N3-5 antibodies targeting the KRS N-terminus derived in the Example 8-2 have similar affinity to KRS, and as shown in the result of the N3-1 antibody in the Example 8-3, it was determined to have an affinity of about 31 nM. In order to obtain more effective antibodies by increasing their affinity for KRS (particularly the N-term region), the heavy chain variable region was intensively improved.

The light chain variable region sequence was fixed with the sequence of the N3-3 antibody (SEQ ID NO: 51), and a library was constructed with various variable sequences in the heavy chain variable region. First, the homology modeling method was used to predict the approximate modeling structure of the N3-3 antibody, and through this, a random mutation was introduced into the CDR predicted to play an important role in antigen binding. Specifically, NNK, a degenerated codon capable of containing all 20 amino acid sequences, was used for the residues of CDR2 and CDR3 of the heavy chain variable region in the N3-3 antibody, and the scFab library was constructed in the same manner as in the Example 8-1.

8-5. Screening ScFab with improved affinity for KRS (residues 1-72) Secondary library screening Using the GST-conjugated KRS (residues 1-72) peptide as an antigen, Fabs with increased affinity were selected in the library constructed in the Example 8-4. Since the affinity of N3-3 and N3-1 was determined to be almost the same and the sequences were almost similar, the comparative experiment was performed with N3-1.

First, GTP-conjugated KRS (residues 1-72) peptide was treated with the library-expressing yeast constructed in the Example 8-4. Subsequently, the yeast expressing the library bound with the GTP-conjugated KRS (resides 1-72) peptide was reacted with Streptavidin Microbead™ (Miltenyi Biotec) at 4° C. for 20 minutes, and yeast expressing scFab having high affinity to the KRS (1-72 aa) peptide was suspended using magnetic activated cell sorting (MACS). The yeast expressing the library selected through the MACS was cultured in SG-CAA (20 g/L Galactose, 6.7 g/L Yeast nitrogen base without amino acids, 5.4 g/L Na$_2$HPO$_4$, 8.6 g/L NaH$_2$PO$_4$, 5 g/L casamino acids) medium to induce library expression. Subsequently, in the same manner as in the Example 8-2, sequential screening was performed using FACS. Briefly, the primary FACS screening was performed with KRS (1-72) peptide bound with 10 nM GST, the secondary FACS screening with KRS (1-72) peptide bound with 1 nM GST, the third FACS screening was performed with the KRS (1-72) peptide bound with 0.5 nM GST, and the forth FACS screening was performed with the KRS (1-72) peptide bound with 0.1 nM GST.

Through the screening process using the magnetic activated cell sorting (MACS) and Fluorescence Activated Cell Sorting (FACS), clones with high affinity dependent on the heavy chain variable region (VH) for the KRS (1-72 aa) peptide compared to the N3-1 antibody (showing similar affinity to N3-3 antibody) were selected. In this way, four excellent clones, N3-6, N3-7, N3-8, and N3-9, with high affinity and specificity for KRS (residues 1-72) peptide were selected through binding ability analysis for individual clones.

The CDR sequences of the light chain variable region and heavy chain variable region of four individual clones, N3-6, N3-7, N3-8, and N3-9, which show high binding ability to the KRS (1-72 aa) peptide, were shown in Table 7, and Table 8 showed the full sequences of heavy chain variable region sequence and light chain variable region.

TABLE 7

|  | Heavy | | | Light | | |
| --- | --- | --- | --- | --- | --- | --- |
|  | CDR H1 | CDR H2 | CDR H3 | CDR L1 | CDR L2 | CDR L3 |
| N3-6 | SYDMS (SEQ ID NO: 1) | AISPQMGRVYYADSVKG (SEQ ID NO: 17) | MALDFDY (SEQ ID NO: 5) | TGSSSNIGSNYVT (SEQ ID NO: 7) | DNSNRPS (SEQ ID NO: 9) | SSFSDELGAYV (SEQ ID NO: 15) |
| N3-7 | SYDMS (SEQ ID NO: 1) | AIDPLGGNIYYADSVKG (SEQ ID NO: 19) | MALDFDY (SEQ ID NO: 5) | TGSSSNIGSNYVT (SEQ ID NO: 7) | DNSNRPS (SEQ ID NO: 9) | SSFSDELGAYV (SEQ ID NO: 15) |
| N3-8 | SYDMS (SEQ ID NO: 1) | AISPYSGRIYYADSVKG (SEQ ID NO: 21) | MALDFDY (SEQ ID NO: 5) | TGSSSNIGSNYVT (SEQ ID NO: 7) | DNSNRPS (SEQ ID NO: 9) | SSFSDELGAYV (SEQ ID NO: 15) |
| N3-9 | SYDMS (SEQ ID NO: 1) | AIGADGGPSYYADSVKG (SEQ ID NO: 23) | MALDFDY (SEQ ID NO: 5) | TGSSSNIGSNYVT (SEQ ID NO: 7) | DNSNRPS (SEQ ID NO: 9) | SSFSDELGAYV (SEQ ID NO: 15) |

TABLE 8

|  | Sequence | SEQ ID NO: (Sequence name) |
| --- | --- | --- |
| N3-6 VH | EVQLLESGGGLVQPGGSLRLSCAASGFTFSSYDMSWVRQAPGKGLEWVSAISPQMGRVYYADSVKGRFTISRDNSKNTLYLQMNSLRAEDTAVYYSARMALDFDYWGQGTLVTVSS | SEQ ID NO: 37 (N3 VH mutant 2) |

TABLE 8-continued

| | Sequence | SEQ ID NO: (Sequence name) |
|---|---|---|
| VL | QSVLTQPPSASGTPGQRVTISCTGSSSNIGSNYVTWYQ QLPGTAPKLLIYDNSNRPSGVPDRFSGSKSGTSASLAI SGLQSEDEADYYCSSFSDELGAYVFGGGTKLTVL | SEQ ID NO: 51 (N3 VL mutant 2) |
| N3-7 VH | EVQLLESGGGLVQPGGSLRLSCAASGFTFSSYDMSWVR QAPGKGLEWVSAIDPLGGNIYYADSVKGRFTISRDNSK NTLYLQMNSLRAEDTAVYYSARMALDFDYWGQGTLVTV SS | SEQ ID NO: 39 (N3 VH mutant 3) |
| VL | QSVLTQPPSASGTPGQRVTISCTGSSSNIGSNYVTWYQ QLPGTAPKLLIYDNSNRPSGVPDRFSGSKSGTSASLAI SGLQSEDEADYYCSSFSDELGAYVFGGGTKLTVL | SEQ ID NO: 51 (N3 VL mutant 2) |
| N3-8 VH | EVQLLESGGGLVQPGGSLRLSCAASGFTFSSYDMSWVR QAPGKGLEWVSAISPYSGRIYYADSVKGRFTISRDNSK NTLYLQMNSLRAEDTAVYYSARMALDFDYWGQGTLVTV SS | SEQ ID NO: 41 (N3 VH mutant 4) |
| VL | QSVLTQPPSASGTPGQRVTISCTGSSSNIGSNYVTWYQ QLPGTAPKLLIYDNSNRPSGVPDRFSGSKSGTSASLAI SGLQSEDEADYYCSSFSDELGAYVFGGGTKLTVL | SEQ ID NO: 51 (N3 VL mutant 2) |
| N3-9 VH | EVQLLESGGGLVQPGGSLRLSCAASGFTFSSYDMSWVR QAPGKGLEWVSAIGADGGPSYYADSVKGRFTISRDNSK NTLYLQMNSLRAEDTAVYYSARMALDFDYWGQGTLVTV SS | SEQ ID NO: 43 (N3 VH mutant 5) |
| VL | QSVLTQPPSASGTPGQRVTISCTGSSSNIGSNYVTWYQ QLPGTAPKLLIYDNSNRPSGVPDRFSGSKSGTSASLAI SGLQSEDEADYYCSSFSDELGAYVFGGGTKLTVL | SEQ ID NO: 51 (N3 VL mutant 2) |

In addition, the affinity of the selected individual clones, N3-6, N3-7, N3-8, and N3-9, for the KRS N-terminus was reconfirmed using the ELISA method. After converting the clones to IgG antibodies in this experiment, they were used in ELISA experiments, and the method is referred to the Example 5-1 above.

Figure 23:
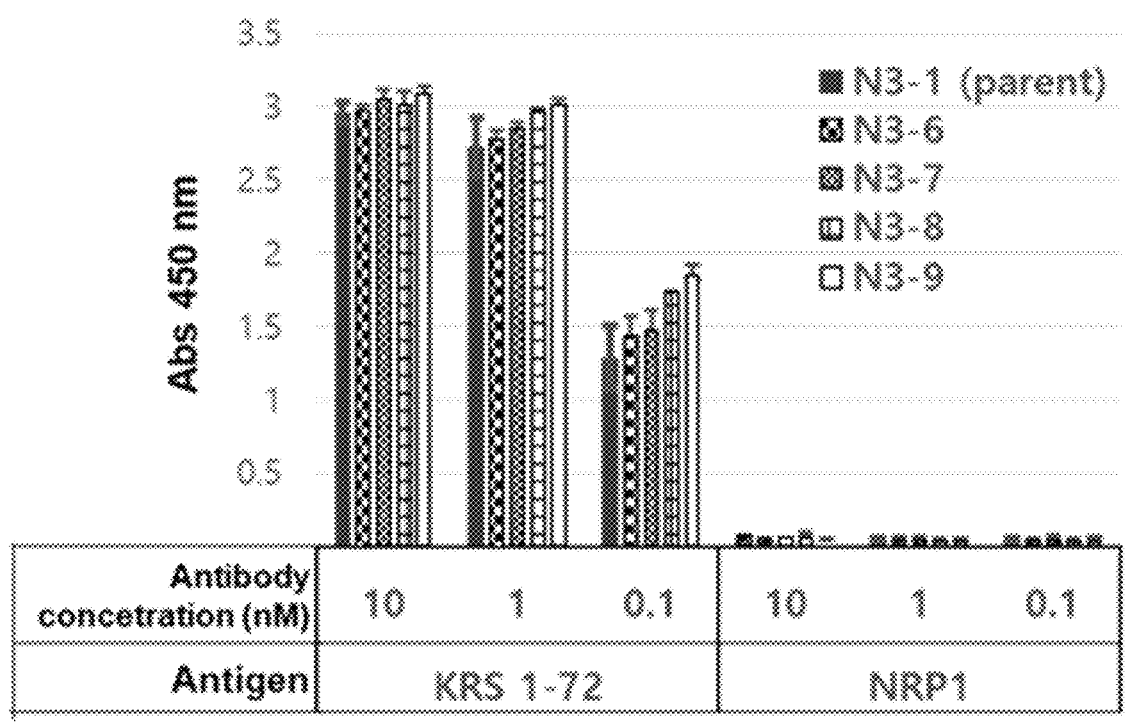
FIG. 23 shows the ELISA results for measuring the affinity of the N3-1 antibody, N3-6 antibody, N3-7 antibody, N3-8 antibody and N3-9 antibody for the N-terminus of KRS.

As a result, as shown in FIG. 23, it was confirmed that the affinity of the improved antibodies, N3-6, N3-7, N3-8, and N3-9, compared to N3-1 antibody (similar to N3-3) was increased. For NRP1-b1 b2 used as a negative control, it was found that no clones were bound.

In addition, the result of inhibitory effects on cell migration by treating N3-6 antibody, N3-7 antibody, N3-8 antibody, and N3-9 antibody (IgG) as improved antibodies (see the above-described Examples for methods) was confirmed that the improved antibodies significantly inhibit cell migration than the N3-1 antibody. There was no significant difference in the inhibitory effect of cell migration among N3-6 antibody, N3-7 antibody, N3-8 antibody, and N3-9 antibody.

8-6. Verification of Epitopes and Affinity of Improved Antibodies N3-6, N3-7, N3-8, and N3-9

Using KRS epitope peptide F4 (EPKLSKNELKRRL-KAEKKVAEKEAKQKE: SEQ ID NO: 136) as an antigen epitope, the binding ability of N3 antibody, N3-6 antibody, N3-7 antibody, N3-8 antibody, and N3-9 antibody was analyzed through Surface Plasmon Resonance (SPR). SPR experiment was carried out in the same manner as in the Example 5-4. The epitope was diluted in PBS solution and diluted 2-fold in the range of 15.7 nM-4000 nM, and allowed to flow for 90 seconds. Thereafter, PBS was flowed for 2400 seconds. The obtained data was analyzed with Biacore T200 Evaluation software v2.0 (GE Healthcare).

Figure 24:
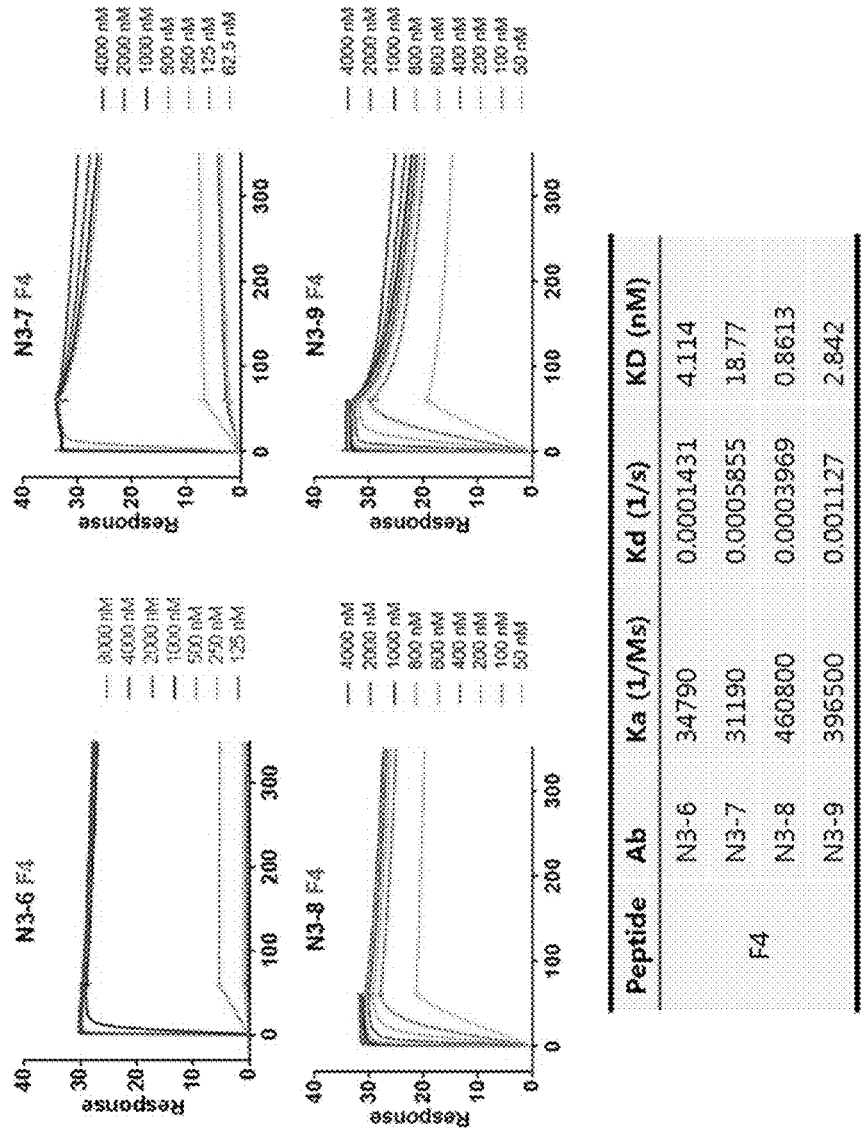
FIG. 24 shows the results of comparing the affinity for KRS by the surface plasmon resonance (SPR) method while confirming the major binding region of the N3-6 antibody, N3-7 antibody, N3-8 antibody and N3-9 antibody.

As a result, as shown in FIG. 24, the improved antibodies N3-6 antibody, N3-7 antibody, N3-8 antibody, and N3-9 antibodies were also confirmed to have a main biding site similar to the N3 antibody (See Example 5-4). Additionally, ELISA was performed to identify residues that are important for antibody-epitope binding, using peptides in which the constituent amino acids of KRS epitope peptide F4 (SEQ ID NO: 136) were substituted with alanine (A), respectively. As a result, the residues that are important in binding to each antibody can be identified in KRS epitope peptide F4.

Also, as shown in FIG. 24, the KD of the N3-8 antibody (KD=0.8613 nM) was exhibited to be excellent, the KD of the N3-9 (KD=2.842 nM) and N3-6 antibodies (KD=4.114 nM) were similar, and the KD value of the N3-7 antibody (KD=18.77 nM) was the largest. The dissociation time of N3-6 antibody was longer than that of N3-7 and N3-9, and showed a sensorgram with longer binding.

8-7. Production of Improved Antibody with Productivity and Stability Based on N3-8 Antibody (N3-8 Antibody Sequence Refinement)

In the above example, it was confirmed that the N3-8 antibody had the best affinity to KRS (especially N-term). Thus, in order to confirm the properties such as productivity and stability of the N3-8 antibody and to make these properties even better, N3-8 derivatives were produced by inducing mutations in sequences expected to affect stability in the N3-8 antibody sequence.

As a result, two heavy chain sequences (SEQ ID NO: 45, SEQ ID NO: 47) in which mutations were introduced into the heavy chain variable region of the N3-8 antibody were obtained. In addition, three light chain sequences (SEQ ID NO: 51, SEQ ID NO: 53, SEQ ID NO: 55) in which mutations were introduced into the light chain variable region were obtained. The seven types of sequences of N3-8 derivatives according to the combination of heavy and light chain sequences are shown in Tables 9 and 10 below, and they maintain the affinity properties of N3-8 antibodies.

TABLE 9

| | Heavy | | | Light | | |
|---|---|---|---|---|---|---|
| | CDR H1 | CDR H2 | CDR H3 | CDR L1 | CDR L2 | CDR L3 |
| N3-8-1 | SYDMS (SEQ ID NO: 1) | AISPYSGRIYY ADSVKG (SEQ ID NO: 21) | MALDFDY (SEQ ID NO: 5) | TGSSSNIGSN YVT (SEQ ID NO: 7) | DNSNRPS (SEQ ID NO: 9) | SSFSDELG AYV (SEQ ID NO: 15) |
| N3-8-2 | SYDMS (SEQ ID NO: 1) | AISPYSGRIYY ADSVKG (SEQ ID NO: 21) | MALDFDY (SEQ ID NO: 5) | TGSSSNIGSN YVT (SEQ ID NO: 7) | SNNQRPS (SEQ ID NO: 27) | SSFSDELG AYV (SEQ ID NO: 15) |
| N3-8-3 | SYDMS (SEQ ID NO: 1) | AISPYSGRIYY ADSVKG (SEQ ID NO: 21) | MALDFDY (SEQ ID NO: 5) | TGSSSNIGSN YVT (SEQ ID NO: 7) | RNNQRPS (SEQ ID NO: 29) | SSFSDELG AYV (SEQ ID NO: 15) |
| N3-8-4 | SYDMS (SEQ ID NO: 1) | AISPYSGRIYY ADSVKG (SEQ ID NO: 21) | LALDFDY (SEQ ID NO: 25) | TGSSSNGSN YVT (SEQ ID NO: 7) | DNSNRPS (SEQ ID NO: 9) | SSFSDELG AYV (SEQ ID NO: 15) |
| N3-8-5 | SYDMS (SEQ ID NO: 1) | AISPYSGRIYY ADSVKG (SEQ ID NO: 21) | LALDFDY (SEQ ID NO: 25) | TGSSSNIGSN YVT (SEQ ID NO: 7) | SNNQRPS (SEQ ID NO: 27) | SSFSDELG AYV (SEQ ID NO: 15) |
| N3-8-6 | SYDMS (SEQ ID NO: 1) | AISPYSGRIYY ADSVKG (SEQ ID NO: 21) | LALDFDY (SEQ ID NO: 25) | TGSSSNIGSN YVT (SEQ ID NO: 7) | RNNQRPS (SEQ ID NO: 29) | SSFSDELG AYV (SEQ ID NO: 15) |
| N3-8-7 | SYDMS (SEQ ID NO: 1) | AISPYSGRIYY ADSVKG (SEQ ID NO: 21) | MALDFDY (SEQ ID NO: 5) | TGSSSNIGSN YVT (SEQ ID NO: 7) | DNSNRPS (SEQ ID NO: 9) | SSFSDELG AYV (SEQ ID NO: 15) |

TABLE 10

| | Sequence | SEQ ID NO: (Sequence name) |
|---|---|---|
| N3-8-1 VH | EVQLLESGGGLVQPGGSLRLSCAASGFTFSSYDMSWVRQAPG KGLEWVSAISPYSGRIYYADSVKGRFTISRDNSKNTLYLQMN SLRAEDTAVYYCARMALDFDYWGQGTLVTVSS | SEQ ID NO: 45 (N3 VH mutant 6) |
| VL | QSVLTQPPSASGTPGQRVTISCTGSSSNIGSNYVTWYQQLPG TAPKLLIYDNSNRPSGVPDRFSGSKSGTSASLAISGLQSEDE ADYYCSSFSDELGAYVFGGGTKLTVL | SEQ ID NO: 51 (N3 VL mutant: 2) |
| N3-8-2 VH | EVQLLESGGGLVQPGGSLRLSCAASGFTFSSYDMSWVRQAPG KGLEWVSAISPYSGRIYIADSVKGRFTISRDNSKNTLYLQMN SLRAEDTAVYYCARMALDFDYWGQGTLVTVSS | SEQ ID NO: 45 (N3 VH mutant 6) |
| VL | QSVLTQPPSASGTPGQRVTISCTGSSSNIGSNYVTWYQQLPG TAPKLLIYSNNQRPSGVPDRFSGSKSGTSASLAISGLQSEDE ADYYCSSFSDELGAYVFGGGTKLTVL | SEQ ID NO: 53 (N3 VL mutant 3) |
| N3-8-3 VH | EVQLLESGGGLVQPGGSLRLSCAASGFTFSSYDMSWVRQAPG KGLEWVSAISPYSGRIYYADSVKGRFTISRDNSKNTLYLQMN SLRAEDTAVYYCARMALDFDYWGQGTLVTVSS | SEQ ID NO: 45 (N3 VH mutant 6) |
| VL | QSVLTQPPSASGTPGQRVTISCTGSSSNIGSNYVTWYQQLPG TAPKLLIYRNNQRPSGVPDRFSGSKSGTSASLAISGLQSEDE ADYYCSSFSDELGAYVFGGGTKLTVL | SEQ ID NO: 55 (N3 VL mutant: 4) |
| N3-8-4 VH | EVQLLESGGGLVQPGGSLRLSCAASGFTFSSYDMSWVRQAPG KGLEWVSAISPYSGRIYYADSVKGRFTISRDNSKNTLYLQMN SLRAEDTAVYYCARLALDFDYWGQGTLVTVSS | SEQ ID NO: 47 (N3 VH mutant 7) |
| VL | QSVLTQPPSASGTPGQRVTISCTGSSSNIGSNYVTWYQQLPG TAPKLLIYDNSNRPSGVPDRFSGSKSGTSASLAISGLQEDE ADYYCSSFSDELGAYVFGGGTKLTVL | SEQ ID NO: 51 (N3 VL mutant 2) |
| N3-8-5 VH | EVQLLESGGGLVQPGGSLRLSCAASGFTFSSYDMSWVRQAPG KGLEWVSAISPYSGRIYYADSVKGRFTISRDNSKNTLYLQMN SLRAEDTAVYYCARLALDFDYWGQGTLVTVSS | SEQ ID NO: 47 (N3 VH mutant V) |

TABLE 10-continued

| Sequence | | SEQ ID NO: (Sequence name) |
|---|---|---|
| | VL QSVLTQPPSASGTPGQRVTISCTGSSSNIGSNYVTWYQQLPG TAPKLLIYSNNQRPSGVPDRFSGSKSGTSASLAISGLQSEDE ADYYCSSFSDELGAYVFGGGTKLTVL | SEQ ID NO: 53 (N3 VL mutant: 3) |
| N3-8-6 | VH EVQLLESGGGLVQPGGSLRLSCAASGFTFSSYDMSWVRQAPG KGLEWVSAISPYSGRIYYADSVKGPFTISRDNSKNTLYLQMN SLRAEDTAVYYCARLALDFDYWGQGTLVTVSS | SEQ ID NO: 47 (N3 VH mutant 7) |
| | VL QSVLTQPPSASGTPGQRVTISCTGSSSNIGSNYVTWYQQLPG TAPKLLIYRNNQRPSGVPDRFSGSKSGTSASLAISGLQSEDE ADYYCSSFSDELGAYVFGGGTKLTVL | SEQ ID NO: 55 (N3 VL mutant 4) |
| N3-8-7 | VH EVQLLESGGGLVQPGGSLRLSCAASGFTFSSYDMSWVRQAPG KGLEWVSAISPYSGRIYYADSVKGRFTISRDNSKNTLYLQMN SLRAEDTAVYYSARMALDFDYWGQGTLVTVSS | SEQ ID NO: 41 (N3 VH mutant 4) |
| | VL QSVLTQPPSASGTPGQRVTISCTGSSSNIGSNYVTWYQQLPG TAPKLLIYDNSNRPSGVPDRFSGSKSGTSASLAISGLQSEDE ADYYCSSFSDELGAYVFGGGTKLTVL | SEQ ID NO: 51 (N3 VL mutant 2) |

Table 11 shows the heavy chain (HC) and light chain (LC) sequences of the entire IgG antibodies used in the above-described examples.

TABLE 11

| | | Amino acid sequence | DNA sequence |
|---|---|---|---|
| N3 | HC | SEQ ID NO: 89 | SEQ ID NO: 90 |
| | LC | SEQ ID NO: 91 | SEQ ID NO: 92 |
| N3-1 | HC | SEQ ID NO: 89 | SEQ ID NO: 90 |
| | LC | SEQ ID NO: 107 | SEQ ID NO: 108 |
| N3-3 | HC | SEQ ID NO: 89 | SEQ ID NO: 90 |
| | LC | SEQ ID NO: 109 | SEQ ID NO: 110 |
| N3-4 | HC | SEQ ID NO: 93 | SEQ ID NO: 94 |
| | LC | SEQ ID NO: 107 | SEQ ID NO: 108 |
| N3-5 | HC | SEQ ID NO: 93 | SEQ ID NO: 94 |
| | LC | SEQ ID NO: 109 | SEQ ID NO: 110 |
| N3-6 | HC | SEQ ID NO: 95 | SEQ ID NO: 90 |
| | LC | SEQ ID NO: 109 | SEQ ID NO: 110 |
| N3-7 | HC | SEQ ID NO: 97 | SEQ ID NO: 98 |
| | LC | SEQ ID NO: 109 | SEQ ID NO: 110 |
| N3-8 | HC | SEQ ID NO: 99 | SEQ ID NO: 100 |
| | LC | SEQ ID NO: 109 | SEQ ID NO: 110 |
| N3-9 | HC | SEQ ID NO: 101 | SEQ ID NO: 102 |
| | LC | SEQ ID NO: 109 | SEQ ID NO: 110 |
| N3-8-1 | HC | SEQ ID NO: 103 | SEQ ID NO: 104 |
| | LC | SEQ ID NO: 111 | SEQ ID NO: 112 |
| N3-8-2 | HC | SEQ ID NO: 103 | SEQ ID NO: 104 |
| | LC | SEQ ID NO: 113 | SEQ ID NO: 114 |
| N3-8-3 | HC | SEQ ID NO: 103 | SEQ ID NO: 104 |
| | LC | SEQ ID NO: 115 | SEQ ID NO: 116 |
| N3-8-4 | HC | SEQ ID NO: 105 | SEQ ID NO: 106 |
| | LC | SEQ ID NO: 111 | SEQ ID NO: 112 |
| N3-8-5 | HC | SEQ ID NO: 105 | SEQ ID NO: 106 |
| | LC | SEQ ID NO: 113 | SEQ ID NO: 114 |
| N3-8-6 | HC | SEQ ID NO: 105 | SEQ ID NO: 106 |
| | LC | SEQ ID NO: 115 | SEQ ID NO: 116 |
| N3-8-7 | HC | SEQ ID NO: 99 | SEQ ID NO: 100 |
| | LC | SEQ ID NO: 111 | SEQ ID NO: 112 |

8-8. Measurement of Productivity and Stability of N3-8 Derivatives (Tm Measurement)

Each antibody protein was expressed and purified by a transient transfection method using plasmids expressing the light and heavy chains of the N3-8 derivative antibodies obtained in the Example 8-7. In HEK293-F cells (Invitrogen) suspended in serum-free FreeStyle 293 expression medium (Invitrogen) in a shake flask, the plasmid and polyethylenimine (Polyethylenimine, Polyscience) were transfected.

Specifically, during transfection into a 200 mL shake flask, HEK293-F cells were seeded in 100 ml of medium at a density of $2 \times 10^6$ cells/ml and cultured at 150 rpm and 37° C. with 8% 002. The heavy chain plasmid and light chain plasmid suitable for the production of each monoclonal antibody were transfected by treating them in a ratio of heavy chain: light chain DNA 1:1 or 1:2 (mixed treatment in 10 ml FreeStyle 293 expression medium). First, when heavy chain: light chain DNA is used in a 1: 1 ratio, 125 μg heavy chain, 125 μg light chain, and 250 μg (2.5 μg/ml) in total are mixed with 10 ml of medium diluted with PEI 750 μg (7.5 μg/ml) at room temperature. The reaction was carried out for 10 minutes. In the case of the ratio 1: 2, the concentration of the light chain DNA was doubled. Thereafter, the mixed medium was treated with HEK293-F cells previously aliquoted with 100 ml, and incubated at 150 rpm and 37° C., with 8% $CO_2$, and for 4 hours. And the remaining 100 ml of FreeStyle 293 expression medium was added and cultured for 6 days.

Then, the cell culture solution was transferred to 50 ml tubes and centrifuged for 5 minutes at 3000 rpm. Protein was then purified from the collected cell culture supernatant. The supernatant was applied to a Protein A Sepharose column, and then washed with PBS (pH 7.4). After eluting the antibody at pH 3.0 with 0.1 M glycine buffer, the sample was immediately neutralized with 1 M Tris buffer. The eluted antibody fraction was concentrated by exchanging buffer with PBS (pH 7.4) through a dialysis method. The purified protein was quantified using absorbance and absorption coefficient at a wavelength of 280 nm.

In addition, the thermal stability of the antibody was measured using 100 μl of the purified antibodies at a concentration of 1 mg/ml. Protein thermal shift Dye kit (Thermofisher) was performed 4 times with Quant Studio 3 Real-time PCR equipment (Thermofisher).

As a result, as shown in Table 12 below, it was confirmed that the yield of all N3-8 derivative antibodies tested was improved over that of the N3-8 antibody. In addition, as shown in Table 12, Tm values were obtained, and thermal transition was observed differently according to the antibody as Tm1-Tm2, but it was found that the Tm value was increased in all N3-8 derivative antibodies.

Through this, it was confirmed that the N3-8 antibody derivatives had higher yield and improved thermal stability than the N3-8 antibody.

TABLE 12

| Antibody | Yield (mg/L) Heavy chain DNA: Light chain DNA 1:1 | Yield (mg/L) Heavy chain DNA: Light chain DNA 1:2 | Thermal stability Tm1 | Thermal stability Tm2 |
|---|---|---|---|---|
| N3-8 | 69.9 | 104.61 | 67.37 | — |
| N3-8-1 | 87.13 | 109.9 | 69.94 | — |
| N3-8-2 | 96.76 | 109.68 | 72.41 | — |
| N3-8-3 | 93.44 | 93.53 | 71.02 | 76.31 |
| N3-8-4 | 86.14 | 89.23 | 70.31 | — |
| N3-8-5 | 84.31 | 107.37 | 72.9 | — |
| N3-8-6 | 105.95 | 92.9 | 71.0 | 76.97 |

(In the above table, '—' refers to the same value as Tm1)

Example 9: Confirmation of Increased Therapeutic Efficacy of N3 Improved Antibody With respect to the N3 improved antibodies produced in the above example, it was confirmed whether the therapeutic effect is remarkable for immune cell migration-related diseases even in vivo. Pulmonary arterial hypertension model was used as a disease model, and N3-6 antibody and N3-8 antibody were typically used as improved antibodies.

To induce pulmonary arterial hypertension in 7-week-old SD rats (Orient Bio), 60 mpk of MCT (monocrotaline) was injected subcutaneously. After inducing disease for 2 weeks, it was divided into four groups (five experiments per group), and PBS, 1 mpk of N3 antibody 1 mpk, 1 mpk of N3-6 antibody, and 1 mpk of N3-8 antibody were administered for 3 weeks, respectively. All antibodies were injected with i.v. twice a week. The measurement of blood flow and blood pressure, and immunohistochemical staining (IHC) were performed for each experimental group in the same manner as described in the Example 6 above. In addition, the lung tissue of each experimental group was stained with Masson's trichrome staining method to measure the degree of lung fibrosis, and Masson's trichrome staining method was performed in the same manner as described in the Example 7.

In the lungs of animals treated with MCT alone, endothelitis of the pulmonary vessels, smooth muscle proliferation of the arterioles, intimal hyperplasia, and vascular occlusion were observed. Therefore, it was confirmed that an animal model of pulmonary arterial hypertension disease was well produced.

Figure 25:
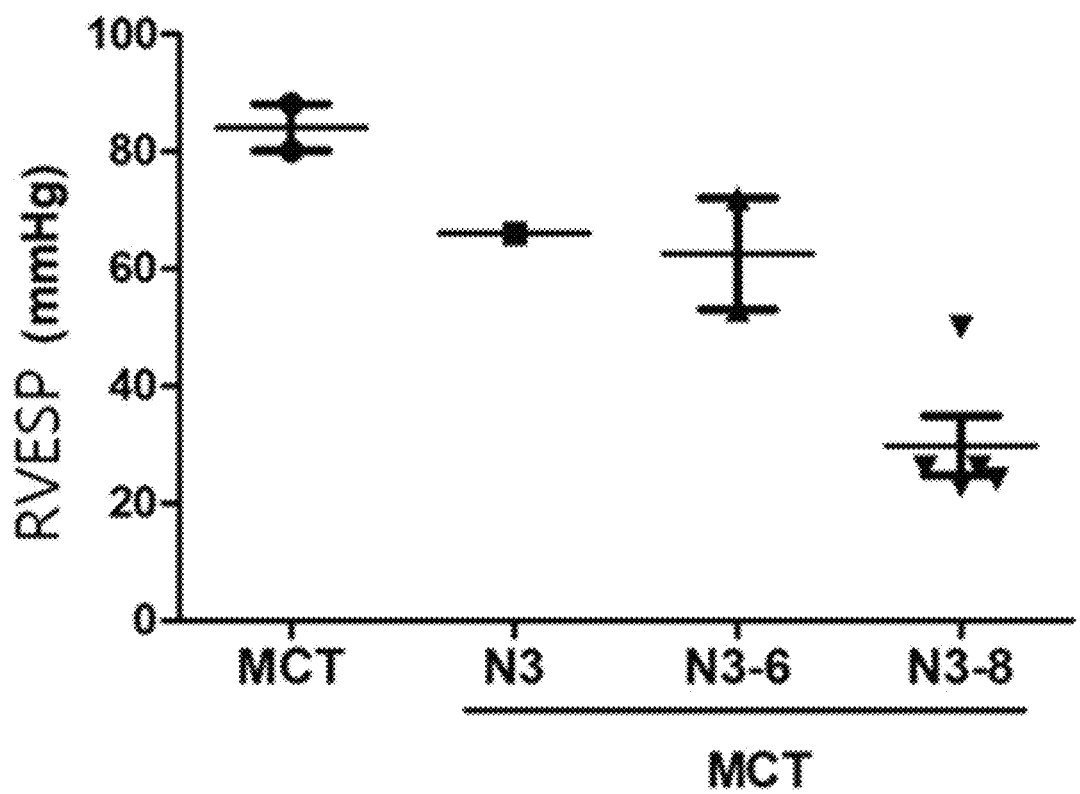
FIG. 25 shows changes in right ventricular end-systolic pressure (RVESP) of pulmonary hypertension (PAH) models by administration of N3 antibody, N3-6 antibody, and N3-8 antibody, respectively.

The phenomena exhibited by the pulmonary arterial hypertension were significantly reduced by treating the antibody of the present invention. Specifically, as shown in FIG. 25, it was confirmed that the increased RVESP in pulmonary arterial hypertension (MCT-only treatment group) was significantly reduced by treating the N3 antibody and the N3 improved antibody of the present invention, and in particular, the N3-8 antibody has a very excellent RVESP reduction effect.

Figure 26:
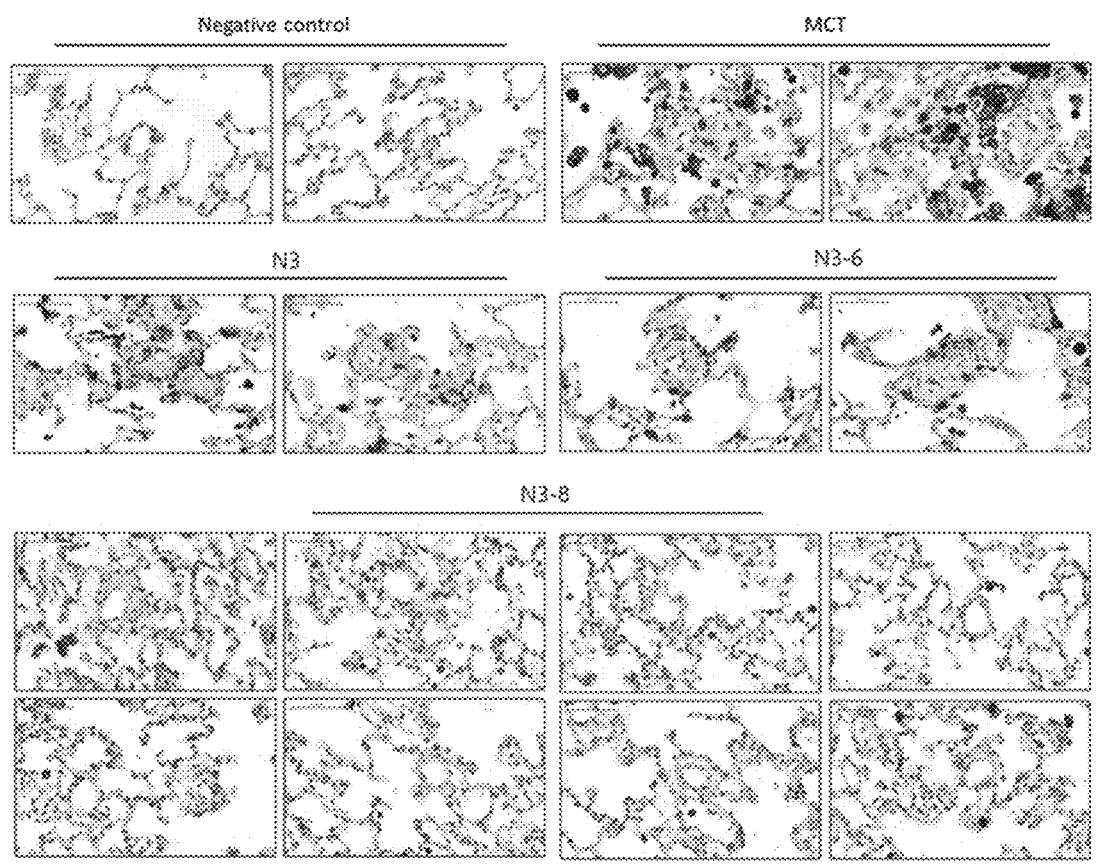
FIG. 26 shows the results of confirming by IHC staining that immune cell migration and invasion were reduced by administration of N3 antibody, N3-6 antibody, and N3-8 antibody of the present invention in pulmonary arterial hypertension (PAH) models, respectively.

FIG. 26 showed the results of IHC staining for each control group and experimental group of lung tissue. It was confirmed that CD68+ monocyte/macrophage staining was strongly observed in the lungs of pulmonary arterial hypertension (MCT-only treatment group) animals, whereas the degree of staining was weakened in the N3 antibody or N3-6 antibody treatment group, and in the N3-8 antibody treatment group, the staining intensity was significantly reduced to a level similar to the negative control. This means that the infiltration of the monocyte/macrophage in the tissue was inhibited by treating the antibody of the present invention, and particularly shows the excellent effect of the N3-8 antibody.

Figure 27:
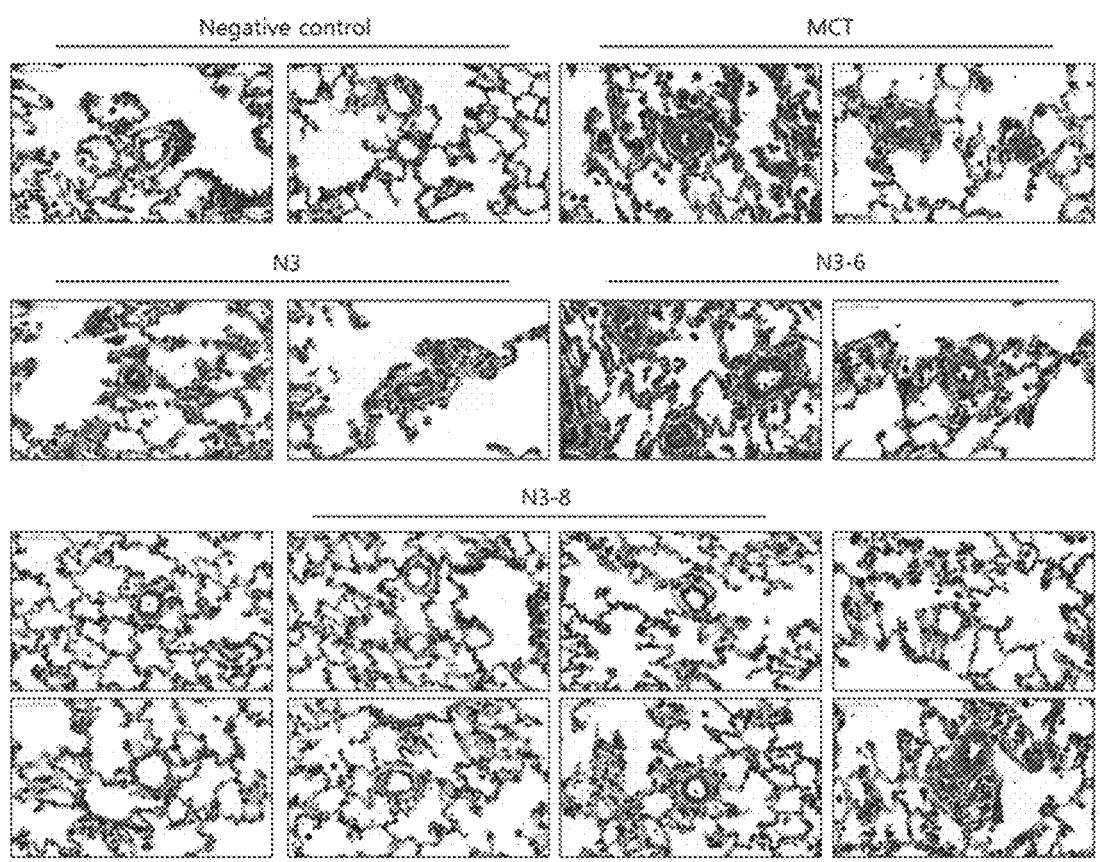
FIG. 27 is a tissue image showing by Masson's trichrome staining that tissue fibrosis advanced in lung tissue of the pulmonary arterial hypertension (PAH) models was inhibited by administration of the N3, N3-6 and N3-8 antibodies of the present invention, respectively.

In addition, as shown in FIG. 27, it was confirmed that the lung fibrosis level was strongly observed in the lung tissue of pulmonary arterial hypertension (MCT-only treatment group) animals, whereas the fibrosis symptom level was significantly weakened in the N3 antibody or N3-6 antibody treatment group, and in the N3-8 antibody treatment group, and fibrosis was reduced to a level similar to that of the negative control. This means that the fibrosis is reduced by treating the antibody of the present invention, and in particular, it shows the excellent effect of the N3-8 antibody.

INDUSTRIAL APPLICABILITY

The present invention relates to a novel use of an antibody biding specifically to the N-terminus of lysyl-tRNA synthetase and, more particularly, to a pharmaceutical composition comprising an antibody biding specifically to an epitope including the sequence of SEQ ID NO: 117 in the N-terminal domain of lysyl-tRNA synthetase (KRS) or a functional fragment thereof as an effective ingredient for preventing and treating an immune cell migration-related disease. A KRS N-terminus-specific antibody provided by the present invention can regulate the migration of immune cells, and thus can be very usefully used in the prevention, alleviation, and treatment of immune cell migration-related diseases, and therefore have high industrial applicability.

What is claimed is:

1. A method for treating an immune cell migration-related disease in a subject, the method comprising administering to the subject in need thereof an effective amount of a composition comprising an antibody binding specifically to an epitope containing the sequence of SEQ ID NO: 117 in the N-terminus of lysyl-tRNA synthetase (KRS) or an antigen binding fragment thereof as an effective ingredient, wherein the antibody or antigen binding fragment thereof comprises:

(a) a heavy chain variable region comprising: a heavy chain complementarity determining region 1 containing the amino acid sequence defined by SEQ ID NO: 1, a heavy chain complementarity determining region 2 containing the amino acid sequence defined by SEQ ID NO: 3 or SEQ ID NO: 151, and a heavy chain complementarity determining region 3 containing the amino acid sequence defined by SEQ ID NO: 5; and a light chain variable region comprising: a light chain complementarity determining region 1 containing the amino acid sequence defined by SEQ ID NO: 7, a light chain complementarity determining region 2 containing the amino acid sequence defined by SEQ ID NO: 9, and a light chain complementarity determining region 3 containing the amino acid sequence defined by SEQ ID NO: 11, SEQ ID NO: 13 or SEQ ID NO: 15;

(b) a heavy chain variable region comprising: a heavy chain complementarity determining region 1 containing the amino acid sequence defined by SEQ ID NO: 1, a heavy chain complementarity determining region 2 containing the amino acid sequence defined by SEQ ID NO: 17, SEQ ID NO: 19, SEQ ID NO: 21 or SEQ ID NO: 23, and a heavy chain complementarity determining region 3 containing the amino acid sequence defined by SEQ ID NO: 5; and a light chain variable region comprising: a light chain complementarity determining region 1 containing the amino acid sequence defined by SEQ ID NO: 7, a light chain complementarity determining region 2 containing the amino acid sequence defined by SEQ ID NO: 9, and a light chain complementarity determining region 3 containing the amino acid sequence defined by SEQ ID NO: 15: or (c) a heavy chain variable region comprising: a heavy chain complementarity determining region 1 containing the amino acid sequence defined by SEQ ID NO: 1, a heavy chain complementarity determining region 2 containing the amino acid sequence defined by SEQ ID NO: 21, and a heavy chain complementarity determining region 3 containing the amino acid sequence defined by SEQ ID NO: 5 or SEQ ID NO: 25; and a light chain variable region comprising: a light chain complementarity determining region 1 containing the amino acid sequence defined by SEQ ID NO: 7, a light chain complementarity determining region 2 containing the amino acid sequence defined by SEQ ID NO: 9, SEQ ID NO: 27, or SEQ ID NO: 29, and a light chain complementarity determining region 3 containing the amino acid sequence defined by SEQ ID NO: 15, wherein the immune cell migration-related disease is a cardiovascular disease, a fibrotic disease, an inflammatory disease, or Alport syndrome.

2. The method of claim 1, wherein the epitope is selected from the group consisting of SEQ ID NO: 133, SEQ ID NO: 134, SEQ ID NO: 135, SEQ ID NO: 136, SEQ ID NO: 138, SEQ ID NO: 139, SEQ ID NO: 140, SEQ ID NO: 141, SEQ ID NO: 143, SEQ ID NO: 144, SEQ ID NO: 145, SEQ ID NO: 146, SEQ ID NO: 148, SEQ ID NO: 149 and SEQ ID NO: 150.

3. The method of claim 1, wherein the antibody or antigen binding fragment thereof decreases the level of KRS on a cell membrane.

4. The method of claim 1, wherein the antibody or antigen binding fragment thereof is a heavy chain variable region containing the amino acid sequence defined by SEQ ID NO: 31; and a light chain variable region containing the amino acid sequence defined by SEQ ID NO: 33.

5. The method of claim 1, wherein the antibody is selected from the group consisting of IgG, IgA, IgM, IgE and IgD, and the antigen binding fragment is selected from the group consisting of diabody, Fab, Fab', F (ab)2, F (ab')2, Fv and scFv.

6. The method of claim 5, wherein the scFv comprises an amino acid sequence defined by SEQ ID NO: 59.

7. The method of claim 1, wherein the cardiovascular disease is selected from the group consisting of hypertension, pulmonary arterial hypertension, atherosclerosis, angina pectoris, myocardial infarction, ischemic cerebrovascular disease, atherosclerosis and mesenteric sclerosis.

8. The method of claim 1, wherein the fibrotic disease is selected from the group consisting of scleroderma, rheumatoid arthritis, Crohn's disease, ulcerative colitis, myelofibrosis, pulmonary fibrosis, hepatic fibrosis, liver cirrhosis, kidney fibrosis, glomerulosclerosis, myofibrosis, myofibrosis cordis, interstitial fibrosis, pancreatic fibrosis, splenic fibrosis, mediastinal fibrosis, vascular fibrosis, skin fibrosis, eye fibrosis, macular degeneration, joint fibrosis, thyroid fibrosis, endomyocardial fibrosis, peritoneal fibrosis, retroperitoneal fibrosis, progressive mass fibrosis, nephrogenic systemic fibrosis, systemic lupus erythematosus, hereditary fibrosis, infectious fibrosis, irritant fibrosis, fibrosis due to chronic autoimmunity, fibrosis due to antigen incompatibility during organ transplantation, fibrotic complications during surgery, fibrosis due to hyperlipidemia, fibrosis due to obesity, diabetic fibrosis, fibrosis due to hypertension, and occlusion due to fibrosis at the time of stent insertion.

9. The method of claim 1, wherein the inflammatory disease is selected from the group consisting of an autoimmune disease, inflammatory bowel disease, dermatitis, atopic dermatitis, eczema, psoriasis, diabetic eye disease, diabetic retinopathy, peritonitis, osteomyelitis, cellulites, meningitis, encephalitis, pancreatitis, trauma-induced shock, bronchial asthma, rhinitis, sinusitis, tympanitis, pneumonia, gastritis, enteritis, cystic fibrosis, apoplexy, stroke, bronchitis, bronchiolitis, hepatitis, cirrhosis, steatohepatitis, non-alcoholic steatohepatitis, nephritis, diabetic renal failure, proteinuria, arthritis, psoriatic arthritis, osteoarthritis, neuritis, diabetic neuropathy, multiple sclerosis, gout, spondylitis, Reiter's syndrome, polyarteritis nodosa, vasculitis, amyotrophic lateral sclerosis, Wegener's granulomatosis, hypercytokinemia, Polymyalgia rheumatica, articular cell arteritis, calcium crystalline arthritis, pseudogout, non-articular rheumatoid, bursitis, tendosynovitis, epicondylitis (tennis elbow), Charcot's joint, hemarthrosis, Henoch-Schonlein purpura, hypertrophic osteoarthritis, multicentric reticulocytoma, sarcoidosis, hemochromatosis, drepanocytosis, hyperlipoproteinemia, hypogammaglobulinemia, hyperparathyroidism, acromegaly, familial Mediterranean fever, systemic lupus erythematosus, recurrent fever, psoriasis, multiple sclerosis, sepsis, septic shock, acute respiratory distress syndrome, multiple organs dysfunction, chronic obstructive pulmonary disease, acute lung injury, and broncho-pulmonary dysplasia.

10. The method of claim 9, wherein the autoimmune disease is selected from the group consisting of rheumatoid arthritis, systemic scleroderma, systemic lupus erythematosus, psoriasis, asthma, ulcerative colitis, Behcet's disease, Crohn's disease, multiple sclerosis, dermatitis, collagen disease, vasculitis, arthritis, granulomatosis, organ specificity autoimmune diseases and GvHD (graft-versus-host disease).

11. The method of claim 5, wherein the scFv comprises an amino acid sequence selected from the group consisting of SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85 and SEQ ID NO: 87.

12. The method of claim 1, wherein the cardiovascular disease is pulmonary arterial hypertension.

* * * * *